(12) United States Patent
Igawa et al.

(10) Patent No.: US 11,332,533 B2
(45) Date of Patent: May 17, 2022

(54) MODIFIED ANTIBODY CONSTANT REGION

(71) Applicant: CHUGAI SEIYAKU KABUSHIKI KAISHA, Tokyo (JP)

(72) Inventors: Tomoyuki Igawa, Shizuoka (JP); Hirotake Shiraiwa, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/614,842

(22) Filed: Jun. 6, 2017

(65) Prior Publication Data

US 2017/0342154 A1    Nov. 30, 2017

Related U.S. Application Data

(62) Division of application No. 12/680,082, filed as application No. PCT/JP2008/067483 on Sep. 26, 2008, now Pat. No. 9,688,762.

(30) Foreign Application Priority Data

Sep. 26, 2007 (JP) .............................. JP2007-250147

(51) Int. Cl.
   *C07K 16/28* (2006.01)
   *C07K 16/00* (2006.01)

(52) U.S. Cl.
   CPC .......... *C07K 16/2866* (2013.01); *C07K 16/00* (2013.01); *C07K 2317/52* (2013.01); *C07K 2317/53* (2013.01); *C07K 2317/71* (2013.01)

(58) Field of Classification Search
   None
   See application file for complete search history.

(56) References Cited

U.S. PATENT DOCUMENTS

| | | |
|---|---|---|
| 4,676,980 A | 6/1987 | Segal et al. |
| 4,737,456 A | 4/1988 | Weng et al. |
| 4,816,567 A | 3/1989 | Cabilly et al. |
| 5,126,250 A | 6/1992 | McDonough et al. |
| 5,208,020 A | 5/1993 | Chari et al. |
| 5,322,678 A | 6/1994 | Morgan et al. |
| 5,416,064 A | 5/1995 | Chari et al. |
| 5,455,030 A | 10/1995 | Ladner et al. |
| 5,468,634 A | 11/1995 | Liu |
| 5,500,362 A | 3/1996 | Robinson et al. |
| 5,571,894 A | 11/1996 | Wells et al. |
| 5,587,458 A | 12/1996 | King et al. |
| 5,624,821 A | 4/1997 | Winter et al. |
| 5,635,483 A | 6/1997 | Pettit et al. |
| 5,639,641 A | 6/1997 | Pedersen et al. |
| 5,648,237 A | 7/1997 | Carter |
| 5,648,260 A | 7/1997 | Winter et al. |
| 5,670,373 A | 9/1997 | Kishimoto |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,750,373 A | 5/1998 | Garrard et al. |
| 5,767,285 A | 6/1998 | Hammann et al. |
| 5,770,429 A | 6/1998 | Lonberg et al. |
| 5,770,701 A | 6/1998 | Mcgahren et al. |
| 5,770,710 A | 6/1998 | Mcgahren et al. |
| 5,773,001 A | 6/1998 | Hamann et al. |
| 5,780,588 A | 7/1998 | Pettit et al. |
| 5,789,199 A | 8/1998 | Joly et al. |
| 5,795,965 A | 8/1998 | Tsuchiya et al. |
| 5,817,790 A | 10/1998 | Tsuchiya et al. |
| 5,821,337 A | 10/1998 | Carter et al. |
| 5,840,523 A | 11/1998 | Simmons et al. |
| 5,859,205 A | 1/1999 | Adair et al. |
| 5,869,046 A | 2/1999 | Presta et al. |
| 5,877,296 A | 3/1999 | Hamann et al. |
| 5,888,510 A | 3/1999 | Kishimoto et al. |
| 5,945,311 A | 8/1999 | Lindhofer et al. |
| 5,959,177 A | 9/1999 | Hein et al. |
| 5,990,286 A | 11/1999 | Khawli et al. |
| 6,018,032 A | 1/2000 | Koike et al. |
| 6,040,498 A | 3/2000 | Stomp et al. |
| 6,075,181 A | 6/2000 | Kucherlapati et al. |

(Continued)

FOREIGN PATENT DOCUMENTS

| | | |
|---|---|---|
| AR | 068564 | 11/2009 |
| AU | 2007/255753 | 12/2007 |

(Continued)

OTHER PUBLICATIONS

U.S. Appl. No. 11/910,128, Igawa et al., filed Oct. 7, 2008.
U.S. Appl. N. 12/295,030, Igawa et al., filed Jan. 20, 2009.
U.S. Appl. No. 12/295,075, Igawa et al., filed Apr. 20, 2009.
U.S. Appl. No. 14/741,786, Igawa et al., filed Jun. 17, 2015.
U.S. Appl. No.13/524,528, Igawa et al., filed Jun. 15, 2012.
U.S. Appl. No. 12/680,082, Igawa et al., filed Jun. 25, 2010.
U.S. Appl. No. 12/680,112, Igawa et al., filed Jun. 23, 2010.
U.S. Appl. No. 13/959,489, Igawa et al., filed Aug. 5, 2013.
U.S. Appl. No. 15/263,617, Igawa et al., filed Sep. 13, 2016.

(Continued)

*Primary Examiner* — Brad Duffy

(74) *Attorney, Agent, or Firm* — Fish & Richardson P.C.

(57) ABSTRACT

The present inventors succeeded in improving the antibody constant region to have increased stability under acid conditions, reduced heterogeneity originated from disulfide bonds in the hinge region, reduced heterogeneity originated from the H chain C terminus, and increased stability at high concentrations as well as in discovering novel constant region sequences having reduced Fcγ receptor-binding, while minimizing the generation of novel T-cell epitope peptides. As a result, the present inventors successfully discovered antibody constant regions with improved physicochemical properties (stability and homogeneity), immunogenicity, safety, and pharmacokinetics.

21 Claims, 24 Drawing Sheets

Specification includes a Sequence Listing.

(56) References Cited

U.S. PATENT DOCUMENTS

| | | |
|---|---|---|
| 6,126,980 A | 10/2000 | Smith et al. |
| 6,129,914 A | 10/2000 | Weiner |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,248,516 B1 | 6/2001 | Winter et al. |
| 6,267,958 B1 | 7/2001 | Andya et al. |
| 6,309,636 B1 | 10/2001 | do Couto et al. |
| 6,329,511 B1 | 12/2001 | Vasquez et al. |
| 6,417,429 B1 | 7/2002 | Hein et al. |
| 6,420,548 B1 | 7/2002 | Vezina et al. |
| 6,485,943 B2 | 11/2002 | Stevens et al. |
| 6,602,684 B1 | 8/2003 | Umana et al. |
| 6,677,436 B1 | 1/2004 | Sato et al. |
| 6,723,319 B1 | 4/2004 | Ito et al. |
| 6,737,056 B1 | 5/2004 | Presta |
| 6,884,879 B1 | 4/2005 | Baca et al. |
| 6,913,747 B1 | 7/2005 | Co et al. |
| 7,052,873 B2 | 5/2006 | Tsuchiya |
| 7,122,637 B2 | 10/2006 | Presta |
| 7,125,978 B1 | 10/2006 | Vezina et al. |
| 7,217,797 B2 | 5/2007 | Hinton et al. |
| 7,276,585 B2 | 10/2007 | Lazar et al. |
| 7,479,543 B2 | 1/2009 | Tsuchiya et al. |
| 7,482,440 B2 | 1/2009 | Maeda et al. |
| 7,615,213 B2 | 11/2009 | Kasaian et al. |
| 7,632,497 B2 | 12/2009 | Stavenhagen et al. |
| 8,562,991 B2 | 10/2013 | Igawa et al. |
| 8,575,317 B2 | 11/2013 | Kuramochi et al. |
| 8,592,562 B2 | 11/2013 | Kannan et al. |
| 8,637,641 B2 | 1/2014 | Dahiyat et al. |
| 9,096,651 B2 | 8/2015 | Igawa et al. |
| 9,228,017 B2 | 1/2016 | Igawa et al. |
| 9,288,017 B2 | 3/2016 | Choi et al. |
| 9,340,615 B2 | 5/2016 | Maeda et al. |
| 9,399,680 B2 | 7/2016 | Kuramochi et al. |
| 9,527,926 B2 | 12/2016 | Ho et al. |
| 9,556,279 B2 | 1/2017 | Niwa et al. |
| 9,637,557 B2 | 5/2017 | Scheer et al. |
| 9,670,269 B2 | 6/2017 | Igawa et al. |
| 9,688,762 B2 | 6/2017 | Igawa et al. |
| 9,828,429 B2 | 11/2017 | Igawa et al. |
| 10,011,858 B2 | 7/2018 | Igawa et al. |
| 10,066,018 B2 | 9/2018 | Igawa et al. |
| 10,150,808 B2 | 12/2018 | Kuramochi et al. |
| 10,253,091 B2 | 4/2019 | Igawa et al. |
| 10,435,458 B2 | 10/2019 | Kuramochi et al. |
| 10,604,561 B2 | 3/2020 | Sampei et al. |
| 10,662,245 B2 | 5/2020 | Igawa et al. |
| 10,774,148 B2 | 9/2020 | Kakehi et al. |
| 10,844,113 B2 | 11/2020 | Sampei et al. |
| 10,934,344 B2 | 3/2021 | Igawa et al. |
| 11,046,784 B2 | 6/2021 | Igawa et al. |
| 11,124,576 B2 | 9/2021 | Igawa et al. |
| 11,142,587 B2 | 10/2021 | Igawa et al. |
| 11,168,344 B2 | 11/2021 | Igawa et al. |
| 2001/0001663 A1 | 5/2001 | Kishimoto et al. |
| 2001/0036923 A1 | 11/2001 | Chari et al. |
| 2002/0142374 A1 | 10/2002 | Gallo et al. |
| 2002/0147326 A1 | 10/2002 | Chaiklin et al. |
| 2002/0164328 A1 | 11/2002 | Shinkawa et al. |
| 2002/0164339 A1 | 11/2002 | Do Couto et al. |
| 2002/0164668 A1 | 11/2002 | Durham et al. |
| 2002/0187150 A1 | 12/2002 | Mihara et al. |
| 2002/0199213 A1 | 12/2002 | Tomizuka et al. |
| 2003/0115614 A1 | 6/2003 | Kanda et al. |
| 2003/0125520 A1 | 7/2003 | Maeda et al. |
| 2003/0144486 A1 | 7/2003 | Rodman |
| 2003/0157108 A1 | 8/2003 | Presta |
| 2003/0166871 A1 | 9/2003 | Barbas et al. |
| 2003/0187225 A1 | 10/2003 | Penichet et al. |
| 2003/0190311 A1 | 10/2003 | Dall'Aqua et al. |
| 2003/0215838 A1 | 11/2003 | Sprecher et al. |
| 2003/0224397 A1 | 12/2003 | Lowman et al. |
| 2003/0224487 A1 | 12/2003 | Sprecher et al. |
| 2004/0071706 A1 | 4/2004 | Ito et al. |
| 2004/0081651 A1 | 4/2004 | Karpusas et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0127688 A1 | 7/2004 | Winter |
| 2004/0132140 A1 | 7/2004 | Satoh et al. |
| 2004/0223970 A1 | 11/2004 | Afar et al. |
| 2004/0236080 A1 | 11/2004 | Aburatani et al. |
| 2005/0014934 A1 | 1/2005 | Hinton et al. |
| 2005/0079574 A1 | 4/2005 | Bond |
| 2005/0095243 A1 | 5/2005 | Chan et al. |
| 2005/0119455 A1 | 6/2005 | Fuh et al. |
| 2005/0123546 A1 | 6/2005 | Umana et al. |
| 2005/0130224 A1 | 6/2005 | Saito et al. |
| 2005/0142133 A1 | 6/2005 | Lazar et al. |
| 2005/0142635 A1 | 6/2005 | Tsuchiya et al. |
| 2005/0158825 A1 | 7/2005 | Power et al. |
| 2005/0164352 A1* | 7/2005 | Lauder ............... A61K 38/2046 435/69.52 |
| 2005/0191293 A1 | 9/2005 | Deshpande et al. |
| 2005/0233382 A1 | 10/2005 | Presta |
| 2005/0238649 A1 | 10/2005 | Doronina et al. |
| 2005/0244403 A1 | 11/2005 | Lazar et al. |
| 2005/0260186 A1 | 11/2005 | Bookbinder et al. |
| 2005/0261229 A1 | 11/2005 | Gillies et al. |
| 2005/0266000 A1 | 12/2005 | Bond et al. |
| 2005/0276802 A1 | 12/2005 | Adams et al. |
| 2006/0019342 A1 | 1/2006 | Acqua et al. |
| 2006/0024298 A1 | 2/2006 | Lazar et al. |
| 2006/0025576 A1 | 2/2006 | Miller et al. |
| 2006/0057149 A1 | 3/2006 | Johnson et al. |
| 2006/0074225 A1 | 4/2006 | Chamberlain |
| 2006/0104968 A1 | 5/2006 | Bookbinder et al. |
| 2006/0121022 A1 | 6/2006 | Koga et al. |
| 2006/0134105 A1* | 6/2006 | Lazar ................. C07K 16/2878 424/133.1 |
| 2006/0134709 A1 | 6/2006 | Stavenhagen et al. |
| 2006/0134805 A1 | 6/2006 | Berg et al. |
| 2006/0141456 A1 | 6/2006 | Edwards et al. |
| 2006/0160184 A1 | 7/2006 | Hoogenboom et al. |
| 2006/0182743 A1 | 8/2006 | Bilsborough |
| 2006/0194280 A1 | 8/2006 | Dillon et al. |
| 2006/0194291 A1 | 8/2006 | Presta |
| 2006/0204493 A1 | 9/2006 | Huang et al. |
| 2006/0275282 A1 | 12/2006 | Moore et al. |
| 2006/0292147 A1 | 12/2006 | Yoshizaki et al. |
| 2007/0036785 A1 | 2/2007 | Kishimoto et al. |
| 2007/0036799 A1 | 2/2007 | Stavenhagen et al. |
| 2007/0041978 A1 | 2/2007 | Hattori et al. |
| 2007/0054354 A1 | 3/2007 | Humphreys et al. |
| 2007/0059312 A1 | 3/2007 | Baca et al. |
| 2007/0061900 A1 | 3/2007 | Murphy et al. |
| 2007/0092940 A1 | 4/2007 | Eigenbrot et al. |
| 2007/0110757 A1 | 5/2007 | Wei et al. |
| 2007/0117126 A1 | 5/2007 | Sidhu et al. |
| 2007/0134234 A1* | 6/2007 | Smith ..................... A61P 3/10 424/133.1 |
| 2007/0148163 A1 | 6/2007 | Takahashi et al. |
| 2007/0148164 A1 | 6/2007 | Farrington et al. |
| 2007/0148167 A1 | 6/2007 | Strohl |
| 2007/0160598 A1 | 7/2007 | Dennis et al. |
| 2007/0160611 A1 | 7/2007 | Yao et al. |
| 2007/0212357 A1 | 9/2007 | Pons et al. |
| 2007/0224174 A1 | 9/2007 | Kang et al. |
| 2007/0237764 A1 | 10/2007 | Birtalan et al. |
| 2007/0280945 A1 | 12/2007 | Stevens et al. |
| 2007/0292936 A1 | 12/2007 | Barthelemy et al. |
| 2008/0063635 A1 | 3/2008 | Takahashi et al. |
| 2008/0069820 A1 | 3/2008 | Fuh et al. |
| 2008/0075712 A1 | 3/2008 | Hattori et al. |
| 2008/0125579 A1 | 5/2008 | Owens et al. |
| 2008/0166756 A1 | 7/2008 | Tsuchiya et al. |
| 2008/0219971 A1 | 9/2008 | Smith et al. |
| 2009/0002360 A1 | 1/2009 | Chen et al. |
| 2009/0117097 A1 | 5/2009 | Igawa et al. |
| 2009/0202556 A1 | 8/2009 | Ohta et al. |
| 2009/0208416 A1 | 8/2009 | Moretta et al. |

(56) References Cited

U.S. PATENT DOCUMENTS

| | | |
|---|---|---|
| 2009/0221803 A1 | 9/2009 | Dall'Acqua et al. |
| 2009/0263392 A1 | 10/2009 | Igawa et al. |
| 2009/0291076 A1 | 11/2009 | Morichika et al. |
| 2009/0324589 A1 | 12/2009 | Igawa et al. |
| 2010/0003254 A1 | 1/2010 | Hattori et al. |
| 2010/0004429 A1 | 1/2010 | Kai et al. |
| 2010/0008907 A1 | 1/2010 | Nishimoto et al. |
| 2010/0015133 A1 | 1/2010 | Igawa et al. |
| 2010/0055092 A1 | 3/2010 | Hasegawa et al. |
| 2010/0239577 A1 | 9/2010 | Igawa et al. |
| 2010/0247523 A1 | 9/2010 | Kano et al. |
| 2010/0285030 A1 | 11/2010 | Bowdish et al. |
| 2010/0286374 A1 | 11/2010 | Kannan et al. |
| 2010/0291072 A1 | 11/2010 | Lowman et al. |
| 2010/0297697 A1 | 11/2010 | Ambrosius et al. |
| 2010/0298542 A1 | 11/2010 | Igawa et al. |
| 2010/0310556 A1 | 12/2010 | Higuchi et al. |
| 2010/0316636 A1 | 12/2010 | Radin et al. |
| 2010/0331527 A1 | 12/2010 | Davis et al. |
| 2011/0044984 A1 | 2/2011 | Azawa et al. |
| 2011/0076275 A1 | 3/2011 | Igawa et al. |
| 2011/0098450 A1 | 4/2011 | Igawa et al. |
| 2011/0111406 A1 | 5/2011 | Igawa et al. |
| 2011/0129459 A1 | 6/2011 | Kuramochi et al. |
| 2011/0229459 A1 | 9/2011 | Kuramochi et al. |
| 2011/0236374 A1 | 9/2011 | Shitara et al. |
| 2011/0245473 A1 | 10/2011 | Igawa et al. |
| 2012/0009188 A1 | 1/2012 | Behrens |
| 2012/0065379 A1 | 3/2012 | Igawa et al. |
| 2012/0071634 A1 | 3/2012 | Igawa et al. |
| 2012/0121587 A1 | 5/2012 | Maeda et al. |
| 2012/0149876 A1 | 6/2012 | Von Kreudenstein |
| 2012/0238729 A1 | 9/2012 | Kuramochi et al. |
| 2012/0253016 A1 | 10/2012 | Igawa et al. |
| 2012/0301460 A1 | 11/2012 | Bao et al. |
| 2013/0011866 A1 | 1/2013 | Igawa et al. |
| 2013/0018174 A1 | 1/2013 | Igawa et al. |
| 2013/0030156 A1 | 1/2013 | Apostolou et al. |
| 2013/0039913 A1 | 2/2013 | Labrun et al. |
| 2013/0052196 A1 | 2/2013 | Apostolou et al. |
| 2013/0085199 A1 | 4/2013 | Tamori et al. |
| 2013/0101581 A1 | 4/2013 | Kuramochi et al. |
| 2013/0195849 A1 | 8/2013 | Spreter et al. |
| 2013/0317203 A1 | 11/2013 | Igawa et al. |
| 2014/0039165 A1 | 2/2014 | Kuramochi et al. |
| 2014/0051833 A1 | 2/2014 | Fischer et al. |
| 2014/0112883 A1 | 4/2014 | Ponath et al. |
| 2014/0154270 A1 | 6/2014 | Wang et al. |
| 2014/0303356 A1 | 10/2014 | Gramer et al. |
| 2014/0377253 A1 | 12/2014 | Harding et al. |
| 2015/0118184 A1 | 4/2015 | Kawai |
| 2015/0166666 A1 | 6/2015 | Igawa et al. |
| 2015/0175704 A1 | 6/2015 | Kuramochi et al. |
| 2015/0274809 A1 | 10/2015 | Igawa et al. |
| 2015/0284465 A1 | 10/2015 | Igawa et al. |
| 2015/0297820 A1 | 10/2015 | Kawai |
| 2015/0315278 A1 | 11/2015 | Igawa et al. |
| 2016/0024147 A1 | 1/2016 | Tustian et al. |
| 2016/0159915 A1 | 6/2016 | Igawa et al. |
| 2016/0229915 A1 | 8/2016 | Igawa et al. |
| 2017/0275332 A1 | 9/2017 | Igawa et al. |
| 2018/0057607 A1 | 3/2018 | Kakehi et al. |
| 2018/0142027 A1 | 5/2018 | Igawa et al. |
| 2018/0148509 A1 | 5/2018 | Kakehi et al. |
| 2018/0162902 A1 | 6/2018 | Igawa et al. |
| 2019/0062368 A1 | 2/2019 | Igawa et al. |
| 2019/0085085 A1 | 3/2019 | Igawa et al. |
| 2019/0211081 A1 | 7/2019 | Igawa et al. |
| 2019/0218277 A1 | 7/2019 | Sampei et al. |
| 2019/0315840 A1 | 10/2019 | Sampei et al. |
| 2019/0330268 A1 | 10/2019 | Tanaka et al. |
| 2019/0352334 A1 | 11/2019 | Igawa et al. |
| 2020/0002429 A1 | 1/2020 | Kuramochi et al. |
| 2020/0207805 A1 | 7/2020 | Igawa et al. |
| 2020/0231688 A1 | 7/2020 | Igawa et al. |
| 2021/0017256 A1 | 1/2021 | Fink et al. |
| 2021/0017286 A1 | 1/2021 | Kakehi et al. |
| 2021/0040147 A1 | 2/2021 | Igawa et al. |
| 2021/0095008 A1 | 4/2021 | Sampei et al. |
| 2021/0206862 A1 | 7/2021 | Igawa et al. |
| 2021/0292360 A1 | 9/2021 | Igawa et al. |
| 2021/0324109 A1 | 10/2021 | Igawa et al. |

FOREIGN PATENT DOCUMENTS

| | | |
|---|---|---|
| AU | 2008332271 | 6/2009 |
| AU | 2009290162 | 4/2010 |
| BR | PI0821145-0 | 6/2015 |
| BR | PI0821110-8 | 7/2015 |
| CA | 1 332 367 | 10/1994 |
| CA | 2 203 182 | 5/1996 |
| CA | 2 443 294 | 10/2002 |
| CA | 2 523 577 | 11/2004 |
| CA | 2 531 482 | 1/2005 |
| CA | 2 549 467 | 7/2005 |
| CA | 2 560 953 | 9/2005 |
| CA | 2 625 773 | 4/2007 |
| CA | 2 626 688 | 4/2007 |
| CA | 2 647 846 | 10/2007 |
| CA | 2 648 644 | 10/2007 |
| CA | 2 700 394 | 4/2009 |
| CA | 2 700 498 | 4/2009 |
| CA | 2 700 986 | 4/2009 |
| CA | 2 708 065 | 6/2009 |
| CA | 2 708 532 | 6/2009 |
| CN | 101198698 | 6/2008 |
| CN | 101849006 | 9/2010 |
| CN | 102946906 | 10/2011 |
| CN | 102471378 | 5/2012 |
| CN | 102782131 | 11/2012 |
| CN | 103476793 | 12/2013 |
| CN | 101874042 | 9/2018 |
| EA | 009026 | 10/2007 |
| EP | 0 361 902 | 4/1990 |
| EP | 0 404 097 | 12/1990 |
| EP | 0 425 235 | 5/1991 |
| EP | 0 329 185 | 4/1994 |
| EP | 0 628 639 | 12/1994 |
| EP | 0 637 593 | 2/1995 |
| EP | 0 783 893 | 7/1997 |
| EP | 0 791 359 | 8/1997 |
| EP | 0 811 691 | 12/1997 |
| EP | 0 983 767 | 3/2000 |
| EP | 1 004 315 | 5/2000 |
| EP | 1 069 185 | 1/2001 |
| EP | 1 074 268 | 2/2001 |
| EP | 1 188 830 | 3/2002 |
| EP | 1 334 731 | 8/2003 |
| EP | 1 374 900 | 1/2004 |
| EP | 1 382 969 | 1/2004 |
| EP | 1 510 943 | 3/2005 |
| EP | 1 690 550 | 8/2006 |
| EP | 1 701 979 | 9/2006 |
| EP | 1 707 215 | 10/2006 |
| EP | 1 728 801 | 12/2006 |
| EP | 1 733 740 | 12/2006 |
| EP | 1 752 471 | 2/2007 |
| EP | 1 772 465 | 4/2007 |
| EP | 1 773 391 | 4/2007 |
| EP | 1 847 602 | 10/2007 |
| EP | 1 870 458 | 12/2007 |
| EP | 1 870 459 | 12/2007 |
| EP | 1 900 814 | 3/2008 |
| EP | 1 941 907 | 7/2008 |
| EP | 1 941 908 | 7/2008 |
| EP | 1 967 207 | 9/2008 |
| EP | 1 967 209 | 9/2008 |
| EP | 1 990 060 | 11/2008 |
| EP | 2 006 3 81 | 12/2008 |
| EP | 2 009 101 | 12/2008 |
| EP | 2 031 064 | 3/2009 |
| EP | 2 047 863 | 4/2009 |
| EP | 2 107 115 | 10/2009 |
| EP | 2 123 302 | 11/2009 |

(56) References Cited

FOREIGN PATENT DOCUMENTS

| | | |
|---|---|---|
| EP | 2 174 667 | 4/2010 |
| EP | 2 194 066 | 6/2010 |
| EP | 2 196 220 | 6/2010 |
| EP | 2 196 541 | 6/2010 |
| EP | 2 202 245 | 6/2010 |
| EP | 2 206 775 | 7/2010 |
| EP | 2 228 392 | 9/2010 |
| EP | 2 236 604 | 10/2010 |
| EP | 2241332 | 10/2010 |
| EP | 2 275 443 | 1/2011 |
| EP | 2 305 306 | 4/2011 |
| EP | 2 330 193 | 8/2011 |
| EP | 2 354 161 | 8/2011 |
| EP | 2 409 991 | 1/2012 |
| EP | 2 522 724 | 11/2012 |
| EP | 2 543 727 | 1/2013 |
| EP | 2 578 233 | 4/2013 |
| EP | 2 644 698 | 10/2013 |
| EP | 2 905 290 | 8/2015 |
| EP | 2 914 634 | 9/2015 |
| EP | 3 059 246 A | 8/2016 |
| JP | 2-028200 | 1/1990 |
| JP | 2-163096 | 6/1990 |
| JP | H03-500644 | 2/1991 |
| JP | 07-67688 | 3/1995 |
| JP | 08-500979 | 2/1996 |
| JP | 09-506001 | 6/1997 |
| JP | 11-500915 | 1/1999 |
| JP | 11-500916 | 1/1999 |
| JP | 2002-514406 | 5/2002 |
| JP | 2004-86862 | 3/2004 |
| JP | 2004-511426 | 4/2004 |
| JP | 2004-321100 | 11/2004 |
| JP | 2005-501514 | 1/2005 |
| JP | 2005-101105 | 3/2005 |
| JP | 2005-532805 | 11/2005 |
| JP | 2005-535341 | 11/2005 |
| JP | 2005-378266 | 12/2005 |
| JP | 2005-537009 | 12/2005 |
| JP | 2008-512995 | 5/2008 |
| JP | 2008-523140 | 7/2008 |
| JP | 2008-538920 | 11/2008 |
| JP | 2009-500458 | 1/2009 |
| JP | 2010-522701 | 7/2010 |
| JP | 2011-508604 | 3/2011 |
| JP | 2012-510281 | 5/2012 |
| JP | 2012-515160 | 7/2012 |
| JP | 2012-522527 | 9/2012 |
| JP | 2012-531439 | 12/2012 |
| JP | 5144499 | 2/2013 |
| JP | 2013-515509 | 5/2013 |
| JP | 2013-529084 | 7/2013 |
| JP | 2013-529190 | 7/2013 |
| JP | 2013-165716 | 8/2013 |
| JP | 2013-541594 | 11/2013 |
| JP | 5334319 | 11/2013 |
| JP | 5484060 | 5/2014 |
| JP | 2015-510764 | 4/2015 |
| JP | 5717624 | 5/2015 |
| JP | 2015-130883 | 7/2015 |
| JP | 5787446 | 9/2015 |
| JP | 2016-69329 | 5/2016 |
| JP | 6534615 | 6/2019 |
| KR | 2006/0010765 | 2/2006 |
| KR | 2007/0035482 | 3/2007 |
| KR | 2010/0074221 | 7/2010 |
| KR | 2010/0097721 | 9/2010 |
| KR | 2012/0123055 | 11/2012 |
| RU | 94028282 | 7/1996 |
| RU | 2195960 | 1/2003 |
| RU | 2232773 | 7/2004 |
| RU | 2266298 | 12/2005 |
| TW | 2007/22517 | 6/2007 |
| TW | 200810778 | 3/2008 |
| TW | 200932266 | 8/2009 |
| WO | WO 89/01343 | 2/1989 |
| WO | WO 91/01335 | 2/1991 |
| WO | WO 92/19759 | 11/1992 |
| WO | WO 93/01161 | 1/1993 |
| WO | WO 93/08829 | 5/1993 |
| WO | WO 93/16185 | 8/1993 |
| WO | WO 94/05690 | 3/1994 |
| WO | WO 94/10354 | 5/1994 |
| WO | WO 94/11026 | 5/1994 |
| WO | WO 94/12215 | 6/1994 |
| WO | WO 94/29351 | 12/1994 |
| WO | WO 95/14710 | 6/1995 |
| WO | WO 95/33844 | 12/1995 |
| WO | WO 96/11020 | 4/1996 |
| WO | WO 96/12503 | 5/1996 |
| WO | WO 96/23071 | 8/1996 |
| WO | WO 96/27011 | 9/1996 |
| WO | WO 97/09351 | 3/1997 |
| WO | WO 97/10354 | 3/1997 |
| WO | WO 97/30087 | 8/1997 |
| WO | WO 98/03546 | 1/1998 |
| WO | WO 98/42377 | 10/1998 |
| WO | WO 98/50431 | 11/1998 |
| WO | WO 98/58964 | 12/1998 |
| WO | WO 99/03495 | 1/1999 |
| WO | WO 99/08707 | 2/1999 |
| WO | WO 99/18212 | 4/1999 |
| WO | WO 99/22764 | 5/1999 |
| WO | WO 99/47170 | 9/1999 |
| WO | WO 99/51642 | 10/1999 |
| WO | WO 99/51743 | 10/1999 |
| WO | WO 99/58572 | 11/1999 |
| WO | WO 00/34317 | 6/2000 |
| WO | WO 00/42072 | 7/2000 |
| WO | WO 00/61739 | 10/2000 |
| WO | WO 00/75314 | 12/2000 |
| WO | WO 01/29246 | 4/2001 |
| WO | WO 01/30854 | 5/2001 |
| WO | WO 01/82899 | 11/2001 |
| WO | WO 02/31140 | 4/2002 |
| WO | WO 02/34292 | 5/2002 |
| WO | WO 02/060919 | 8/2002 |
| WO | WO 02/072605 | 9/2002 |
| WO | WO 02/080969 | 10/2002 |
| WO | WO 03/000883 | 1/2003 |
| WO | WO 03/011878 | 2/2003 |
| WO | WO 03/012069 | 2/2003 |
| WO | WO 03/020949 | 3/2003 |
| WO | WO 03/057881 | 7/2003 |
| WO | WO 03/060090 | 7/2003 |
| WO | WO 03/074679 | 9/2003 |
| WO | WO 03/084570 | 10/2003 |
| WO | WO 03/085107 | 10/2003 |
| WO | WO 03/085119 | 10/2003 |
| WO | WO 03/105757 | 12/2003 |
| WO | WO 2004/008147 | 1/2004 |
| WO | WO 2004/016740 | 2/2004 |
| WO | WO 2004/020579 | 3/2004 |
| WO | WO 2004/035752 | 4/2004 |
| WO | WO 2004/056312 | 7/2004 |
| WO | WO 2004/068931 | 8/2004 |
| WO | WO 2004/085476 | 10/2004 |
| WO | WO 2004/091543 | 10/2004 |
| WO | WO 2004/092219 | 10/2004 |
| WO | WO 2004/096273 | 11/2004 |
| WO | WO 2004/113387 | 12/2004 |
| WO | WO 2005/005604 | 1/2005 |
| WO | WO 2005/035586 | 4/2005 |
| WO | WO 2005/035753 | 4/2005 |
| WO | WO 2005/035754 | 4/2005 |
| WO | WO 2005/035756 | 4/2005 |
| WO | WO 2005/035778 | 4/2005 |
| WO | WO 2005/037315 | 4/2005 |
| WO | WO 2005/037867 | 4/2005 |
| WO | WO 2005/047327 | 5/2005 |
| WO | WO 2005/053742 | 6/2005 |
| WO | WO 2005/056606 | 6/2005 |
| WO | WO 2005/059106 | 6/2005 |
| WO | WO 2005/061000 | 7/2005 |

(56) References Cited

FOREIGN PATENT DOCUMENTS

| | | |
|---|---|---|
| WO | WO 2005/062916 | 7/2005 |
| WO | WO 2005/067620 | 7/2005 |
| WO | WO 2005/080429 | 9/2005 |
| WO | WO 2005/090405 | 9/2005 |
| WO | WO 2005/092925 | 10/2005 |
| WO | WO 2005/100402 | 10/2005 |
| WO | WO 2005/112564 | 12/2005 |
| WO | WO 2005/121180 | 12/2005 |
| WO | WO 2005/123126 | 12/2005 |
| WO | WO 2005/123780 | 12/2005 |
| WO | WO 2006/004663 | 1/2006 |
| WO | WO 2006/019447 | 2/2006 |
| WO | WO 2006/023144 | 3/2006 |
| WO | WO 2006/029879 | 3/2006 |
| WO | WO 2006/030200 | 3/2006 |
| WO | WO 2006/030220 | 3/2006 |
| WO | WO 2006/031370 | 3/2006 |
| WO | WO 2006/033386 | 3/2006 |
| WO | WO 2006/044908 | 4/2006 |
| WO | WO 2006/047340 | 5/2006 |
| WO | WO 2006/047350 | 5/2006 |
| WO | WO 2006/050166 | 5/2006 |
| WO | WO 2006/050491 | 5/2006 |
| WO | WO 2006/053301 | 5/2006 |
| WO | WO 2006/065208 | 6/2006 |
| WO | WO 2006/067913 | 6/2006 |
| WO | WO 2006/070286 | 7/2006 |
| WO | WO 2006/071877 | 7/2006 |
| WO | WO 2006/075668 | 7/2006 |
| WO | WO 2006/088855 | 8/2006 |
| WO | WO 2006/106903 | 10/2006 |
| WO | WO 2006/106905 | 10/2006 |
| WO | WO 2006/109592 | 10/2006 |
| WO | WO 2006/113767 | 10/2006 |
| WO | WO 2006/116260 | 11/2006 |
| WO | WO 2006/118959 | 11/2006 |
| WO | WO 2006/119062 | 11/2006 |
| WO | WO 2006/119115 | 11/2006 |
| WO | WO 2006/121852 | 11/2006 |
| WO | WO 2007/009065 | 1/2007 |
| WO | WO 2007/024535 | 3/2007 |
| WO | WO 2007/043641 | 4/2007 |
| WO | WO 2007/046489 | 4/2007 |
| WO | WO 2007/058194 | 5/2007 |
| WO | WO 2007/060411 | 5/2007 |
| WO | WO 2007/061029 | 5/2007 |
| WO | WO 2007/074880 | 7/2007 |
| WO | WO 2007/086490 | 8/2007 |
| WO | WO 2007/108559 | 9/2007 |
| WO | WO 2007/108756 | 9/2007 |
| WO | WO 2007/114319 | 10/2007 |
| WO | WO 2007/114325 | 10/2007 |
| WO | WO 2007/133816 | 11/2007 |
| WO | WO 2007/137984 | 12/2007 |
| WO | WO 2007/142325 | 12/2007 |
| WO | WO 2007/143168 | 12/2007 |
| WO | WO 2008/022152 | 2/2008 |
| WO | WO 2008/043822 | 4/2008 |
| WO | WO 2008/077546 | 7/2008 |
| WO | WO 2008/090901 | 7/2008 |
| WO | WO 2008/090960 | 7/2008 |
| WO | WO 2008/092117 | 7/2008 |
| WO | WO 2008/103432 | 8/2008 |
| WO | WO 2008/119353 | 10/2008 |
| WO | WO 2008/132453 | 11/2008 |
| WO | WO 2008/145141 | 12/2008 |
| WO | WO 2008/145142 | 12/2008 |
| WO | WO 2009/014263 | 1/2009 |
| WO | WO 2009/036209 | 3/2009 |
| WO | WO 2009/041062 | 4/2009 |
| WO | WO 2009/041613 | 4/2009 |
| WO | WO 2009/041621 | 4/2009 |
| WO | WO 2009/041643 | 4/2009 |
| WO | WO 2009/041734 | 4/2009 |
| WO | WO 2009/044774 | 4/2009 |
| WO | WO 2009/052439 | 4/2009 |
| WO | WO 2009/053368 | 4/2009 |
| WO | WO 2009/058492 | 5/2009 |
| WO | WO 2009/063965 | 5/2009 |
| WO | WO 2009/072598 | 6/2009 |
| WO | WO 2009/072604 | 6/2009 |
| WO | WO 2009/079649 | 6/2009 |
| WO | WO 2009/086320 | 7/2009 |
| WO | WO 2009/089004 | 7/2009 |
| WO | WO 2009/100309 | 8/2009 |
| WO | WO 2009/125825 | 10/2009 |
| WO | WO 2009/13 9822 | 11/2009 |
| WO | WO 2009/148148 | 12/2009 |
| WO | WO 2010/035769 | 4/2010 |
| WO | WO 2010/043977 | 4/2010 |
| WO | WO 2010/045193 | 4/2010 |
| WO | WO 2010/063746 | 6/2010 |
| WO | WO 2010/064090 | 6/2010 |
| WO | WO 2010/064456 | 6/2010 |
| WO | WO 2010/064697 | 6/2010 |
| WO | WO 2010/065078 | 6/2010 |
| WO | WO 2010/080065 | 7/2010 |
| WO | WO 2010/106180 | 9/2010 |
| WO | WO 2010/107109 | 9/2010 |
| WO | WO 2010/107110 | 9/2010 |
| WO | WO 2010/115589 | 10/2010 |
| WO | WO 2010/131733 | 11/2010 |
| WO | WO 2010/151792 | 12/2010 |
| WO | WO 2011/037158 | 3/2011 |
| WO | WO 2011/078332 | 6/2011 |
| WO | WO 2011/090754 | 7/2011 |
| WO | WO 2011/090762 | 7/2011 |
| WO | WO 2011/091078 | 7/2011 |
| WO | WO 2011/091177 | 7/2011 |
| WO | WO 2011/091181 | 7/2011 |
| WO | WO 2011/108502 | 9/2011 |
| WO | WO 2011/108714 | 9/2011 |
| WO | WO 2011/111007 | 9/2011 |
| WO | WO 2011/122011 | 10/2011 |
| WO | WO 2011/125674 | 10/2011 |
| WO | WO 2011/131746 | 10/2011 |
| WO | WO 2011/133886 | 10/2011 |
| WO | WO 2011/143545 | 11/2011 |
| WO | WO 2011/149046 | 12/2011 |
| WO | WO 2012/016227 | 2/2012 |
| WO | WO 2012/020096 | 2/2012 |
| WO | WO 2012/064627 | 5/2012 |
| WO | WO 2012/067176 | 5/2012 |
| WO | WO 2012/073985 | 6/2012 |
| WO | WO 2012/073992 | 6/2012 |
| WO | WO 2012/082073 | 6/2012 |
| WO | WO 2012/132067 | 10/2012 |
| WO | WO 2012/145238 | 10/2012 |
| WO | 2013/02219 | 1/2013 |
| WO | WO 2013/046704 | 4/2013 |
| WO | WO 2013/047752 | 4/2013 |
| WO | WO 2013/060867 | 5/2013 |
| WO | WO 2013/089647 | 6/2013 |
| WO | WO 2013/124450 | 8/2013 |
| WO | WO 2013/136186 | 9/2013 |
| WO | WO 2013/151764 | 10/2013 |
| WO | WO 2013/157954 | 10/2013 |
| WO | WO 2013/173348 | 11/2013 |
| WO | WO 2013/180200 | 12/2013 |
| WO | WO 2013/180201 | 12/2013 |
| WO | WO 2014/025546 | 2/2014 |
| WO | WO 2014/028354 | 2/2014 |
| WO | WO 2014/054804 | 4/2014 |
| WO | WO 2014/067011 | 5/2014 |
| WO | WO 2014/145159 | 9/2014 |
| WO | WO 2015/046467 | 4/2015 |
| WO | WO 2015/063339 | 5/2015 |
| WO | WO 2015/122995 | 8/2015 |
| WO | WO 2015/123362 | 8/2015 |
| WO | WO 2016/012800 | 1/2016 |
| WO | WO 2016/098357 | 6/2016 |
| WO | WO 2016/125495 | 8/2016 |
| WO | WO 2016/136933 | 9/2016 |
| WO | WO2016/136933 | 9/2016 |

(56) References Cited

FOREIGN PATENT DOCUMENTS

| WO | WO 2016/159213 | 10/2016 |
|---|---|---|
| WO | WO 2017/115773 | 7/2017 |
| WO | WO 2017/212291 | 12/2017 |
| WO | WO 2018/052375 | 3/2018 |
| WO | WO 2019/177543 | 9/2019 |

OTHER PUBLICATIONS

U.S. Appl. No. 12/745,781, Kuramochi et al., filed Sep. 13, 2010.
U.S. Appl. No. 14/340,883, Kuramochi et al., filed Jul. 25, 2014.
U.S. Appl. No. 14/047,316, Kuramochi et al., filed Oct. 7, 2013.
U.S. Appl. No. 13/257,112, Igawa et al., filed Nov. 22, 2011.
U.S. Appl. No. 14/962,293, Igawa et al., filed Dec. 8, 2015.
U.S. Appl. No. 13/257,145, Igawa et al., filed Nov. 22, 2011.
U.S. Appl. No. 14/680,250, Igawa et al., filed Apr. 7, 2015.
U.S. Appl. No. 13/320,317, Maeda et al., filed Feb. 1, 2012.
U.S. Appl. No. 13/497,269, Kuramochi et al., filed Jun. 1, 2012.
U.S. Appl. No. 13/518,861, Igawa et al., filed Oct. 4, 2012.
U.S. Appl. No. 13/582,073, filed Aug. 31, 2012, Kuramochi et al.
U.S. Appl. No. 13/959,489, filed Aug. 5, 2013, Igawa et al.
U.S. Appl. No. 14/047,316, filed Oct. 7, 2013, Kuramochi et al.
U.S. Appl. No. 15/263,617, filed Sep. 13, 2016, Igawa et al.
U.S. Appl. No. 15/490,936, filed Apr. 19, 2017, Igawa et al.
U.S. Appl. No. 15/614,842, filed Jun. 6, 2017, Igawa et al.
Abe et al., "Purification of monoclonal antibodies with light-chain heterogeneity produced by mouse hybridomas raised with NS-1 myelomas: application of hydrophobic interaction high-performance liquid chromatography," J. Biochem. Biophys. Methods, 27:215-227 (1993).
Adams et al., "Humanization of a recombinant monoclonal antibody to produce a therapeutic HER dimerization inhibitor, pertuzumab," Cancer Immunol. Immunother., 55:717-727 (2006).
Algonomics—Tripole® applications [online] Retrieved from the Internet on Feb. 29, 2012: http://web.archive.org/web20090221052902/http://www.algonomics.com/proteinengineering/tripole_applications.php, 2 pages (Feb. 21, 2009).
Allard et al., "Antigen binding properties of highly purified bispecific antibodies," Mol Immunol., Oct. 1992;29(10):1219-27.
Allen et al., "Novel mechanism for gonadotropin-releasing hormone neuronal migration involving Gas6/Ark signaling to p38 mitogen-activated protein kinase," Mol. Cell. Biol., 22(2):599-613 (2002).
Allen et al., "Interchain disulfide bonding in human IgG2 antibodies probed by site-directed mutagenesis," Biochemistry, 48(17):3755-66 (2009).
Almagro et al., "Humanization of antibodies," Front Biosci., 13:1619-33 (2008).
Amersham Biosciences, "Affinity Chromatography: Principles and Methods," Edition AC, pp. 16-18, 137 (2002).
Amersham Biosciences, "Protein Purification Handbook, " Edition AC, 98 pages (2001).
Arndt et al., "Factors influencing the dimer to monomer transition of an antibody single-chain Fv fragment," Biochemistry, Sep. 15, 1998;37(37):12918-26.
Armour et al., "Recombinant human IgG molecules lacking Fegamma receptor I binding and monocyte triggering activities," Eur. J. Immunol., 29(8):2613-24 (1999).
Aslan et al., "Engineering a novel, stable dimeric streptavidin with lower isoelectric point," J. Biotechnol., 128(2):213-25 (2007).
Atwell et al., "Stable heterodimers from remodeling the domain interface of a homodimer using a phage display library," J. Mol. Biol., 270:26-35 (1997).
Baerga-Ortiz et al., "Two different proteins that compete for binding to thrombin have opposite kinetic and thermodynamic profiles," Protein Sci., 13(1):166-76 (2004).
Baker et al., "Conversion of a T cell antagonist into an agonist by repairing a defect in the TCR/peptide/MHC interface: implications for TCR signaling," Immunity, 13:475-484 (2000).
Bartelds et al., "Clinical response to adalimumab: relationship to anti-adalimumab antibodies and serum adalimumab concentrations in rheumatoid arthritis," Ann Rheum. Dis., 66(7):921-6 (2007).
Batra et al., "Pharmacokinetics and biodistribution of genetically engineered antibodies," Curr Opin Biotechnol., Dec. 2002;13(6):603-8.
Bayry et al., "Immuno affinity purification of foot and mouth disease virus type specific antibodies using recombinant protein adsorbed to polystyrene wells," J. Virol. Methods, 81:21-30 (1999).
Bellosta et al., "Signaling through the ARK tyrosine kinase receptor protects from apoptosis in the absence of growth stimulation," Oncogene., 15(20):2387-97 (1997).
Bender et al., "Immunogenicity, efficacy and adverse events of adalimumab in RA patients," Rheumatol. Int., 27(3):269-74 (2007).
Bendig, "Humanization of rodent monoclonal antibodies by CDR grafting," Methods: A Comparison to Methods in Enzymology, 8:83-93 (1995).
Berglund et al., "The epitope space of the human proteome," Protein Sci., Apr. 2008;17(4):606-13.
Bian et al., "Discovery of promiscuous HLA-II-restricted T cell epitopes with TEPITOPE," Methods, Dec. 2004;34(4):468-75.
Bilsborough, "IL-31 is associated with cutaneous lymphocyte antigen-positive skin homing T cells inpatients with atopic dermatitis," J. Allergy Clin. Immunol., 117(2):418-25 (2006).
Binz et al., "Engineering novel binding proteins from nonimmunoglobulin domains," Nat. Biotechnol., 23:1257-68 (2005).
Bowie et al., "Deciphering the message in protein sequences: tolerance to amino acid substitutions," Science, 247:1306-1310 (1990).
Branden and Tooze, "Recognition of Foreign Molecules by the Immune System," Introduction to Protein Structure, 2d Ed., Garland Publishing, pp. 299-323 (1999).
Brenner et al., "Errors in genome annotation," Trends in Genetics, Apr. 1999;15:132-133.
Brown et al., "Tolerance of single, but not multiple, amino acid replacements in antibody $V_H$ CDR 2: a means of minimizing B cell wastage from somatic hypermutation?," J. Immunol., 156(9):3285-91 (1996).
Budagian et al., "A promiscuous liaison between IL-15 receptor and Axl receptor tyrosine kinase in cell death control," EMBO J., 24(24):4260-70 (2005).
Burges et al., "Effective relief of malignant ascites in patients with advanced ovarian cancer by a trifunctional anti-EpCAM x anti-CD3 antibody: a phase I/II study," Clin. Cancer Res., 13(13):3899-905 (2007).
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell. Biol., 111:2129-2138 (1990).
Calbiochem® Buffers, "A guide for the preparation and use of buffers in biological systems," by Chandra Mohan, Ph.D., Copyright© 2003 EMD Biosciences, Inc., an Affiliate of Merck KGaA, Darmstadt, Germany, 37 pages.
Carter, "Bispecific human IgG by design," J. Immunol. Methods, 248:7-15 (2001).
Casset et al., "A peptide mimetic of an anti-CD4 monoclonal antibody by rational design," Biochem Biophys Res Commun., Jul. 18, 2003;307:198-205.
Chamow et al., "A humanized, bispecific immunoadhesin-antibody that retargets CD3+ effectors to kill HIV-1-infected cells," J. Immunol., 153(9):4268-80 (1994).
Chappel et al., "Identification of a secondary Fc gamma RI binding site within a genetically engineered human IgG antibody," J Biol Chem., Nov. 25, 1993;268(33):25124-31.
Chappel et al., "Identification of the Fc gamma receptor class I binding site in human IgG through the use of recombinant IgG1/IgG2 hybrid and point-mutated antibodies," Proc Natl Acad Sci U S A., Oct. 15, 1991;88(20):9036-40.
Chatellier et al., "Functional mapping of conserved residues located at the VL and VH domain interface of a Fab," J. Mol. Biol., Nov. 22, 1996;264(1):1-6.
Chau et al., "HuM291(Nuvion), a humanized Fc receptor-nonbinding antibody against CD3, anergizes peripheral blood T cells as partial agonist of the T cell receptor," Transplantation, 71(7):941-50 (2001).

(56) References Cited

OTHER PUBLICATIONS

Chen et al., "Generation and analysis of random point mutations in an antibody CDR2 sequence: many mutated antibodies lose their ability to bind antigen," J. Exp. Med., 176(3):855-66 (1992).
Chen et al., "Defective secretion of an immunoglobulin caused by mutations in the heavy chain complementarity determining region 2," J. Exp. Med., 180(2):577-86 (1994).
Chien et al., "Significant structural and functional change of an antigen-binding site by a distant amino acid substitution: proposal of a structural mechanism," Proc. Natl. Acad. Sci. U.S.A., 86(14):5532-6 (1989).
Chen et al., "Selection and analysis of an optimized anti-VEGF antibody: crystal structure of an affinity-matured Fab in complex with antigen," J Mol Biol., Nov. 5, 1999;293(4):865-81.
Chirino et al., "Minimizing the immunogenicity of protein therapeutics," Drug Discov. Today., 9(2):82-90 (2004).
Choi et al., "Engineering of Immunoglobulin Fc Heterodimers Using Yeast Surface-Displayed Combinatorial Fc Library Screening," PLoS One, Dec. 16, 2015;10(12):e0145349. doi: 10.1371/journal.pone.0145349. eCollection 2015.
Chu et al., "Accumulation of succinimide in a recombinant monoclonal antibody in mildly acidic buffers under elevated temperatures," Pharm. Res., 24(6): 1145-56 (2007).
Chung et al., "Expression of the proto-oncogene Axl in renal cell carcinoma," DNA Cell Biol., 22(8):533-40 (2003).
Cole et al., "Human IgG2 variants of chimeric anti-CD3 are nonmitogenic to T cells," J. Immunol., 159(7):3613-21 (1997).
Coloma et al., "Position effects of variable region carbohydrate on the affinity and in vivo behavior of an anti-(1—>6) dextran antibody," J Immunol., Feb. 15, 1999;162(4):2162-70.
Comper and Glasgow, "Charge selectivity in kidney ultrafiltration," Kidney Int., 47:1242-51 (1995).
Cordoba et al., "Non-enzymatic hinge region fragmentation of antibodies in solution," J. Chromatogr. B. Analyt. Technol. Biomed. Life Sci., 818(2):115-21 (2005).
Couto et al., "Anti-B A46 Monoclonal Antibody Mc3: Humanization Using a Novel Positional Consensus and in Vivo and in Vitro Characterization," Cancer Research, 55:1717-1722 (1995).
Craven et al., "Receptor tyrosine kinases expressed in metastatic colon cancer," Int. J. Cancer, 60(6):791-7 (1995).
Dall'Acqua et al., "Antibody humanization by framework shuffling," Methods, 36(1):43-60 (2005).
Dall'Acqua et al., "Modulation of the effector functions of a human IgG1 through engineering of its hinge region," J. Immunol., 177(2): 1129-38 (2006).
Dall'Acqua et al., "Increasing the affinity of a human IgG1 for the neonatal Fc receptor: biological consequences," J. Immunol., Nov. 1, 2002;169(9):5171-80.
Damschroder et al., "Framework shuffling of antibodies to reduce immunogenicity and manipulate functional and biophysical properties," Mol. Immunol., 44(11):3049-60 (2007).
Datta-Mannan et al., "Monoclonal antibody clearance. Impact of modulating the interaction of IgG with the neonatal Fc receptor," J Biol Chem., 282(3): 1709-17 (2007).
Davies et al., "Affinity improvement of single antibody VH domains: residues in all three hypervariable regions affect antigen binding," Immunotechnology, 2(3):169-79 (1996).
Davies et al., "Antibody VH domains as small recognition units," Biotechnology (N.Y.), May 1995;13(5):475-9.
De Pascalis et al., "Grafting of "abbreviated" complementarity-determining regions containing specificity—determining residues essential for ligand contact to engineer a less immunogenic humanized monoclonal antibody," J. Immunol., 169(6):3076-84 (2002).
Deen et al., "Structural determinants of glomerular permeability," Am. J. Physiol. Renal. Physiol., 281:F579-F596 (2001).
De Groot et al., "De-immunization of therapeutic proteins by T-cell epitope modification," Dev. Biol. (Basel), 122:171-94 (2005).
Del Rio et al., "An Engineered Penicillin Acylase with Altered Surface Charge is More Stable in Alkaline pH," Ann. NY Acad. Sci., 799:61-64 (1996).

Deng et al., "An Agonist Murine Monoclonal Antibody to the Human c-Mpl Receptor Stimulates Megakaryocytopoiesis," Blood, 92:1981-88 (1998).
Dhiman et al., "Gene expression microarrays: a 21st century tool for directed vaccine design," Vaccine, Oct. 12, 2001;20(1-2):22-30.
Diaz et al., "Effects of engineering charged amino acids in the CH3 domains on antibody heavy chain dimerization," Philippine Science Letters. 2011;4(1):48-55.
Dillon et al., "Structural and functional characterization of disulfide isoforms of the human IgG2 subclass," J. Biol. Chem., 283(23):16206-15 (2008).
Dillon et al., "Interleukin 31, a cytokine produced by activated T cells, induces dermatitis in mice," Nat. Immunol., 5(7):752-760 (2004).
Diveu et al., "GPL, a novel cytokine receptor related to GP130 and leukemia inhibitory factor receptor," J. Biol. Chem., 278(50):49850-49859 (2003).
Dumont et al., "Monomeric Fc fusions: impact on pharmacokinetic and biological activity of protein therapeutics," BioDrugs., 20(3):151-60 (2006).
Ejima et al., "Effects of Acid Exposure on the Conformation, Stability, and Aggregation of Monoclonal Antibodies," Proteins. Mar. 1, 2007;66(4):954-62.
Elliott et al., "Activation of the erythropoietin (EPO) receptor by bivalent anti-EPO receptor antibodies," J Biol Chem., Oct. 4, 1996;271(40):24691-7.
Ewert et al., "Stability improvement of antibodies for extracellular and intracellular applications: CDR grafting to stable frameworks and structure-based framework engineering," Methods, 34:184-199 (2004).
Fridell et al., "GAS6 induces Axl-mediated chemotaxis of vascular smooth muscle cells," J. Biol. Chem., 273(12):7123-6 (1998).
Fujii, "Antibody affinity maturation by random mutagenesis," Methods Mol. Biol., 248:345-59 (2004).
Gen Bank Accession No. AAG00910.2, "recombinant IgG2 heavy chain, partial [*Homo sapiens*]," May 14, 2001, 1 page.
Gerstner et al., "Sequence plasticity in the antigen-binding site of a therapeutic anti-HER2 antibody," J. Mol. Biol., 321(5):851-62 (2002).
Gessner et al., "The IgG Fc receptor family," Ann Hematol., 76(6):231-48 (1998).
Ghetie and Ward, "FcRn: the MHC class I-related receptor that is more than an IgG transporter," Immunol. Today, 18:592-598 (1997).
Ghetie et al., "Increasing the serum persistence of an IgG fragment by random mutagenesis," Nat. Biotechnol., 15:637-640 (1997).
Ghetie et al., "Multiple roles for the major histocompatibility complex class I- related receptor FcRn," Annu. Rev. Immunol., 18:739-766 (2000).
Gobburu et al., "Pharmacokinetics/dynamics of 5c8, a monoclonal antibody to CD 154 (CD40 ligand) suppression of an immune response in monkeys," J. Pharmacol. Exp. Ther., 286:925-930 (1998).
Goode et al., "The glomerular basement membrane charge-selectivity bamer: an oversimplified concept?," Nephrol. Dial. Transplant., 11:1714-16 (1996).
Goruppi et al., "Requirement of phosphatidylinositol 3-kinase-dependent pathway and Src for Gas6-Axl mitogenic and survival activities in NIH 3T3 fibroblasts," Mol. Cell Biol., 17(8):4442-53 (1997).
Gramer et al., "Production of stable bispecific IgG1 by controlled Fab-arm exchange: scalability frombenchto large-scale manufacturing by application of standard approaches," MAbs., Nov.-Dec. 2013;5(6):962-73. doi: 10.4161/mabs.26233. Epub Aug. 22, 2013.
Graves et al., "Molecular modeling and preclinical evaluation of the humanized NR-LU-13 antibody," Clin. Cancer Res., 5:899-908 (1999).
Greenwood et al., "Structural motifs involved in human IgG antibody effector functions," Eur J Immunol., May 1993;23(5): 1098-104.
Griffin et al., "Analysis of heavy and light chain sequences of conventional camelid antibodies from Camelus dromedarius and Camelus bactrianus species," J Immunol Methods, Mar. 2014;405:35-46, doi: 10.1016/j.jim.2014.01.003. Epub Jan. 18, 2014.

(56) References Cited

OTHER PUBLICATIONS

Gunasekaran et al., "Enhancing antibody Fc heterodimer formation through electrostatic steering effects: applications to bispecific molecules and monovalent IgG," J. Biol. Chem., 285(25):19637-46 (2010).
Gupta et al., "Affinity chromatography and co-chromatography of bispecific monoclonal antibody immunoconjugates," J. Biochem. Biophys. Methods, 51:203-216 (2002).
Gussow et al., "Humanization of monoclonal antibodies," Methods Enzymol., 203:99-121 (1991).
Guyre et al., "Increased potency of Fc-receptor-targeted antigens," Cancer Immunol. Immunother., 45(3-4):146-8 (1997).
Haagen et al., "Unprimed CD4+ and CD8+ T cells can be rapidly activated by a CD3 × CD 19 bispecific antibody to proliferate and become cytotoxic," Cancer Immunol Immunother., Dec. 1994;39(6):391-6.
Hafizi et al., "Interaction of Axl receptor tyrosine kinase with C1-TEN, a novel C1 domaincontaining protein with homology to tensin," Biochem. Biophys. Res. Commun., 299(5):793-800 (2002).
Hafizi et al., "Signalling and functional diversity within the Axl subfamily of receptor tyrosine kinases," Cytokine Growth Factor Rev., 17(4):295-304 (2006).
Hamers-Casterman et al., "Naturally occurrng antibodies devoid of light chains," Nature, Jun. 3, 1993;363(6428):446-8.
Hanes et al., "Picomolar affinity antibodies from a fully synthetic naive library selected and evolved by ribosome display," Nat. Biotechnol., 18(12):1287-1292 (2000).
Hanson et al., "Catalytic antibodies and their applications," Curr. Opin. Biotechnol., 16:631-636 (2005).
He et al., "Humanization and pharmacokinetics of a monoclonal antibody with specificity for both E- and P-selectin," J. Immunol., 160:1029-35 (1998).
Hinton et al., "An engineered human IgG1 antibody with longer serum half-life," J. Immunol., Jan. 1, 2006;176:346-56.
Hinton et al., "Engineered human IgG antibodies with longer serum half-lives in primates," J Biol Chem., Feb. 20, 2004;279(8):6213-6, Epub Dec. 29, 2003.
Hird et al., "Tumour localisation with a radioactively labelled reshaped human monoclonal antibody," Br J Cancer, Nov. 1991;64(5):911-4.
Holland et al., "Multiple roles for the receptor tyrosine kinase axl in tumor formation," Cancer Res., Oct. 15, 2005;65(20):9294-303.
Holm et al., "Functional mapping and single chain construction of the anti-cytokeratin 8 monoclonal antibody TS1," Mol Immunol., Feb. 2007;44(6):1075-84.
Holt et al., "Domain antibodies: proteins for therapy," Trends Biotechnol., 21(11):484-90 (2003).
Hombach et al., "A CD16/CD30 bispecific monoclonal antibody induces lysis of Hodgkin's cells by unstimulated natural killer cells in vitro and in vivo," Int J Cancer, 55:830-6 (1993).
Hong et al., "Enhanced cellular uptake and transport of polyclonal immunoglobulin G and fab after their cationization," J Drug Target, 2000;8(2):67-77.
Hwang et al., "Use of human germline genes in a CDR homology-based approach to antibody humanization," Methods., 36(1):35-42 (2005).
Igawa et al., "VH/VL interface engineering to promote selective expression and inhibit conforrnnational isomerization of thrombopoietin receptor agonist single-chain diabody," Protein Eng Des Sel., Aug. 2010;23(8):667-77. doi: 10.1093/protein/gzq034. Epub Jun. 24, 2010.
Igawa et al., "Engineering the variable region of therapeutic IgG antibodies," MAbs, 3(3):243-52 (2011).
Igawa et al., "Reduced elimination of IgG antibodies by engineering the variable region," Protein Eng. Des. Sel., 23(5):385-92 (2010).
Igawa et al., "Antibody recycling by engineered pH-dependent antigen binding improves the duration of antigen neutralization," Nat. Biotechnol., 28(11):1203-7 (2010).

IMGT Scientific charts depicting the correspondence between Eu and Kabat numberings for the human IgG constant region, created May 17, 2001 and last updated Aug. 13, 2014.
Ito et al., "The His-probe method: effects of histidine residues introduced into the complementarity-determining regions of antibodies on antigen-antibody interactions at different pH values," FEBS Lett., 309:85-88 (1992).
Ito et al., "Expression of receptor-type tyrosine kinase, Axl, and its ligand, Gas6, in pediatric thyroid carcinomas around Chernobyl," Thyroid., 12(11):971-5 (2002).
Jackman et al., "Development of a two-part strategy to identify a therapeutic human bispecific antibody that inhibits IgE receptor signaling," J Biol Chem., Jul. 2, 2010;285(27): 20850-9. doi: 10.1074/jbc.M110.113910. Epub May 5, 2010.
Jain et al., "Engineering antibodies for clinical applications," Trends Biotechnol., 25(7):307-16 (2007).
Jefferis et al., "Recognition sites on human IgG for Fc gamma receptors: the role of glycosylation," Immunol. Lett., 44(2-3):111-7 (1995).
Jendeberg et al., "Engineering of Fc(1) and Fc(3) from human immunoglobulin G to analyse subclass specificity for staphylococcal protein A," J. Immunol. Methods., 201(1):25-34 (1997).
Johnson et al., "Cation exchange-HPLC and mass spectrometry reveal C-terminal amidation of an IgG1 heavy chain," Anal. Biochem., 360(1):75-83 (2007).
Johnson et al., "Kabat database and its applications: 30 years after the first variability plot," Nucleic Acids Res., Jan. 1, 2000;28(1):214-8.
Jones et al., "Identification and removal of a promiscuous CD4+ T cell epitope from the C1 domain of factor VIII," Thromb. Haemost, 3(5):991-1000 (2005).
Ju et al., "Conversion of the interleukin 1 receptor antagonist into an agonist by site-specific mutagenesis," Proc. Natl. Acad. Sci. U.S.A., 88:2658-2662 (1991).
Jung et al., "The importance of framework residues H6, H7 and H10 in antibody heavy chains: experimental evidence for a new structural subclassification of antibody V(H) domains," J. Mol. Biol., Jun. 8, 2001;309(3):701-16.
Kabat et al., National Institutes of Health, Publ'n No. 91-3242, Sequences of Proteins of Immunological Interest, vol. 1, pp. 647-660 (5$^{th}$ ed. 1991).
Kabat et al., Sequence of Proteins of Immunological Interest, 5$^{th}$ Edition 1991, p. 690 and p. 693.
Kai et al., "Switching constant domains enhances agonist activities of antibodies to a thrombopoietin receptor," Nat Biotechnol., Feb. 2008;26(2):209-11. Epub Dec. 23, 2007.
Kashmiri et al., "Generation, characterization, and in vivo studies of humanized anticarcinoma antibody CC49," Hybridoma, 14:461-473 (1995).
Katayose et al., "MUC1-specific targeting immunotherapy with bispecific antibodies: inhibition of xenografted human bile duct carcinoma growth," Cancer Res., 56(18):4205-12 (1996).
Kenanova et al., "Tailoring the pharmacokinetics and positron emission tomography imaging properties of anti-carcinoembryonic antigen single-chain Fv-Fc antibody fragments," Cancer Res., Jan. 15, 2005;65(2):622-31.
Khalifa et al., "Effects on interaction kinetics of mutations at the VH-VL interface of Fabs depend on the structural context," J. Mol. Recognit., May-Jun. 2000;13(3):127-39.
Khawli et al., "Improved tumor localization and radioimaging with chemically modified monoclonal antibodies," Cancer Biother. Radiopharm., 11:203-215 (1996).
Kim et al., "Antibody Engineering for the Development of Therapeutic Antibodies," Mol. Cells, 20:17-29 (2005).
Kim et al., "Chemical modification to reduce renal uptake of disulfide-bonded variable region fragment of anti-tac monoclonal antibody labeled with 99mTc," Bioconjugate Chem., 10:447-453 (1999).
Kim et al., "Lowering of pI by acylation improves the renal uptake of 99mTc-labeled anti-Tac dsFv: effect of different acylating reagents," Nucl. Med. Biol., 29:795-801 (2002).

(56) References Cited

OTHER PUBLICATIONS

Kim et al., "Mapping the site on human IgG for binding of the MHC class I-related receptor, FcRn," Eur. J. Immunol., Sep. 1999;29(9):2819-25.
Kipriyanov et al., "Bispecific tandem diabody for tumor therapy with improved antigen binding and pharmacokinetics," J. Mol. Biol., Oct. 15, 1999;293(1):41-56.
Kipriyanov et al., "Effect of domain order on the activity of bacterially produced bispecific single-chain Fv antibodies," J. Mol. Biol., Jun. 27, 2003;330(1):99-111.
Klein et al., "Progress in overcoming the chain association issue in bispecific heterodimeric IgG antibodies," MAbs., Nov.-Dec. 2012;4(6):653-63, doi: 10.4161/mabs.21379. Epub Aug. 27, 2012.
Kobayashi et al., "A monoclonal antibody specific for a distinct region of hen egg-white lysozyme," Mol. Immunol., 19:619-30 (1982).
Kobayashi et al., "The pharmacokinetic characteristics of glycolated humanized anti-Tac Fabs are determined by their isoelectric points," Cancer Res., 59:422-430 (1999).
Komissarov et al., "Site-specific mutagenesis of a recombinant anti-single-stranded DNA Fab. Role of heavy chain complementarity-determining region 3 residues in antigen interaction," J. Biol. Chem., 272(43):26864-70 (1997).
Kontermann, "Recombinant bispecific antibodies for cancer therapy," Acta Pharmacol Sin., Jan. 2005;26(1):1-9.
Korn et al., "Recombinant bispecific antibodies for the targeting of adenoviruses to CEA-expressing tumour cells: a comparative analysis of bacterially expressed single-chain diabody and tandem scFv," J. Gene Med., Jun. 2004;6(6):642-51.
Kranenborg et al., "Development and characterization of anti-renal cell carcinoma x antichelate bispecific monoclonal antibodies for two-phase targeting of renal cell carcinoma," Cancer Res., 55:5864s-5867s (1995).
Krauss et al., "Impact of antibody framework residue VH-71 on the stability of a humanised anti-MUC1 scFv and derived immunoenzyme," Br. J. Cancer, 90:1863-70 (2004).
Kufer et al., "A revival of bispecific antibodies," Trends Biotechnol., 22(5):238-44 (2004).
Kumar et al., "The second PDZ domain of INAD is a type I domain involved in binding to eye protein kinase C. Mutational analysis and naturally occurring variants," J. Biol. Chem., Jul. 6, 2001;276(27):24971-7, Epub May 7, 2001.
Kurfis et al., "Role of Arg182 in the second extracellular loop of angiotensin II receptor AT2 in ligand binding," Biochem. Biophys. Res. Commun., 263:816-819 (1999).
Kreutz et al., "Efficient bispecific monoclonal antibody purification using gradient thiophilic affinity chromatography," J. Chromatogr. B, 714:161-170 (1998).
Labrun et al., "Efficient generation of stable bispecific IgG1 by controlled Fab-arm exchange," Pro Natl Acad Sci U S A., Mar. 26, 2013;110(13):5145-50. doi: 10.1073/pnas.1220145110. Epub Mar. 11, 2013.
Labrun et al., "Species-specific determinants in the IgG CH3 domain enable Fab-arm exchange by affecting the noncovalent CH3—CH3 interaction strength," J Immunol., Sep. 15, 2011;187(6):3238-46. doi: 10.4049/jimmunol.1003336. Epub Aug. 12, 2011.
Lansdorp et al., "Purification and analysis of bispecific tetrameric antibody complexes," Mol. Immunol., 27:659-666 (1990).
Lay et al., "Sulfasalazine suppresses drug resistance and invasiveness of lung adenocarcinoma cells expressing AXL," Cancer Res., 67(8):3878-87 (2007).
Lazar et al., "Transforming growth factor alpha: mutation of aspartic acid 47 and leucine 48 results in different biological activities," Mol. Cell. Biol., 8:1247-1252 (1988).
Lebegue et al., "Production and characterization of hybrid monoclonal antibodies with IgG1/IgG3 double isotype," C R Acad Sci III., 1990;310(9):377-82.
Le Gall et al., "Effect of linker sequences between the antibody variable domains on the formation, stability and biological activity of a bispecific tandem diabody," Protein Eng. Des. Sel., Apr. 2004;17(4):357-66, Epub May 4, 2004.
Leong et al., "Adapting pharmacokinetic properties of a humanized anti-interleukin-8 antibody for therapeutic applications using site-specific pegylation," Cytokine, 16(3):106-19 (2001).
Levin et al., "Optimizing the affinity and specificity of proteins with molecular display," Mol. Biosyst, 2(1):49-57 (2006) (Epub Nov. 8, 2005).
Li et al., "Construction and characterization of a humanized anti-human CD3 monoclonal antibody 12F6 with effective immunoregulation functions," Immunology, Dec. 2005;116(4):487-98.
Lin et al., "Preclinical pharmacokinetics, interspecies scaling, and tissue distribution of a humanized monoclonal antibody against vascular endothelial growth factor," J Pharmacol Exp Ther., 288(1):371-8 (1999).
Lindhofer et al., "Preferential Species-Restricted Heavy/Light Chain Pairing in Rat/Mouse Quadromas," J. Immunol., 155:219-225 (1995).
Liu et al., "Functional interactions between arginine-133 and aspartate-88 in the human reduced folate carrier: evidence for a charge-pair association," Biochem. J., Sep. 2001;358(Pt. 2): 511-6.
Liu et al., "Heterogeneity of monoclonal antibodies," J. Pharm. Sci., 97(7):2426-47 (2008).
Lloyd et al., "The production of a bispecific anti-CEA, anti-hapten (4-amino-phthalate) hybrid-hybridoma," J Natl Med Assoc., Oct. 1991;83(10):901-4.
Lobo et al., "Antibody pharmacokinetics and pharmacodynamics," J. Pharm. Sci., 93:2645-68 (2004).
Lund et al., "Expression and characterization of truncated forms of humanized L243 IgG1. Architectural features can influence synthesis of its oligosaccharide chains and affect superoxide production triggered through human Fcgamma receptor I," Eur J Biochem., Dec. 2000;267(24):7246-56.
MacCallum et al., "Antibody-antigen interactions: contact analysis and binding site topography," J. Mol. Biol., 262:732-45 (1996).
Maeda et al., "pH-dependent receptor/ligand dissociation as a determining factor for intracellular sorting of ligands for epidermal growth factor receptors in rat hepatocytes," J. Control Release, 82(1):71-82 (2002).
Male et al., "Antibodies" Immunology, 7th Edition (2006), published by Elsevier Ltd., pp. 59-86.
Maini et al., "Double-blind randomized controlled clinical trial of the interleukin-6 receptor antagonist, tocilizumab, in European patients with rheumatoid arthntis who had an incomplete response to methotrexate," Arthritis Rheum., 54(9):2817-29 (2006).
Maity et al., "Equilibrium unfolding of dimeric and engineered monomeric forms of lambda Cro (F58W) repressor and the effect of added salts: evidence for the formation of folded monomer induced by sodium perchlorate," Arch. Biochem. Biophys., Feb. 1, 2005;434(1):93-107.
Manz et al., Bioanalytical Chemistry, World Scientific Publishing Co. (2003).
Manzke et al., "Single-step purification of bispecific monoclonal antibodies for immunotherapeutic use by hydrophobic interaction chromatography," J. Immunol. Methods, 1997;208:65-73.
Mariuzza et al., "The structural basis of antigen-antibody recognition," Annu. Rev. Biophys. Chem., 16:139-59 (1987).
Marks et al., "By-passing immunization: building high affinity human antibodies by chain shuffling," Biotechnology (N.Y.), 10(7):779-83 (1992).
Marshall et al., "Rational design and engineering of therapeutic proteins," Drug Discov Today, Mar. 1, 2003;8(5):212-21.
Marti et al., "Inverse electrostatic effect: electrostatic repulsion in the unfolded state stabilizes a leucine zipper," Biochemistry, 43(39): 12436-47 (2004).
Martin et al., "Crystal structure at 2.8 A of an FcRn/heterodimeric Fc complex: mechanism of pH-dependent binding," Mol. Cell, 7:867-877 (2001).
Martinez et al., "Disulfide connectivity of human immunoglobulin G2 structural isoforms," Jul. 15, 2008;47(28):7496-508. doi: 10.1021/bi800576c. Epub Jun. 13, 2008.
Marvin et al., "Recombinant approaches to IgG-like bispecific antibodies," Acta. Pharmacol. Sin., 26:649-658 (2005).

(56) References Cited

OTHER PUBLICATIONS

Marvin et al., "Redesigning an antibody fragment for faster association with its antigen," Biochemistry, 42:7077-83 (2003).
Maxfield et al., "Endocytic recycling," Nat. Rev. Mol. Cell Biol., 5(2):121-32 (2004).
Maynard et al., "Antibody engineering," Annu. Rev. Biomed. Eng., 2:339-76 (2000).
McCloskey et al., "GAS6 mediates adhesion of cells expressing the receptor tyrosine kinase Axl," J. Biol. Chem., 272(37):23285-91 (1997).
McPhee et al., "Engineering human immunodeficiency virus 1 protease heterodimers as macromolecular inhibitors of viral maturation," Proc Natl Acad Sci U S A., Oct. 15, 1996;93(21):11477-81.
Medesan et al., "Delineation of the amino acid residues involved in transcytosis and catabolism of mouse IgG1," J Immunol., Mar. 1, 1997;158(5):2211-7.
Merchant et al., "An efficient route to human bispecific IgG," Nat. Biotechnol., 16:677-681 (1998).
Meric et al., "Expression profile of tyrosine kinases in breast cancer," Clin Cancer Res., 8(2):361-7 (2002).
Michaelsen et al., "A mutant human IgG molecule with only one C1q binding site can activate complement and induce lysis of target cells," Eur J Immunol., Jan. 2006;36(1):129-38.
Mihara et al., "Tocilizumab inhibits signal transduction mediated by both mIL-6R and sIL-6R, but not by the receptors of other members of IL-6 cytokine family," Int. Immunopharmnacol., 5(12):1731-40 (2005).
Morell et al., "Metabolic properties of IgG subclasses in man," J. Clin. Invest, 49(4):673-80 (1970).
Morimoto et al., "Single-step purification of F(ab')2 fragments of mouse monoclonal antibodies (immunoglobulins G1) by hydrophobic interaction high performance liquid chromatography using TSKgel Phenyl-5PW," J. Biochem. Biophys. Methods, 24:107-117 (1992).
Murtaugh et al., "A combinatorial histidine scanning library approach to engineer highly pH-dependent protein switches," Protein Sci., 20(9): 1619-31 doi:10.1002/pro 696 (2011).
Nakano et al., "Vascular smooth muscle cell-derived, Gla-containing growth-potentiating factor for Ca(2+)-mobilizing growth factors," J. Biol. Chem., 270(11):5702-5 (1995).
Nakano et al., "Prevention of growth arrest-induced cell death of vascular smooth muscle cells by a product of growth arrest-specific gene, gas6," FEBS Lett., 387(1):78-80 (1996).
Narhi et al., "Asn to Lys mutations at three sites which are N-glycosylated in the mammalian protein decrease the aggregation of *Escherichia coli*-derived erythropoietin," Protein Eng., Feb. 2001;14(2):135-40.
Neis et al., "Enhanced expression levels of IL-31 correlate with IL-4 and IL-13 in atopic and allergic contact dermatitis," J. Allergy Clin. Immunol., 118(4):930-937 (2006).
Nemoto et al., "Overexpression of protein tyrosine kinases in human esophageal cancer," Pathobiology., 65(4):195-203 (1997).
Nesterova et al., "Glypican-3 as a novel target for an antibody-drug conjugate," AACR Abstract No. 656, Los Angeles, CA (Apr. 4-18, 2007).
Neubauer et al., "Expression of axl, a transforming receptor tyrosine kinase, in normal and malignant hematopoiesis," Blood, 84(6):1931-41 (1994).
Newman et al., "Modification of the Fc Region of a Primatized IgG Antibody to Human CD4 Retains Its Ability to Modulate CD4 Receptors but Does Not Deplete CD4 T Cells in Chimpanzees," Clin Immunol. Feb. 2001;98(2):164-74.
Nieba et al., "Disrupting the hydrophobic patches at the antibody variable/constant domain interface: improved in vivo folding and physical characterization of an engineered scFv fragment," Protein Eng., Apr. 1997;10(4):435-44.
Nishimoto et al., "Humanized anti-interleukin-6 receptor antibody treatment of multicentric Castleman disease," Blood, 106(8):2627-32 (2005).
Nishimoto et al., "Interleukin 6: from bench to bedside," Nat. Clin. Pract. Rheumatol., 2(11):619-26 (2006).
Nohaile et al., "Altering dimerization specificity by changes in surface electrostatics," Proc. Natl. Acad. Sci. U.S.A., Mar. 13, 2001;98(6):3109-14.
O'Bryan et al., "axl, a transforming gene isolated from primary human myeloid leukemia cells, encodes a novel receptor tyrosine kinase," Mol. Cell Biol., 11(10):5016-31 (1991).
O'Shea et al., "Peptide 'Velcro': design of a heterodimeric coiled coil," Curr Biol., Oct. 1, 1993;3(10):658-67.
Ohno et al., "Antigen-binding specificities of antibodies are primarily determined by seven residues of VH," Proc. Natl. Acad. Sci. U.S.A., 82(9):2945-9 (1985).
Ohsugi et al., Pharm Stage, 7(5): 13-18 (2007) (English translation included).
Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Ono et al., "The humanized anti-HM1.24 antibody effectively kills multiple myeloma cells by human effector cell-mediated cytotoxicity," Mol. Immunol., 36(6):387-95 (1999).
Ozhegov et al., Tolkovyi Slovar Russkogo iazyka: 2004, p. 292 (with an English translation of the relevant passage defining "control").
Padlan et al., "Identification of specificity-determining residues in antibodies," FASEB J., 9:133-139 (1995).
Padlan et al., "Structure of an antibody-antigen complex: crystal structure of the HyHEL-10 Fab-lysozyme complex," Proc. Natl. Acad. Sci. USA, 86:5938-5942 (1989).
Padlan et al., "X-ray crystallography of antibodiesm," Adv Protein Chem., 1996;49:57-133.
Pakula et al., "Genetic Analysis of Protein Stability and Function," Annu. Rev. Genet., 23:289-310 (1989).
Pan et al., "Blocking neuropilin-1 function has an additive effect with anti-VEGF to inhibit tumor growth," Cancer Cell, Jan. 2007;11(1):53-67.
Pardridge et al., "Enhanced endocytosis in cultured human breast carcinoma cells and in vivo biodistribution in rats of a humanized monoclonal antibody after cationization of the protein," J. Pharmacol. Exp. Ther., 286(1):548-54 (1998).
Pardridge et al., "Enhanced cellular uptake and in vivo biodistribution of a monoclonal antibody following cationization," J Pharm Sci., Aug. 1995;84(8):943-8.
Paul, "Structure and function of immunoglobulins," Fundamental Immunology, Third Edition, 292-295 (1993).
Pavlaki et al., "Matrix metalloproteinase inhibitors (MMPIs): the beginning of phase I or the termination of phase III clinical trials," Cancer Metastasis Rev., 22(2-3):177-203 (2003).
Pavlinkova et al., "Charge-modified single chain antibody constructs of monoclonal antibody CC49: Generation, characterization, pharmacokinetics, and biodistribution analysis," Nucl. Med. Biol., 26:27-34 (1999).
Pavlou et al., "The therapeutic antibodies market to 2008," Eur. J. Pharm. Biopharm., 59:389-396 (2005).
Pini et al., "Design and use of a phage display library. Human antibodies with subnanomolar affinity against a marker of angiogenesis eluted from a two-dimensional gel," J. Biol. Chem., 273(34):21769-76 (1998).
Poduslo et al., "Polyamine modification increases the permeability of proteins at the blood-nerve and blood-brain barriers," J. Neurochem., 66:1599-1609 (1996).
Pokkuluri et al., "A domain flip as a result of a single amino-acid substitution," Structure, Aug. 15, 1998 ;6(8):1067-73.
Pons et al., "Energetic analysis of an antigen/antibody interface: alanine scanning mutagenesis and double mutant cycles on the HyHEL-10/lysozyme interaction," Protein Sci., 8(5):958-68 (1999).
Presta, "Engineering of therapeutic antibodies to minimize immunogenicity and optimize function," Adv. Drug Deliv. Rev., 58(5-6):640-56 (2006).
Presta et al., "Molecular engineering and design of therapeutic antibodies," Curr. Opin. Immunol., 20(4):460-70, doi: 10.1016/j.coi.2008.06.012 (2008).
Queen et al., "A humanized antibody that binds to the interleukin 2 receptor," Proc. Natl. Acad. Sci. U.S.A., 86(24):10029-10033 (1989).

(56) References Cited

OTHER PUBLICATIONS

R&D Systems (R&D Systems, Anti-human IL-31 RA Antibody, Catalog #AF2769, Oct. 2008).
R&D Systems (R&D Systems, Biotinylated Anti-human IL-31 RA Antibody, Catalog #BAF2769, Nov. 2005), 1 page.
Raap et al., "Correlation of IL-31 serum levels with severity of atopic dermatitis," J. Allergy Clin. Immunol., 122(2):421-423 (2008).
Rader et al., "A phage display approach for rapid antibody humanization: designed combinatorial V gene libraries," Proc. Natl. Acad. Sci. U.S.A,, Jul. 21, 1998;95(15):8910-5.
Raffen et al., "Reengineering immunoglobulin domain interactions by introduction of charged residues," Protein Eng., Apr. 1998;11:303-9.
Rajpal et al., A general method for greatly improving the affinity of antibodies by using combinatorial libraries, Proc. Natl. Acad. Sci. USA, 102:8466-71 (2005).
Rathanaswami et al., "Demonstration of an in vivo generated sub-picomolar affinity fully human monoclonal antibody to interleukin-8," Biochem. Biophys. Res. Commun., 334:1004-13 (2005).
Reddy et al., "Elimination of Fc receptor-dependent effector functions of a modified IgG4 monoclonal antibody to human CD4," J. Immunol., 164(4):1925-33 (2000).
Reichert et al., "Monoclonal antibody successes in the clinic," Nat. Biotechnol., 23:1073-78 (2005).
Reichert et al., "Development trends for monoclonal antibody cancer therapeutics," Nat. Rev. Drug Discov., 6(5):349-56 (2007).
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997;13(11):933-43.
Reist et al., "Human IgG2 constant region enhances in vivo stability of anti-tenascin antibody 81C6 compared with its murine parent," Clin Cancer Res., Oct. 1998;4(10):2495-502.
Ridgway et al., "'Knobs-into-holes' engineering of antibody $C_H3$ domains for heavy chain heterodimerization," Protein Eng., 9:617-621 (1996).
Rispens et al., "Dynamics of inter-heavy chain interactions in human immunoglobulin G (IgG) subclasses studied by kinetic Fab arm exchange," J Biol Chem., Feb. 28, 2014;289(9):6098-109. doi: 10.1074/jbc.M113.541813. Epub Jan. 14, 2014.
Roguska et al., "Humanization of murine monoclonal antibodies through variable domain resurfacing," Proc Natl Acad Sci U.S.A., 91:969-73 (1994).
ROITT et al., Immunology, M., Mir, (2000), pp. 110, 150, and 537-539 (in Russian, with what is believed to be a published English equivalent of those pages).
ROITT et al., Immunology, M., Mir, (2000), pp. 110-111 (in Russian, with what is believed to be a published English equivalent of those pages taken from ROITT et al., "Antibody Structure and Function," Immunology, Fifth Ed., (1998), pp. 80-81).
ROITT et al., Immunology, M., Mir, 5th Edition (2000), pp. 97-113 [In Russian: ROITT et al. (Document ID 611) is pages from a 2000 Russian edition of Immunology. In lieu of an English translation, applicant cites MALE et al. (Document ID 534 which is believed to be the corresponding pages from an English language edition of Immunology].
Roopenian et al., "FcRn: the neonatal Fc receptor comes of age," Nat Rev. Immunol., Sep. 2007;7(9):715-25 Epub Aug. 17, 2007.
Rothe et al., "Ribosome display for improved biotherapeutic molecules," Expert Opin. Biol. Ther., 6(2):177-87 (2006).
Rudikoff et al., "Single amino acid substitution altering antigen-binding specificity," Proc. Natl. Acad. Sci. U.S.A.,79(6):1979-83 (1982).
Ruf et al., "Pharmacokinetics and in vivo stability of intraperitoneally administered therapeutic antibody catumaxomab," J. Clin. Oncol., 26 (May 20 suppl) (2008), abstr 14006.
Sainaghi et al., "Gas6 induces proliferation in prostate carcinoma cell lines expressing the Axl receptor," J. Cell. Physiol., 204(1):36-44 (2005).

Salfeld et al., "Isotype selection in antibody engineering," Nat. Biotechnol., 25(12):1369-72 (2007).
Sal-Man et al., "Arginine mutations within a transmembrane domain of Tar, an *Escherichia coli* aspartate receptor, can drive homodimer dissociation and heterodimer association in vivo," Biochem. J., 385:29-36 (2005).
Sarkar et al., "Rational cytokine design for increased lifetime and enhanced potency using pH-activated "histidine switching"," Nat Biotechnol., Sep. 2002;20(9):908-13, Epub Aug. 5, 2002.
Sarmay et al., "Mapping and comparison of the interaction sites on the Fc region of IgG responsible for triggering antibody dependent cellular cytotoxicity (ADCC) through different types of human Fc gamma receptor," Mol. Immunol., 29(5):633-9 (1992).
Sato et al., "Reshaping a human antibody to inhibit the interleukin 6-dependent tumor cell growth," Cancer Res., 53(4):851-6 (1993).
Sawabu et al., "Growth arrest-specific gene 6 and Axl signaling enhances gastric cancer cell survival via Akt pathway," Mol. Carcinog., 46(2):155-64 (2007).
Schaeffer et al., "The Rat Glomerular Filtration Barrier Does Not Show Negative Charge Selectivity," Microcirculation, 9:329-342 (2002).
Schaefer et al., "Immunoglobulin domain crossover as a generic approach for the production of bispecific IgG antibodies," Proc Natl Acad Sci U S A., Jul. 5, 2011; 108(27):11187-92. doi: 10.1073/pnas.1019002108. Epub Jun. 20, 2011.
Schmitz et al., "Phage display: a molecular tool for the generation of antibodies—a review," Placenta., 21 Suppl A:S106-12 (2000).
Schuurman et al., "Normal human immunoglobulin G4 is bispecific: it has two different antigen-combining sites," Immunology, Aug. 1999;97(4):693-8.
Schuurman et al., "The inter-heavy chain disulfide bonds of IgG4 are in equilibrium with intrachain disulfide bonds," Mol Immunol., Jan. 2001;38(1):1-8.
Sebba et al., "Tocilizumab: the first interleukin-6-receptor inhibitor," Am J Health Syst Pharm., Aug. 1, 2008;65(15):1413-8. doi: 10.2146/ajhp070449.
Segal et al., "Bispecific antibodies in cancer therapy," Curr. Opin. Immunol., 11:558-562 (1999).
Shaul, "Exploring the charge space of protein-protein association: a proteomic study," Proteins, 60:341-352 (2005).
Sharifi et al., "Improving monoclonal antibody pharmacokinetics via chemical modification," Q J Nucl Med., Dec. 1998;42(4):242-9.
Shieh et al., "Expression of axl in lung adenocarcinoma and correlation with tumor progression," Neoplasia., 7(12):1058-64 (2005).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001) (Epub Nov. 28, 2000).
Shire et al., "Challenges in the development of high protein concentration formulations," J. Pharm. Sci., 93(6):1390-402 (2004).
Singer et al., Genes & Genomes, 1998; 1:63-64 (In Russian—with English translation).
Singer et al., Genes & Genomes, 1991; 67-69 (English translation is Singer et al., Genes & Genomes, 1998;1:63-64).
Sinha et al., "Electrostatics in protein binding and function," Curr. Protein Pept. Sci., 3(6):601-14 (2002).
Smans et al., "Bispecific antibody-mediated lysis of primary cultures of ovarian carcinoma cells using multiple target antigens," Int. J. Cancer, 83:270-277 (1999).
Smith et al., "The challenges of genome sequence annotation or 'the devil is in the details'," Nature Biotechnology, Nov. 1997;15:1222-1223.
Smolen et al., "Interleukin-6: a new therapeutic target," Arthritis Res Then, 2006;8 Suppl 2:S5. Epub Jul. 28, 2006.
Sonkoly et al., "IL-31: a new link between T cells and pruritus in atopic skin inflammation," J. Allergy Clin. Immunol., 117:411-417 (2006).
Spiess et al., "Bispecific antibodies with natural architecture produced by co-culture of bacteria expressing two distinct half-antibodies," Nat Biotechnol., Aug. 2013; 31(8):753-8. doi: 10.1038/nbt.2621. Epub Jul. 7, 2013.

(56) References Cited

OTHER PUBLICATIONS

Staerz et al., "Hybrid hybridoma producing a bispecific monoclonal antibody that can focus effector T-cell activity," Proc Natl Acad Sci U.S.A., 83:1453-7 (1986).
Stenhoff et al., "Vitamin K-dependent Gas6 activates ERK kinase and stimulates growth of cardiac fibroblasts," Biochem. Biophys. Res. Commun., 319(3):871-8 (2004).
Strand et al., "Biologic therapies in rheumatology: lessons learned, future directions," Nat. Rev. Drug Discov., 6(1):75-92 (2007).
Sun et al., "Coexpression of Gas6/Axl in human ovarian cancers," Oncology, 66(6):450-7 (2004).
Suresh et al., "Bispecific monoclonal antibodies from hybrid hybridomas," Methods Enzymol., 1986;121:210-228.
Tabrizi et al., "Elimination mechanisms of therapeutic monoclonal antibodies," Drug Discov Today, Jan. 2006;111(1-2):81-8.
Takkinen et al., "Affinity and Specificity Maturation by CDR Walking," Antibody Engineering, Springer Lab Manuals, pp. 540-545 (2001).
Tan et al., "Contributions of a highly conserved VH/VL hydrogen bonding interaction to scFv folding stability and refolding efficiency," Biophys. J., Sep. 1998;75(3):1473-82.
Tan et al., "Engineering the isoelectric point of a renal cell carcinoma targeting antibody greatly enhances scFv solubility," Immunotechnology, 4(2):107-114 (1998).
Tarditi et al., "Selective high-performance liquid chromatographic purification of bispecific monoclonal antibodies," J. Chromatogr., 599:13-20 (1992).
Teeling et al., "The biological activity of human CD20 monoclonal antibodies is linked to unique epitopes on CD20," J. Immunol., 177(1):362-71 (2006).
Ten Kate et al., "Effect of isoelectric point on biodistribution and inflammation: imaging with indium-111-labelled IgG," Eur. J. Nucl. Med., 17:305-309 (1990).
Thies et al., "The alternatively folded state of the antibody C(H)3 domain," J Mol Biol., Jun. 22, 2001;309(5):1077-85.
Tsubaki et al., "C-terminal modification of monoclonal antibody drugs: amidated species as a general product-related substance," Int J Biol Macromol., 52:139-47. doi: 10.1016/j.ijbiomac.2012.09.016. Epub Sep. 25, 2012.
Tsuchiya, Credit Suisse Seminar, "Therapeutic Antibody," at Fuji-Gotemba Laboratories, p. 21 (2006) [Translation].
Tsurushita et al., "Design of humanized antibodies: From anti-Tac to Zenapax," Methods, 36:69-83 (2005).
Vaisitti et al., "Cationization of monoclonal antibodies: another step towards the "magic bullet"?," J. Biol. Regul. Homeost. Agents., 19(3-4):105-12 (2005).
Vajdos et al., "Comprehensive functional maps of the antigen-binding site of an anti-ErbB2 antibody obtained with shotgun scanning mutagenesis," J. Mol. Biol., 320(2):415-28 (2002).
Vajkoczy et al., "Dominant-negative inhibition of the Axl receptor tyrosine kinase suppresses brain tumor cell growth and invasion and prolongs survival," Proc. Natl. Acad. Sci. U.S.A., 103(15):5799-804 (2006).
Van Der Neut Kolfschoten et al., "Anti-inflammatory activity of human IgG4 antibodies by dynamic Fab arm exchange," Science, Sep. 14, 2007;317(5844):1554-7.
Van Loghem et al., "Staphylococcal protein A and human IgG subclasses and allotypes," Scand. J. Immunol., 15(3):275-8 (1982).
Van Walle et al., Immunogenicity screening in protein drug development, Expert Opin. Biol. Ther., 7(3):405-18 (2007).
Vargas-Madrazo et al., "An improved model of association for VH-VL immunoglobulin domains: asymmetries between VH and VL in the packing of some interface residues," J. Mol. Recognit., May 2003-Jun. 16(3):113-20.
Varnum et al., "Axl receptor tyrosine kinase stimulated by the vitamin K-dependent protein encoded by growth-arrest-specific gene 6," Nature, 373(6515):623-6 (1995).
Verhoeyen et al., "Construction of a reshaped HMFG1 antibody and comparison of its fine specificity with that of the parent mouse antibody," Immunology, Mar. 1993;78(3):364-70.

Verhoeyen et al., "Monoclonal Antibodies in Clinical Oncology," 1991, Edited by AA Epenetos, Chapter 5, pp. 37-43, Chapman and Hall.
Wally et al., "Identification of a novel substitution in the constant region of a gene coding for an amyloidogenic kappa1 light chain," Biochim Biophys Acta., May 31, 1999;1454(1):49-56.
Wang et al., "Polyethylene Glycol-modified Chimeric Toxin Composed of Transforming Growth Factor alpha and Pseudomonas Exotoxin," Cancer Res., Oct. 1, 1993;53:4588-94.
Wang et al., "Conserved amino acid networks involved in antibody variable domain interactions," Proteins, Jul. 2009;76(1):99-114. doi: 10.1002/prot.22319.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," Biochemistry, Jun. 30, 1987;26(13):4131-8.
Ward et al., "Binding activities of a repertoire of single immunoglobulin variable domains secreted from *Escherichia coli*," Nature, 1989;341:544-546.
Warnaar et al., "Purification of bispecific F(ab')2 from murine trinoma OC/TR with specificity for CD3 and ovarian cancer," Hybridoma, 13:519-526 (1994).
Wiens et al., "Somatic mutation in VH complementarity-determining region 2 and framework region 2: differential effects on antigen binding and Ig secretion," J. Immunol., 159(3):1293-302 (1997).
Wiens et al., "Mutation of a single conserved residue in VH complementarity-determining region 2 results in a severe Ig secretion defect," J. Immunol., 167(4):2179-86 (2001).
Winkler et al., "Changing the antigen binding specificity by single point mutations of an anti-p24 (HIV-1) antibody," J. Immunol., 165:4505-14 (2000).
Worn et al., "Stability engineering of antibody single-chain Fv fragments," J. Mol. Biol., Feb. 2, 2001;305(5):989-1010.
Wu et al., "Development of motavizumab, an ultra-potent antibody for the prevention of respiratory syncytial virus infection in the upper and lower respiratory tract," J. Mol. Biol., 368(3):652-65 (2007).
Wu et al., "Humanization of a murine monoclonal antibody by simultaneous optimization of framework and CDR residues," J. Mol. Biol., 294(1):151-62 (1999).
Wu et al., "Multimerization of a chimeric anti-CD20 single-chain Fv-Fc fusion protein is mediated through variable domain exchange," Protein Eng., Dec. 2001;14(12):1025-33.
Wypych et al., "Human IgG2 antibodies display disulfide-mediated structural isoforms," J. Biol. Chem., Jun. 6, 2008;283(23):16194-205. Epub Mar. 13, 2008.
Xiang et al., "Study of B72.3 combining sites by molecular modeling and site-directed mutagenesis," Protein Eng., 13(5):339-44 (2000).
Yagi et al., "Interleukin-31 stimulates production of inflammatory mediators from human colonic subepithelial myofibroblasts," Int. J. Mol. Med., 19(6):941-946 (2007).
Yamagata et al., "Synaptic adhesion molecules," Curt. Opin. Cell Biol., 15(5):621-32 (2003).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).
Yang et al., "Tailoring structure-function and pharmacokinetic properties of single-chain Fv proteins by site-specific PEGylation," Protein Eng., 16:761-770 (2003).
Yang et al., "CDR walking mutagenesis for the affinity maturation of a potent human anti-HIV-1 antibody into the picomolar range," J. Mol. Biol., 254(3):392-403 (1995).
Zhu et al., "MHC class I-related neonatal Fc receptor for IgG is functionally expressed in monocytes, intestinal macrophages, and dendritic cells," J. Immunol., 166(5):3266-76 (2001).
Zhu et al., "Remodeling domain interfaces to enhance heterodimer formation," Protein Sci., Apr. 1997;6(4):781-8.

(56) References Cited

OTHER PUBLICATIONS

Zuckier et al., "Chimeric human-mouse IgG antibodies with shuffled constant region exons demonstrate that multiple domains contribute to in vivo half-life," Cancer Res., 58:3905-08 (1998).
Zwick et al., "The long third complementarity-determining region of the heavy chain is important in the activity of the broadly neutralizing anti-human immunodeficiency virus type 1 antibody 2F5," J. Virol., 78(6):3155-61 (2004).
International Search Report for App. Ser. No. PCT/JP2008/067483, dated Oct. 21, 2008, 2 pages.
International Preliminary Report on Patentability for App. Ser. No. PCT/JP2008/067483, dated Apr. 7, 2010, 13 pages.
International Search Report for App. Ser. No. PCT/JP2009/066590, dated Oct. 20, 2009, 2 pages.
International Preliminary Report on Patentability for PCT App. Ser. No. PCT/JP2008/067499, dated Apr. 7, 2010, 6 pages.
USPTO Restriction Requirement in U.S. Appl. No. 12/680,112, dated Oct. 7, 2011, 6 pages.
Fish & Richardson P.C., Amendment and Response to Species Election Requirement dated Oct. 7, 2011 in U.S. Appl. No. 12/680,112, filed on Dec. 6, 2011, 15 pages.
USPTO Non Final Office Action in U.S. Appl. No. 12/680,112, dated Feb. 29, 2012, 8 pages.
Fish & Richardson P.C., Amendment in Reply to Action of Feb. 29, 2012 in U.S. Appl. No. 12/680,112, filed on Aug. 27, 2012, 12 pages.
USPTO Restriction Requirement in U.S. Appl. No. 12/680,112, dated Sep. 19, 2012, 6 pages.
Fish & Richardson P.C., Amendment and Reply to Restriction Requirement dated Sep. 19, 2012 in U.S. Appl. No. 12/680,112, filed on Oct. 17, 2012, 13 pages.
USPTO Non Final Office Action in U.S. Appl. No. 12/680,112, dated Feb. 4, 2013, 9 pages.
USPTO Restriction Requirement in U.S. Appl. No. 13/257,112, dated Oct. 15, 2013, 10 pages.
Fish & Richardson P.C., Amendment and Response to Election Requirement dated Oct. 15, 2013 in U.S. Appl. No. 13/257,112, filed on Nov. 15, 2013, 6 pages.
USPTO Non-Final Office Action in U.S. Appl. No. 13/257,112, dated Jan. 30, 2014, 18 pages.
Fish & Richardson P.C., Amendment and Reply to Non-Final Office Action dated Jan. 30, 2014 in U.S. Appl. No. 13/257,112, filed on Jul. 1, 2014, 12 pages.
USPTO Final Office Action in U.S. Appl. No. 13/257,112, dated Sep. 5, 2014, 16 pages.
Fish & Richardson P.C., Amendment and Reply to Final Office Action dated Sep. 5, 2014 in U.S. Appl. No. 13/257,112, filed on Feb. 5, 2015, 6 pages.
USPTO Notice of Allowance in U.S. Appl. No. 13/257,112, dated Feb. 23, 2015, 8 pages.
USPTO Notice of Allowance in U.S. Appl. No. 13/257,112, dated Apr. 2, 2015, 7 pages.
USPTO Notice of Allowance in U.S. Appl. No. 13/257,112, dated Aug. 26, 2015, 7 pages.
International Search Report for App. Ser. No. PCT/JP2010/054769, dated Apr. 20, 2010, 4 pages.
International Preliminary Report on Patentability for App. Ser. No. PCT/JP2010/054769, dated Oct. 18, 2011, 6 pages.
USPTO Restriction Requirement in U.S. Appl. No. 13/257,145, dated Mar. 20, 2013, 11 pages.
Fish & Richardson P.C., Preliminary Amendment and Response to Restriction Requirement dated Mar. 20, 2013 in U.S. Appl. No. 13/257,145, filed on Apr. 22, 2013, 7 pages.
USPTO Non-Final Office Action in U.S. Appl. No. 13/257,145, dated Jul. 2, 2013, 20 pages.
Fish & Richardson P.C., Amendment in Reply to Office Action dated Jul. 2, 2013 in U.S. Appl. No. 13/257,145, filed on Dec. 2, 2013, 12 pages.
USPTO Final Office Action in U.S. Appl. No. 13/257,145, dated Feb. 6, 2014, 12 pages.
Fish & Richardson P.C., Amendment in Reply to Office Action dated Feb. 6, 2014 in U.S. Appl. No. 13/257,145, filed on May 6, 2014, 10 pages.
USPTO Notice of Allowance in U.S. Appl. No. 13/257,145, dated Oct. 1, 2014, 9 pages.
USPTO Notice of Allowance in U.S. Appl. No. 13/257,145, dated Jan. 9, 2015, 7 pages.
USPTO Notice of Allowance in U.S. Appl. No. 13/257,145, dated Mar. 11, 2015, 7 pages.
USPTO Advisory Action in U.S. Appl. No. 13/257,145, dated May 14, 2014, 5 pages.
Reply to Advisory Action in U.S. Appl. No. 13/257,145 dated May 14, 2014, filed on Jun. 3, 2014, 8 pages.
International Search Report for App. Ser. No. PCT/JP2010/054767, dated Jun. 15, 2010, 7 pages.
International Preliminary Report on Patentability for App. Ser. No. PCT/JP2010/054767, dated Oct. 18, 2011, 12 pages.
International Search Report for App. Ser. No. PCT/JP2008/067534, dated Oct. 21, 2008, 4 pages.
International Preliminary Report on Patentability for App. Ser. No. PCT/JP2008/067534, dated Apr. 7, 2010, 7 pages.
International Search Report for App. Ser. No. PCT/JP2009/057309, dated Jul. 7, 2009, 8 pages.
International Preliminary Report on Patentability for App. Ser. No. PCT/JP2009/057309, dated Nov. 30, 2010, 7 pages.
European Search Report for App. Ser. No. EP 09 72 9337, dated Nov. 3, 2011, 3 pages.
USPTO Restriction Requirement in U.S. Appl. No. 12/295,039, dated Oct. 12, 2010, 9 pages.
Fish & Richardson P.C., Response to Restriction Requirement dated Oct. 12, 2010 in U.S. Appl. No. 12/295,039, filed on Apr. 11, 2011, 9 pages.
USPTO Non-Final Office Action in U.S. Appl. No. 12/295,039, dated Jun. 28, 2011, 9 pages.
Fish & Richardson P.C., Amendment in Reply to Action dated Jun. 28, 2011 in U.S. Appl. No. 12/295,039, filed on Dec. 27, 2011, 14 pages.
USPTO Final Office Action in U.S. App. U.S. Appl. No. 12/295,039, dated Apr. 12, 2012, 8 pages.
Fish & Richardson P.C., Amendment in Reply to Action dated Apr. 12, 2012 in U.S. Appl. No. 12/295,039, filed on Sep. 11, 2012, 12 pages.
International Preliminary Report on Patentability for App. Ser. No. PCT/JP2007/057036, dated Oct. 21, 2008, 6 pages.
International Search Report for App. Ser. No. PCT/JP2007/057036, dated May 1, 2007, 2 pages.
European Search Report for App. Ser. No. 07 74 0494, dated Sep. 3, 2009, 3 pages.
International Preliminary Report on Patentability for App. Ser. No. PCT/JP2007/057058, dated Oct. 21, 2008, 11 pages.
International Search Report App. Ser. No. PCT/JP2007/057058, dated May 7, 2001, 2 pages.
USPTO Restriction Requirement in U.S. Appl. No. 12/295,075, dated Feb. 22, 2011, 9 pages.
Fish & Richardson P.C., Response to Restriction Requirement dated Feb. 22, 2011 in U.S. Appl. No. 12/295,075, filed Aug. 18, 2011, 2 pages.
USPTO Non-Final Office Action in U.S. Appl. No. 12/295,075, dated Nov. 4, 2011, 14 pages.
Fish & Richardson P.C., Amendment in Reply to Action dated Nov. 4, 2011 in U.S. Appl. No. 12/295,075, filed May 3, 2012, 12 pages.
USPTO Final Office Action in U.S. App. U.S. Appl. No. 12/295,075, dated Jul. 19, 2012, 12 pages.
Fish & Richardson P.C., Amendment in Reply to Action dated Jul. 19, 2012 in U.S. Appl. No. 12/295,075, filed Jan. 17, 2013, 113 pages.
USPTO Non-Final Office Action in U.S. Appl. No. 12/295,075, dated Jun. 7, 2013, 17 pages.
USPTO Restriction Requirement in U.S. App. U.S. Appl. No. 11/910,128, dated Jun. 9, 2011, 10 pages.
Fish & Richardson P.C., Response to Restriction Requirement dated Jun. 9, 2011 in U.S. Appl. No. 11/910,128, filed Dec. 2, 2011, 1 page.

(56) References Cited

OTHER PUBLICATIONS

USPTO Non-Final Office Action in U.S. Appl. No. 11/910,128, dated Apr. 25, 2012, 21 pages.
Fish & Richardson P.C., Amendment in Reply to Office Action dated Apr. 25, 2012 in U.S. Appl. No. 11/910,128, filed Oct. 25, 2012, 32 pages.
Fish & Richardson P.C., Supplemental Amendment in U.S. Appl. No. 11/910,128, filed Nov. 14, 2012, 20 pages.
USPTO Final Office Action in U.S. Appl. No. 11/910,128, dated Sep. 10, 2013, 12 pages.
International Preliminary Report on Patentability for App. Ser. No. PCT/JP2009/066590, dated May 10, 2011, 6 pages.
International Preliminary Report on Patentability for App. Ser. No. PCT/JP2009/070376, dated Jul. 5, 2011, 11 pages.
USPTO Non-Final Office Action U.S. Appl. No. 12/680,087, dated Oct. 27, 2011, 6 pages.
Fish & Richardson P.C., Amendment and Reply to Action dated Oct. 27, 2011 in U.S. Appl. No. 12/680,087, filed on Jan. 26, 2012, 6 pages.
USPTO Notice of Allowance in U.S. Appl. No. 12/680,087, dated Feb. 24, 2012, 5 pages.
USPTO Notice of Allowance in U.S. Appl. No. 12/680,087, dated Jun. 25, 2012, 11 pages.
USPTO Notice of Allowance in U.S. Appl. No. 12/680,087, dated Nov. 26, 2012, 7 pages.
USPTO Notice of Allowance in U.S. Appl. No. 12/680,087, dated Apr. 15, 2013, 9 pages.
USPTO Notice of Allowance in U.S. Appl. No. 12/680,087, dated Aug. 2, 2013, 8 pages.
USPTO Restriction Requirement in U.S. Appl. No. 12/936,587, dated Dec. 6, 2011, 5 pages.
Fish & Richardson P.C., Third Preliminary Amendment and Response to Restriction Requirement dated Dec. 6, 2011 in U.S. Appl. No. 12/936,587, filed on Jun. 5, 2012, 7 pages.
USPTO Restriction Requirement in U.S. Appl. No. 12/936,587, dated Jun. 25, 2012, 5 pages.
Fish & Richardson P.C., Response to Species Election Requirement dated Jun. 25, 2012 in U.S. Appl. No. 12/936,587, filed on Jul. 25, 2012, 1 page.
USPTO Non-Final Office Action in U.S. Appl. No. 12/936,587, dated Nov. 7, 2012, 13 pages.
International Preliminary Report on Patentability for App. Ser. No. PCT/JP2010/058166, dated Dec. 16, 2011, 15 pages.
International Search Report for App. Ser. No. PCT/JP2010/066490, dated Nov. 9, 2010, 5 pages.
International Preliminary Report on Patentability for App. Ser. No. PCT/JP2010/066490, dated Apr. 11, 2012, 6 pages.
USPTO Restriction Requirement in U.S. Appl. No. 12/745,781, dated Sep. 4, 2012, 10 pages.
Response to Restriction Requirement dated Sep. 4, 2012 in U.S. Appl. No. 12/745,781, fded on Sep. 21, 2012, 176 pages.
USPTO Non-Final Office Action in U.S. Appl. No. 12/745,781, dated Oct. 18, 2012, 21 pages.
Fish & Richardson P.C., Amendment in Reply to Office Action dated Oct. 18, 2012 in U.S. Appl. No. 12/745,781, filed on Apr. 17, 2013, 23 pages.
USPTO Final Office Action in U.S. Appl. No. 12/745,781, dated May 21, 2013, 16 pages.
USPTO Restriction Requirement in U.S. Appl. No. 12/679,922, dated Oct. 2, 2012, 9 pages.
Fish & Richardson P.C., Response to Restriction Requirement dated Oct. 2, 2012 in U.S. Appl. No. 12/679,922, filed on Nov. 1, 2012, 2 pages.
USPTO Non-Final Office Action in U.S. Appl. No. 12/679,922, dated Jan. 3, 2013, 25 pages.
Fish & Richardson P.C., Amendment in Reply to Action dated Jan. 3, 2013 in U.S. Appl. No. 12/679,922, filed on Jul. 2, 2013, 18 pages.
USPTO Final Office Action in U.S. Appl. No. 12/679,922, dated Aug. 2, 2013, 12 pages.
International Preliminary Report on Patentability for App. Ser. No. PCT/JP2010/073361, dated Aug. 14, 2012, 7 pages.
USPTO Non-Final Office Action in U.S. Appl. No. 13/595,139, dated Nov. 14, 2012, 10 pages.
International Search Report for App. Ser. No. PCT/JP2011/055101, dated May 10, 2011, 4 pages.
International Preliminary Report on Patentability for App. Ser. No. PCT/JP2011/055101, dated Oct. 2, 2012, 6 pages.
USPTO Restriction Requirement in U.S. Appl. No. 13/497,269, dated Dec. 6, 2012, 9 pages.
Fish & Richardson P.C., Response to Restriction Requirement dated Dec. 6, 2012 in U.S. Appl. No. 13/497,269, filed May 1, 2013, 2 pages.
USPTO Non-Final Office Action in U.S. Appl. No. 13/497,269, dated Aug. 15, 2013, 13 pages.
USPTO Restriction Requirement in U.S. Appl. No. 12/809,138, dated Dec. 13, 2012, 8 pages.
Fish & Richardson P.C., Response to Restriction Requirement dated Dec. 13, 2012 in U.S. Appl. No. 12/809,138, filed Apr. 5, 2013, 2 pages.
USPTO Notice of Allowance in U.S. Appl. No. 12/809,138, dated Aug. 23, 2013, 9 pages.
USPTO Restriction Requirement in U.S. Appl. No. 13/320,317, dated Dec. 18, 2012, 13 pages.
Fish & Richardson P.C., Response to Restriction Requirement dated Dec. 18, 2012 in U.S. Appl. No. 13/320,317, filed Jan. 18, 2013, 3 pages.
USPTO Non-Final Office Action in U.S. Appl. No. 13/320,317, dated Dec. Apr. 25, 2013, 25 pages.
USPTO Restriction Requirement in U.S. Appl. No. 13/524,528, dated Mar. 21, 2013, 7 pages.
Fish & Richardson P.C., Reply to Restriction Requirement dated Mar. 21, 2013 in U.S. Appl. No. 13/524,528, filed on Sep. 13, 2013, 1 page.
USPTO Non-Final Office Action in U.S. App. U.S. Appl. No. 13/524,528, dated Sep. 30, 2013, 9 pages.
U.S. Appl. No. 15/617,008, Igawa et al., filed Jun. 8, 2017.
U.S. Appl. No. 15/875,847, Igawa et al., filed Jan. 19, 2018.
U.S. Appl. No. 16/155,673, Igawa et al., filed Oct. 9, 2018.
Chihara et al., "Interleukin 6 signaling promotes anti-aquaporin 4 autoantibody production from plasmablasts in neuromyelitis optica," Proc Natl Acad Sci USA, Mar. 1, 2011, 108(9):3701-3706.
Sampei et al., Non-antigen-contacting region of an asymmetric bispecific antibody to factors IXa/X significantly affects factor VII-mimetic activity, mAbs, 2015, 7(1):120-8. doi: 10.4161/19420862.2015.989028.
USPTO Restriction Requirement in U.S. Appl. No. 12/680,082, dated Jun. 6, 2012, 12 pages.
USPTO Restriction Requirement in U.S. Appl. No. 12/680,082, dated Sep. 14, 2012, 6 pages.
USPTO Non-Final Office Action in U.S. Appl. No. 12/680,082, dated Feb. 14, 2013, 12 pages.
USPTO Final Office Action in U.S. Appl. No. 12/680,082, dated Oct. 22, 2013, 12 pages.
USPTO Interview Summary in U.S. Appl. No. 12/680,082, dated Feb. 25, 2014, 3 pages.
USPTO Non-Final Office Action in U.S. Appl. No. 12/680,082, dated Feb. 5, 2015, 9 pages.
USPTO Final Office Action in U.S. Appl. No. 12/680,082, dated May 13, 2015, 10 pages.
USPTO Non-Final Office Action in U.S. Appl. No. 12/680,082, dated Apr. 27, 2016, 15 pages.
USPTO Notice of Allowance in U.S. Appl. No. 12/680,082, dated Feb. 14, 2017, 8 pages.
U.S. Appl. No. 15/725,692, filed Oct. 5, 2017, Igawa et al.
U.S. Appl. No. 15/782,256, filed Oct. 12, 2017, Igawa et al.
Akira et al., "Interleukin-6 in Biology and Medicine," Adv Immunol. Dec. 31, 1993; 54: 1-78.
Annual Report 2012 (Integrated Edition Inluding CSR Report) Mar. 27, 2013, 154 pages.
Araki et al., "Clinical improvement in a patient with neuromyelitis optica following therapy with the anti-IL-6 receptor monoclonal

(56) References Cited

OTHER PUBLICATIONS antibody tocilizumab," Mod Rheumatol. Jul. 2013;23(4):827-31. doi: 10. 1007/s10165-012-0715-9. Epub Jul. 11, 2012.
Aricha et al., "Blocking of IL-6 suppresses experimental autoimmune myasthenia gravis," J Autoimmun. Mar. 2011;36(2):135-41. doi: 10. 1016/j.jaut. 2010. 12. 001. Epub Dec. 30, 2010.
Davies et al., "Structural determinants of unique properties of human IgG4-Fc," J. Mol. Biol., Feb. 6, 2014; 426(3): 630-644. doi: 10.1016/j.jmb.2013.10.039.Epub Nov. 6, 2013.
Gunawardane et al., "Agonistic Hman Antibodies Binding to Lecithin-Cholesterol Acyltransferase Modulate High Density Lipoprotein Metabolism," J Biol Chem. Feb. 5, 2016;291(6):2799-811. doi: 10.1071/ibc.M11S.672790. Epub Dec. 7, 2015.
Hirano et al., "Complementary DNA for a novel human interleukin (BSF-2) that induces B lymphocytes to produce immunoglobulin," Nature, 324: 73-76 (Nov. 1986).
Hirata et al., "Characterization of IL-6 Receptor Expression by Monoclonal and Polyclonal Antibodies," J Immunol. Nov. 1, 1989;143(9):2900-6.
Huang et al., "A Monoclonal Anti-Human IL-6 Receptor Antibody Inhibitis the Proliferation of Human Myeloma Cells," Hybridoma. Oct. 1993:12(5):621-30.
Janeway et al. "Antigen Recognition by B-cell and T-cell Receptors," Immunobiology, 5th edition. 2001 :Extract from Chapter 3, pp. 93-122.
Janeway et al., "The Generation of Lymphocyte Antigen Receptors," Immunobiology, 5th edition. 2001 :Extract from Chapter 4, pp. 123-154.
Krieckaert et al., "Immunogenicity of biologic therapies—we need tolerance," Nat Rev Rheumatol. Oct. 2010;6(10) : 558-9. doi: 10. 1038/nrrheum. 2010. 153.
Lotz et al., "B Cell Stimulating Factor 2/Interleukin 6 is a Costimulant for Human Thymocytes and T Lymphocytes," J. Exp. Med., Mar. 1, 1988; 167(3): 1253-1258.
Matsumiya et al., "Structural Comparison of Fucosylated and Nonfucosylated Fc Fragments of Human Immunoglobulin G1," J. Mol. Biol. May 4, 2007; 368(3):767-79. Epb Feb. 22, 2007.
Murata et al., "Anti-Digoxin Fab Variants Generated by Phage Display," Mol Biotechnol. Jun. 2013 :54 (2) :269-77. doi : 10. 1007/s12033-012-9564-1.
Nishimoto et al., "Humanized anti-interleukin-6 receptor antibody treatment of multicentric Castleman disease," Blood, Oct. 15, 2005; 106:2627-32).
Novick et al., "Monoclonal Antibodies to the Soluble Human IL-6 Receptor: Affinity Purification, ELISA, and Inhibition of Ligand Binding," Hybridoma. Feb. 1991;10(1) :137-46.
Okabe, Proprietary Innovative Antibody Engineering Technologies in Chugai Pharmaceutical: Dec. 18, 2012, 78 pages.
Pejchal et al., "A Conformational Switch in Human Immunodeficiency Virus gp41 Revealed by the Structures of Overlapping Epitopes Recognized by Neutralizing Antibodies," J Virol. Sep. 2009;83 (17) : 8451-62. do i : 10. 1128/ JVI. 00685- 09. Epub Jun. 10, 2009.
Raposo et al., "Epitope-specific antibody response is controlled by immunoglobulin Vh polymorphisms," J Exp Med. Mar. 10, 2014:211(3) :405-11. do i : 10. 1084/ jem. 20130968. Epub Feb. 17, 2014.
Reichert, "Antibodies to watch in 2014," mAbs, 6(4): 799-802 (Jul.-Aug. 2014).
Taga et al., "Interleukin-6 Triggers the Association of Its Receptor with a Possible Signal Transducer, gp130," Cell. Aug. 11, 1989; 58(3): 873-581.
Taga et al., "Receptors for B Cell Stimulatory Factor 2," J. Exp. Med. Oct. 1, 1987; 166(4): 967-981.
Yamasaki et al., "Cloning and Expression of the Human Interleukin-6 (BSF-2/IFNb 2) Receptor," Science. Aug. 12, 1988:241 (4867):825-8.
U.S. Appl. No. 12/745,781, Kuamochi et al., filed Sep. 13, 2010.
U.S. Appl. No. 15/782,256, Igawa et al., filed Oct. 12, 2017.
U.S. Appl. No. 15/614,842, Igawa et al., filed Jun. 6, 2017.
U.S. Appl. No. 12/295,039, Igawa et al., fied Jan. 20, 2009.
U.S. Appl. No. 15/553,609, filed Aug. 25, 2017, Kakehi et al.
U.S. Appl. No. 15/562,186, filed Sep. 27, 2017, Igawa et al.
Gershoni et al., "Epitope Mapping," BioDrugs, May 2007;21(3):145-56.
Hattori, "Introduction of ART-Ig and application to hemophilia A treatment," Chugai Seiyaku ni Okeru Dokuji no Kakushinteki Kotai Gijutsu. Dec. 2012; 18: 42-57 (with English translation).
Labrun et al., "Controlled Fab-arm exchange for the generation of stable bispecific IgG1," Nat Protoc. Oct. 2014; 9(10): 2450-63. doi: 10.1038/nprot.2014.169. Epub Sep. 25, 2014.
Peters et al., "Engineering an improved IgG4 molecule with reduced disulfide bond heterogeneity and increased Fab domain thermal stability," J Biol Chem. Jul. 13, 2012; 287(29): 24525-33. doi: 10.1074/jbc.M112.369744. Epub May 18, 2012.
U.S. Appl. No. 14/897,498, Yamura et al., filed Dec. 10, 2015.
U.S. Appl. No. 15/562,186, Igawa et al., filed Sep. 27, 2017 (attorney docket No. 14875-0260US1).
U.S. Appl. No. 15/875,847, filed Jan. 19, 2018, Igawa et al.
U.S. Appl. No. 16/041,976, filed Jul. 23, 2018, Igawa et al.
U.S. Appl. No. 16/061,454, filed Jun. 12, 2018, Tanaka et al.
Besada, "Potential patient benefit of a subcutaneous formulation of a tocilizumab for the treatment of rheumatoid arthritis: a critical review." Patient Prefer and Adherence, Aug. 1, 2014, 8:1051-9. doi: 10.2147/PPA. S34958. eCollection 2014.
Canfield et al., "The Binding Affinity of Human IgG for its High Affinity Fc Receptor is Determined by Multiple Amino Acids in the CH2 Domain and is Modulated by the Hinge Region," J Exp Med, Jun. 1, 1991, 173(6):1483-91.
Dall'Acqua et al., "Properties of Human IgG1s Engineered for Enhanced Binding to the Neonatal Fc Receptor (FcRn)," J Biol Chem., Aug. 18, 2006, 281(33):23514-24, Epub Jun. 21, 2006.
EPO Register Extract EP 1915397 (document submitted in EP opposition and posted by EPO on Feb. 2, 2018); 4 pages.
Geneseq Accession No. AEM45140, Feb. 22, 2007, "Light chain constant region of therapeutic human IgG antibody," 1 page.
Golay et al., "Mechanism of action of therapeutic monoclonal antibodies: Promises and pitfalls of in vitro and in vivo assays," Archives of Biochemistiy and Biophysics, Oct. 15, 2012, 526:146-153.
Hotzel et al., "A strategy for risk mitigation of antibodies with fast clearance," mAbs., Nov.-Dec. 2012, 4(6):753-60. doi: 10.4161/mabs. 22189.
Huizinga et al., "Sarilumab, a fully human monoclonal antibody against IL-6Rα in patients with rheumatoid arthritis and an inadequate response to methotrexate: efficacy and safety results from the randomised SARIL-RA-MOBILITY Part A trial," Ann Rheum Dis., Sep. 2014, 73(9):1626-34. doi: 10. 1136/annrheumdis-2013-204405. Epub Dec. 2, 2013.
Ryman et al., "Pharmacokinetics of Monoclonal Antibodies," CPT Pharmacometrics Syst Pharmacol., Sep. 2017, 6(9):576-588, doi: 10.1002/psp4.12224, Epub Jul. 29, 2017.
Sampei et al., "Identification and multidimensional optimization of an asymmetric bispecific IgG antibody mimicking the function of factor VIII cofactor activity," PLoS One, Feb. 2013, 8(2):e57479, doi: 10.1371/joumal.pone.0057479. Epub Feb. 28, 2013.
Stancovski et al., "Mechanistic Aspects of the Opposing Effects of Monoclonal Antibodies to the ERBB2 Receptor on Tumor Growth," Proc Natl Acad Sci USA, Oct. 1, 1991, 88:8691-8695.
Summary of information about antibodies in Examples of patent (document submitted in EP opposition and posted by EPO on Apr. 13, 2018); 3 pages.
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 20063 81 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol., Jul. 1, 2005, 350(1):126-44.
Yarilin, Fundamentals of Immunology M:Medicina, 1999, pp. 169-172, 354-8 (With English translation) 21 pages.

(56) References Cited

OTHER PUBLICATIONS

Yarilin, Fundamentals of Immunology M:Medicina, 1999, pp. 172-174 (With English translation), 8 pages.
Choi et al., "Crystal structures of immunoglobulin Fc heterodimers reveal the molecular basis for heterodimer formation," Mol Immunol, Jun. 2015, 65(2):377-83. doi: 10.1016/j.molimm.2015.02.017. Epub Mar. 2, 2015.
Feige et al., "How antibodies fold," Trends Biochem Sci, Apr. 2010, 35(4): 189-98. doi: 10.1016/j.tibs.2009.11.005. Epub Dec. 21, 2009.
Goulet et al., "Kinetic mechanism of controlled Fab-arm exchange for the formation of bispecific immunoglobulin G1 antibodies," J Biol Chem, Jan. 12, 2018, 293(2):651-661. doi: 10.1074/jbc.RA117.000303. Epub Nov. 17, 2017.
Rispens et al., "Mechanism of Immunoglobulin G4 Fab-arm Exchange," J Am Chem Soc, Jul. 6, 2011, 133(26):10302-11, doi: 10.1021/ja203638y, Epub Jun. 15, 2011.
U.S. Appl. No. 15/553,609, Kakehi et al., filed on Aug. 25, 2017.
Abe et al., "Novel Protein A Resin: Synthetic Polymer Matrix Design Impact on Antibody Binding Capacity," JSR Technical Review No. 119, 2012, pp. 1-5 [online], [retrieved on Feb. 17, 2017], retrieved from the internet: <URL:http://www.jsr.co.jp/pdf/rd/tec119-1.pdf> (with English translation).
Cruse et al., Atlas of Immunology, CRC Press LLC, 2004, Chapter 3 "Antigens and Immunogens", p. 109.
Decision of the EPO Opposition Division for EP 2 006 3 81 on Jul. 25, 2018, 17 pages.
GE Healthcare Life Sciences, Dynamic binding capacity study on MabSelect SuReTM LX for capturing high-titer monoclonal antibodies, Application note 28-9875-25-AA, 2011, [online], [retrieved on Feb. 17, 2017], retrieved from the internet:,http://www.processdevelopmentforum.com/images/articles/28-9875-25_AA_AN_DBC_study_on_MabSelect_SuRe_LX_final.pdf>.
Geneseq Accession No. ARZ17615, Aug. 21, 2008, "Human antibody IgG2 heavy chain constant region SEQ ID No. 36".
Sequence alignments and modification scheme (document filed during Oral Proceedings in EPO opposition for EP 2 006 381 mentioned in minutes of the Oral Proceedings posted by EPO on Jul. 25, 2018); 3 pages.
Van Den Abbeele et al., "Antigen-Binding Site Protection During Radiolabeling Leads to a Higher Immunoreactive Fraction," J Nucl Med, Jan. 1991, 32(1):116-22.
U.S. Appl. No. 14/520,423, Igawa et al., filed Oct. 22, 2014.
U.S. Appl. No. 16/448,088, Igawa et al., filed Jun. 21, 2019.
USSN 13/5 82,073, Kuramochi et al., filed Dec. 20, 2012.
USSN 15/490,936, Igawa et al., filed Apr. 19, 2017.
U.S. Appl. No. 16/298,032, filed Mar. 11, 2019, Igawa et al.
U.S. Appl. No. 16/448,088, filed Jun. 21, 2019, Igawa et al.
U.S. Appl. No. 16/560,143, filed Sep. 4, 2019, Kuramochi et al.
ACTEMRA (tocilizumab), Highlights of Prescribing Information, as revised in Aug. 2017 (1 page).
Ando et al., "Tocilizumab, a Proposed Therapy for the Cachexia of Interlenkin6-Expressing Lung Cancer," PLOS One, Jul. 10, 2014, 9(7):e102436. doi: 10.1371/journal.pone.0102436. eCollection 2014.
Barrabes et al., "Effect of sialic acid content on glycoprotein pI analyzed by two-dimensional electrophoresis," Electrophoresis, Sep. 2010, 31(17):2903-12, doi: 10,1002/elps.200900764.
Beiboer et al., "Guided Selection of a Pan Carcinoma Specific Antibody Reveals Similar Binding Characteristics yet Structural Divergence Between the Original Murine Antibody and its Human Equivalent," J Mol Biol, Feb. 25, 2000, 296(3):833-49.
Costa et al., "Efficacy of tocilizumab in a patient with refractory psoriatic arthritis," Clin Rheumatol, Sep. 2014, 33(9):1355-7.
Decision of the Opposition Division in EP 2 275 443, dated Apr. 26, 2018 (submitted on May 24, 2019 by the Patentee during EPO Opposition Procedure for EP 2 202 245), 29 pages.
Declaration of Taichi Kuramochi (submitted on May 24, 2019 by the Patentee during EPO Opposition Procedure for EP 2 202 245), 11 pages.
Declaration of Dr. Anette Henriksen, signed Apr. 17, 2019 (which was submitted by the Opponent during EPO opposition procedure for EP 2 006 381).
Do et al., "A rapid method for determining dynamic binding capacity of resins for the purification of proteins," Protein Expr Purif, Aug. 2008, 60(2):147-50. doi: 10.1016/j.pep.2008.04.009. Epub May 3, 2008.
Furuya et al., "Interleukin-6 as a Potential Therapeutic Target for Pulmonary Arterial Hypertension," Int J Rheumatol, Aug. 2010, 2010:720305:1-8. doi: 10.1155/2010/720305. Epub Aug. 2, 2010.
Granted claims of EP 2 275 443 (submitted on May 24, 2019 by the Patentee during EPO Opposition Procedure for EP 2 202 245), 1 page.
Hashizume et al., "Tocilizumab, a humanized anti-interleukin-6 receptor antibody, improved anemia in monkey arthritis by suppressing IL-6-induced hepcidin production," Rheumatol Int, May 2010, 30(7):917-23, doi: 10.1007/s00296-009-1075-4. Epub Jul. 2, 20099.
Honda et al., "Marginal zone B cells exacerbate endotoxic shock via interleukin-6 secretion induced by Fca/mR-coupled TLR4 signalling," Nat Commun, May 5, 2016, 7:11498. doi: 10.1038/ncomms11498.
Iijima et al., "Tocilizumab improves systemic rheumatoid vasculitis with necrotizing crescentic glomerulonephritis," Mod Rheumatol, Jan. 2015, 25(1):138-42. doi: 0.3109/14397595.2013.874748. Epub Feb. 18, 2014.
Kishimoto, "Interleukin-6 and its Receptor in Autoimmunity," J Autoimmun, Apr. 1992, 5 Suppl A:123-32.
Klimka et al., "Human anti-CD30 recombinant antibodies by guided phage antibody selection using cell panning," Br J Cancer, Jul. 2000, 83(2):252-60.
Kondo et al., "A case of overlap syndrome successfully treated with tocilizumab: a hopeful treatment strategy for refractory dermatomyositis?," Rheumatology (Oxford), Oct. 2014, 53(10):1907-8, doi: 10.1093/rheumatology/keu234. Epub May 23, 2014.
Mihara et al., "Anti-interleukin 6 receptor antibody inhibits murine AA-amyloidosis," J Rheumatol, Jun. 2004, 31(6):1132-8.
Mori et al., "Novel models of cancer-related anemia in mice inoculated with IL-6-producing tumor cells," Biomed Res, Feb. 2009, 30(1):47-51.
Motozawa et al., "Unique circumferential peripheral keratitis in relapsing polychondritis," Medicine (Baltimore), Oct. 2017, 96(41):e7951. doi: 10.1097/MD.0000000000007951.
Narazaki et al., "Therapeutic effect of tocilizumab on two patients with polymyositis," Rheumatology (Oxford), Jul. 2011, 50(7):1344-6. doi: 10.1093/rheumatology/ker152. Epub Apr. 22, 2011.
Okiyama et al., "Therapeutic Effects of Interleukin-6 Blockade in a Murine Model of Polymyositis That Does Not Require Interleukin-17A," Arthritis Rheum, Aug. 2009, 60(8):2505-12.
Pabst et al., "Engineering of novel Staphylococcal Protein A ligands to enable milder elution pH and high dynamic binding capacity," J Chromatogr A, Oct. 3, 2014, 1362:180-5. doi: 10.1016/j.chroma.2014.08.046. Epub Aug. 19, 2014.
Pabst et al., "Evaluation of recent Protein A stationary phase innovations for capture of biotherapeutics," J Chromatogr A, Jun. 15, 2018, 1554:45-60. doi: 10.1016/j.chroma.2018.03.060. Epub Apr. 7, 2018.
Petkova et al., "Enhanced half-life of genetically engineered human IgG1 antibodies in a humanized FcRn mouse model: potential application in humorally mediated autoimmune disease," Int Immunol, Dec. 2006, 18(12):1759-69, Epub Oct. 31, 2006.
Serada et al., "IL-6 blockade inhibits the induction of myelin antigen-specific Th17 cells and Th1 cells in experimental autoimmune encephalomyelitis," Proc Natl Acad Sci USA, Jul. 1, 2008, 105(26):9041-6, doi: 10.1073/pnas.0802218105. Epub Jun. 24, 2008.
Shima et al., "Tocilizumab, a humanized anti-interleukin-6 receptor antibody, ameliorated clinical symptoms and MRI findings of a patient with ankylosing spondylitis," Mod Rheumatol, Aug. 2011, 21(4):436-9. doi: 10,1007/s 10165-011-0416-9, Epub Feb. 9, 2011.
Shimizu et al., "Successful treatment with tocilizumab for refractory scleritis associated with relapsing polychondritis," Scand J Rheumatol, Sep. 2017, 46(5):418-419. doi: 10.1080/03009742,2016.1275774. Epub Jan. 25, 2017.

(56) References Cited

OTHER PUBLICATIONS

Silpa-Archa et al., "Outcome of tocilizumab treatment in refractory ocular inflammatory diseases," Acta Ophthalmol, Sep. 2016, 94(6):e400-6, doi: 10.1111/aos. 13015, Epub Mar. 24, 2016.
Supplemental Material to RAPOSO et al., "Epitope-specific antibody response is controlled by immunoglobulin VH polymorphisms," J Exp Med, Mar. 10, 2014, 211 (3):405-11. doi: 10.1084/jem. 20130968. Epub Feb. 17, 2014 (submitted on May 24, 2019 by the Patentee during EPO Opposition Procedure for EP 2 202 245), 4 pages.
Suzuki et al., "Anti-murine IL-6 receptor antibody inhibits IL-6 effects in vivo," Immunol Lett, Sep. 1991,30(1):17-21.
Vaccaro et al., "Divergent activities of an engineered antibody in murine and human systems have implications for therapeutic antibodies," Proc Natl Acad Sci USA. Dec. 5, 2006, 103(49): 18709-14, Epub Nov. 20, 2006.
U.S. Appl. No. 16/041,976, Igawa et al., filed Jul. 23, 2018.
U.S. Appl. No. 16/815,089, Igawa et al., filed Mar. 11, 2020.
U.S. Appl. No. 13/582,073, Kuramochi et al., filed Dec. 20, 2012.
U.S. Appl. No. 15/553,609, Kakehi et al., filed Aug. 25, 2017.
U.S. Appl. No. 15/490,93 6, Igawa et al., filed Apr. 19, 2017.
U.S. Appl. No. 16/815,089, filed Mar. 11, 2020, Igawa et al.
U.S. Appl. No. 16/838,415, filed Apr. 2, 2020, Igawa et al.
"Interleukin 6," Wikipedia, Feb. 22, 2019, XP055598802, Retrieved from the Internet: URL:https://protect-us.mimecast.com/s/6UxpCmZ28nsAp18JuGhTki?domain=en. wikipedia.org [retrieved on Jun. 24, 2019].
Baca et al., "Antibody Humanization Using Monovalent Phage Display," J Biol Chem, Apr. 18, 1997, 272(16):10678-84.
Boerner et al., "Production of antigen-specific human monoclonal antibodies from in vitro-primed human splenocytes," J Immunol, Jul. 1, 1991, 147(1):86-95.
Brooks et al., "Structure and Function of Human IgG FcRII(CD32)—Functional Heterogeneity is Encoded by the Alternatively Spliced Products of Multiple Genes," J Exp Med, Oct. 1, 1989, 170(4):1369-85.
Bruggemann et al., "Comparison of the Effector Functions of Human Immunoglobulins Using a Matched Set of Chimeric Antibodies," J Exp Med, Nov. 1, 1987, 166(5):1351-61.
Capel et al., "Heterogeneity of Human IgG Fc Receptors," Immunomethods, Feb. 1994, 4(1):25-34.
Carter et al., "Humanization of an anti-p185$^{HER2}$ antibody for human cancer therapy," Proc Natl Acad Sci USA, May 15, 1992, 89(10):4285-9.
Chan et al., "Therapeutic antibodies as a treatment option for dengue fever," Expert Rev Anti Infect Ther, Nov. 2013, 11(11):1147-57. doi: 10,1586/14787210.2013.839941. Epub Oct. 4, 2013.
Chari et al., Immunoconjugates Containing Novel Maytansinoids: Promising Anticancer Drugs, ancer Res, Jan. 1, 1992, 52(1):127-31.
Chothia et al., "Canonical Structures for the Hypervariable Regions of Immunoglobulins," J Mol Biol, Aug. 20, 1987, 196(4);901-17.
Chowdhury et al., "Engineering scFvs for Improved Stability," Methods Mol Biol, 2003, 207:179-96.
Chugai NMO Clinical Trial Webinar, Sakura Star Study, dated Dec. 12, 2014, downloaded on Sep. 5, 2019 from https://s3.amazonaws.com/gjcf-wp-uploads/wpcontent/uploads/2016/05/16162202/12_12_14_Chugai_Webinar_PPT_Complete_Deck_FINAL.pdf, 18 pages.
Chugai Pharmaceutical, A phase I, multiple-dose study of SA237, Study JapicCTI-No. 121786; submitted to Clinicaltrials.jp on Jan. 31, 2014; downloaded from clinicaltrials.jp archive on Sep. 5, 2019 as https://www.clinicaltrials.jp/ctiuser/trial/Show.jsp, 5 pages.
Chugai Pharmaceutical, A phase I, multiple-dose study of SA237, Study JapicCTI-No. 121786; submitted to Clinicaltrials.jp on Mar. 19, 2012; downloaded from clinicaltrials.jp archive on Sep. 5, 2019 as https://www.clinicaltrials.jp/ctiuser/trial/Show.jsp, 5 pages.
Chugai Pharmaceutical, A phase I, multiple-dose study of SA237, Study JapicCTI-No. 121786; submitted to Clinicaltrials.jp on Jun. 19, 2012; downloaded from clinicaltrials.jp archive on Sep. 5, 2019 as https://www.clinicaltrials.jp/ctiuser/trial/Show.jsp, 5 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 1; submitted to ClinicalTrials.gov on Jan. 6, 2014; downloaded from ClinicalTrials.gov archive on Sep. 4, 2019 as https://clinicaltrials.gov/ct2/history/NCT020288847V_1=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT020288847V_2=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep. 4, 2015; downloaded from ClinicalTrials.gov archive on Sep. 4, 2019 as https://clinicaltrials.gov/ct2/history/NCT020288847V_3=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 4; submitted to ClinicalTrials.gov on Dec. 8, 2015; downloaded from ClinicalTrials.gov archive on Sep. 4, 2019 as https://clinicaltrials.gov/ct2/history/NCT020288847V_4=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 1; submitted to ClinicalTrials.gov on Feb. 25, 2014; downloaded from ClinicalTrials.gov archive on Sep. 4, 2019 as https://clinicaltrials.gov/ct2/history/NCT020732797V_1=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov on Jul. 7, 2015; downloaded from ClinicalTrials.gov archive on Sep. 5, 2019 as https://clinicaltrials.gov/ct2/history/NCT020732797V_10=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT020732797V_11=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 12; submitted to ClinicalTrials.gov on Sep. 3, 2015; downloaded from ClinicalTrials.gov archive on Sep. 5, 2019 as https://clinicaltrials.gov/ct2/history/NCT020732797V_12=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 13; submitted to ClinicalTrials.gov on Oct. 5, 2015; downloaded from ClinicalTrials.gov archive on Sep. 5, 2019 as https://clinicaltrials.gov/ct2/history/NCT020732797V_13=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT020732797V_14=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD),

(56) References Cited

OTHER PUBLICATIONS

Study NCT02073279, version 2; submitted to ClinicalTrials.gov on Jul. 22, 2014; downloaded from ClinicalTrials.gov archive on Sep. 5, 2019 as https://clinicaltrials.gov/ct2/history/NCT020732797V_2=View#StudyPageTop, 6 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 3; submitted to ClinicalTrials.gov on Dec. 15, 2014; downloaded from ClinicalTrials.gov archive on Sep. 5, 2019 as https://clinicaltrials.gov/ct2/history/NCT020732797V_3=View#StudyPageTop, 7 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 4; submitted to ClinicalTrials.gov on Feb. 5, 2015; downloaded from ClinicalTrials.gov archive on Sep. 5, 2019 as https://clinicaltrials.gov/ct2/history/NCT020732797V_4=View#StudyPageTop, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 5; submitted to ClinicalTrials.gov on Feb. 6, 2015; downloaded from ClinicalTrials.gov archive on Sep. 5, 2019 as https://clinicaltrials.gov/ct2/history/NCT020732797V_5=View#StudyPageTop, 8 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT020732797V_6=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT020732797V_7=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT020732797V_8=View#StudyPageTop, 9 pages.

Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 9; submitted to ClinicalTrials.gov on Jun. 5, 2015; downloaded from ClinicalTrials.gov archive on Sep. 5, 2019 as https://clinicaltrials.gov/ct2/history/NCT020732797V_9=View#StudyPageTop, 9 pages.

Clackson et al., "Making antibody fragments using phage display libraries," Nature, Aug. 15, 1991, 352(6336):624-8.

Clynes et al., "Fc receptors are required in passive and active immunity to melanoma," Proc Natl Acad Sci USA, Jan. 20, 1998, 95(2):652-6.

Cragg et al., "Complement-mediated lysis by anti-CD20 mAb correlates with segregation into lipid rafts," Blood, Feb. 1, 2003, 101(3):1045-52. Epub Sep. 19, 2002.

Cragg et al., "Antibody specific controls in vivo effector mechanisms of anti-CD reagents," Blood, Apr. 1, 2004, 103(7):2738-43, Epub Oct. 9, 2003.

Daeron et al., "Fc Receptor Biology," Annu Rev Immunol, Apr. 1997, 15:203-34.

Deng et al., "Pharmacokinetics of Humanized Monoclonal Anti-Tumor Necrosis Factor-α Antibody and Its Neonatal Fc Receptor Variants in Mice and Cynomolgus Monkeys," Drug Metab Dispos, Apr. 2010, 38(4):600-5, doi: 10.1124/dmd.109.031310. Epub Jan. 13, 2010.

Dubowchik et al., "Doxorubicin Immunoconjugates Containing Bivalent, Lysosomally-Cleavable Dipeptide Linkages," Bioorg Med Chem Lett, Jun. 3, 2002, 12(11):1529-32.

Duncan et al., "The binding site for C1q and IgG," Nature, Apr. 21, 1988, 332(6166):738-40.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Germany; submitted to clinicaltrialsregister.eu on Dec. 20, 2013; downloaded from clinicaltrialsregister.eu archive on Sep. 5, 2019 as https://www.clinicaltrialsregister.eu/ctrsearch/trial/2013-003752-21/DE, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 as https://www.clinicaltrialsregister.eu/ctrsearch/trial/2013-003752-21/HU, 6 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from clinicaltrialsregister.eu archive on Sep. 5, 2019 as https://www.clinicaltrialsregister.eu/ctrsearch/trial/2013-003752-21/IT, 5 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Oct. 15, 2013; downloaded from clinicaltrialsregister.eu archive on Sep. 5, 2019 as https://www.clinicaltrialsregister.eu/ctrsearch/trial/2013-003752-21/PL, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltrialsregister.eu archive on Sep. 5, 2019 as https://www.clinicaltrialsregister.eu/ctrsearch/trial/2013-003752-21/ES, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 as https://www.clinicaltrialsregister.eu/ctrsearch/trial/2013-003752-21/GB, 6 pages.

F. Hoffmann-La Roche Ltd., A Multicenter, Randomized, Double-blind, Placebo controlled, Phase 3 Study to Evaluate the Efficacy and Safety of Satralizumab (SA237) as Monotherapy in Patients With Neuromyelitis Optica (NMO) and Neuromyelitis Optica Spectrum Disorder(NMOSD), Study EudraCT 2015-005431-41 in Croatia; submitted to clinicaltrialsregister.eu on Dec. 15, 2016; downloaded from clinicaltrialsregister.eu archive on Sep. 5, 2019 as https://www.clinicaltrialsregister.eu/ctr-search/triaF2015-005431-41/HR, 6 pages.

F. Hoffmann-La Roche Ltd., A Multicenter, Randomized, Double-blind, Placebo controlled, Phase 3 Study to Evaluate the Efficacy and Safety of Satralizumab (SA237) as Monotherapy in Patients With Neuromyelitis Optica (NMO) and Neuromyelitis Optica Spectrum Disorder(NMOSD), Study EudraCT 2015-005431-41 in Poland; submitted to clinicaltrialsregister.eu on Apr. 7, 2016; downloaded

(56) References Cited

OTHER PUBLICATIONS from clinicaltrialsregister.eu archive on Sep. 5, 2019 as https://www.clinicaltrialsregister.eu/ctrsearch/trial/2015-005431-41/PL, 6 pages.
Fellouse et al., "Synthetic antibodies from a four-amino-acid code: A dominant role for tyrosine in antigen recognition," Proc Natl Acad Sci USA, Aug. 24, 2004, 101(34):12467-72. Epub Aug. 11, 2004.
Flatman et al., "Process analytics for purification of monoclonal antibodies," J Chromatogr B Analyt Technol Biomed Life Sci, Mar. 15, 2007, 848(1):79-87, Epub Dec. 11, 2006.
Gazzano-Santoro et al., "A non-radioactive complement-dependent cytotoxicity assay for anti-CD20 monoclonal antibody," J Immunol Methods, Mar. 28, 1997, 202(2):163-71.
Gerngross et al., "Advances in the production of human therapeutic proteins in yeasts and filamentous fungi," Nat Biotechnol, Nov. 2004, 22(11): 1409-14.
Graham et al., "Characteristics of a Human Cell Line Transformed by DNA from Human Adenovirus Type 5," J Gen Virol, Jul. 1977, 36(1):59-74.
Griffiths et al., Human anti-self antibodies with high specificity from phage display libraries, EMBO J, Feb. 1993, 12(2):725-34.
Gruber et al., "Efficient Tumor Cell Lysis Mediated by a Bispecific Single Chain Antibody in *Escherichia coli*" J Immunol, Jun. 1, 1994, 152(11):5368-74.
Guyer et al., "Immunoglobulin Binding by Mouse Intestinal Epithelial Cell Receptors," J Immunol, Aug. 1976, 117(2):587-93.
Haas et al., "Fcy receptors of phagocytes," J Lab Clin Med, Oct. 1995, 126(4):330-41.
Hashimoto-Gotoh et al., "An oligodeoxyribonucleotide-directed dual amber method for site-directed mutagenesis," Gene, Jan. 23, 1995, 152(2):271-5.
Hellstrom et al., "Antitumor effects of L6, an IgG2a antibody that reacts with most human carcinomas," Proc Natl Acad Sci USA, Sep. 1986, 83(18):7059-63.
Hellstrom et al., "Strong antitumor activities of IgG3 antibodies to a human melanoma-associated ganglioside," Proc Natl Acad Sci USA, Mar. 1985, 82(5):1499-502.
Hinman et al., "Preparation and Characterization of Monoclonal Antibody Conjugates of the Calicheamicins: A Novel and Potent Family of Antitumor Antibiotics," Cancer Res, Jul. 15, 1993, 53(14):3336-42.
Holliger et al., "'Diabodies': Small bivalent and bispecific antibody fragments," Prop Natl Acad Sci USA, Jul. 15, 1993, 90(14):6444-8.
Hoogenboom, "Overview of Antibody Phage-Display Technology and Its Applications," Methods in Molecular Biology, O'Brien et al., eds., Human Press, 2001, 178:1-37.
Hoogenboom et al., "By-passing Immunisation Human Antibodies from Synthetic Repertoires of Germline $V_H$ Gene Segments Rearranged in Vitro," J Mol Biol, Sep. 20, 1992, 227(2):381-8.
Hudson et al., "Engineered antibodies," Nat Med, Jan. 2003, 9(1):429-34.
Idusogie et al., "Mapping of the C1q Binding Site on Rituxan, a Chimeric Antibody with a Human IgG1 Fc," J Immunol, Apr. 15, 2000, 164(8):4178-84.
Igawa et al., "pH-dependent antigen-binding antibodies as a novel therapeutic modality," Biochim Biophys Acta, Nov. 2014, 1844(11):1943-1950. doi: 10.1016/j.bbapap.2014.08.003. Epub Aug. 12, 2014.
Jeffrey et al., "Dipeptide-based highly potent doxorubicin antibody conjugates," Bioorg Med Chem Lett, Jan. 15, 2006, 16(2):358-62, Epub Nov. 3, 2005.
Kam et al., "Carbon nanotubes as multifunctional biological transporters and near-infrared agents for selective cancer cell destruction," Proc Natl Acad Sci USA, Aug. 16, 2005, 102(33):11600-5. Epub Aug. 8, 2005.
Kanda et al., "Comparison of Cell Lines for Stable Production of Fucose-Negative Antibodies With Enhanced ADCC," Biotechnol Bioeng, Jul. 5, 2006, 94(4):680-8.
Kashmiri et al., "SDR grafting—a new approach to antibody humanization," Methods, May 2005, 36(1):25-34.

King et al., "Monoclonal Antibody Conjugates of Doxorubicin Prepared with Branched Peptide Linkers: Inhibition of Aggregation by Methoxytriethyleneglycol Chains," J Med Chem, Sep. 12, 2002, 45(19):4336-43.
Kohler et al., "Continuous cultures of fused cells secreting antibody of predefined specificity," Nature, Aug. 7, 1975, 256(5517):495-7.
Kono et al., "FcγRIIB Ile232Thr transmembrane polymorphism associated with human systemic lupus erythematosus decreases affinity to lipid rafts and attenuates inhibitory effects on B cell receptor signaling," Hum Mol Genet, Oct. 1, 2005, 14(19):2881-92, Epub Aug. 22, 2005.
Kostelny et al., "Formation of a bispecific antibody by the use of leucine zippers," J Immunol, Mar. 1, 1992, 148(5):1547-53.
Kozbor, "A human hybrid myeloma for production of human monoclonal antibodies," J Immunol, Dec. 1984, 133(6):3001-5.
Kramer et al., "The gapped duplex DNA approah to oligonudeotde-directed mutation construction," Nucleic Acids Res, Dec. 21, 1984, 12(24):9441-56.
Kramer et al., "Oligonucleotide-Directed Construction of Mutations via Gapped Duplex DNA," Methods Enzymol, 1987, 154:350-67.
Kratz et al., "Prodrugs of Anthracyclines in Cancer Chemotherapy," Curr Med Chem, 2006, 13(5):477-523.
Kunkel et al., "Rapid and efficient site-specific mutagenesis without phenotypic selection," Proc Natl Acad Sci USA, Jan. 1985, 82(2):488-92.
Kyogoju et al., "Fcγ Receptor Gene Polymorphisms in Japanese Patients With Systemic Lupus Eiythematosus," Arthritis Rheum, May 2002, 46(5):1242-54.
Labrun et al., "Therapeutic IgG4 antibodies engage in Fab-arm exchange with endogenous human IgG4 in vivo" Nat Biotechnol, Aug. 2009, 27, 767-771.
Lazar et al., "Engineered antibody Fc variants with enhanced effector function," Proc Natl Acad Sci USA, Mar. 14, 2006, 103(11):4005-10. Epub Mar. 6, 2006.
Lee et al., "High-affinity Human Antibodies from Phage-displayed Synthetic Fab Libraries with a Single Framework Scaffold," J Mol Biol, Jul. 23, 2004, 340(5):1073-93.
Lee et al., "Bivalent antibody phage display mimics natural immunoglobulin," J Immunol Methods, Jan. 2004, 284(1-2):119-32.
Li et al., "Optimization of humanized IgGs in glycoengineered *Pichia pastoris*," Nat Biotechnol, Feb. 2006, 24(2):210-5. Epub Jan. 22, 2006.
Li et al., "Human antibodies for immunotherapy development generated via a human B cell hybridoma technology," Proc Natl Acad Sci USA, Mar. 7, 2006, 103(10):3557-62, Epub Feb. 27, 2006.
Li et al., "A Novel Polymorphism in the Fcγ Receptor Iib (CD32B) Transmembrane Region Alters Receptor Signaling," Arthritis Rheum, Nov. 2003, 48(11):3242-52.
Lode et al., "Targeted Therapy with a Novel Enediyene Antibiotic Calicheamicin $\phi_1^I$ Effectively Suppresses Growth and Dissemination of Liver Metastases in a Syngeneic Model of Murine Neuroblastoma," Cancer Res, Jul. 15, 1998, 58(14):2925-8.
Lonberg, "Fully human antibodies from transgenic mouse and phage display platforms," Curr Opin Immunol, Aug. 2008, 20(4):450-9, doi: 10.1016/j.coi.2008.06.004. Epub Jul. 21, 2008.
Lonberg, "Human antibodies from transgenic animals," Nat Biotechnol, Sep. 2005, 23(9):1117-25.
Lund et al., "Multiple Interactions of IgG with Its Core Oligosaccharide Can Modulate Recognition by Complement and Human Fcγ Receptor I and Influence the Synthesis of Its Oligosaccharide Chains," The Journal of Immunology, Dec. 1, 1996, 157:4963-4969.
Marks et al., "Bi-passing Immunization—Human Antibodies from V-gene Libraries Displayed on Phage," J Mol Biol, Dec. 5, 1991, 222(3):581-97.
Marks et al., "Selection of Human Antibodies from Phage Display Libraries," Methods Mol Biol, 2004, 248:161-76.
Mather et al., "Establishment and Characterization of Two Distinct Mouse Testicular Epithelial Cell Lines," Biol Reprod, Aug. 1980, 23(1):243-52.
Mather et al., "Culture of Testicular Cells in Hormone-Supplemented Serum-Free Medium," Ann NY Acad Sci, Jun. 1982, 383:44-68.

(56) References Cited

OTHER PUBLICATIONS

McCafferty et al., "Phage antibodies: filamentous phage displaying antibody variable domains," Nature, Dec. 6, 1990, 348(6301):552-4.
Milstein et al., "Hybrid hybridomas and their use in immunohistochemistry," Nature, Oct. 6-12, 1983, 305(5934):537-40.
Morrison et al., "Chimeric human antibody molecules: Mouse antigen-binding domains with human constant region domains," Proc Natl Acad Sci USA, Nov. 1984, 81(21):6851-5.
Munson et al., "LIGAND: A Versatile Computerized Approach for Characterization of Ligand-Binding Systems," AnalBiochem, Sep. 1, 1980, 107(1):220-39.
Nagy et al., "Stability of cytotoxic luteinizing hormone-releasing hormone conjugate (AN-152) containing doxorubicin 14-O-hemiglutarate in mouse and human serum in vitro: Implications for the design of preclinical studies," Proc Natl Acad Sci USA, Jan. 18, 2000, 97(2):829-34.
Okazaki et al., "Fucose Depletion from Human IgG1 Oligosaccharide Enhances Binding Enthalpy and Association Rate Between IgG1 and FcγRIIIa," J Mol Biol, Mar. 5, 2004, 336(5):1239-49.
Ory et al., "Sequences of Complementary DNAs That Encode the NA1 and NA2 Forms of Fc Receptor III on Human Neutrophils," J Clin Invest, Nov. 1989, 84(5):1688-91.
Osbourn et al., "From rodent reagents to human therapeutics using antibody guided selection," Methods, May 2005, 36(1):61-8.
Pace et al., "How to measure and predict the molar absorption coefficient of a protein," Protein Sci, Nov. 1995, 4(11):2411-23.
Padlan, "A Possible Procedure for Reducing the Immunogenicity of Antibody Variable Domains While Preserving Their Ligand-Binding Properties," Mol Immunol, Apr.-May 1991, 28(4-5):489-98.
Portolano et al., "Lack of Promiscuity in Autoantigen-Specific H and L Chain Combinations as Revealed by Human H and L Chain 'Roulette'," J Immunol, Feb. 1, 1993, 150(3):880-7.
Presta et al., "Humanization of an Anti-Vascular Endothelial Growth Factor Monoclonal Antibody for the Therapy of Solid Tumors and Other Disorders," Cancer Res, Oct. 15, 1997; 57(20):4593-9.
Presta et al., "Humanization of an antibody directed against IgE," J Immunol, Sep. 1, 1993, 151(5):2623-32.
Ravetch et al., "Fc Receptors," Annu Rev Immunol, 1991, 9:457-92.
Riechmann et al., "Reshaping human antibodies for therapy," Nature, Mar. 24, 1988, 332(6162):323-7.
Ripka et al., "Two Chinese Hamster Ovary Glycosylation Mutants Affected in the Conversion of GDP-Mannose to GDP-Fucose," Arch Biochem Biophys, Sep. 1986, 249(2):533-45.
Pluckthun, Chapter 11 "Antibodies from *Escherichia coli*," The Pharmacology of Monoclonal Antibodies, M. Rosenberg et al. (eds.), Springer-Verlag Berlin Heidelberg, 1994, 113:269-315.
Rosok et al., "A Combinatorial Library Strategy for the Rapid Humanization of Anticarcinoma BR96 Fab," J Biol Chem, Sep. 13, 1996, 271(37):22611-8.
Sidhu et al., "Phage-displayed Antibody Libraries of Synthetic Heavy Chain Complementarity Determining Regions," J Mol Biol, Apr. 23, 2004, 338(2):299-310.
Story et al., "A Major Histocompatibility Complex Class I-like Fc Receptor Cloned from Human Placenta: Possible Role in Transfer of Immunoglobulin G from Mother to Fetus," J Exp Med, Dec. 1, 1994, 180(6):2377-81.
Strausberg et al., "Generation and initial analysis of more than 15,000 full-length human and mouse cDNA sequences," Proc Natl Acad Sci USA, Dec. 24, 2002, 99(26):16899-903. Epub Dec. 11, 2002.
Tan et al., "A Non Mouse-Adapted Dengue Virus Strain as a New Model of Severe Dengue Infection in AG129 Mice," PLoS Negl Trop Dis, Apr. 27, 2010, 4(4):e672. doi: 10.1371/journal.pntd.0000672.
Tan, Review of "Current Protocols in Immunology," eds. Coligan et al., 1991, 1 page.
Torgov et al., "Generation of an Intensely Potent Anthracycline by a Monoclonal Antibody 3-Galactosidase Conjugate," Bioconjug Chem, May-Jun. 2005, 16(3):717-21.
Traunecker et a., "Bispecific single chain molecules (Janusins) target cytotoxic lymphcytes on HIV infected cells," EMBO J, Dec. 1991, 10(12):3655-9.
Tutt et al. "Trispecific F(ab')3 derivatives that use cooperative signaling via the TCR/CD3 complex and CD2 to activate and redirect resting cytotoxic T cells," J Immunol, Jul. 1, 1991, 147(1):60-9.
Urlaub et al., "Isolation of Chinese hamster cell mutants deficient in dihydrofolate reductase activity," Proc Natl Acad Sci USA, Jul. 1980, 77(7):4216-20.
Van Dijk et al., "Human antibodies as next generation therapeutics," Curr Opin Chem Biol, Aug. 2001, 5(4):368-74.
Vitetta et al., "Redesigning Nature's Poisons to Create Anti-Tumor Reagents," Science, Nov. 20, 1987, 238(4830):1098-104.
Vollmers et al., "The 'early birds': natural IgM antibodies and immune surveillance," Histol Histopathol, Jul. 2005, 20(3):927-37, doi: 10.14670/HH-20.927.
Vollmers et al., "Deathby Stress: Natural IgM-Induced Apoptosis," Methods Find Exp Clin Pharmacol, Apr. 2005, 27(3):185-91.
Warmerdam et al., "Molecular Basis for a Polymorphism of Human Fcγ Receptor II (CD32)," J Exp Med, Jul. 1, 1990, 172(1):19-25.
Winter et al., "Making Antibodies by Phage Display Technology," Annu Rev Immunol, Apr. 1994, 12:433-55.
Wright et al., "Effect of glycosylation on antibody function: implications for genetic engineering," Trends Biotechnol, Jan. 1997, 15(1):26-32.
Wu et al., "A novel polymorphism of FcgammaRIIIa (CD 16) alters receptor function and predisposes to autoimmune disease," J Clin Invest, Sep. 1, 1997, 100(5):1059-70.
Yamane-Ohnuki et al., "Establishment of *FUT8* Knockout Chinese Hamster Ovary Cells: An Ideal Host Cell Line for Producing Completely Defucosylated Antibodies With Enhanced Antibody-Dependent Cellular Cytotoxicity," Biotechnol Bioeng, Sep. 5, 2004, 87(5):614-22.
Yazaki et al., "Expression of Recombinant Antibodies in Mammalian Cell Lines," Methods Mol Biol, 2004, 248:255-68.
Zalevsky et al., "Enhanced antibody half-life improves in vivo activity," Nat Biotechnol, Feb. 2010, 28(2)457-9. Epub Jan. 17, 2010.
Zheng et al., "Translational Pharmacokinetics and Pharmacodynamics of an FcRn-Variant Anti-CD4 Monoclonal Antibody From Preclinical Model to Phase I Study," Clin Pharmacol Ther, Feb. 2011, 89(2):283-90, doi: 10.1038/clpt.2010.31L Epub Dec. 29, 2010.
Zola, Chapter 6 "Using Monoclonal Antibodies: Soluble Antigens," Monoclonal Antibodies: A Manual of Techniques, 1987, pp. 147-158.
Zoller, "Oligonucleotide-Directed Mutagenesis of DNA Fragments Cloned into M13 Vectors," Methods Enzymol, 1983, 100:468-500.
Zust et al., "Type I Interferon Signals in Macrophages and Dendritic Cells Control Dengue Virus Infection: Implications for a New Mouse Model To Test Dengue Vaccines," J Virol, Jul. 2014, 88(13):7276-85. doi: 10.1128/JVI.03827-13. Epub Apr. 16, 2014.
U.S. Appl. No. 16/83 8,415, Igawa et al., filed Apr. 2, 2020.
U.S. Appl. No. 16/298,032, Igawa et al., filed Mar. 11, 2019.
U.S. Appl. No. 16/448,088, Igawa et al., filed June 21, 2019 (abandoned)
U.S. Appl. No. 17/076,938, Igawa et al., filed Oct. 22, 2020.
U.S. Appl. No. 15/024,063, Igawa et al., filed Mar. 23, 2016.
U.S. Appl. No. 15/562,186, Igawa et al., filed Sep. 27, 2017.
U.S. Appl. No. 15/782,256, Igawa et al., filed Oct. 12, 2107.
U.S. Appl. No. 12/295,039, Igawa et al., filed Jan. 20, 2009.
U.S. Appl. No. 16/983,115, filed Aug. 3, 2020, Kakehi et al.
U.S. Appl. No. 17/076,938, filed Oct. 22, 2020, Igawa et al.
U.S. Appl. No. 17/097,298, filed Nov. 13, 2020, Igawa et al.
Adlersberg et al., "The Immunoglobulin Hinge (Interdomain) Region," Ric Clin Lab, Jul.-Sep. 1976, 6(3):191-205.

(56) References Cited

OTHER PUBLICATIONS

Chattopadhyay et al., "Interleukin-31 and Oncostatin-M Mediate Distinct Signaling Reactions and Response Patterns in Lung Epithelial Cells," J Biol Chem, Feb. 2, 2007, 282(5):3014-3026, doi:10.1074/jbc.M609655200.
Dall'Acqua et al., "Contribution of Domain Interface Residues to the Stability of Antibody $C_H3$ Domain Homodimers," Biochemistry, Jun. 30, 1998, 37(26):9266-9273. doi: 10.1021/bi980270i PMID: 9649307.
Declaration of Christian Beil, signed Jun. 18, 2020, submitted by the opponent in Opposition of EP 3 050 963, 6 pages.
Helguera et al., "Antibody-Cytokine Fusion Proteins for the Therapy of Cancer," Methods Mol Med, 2005, 109:347-374. doi: 10.1385/1-59259-862-5:347. PMID: 15585931.
Hugo et al., "Functional aspects of co-variant surface charges in an antibody fragment," Protein Sci, Nov. 2002, 11(11):2697-2705. doi: 10.1110/ps.0209302. PMID: 12381851; PMCID: PMC2373727.
Otomo et al., "Structure of the heterodimeric complex between CAD domains of CAD and ICAD," Nat Struct Biol, Aug. 2000, 7(8):658-662, doi: 10.1038/77957. PMID: 10932250.
Raghavan et al., "Fc Receptors and Their Interactions with Immunoglobulins," Annu Rev Cell Dev Biol, Nov. 1996, 12:181-220.
Reference table: IMGT exon, EU and Kabat numbering of residues within the human IgG1 sequence; retrieved from http://www.imgt.org/IMGTScientificChart/Numbering/Hu_IGHGnber.html on Jun. 1, 2020, 4 pages (cited by the opponents in an Opposition procedure in European Patent No. 3 050 963).
Vincent et al., "Current strategies in antibody engineering: Fc engineering and pH-dependent antigen binding, bispecific antibodies and antibody drug conjugates," Biotechnol J, Nov. 1, 2012, 7(12):1444-1450. doi: 10.1002/biot.201200250.
Wenig et al., "Structure of the streptococcal endopeptidase IdeS, a cysteine proteinase with strict specificity for IgG," Proc Nat Acad Sci USA, Oct. 28, 2004, 101:17371-17376.
USPTO Non-Final Office Action in U.S. Appl. No. 11/910,128, dated Nov. 28, 2016, 17 pages.
Aalberse et al., "IgG4 breaking the rules," Immunology, Jan. 2002, 105(1):9-19.
U.S. Appl. No. 13/524,528, Igawa et al., filed Jun. 15, 2012 (abandoned).
U.S. Appl. No. 16/838,415, Igawa et al., filed Apr. 2, 2020 (abandoned).
U.S. Appl. No. 17/509,128, Igawa et al., filed Oct. 25, 2021.
U.S. Appl. No. 12/680,112, Igawa et al., filed Jun. 23, 2010 (abandoned).
U.S. Appl. No. 13/959,489, Igawa et al., filed Aug. 5, 2013 (abandoned).
U.S. Appl. No. 15/263,617, Igawa et al., filed Sep. 13, 2016 (abandoned).
U.S. Appl. No. 16/041,976, Igawa et al., filed Jul. 23, 2018 (abandoned).
U.S. Appl. No. 17/097,298, Igawa et al., filed Nov. 13, 2020.
U.S. Appl. No. 12/745,781, Kuramochi et al., filed Sep. 13, 2010 (abandoned).
U.S. Appl. No. 14/340,883, Kuramochi et al., filed Jul. 25, 2014 (abandoned).
U.S. Appl. No. 16/560,143, Kuramochi et al., filed Sep. 4, 2019.
U.S. Appl. No. 13/257,145, Igawa et al., filed Nov. 22, 2011 (abandoned).
USSN 16/298,03 2, Igawa et al., filed Mar. 11, 2019 (abandoned).
U.S. Appl. No. 17/530,542, Igawa et al., filed Nov. 19, 2021.
U.S. Appl. No. 13/518,861, Igawa et al., filed Oct. 4, 2012 (abandoned).
U.S. Appl. No. 15/617,008, Igawa et al., filed Jun. 8, 2017 (abandoned).
U.S. Appl. No. 15/875,847, Igawa et al., filed Jan. 19, 2018 (abandoned).
U.S. Appl. No. 16/155,673, Igawa et al., filed Oct. 9, 2018 (abandoned).
U.S. Appl. No. 16/448,088, Igawa et al., filed Jun. 21, 2019 (abandoned).
U.S. Appl. No. 16/815,089, Igawa et al., filed Mar. 11, 2020 (abandoned).
U.S. Appl. No. 17/076,938, Igawa et al., filed Oct. 22, 2020 (abandoned).
U.S. Appl. No. 17/336,538, Igawa et al., filed Jun. 2, 2021.
U.S. Appl. No. 17/483,898, Igawa et al., filed Sep. 24, 2021.
U.S. Appl. No. 16/983,115, Kakehi et al., filed Aug. 3, 2020.
U.S. Appl. No. 17/520,368, Igawa et al., filed Nov. 5, 2021.
U.S. Appl. No. 17/359,867, Igawa et al., filed Jun. 28, 2021.
U.S. Appl. No. 15/725,692, Igawa et al., filed Oct. 5, 2017.
U.S. Appl. No. 16/061,454, Tanaka et al., filed Jun. 12, 2018.
U.S. Appl. No. 16/980,611, Fink et al., filed Sep. 14, 2020.
U.S. Appl. No. 17/066,092, Sampei et al., filed Oct. 8, 2020.
U.S. Appl. No. 17/336,538, filed Jun. 2, 2021, Igawa et al.
U.S. Appl. No. 17/359,867, filed Jun. 28, 2021, Igawa et al.
U.S. Appl. No. 17/483,898, filed Sep. 24, 2021, Igawa et al.
U.S. Appl. No. 17/509,128, filed Oct. 25, 2021, Igawa et al.
U.S. Appl. No. 17/520,368, filed Nov. 5, 2021, Igawa et al.
U.S. Appl. No. 17/530,542, filed Nov. 19, 2012, Igawa et al.
Annex from opponent 2's submission of Jun. 7, 2018, 13 pages (cited by the opponent during the EPO opposition proceedings of EP 2 202 245 on May 19, 2020).
Antibodies in Example 29 of EP 2 202 245, 2 pages (cited by the opponent during the EPO opposition proceedings of EP 2 202 245 on May 19, 2020).
Barba-Spaeth et al., "Structural basis of potent Zika-dengue virus antibody cross-neutralization," Nature, Aug. 4, 2016, 536(7614):48-53.
Dejnirattisai et al., "Dengue virus sero-cross-reactivity drives antibody-dependent enhancement of infection with zika virus," Nat Immunol, Sep. 2016, 17(9):1102-1108.
Fernandez et al., "Anti-Dengue E-dimer epitope human antibodies have therapeutic activity against Zika virus infection," Nat Immunol, Nov. 2017, 18(11):1261-1269.
Golay et al., "Design and Validation of a Novel Generic Platform for the Production of Tetravalent IgG1-like Bispecific Antibodies," J Immunol, Apr. 1, 2016, 196 (7):3199-3211.
Ho et al., "In vitro antibody evolution targeting germline hot spots to increase activity of an anti-CD22 immunotoxin," J Biol Chem, Jan. 7, 2005, 280(1):607-617. doi: 10.1074/jbc.M409783200. Epub Oct. 18, 2004.
Kam et al., "Cross-reactive dengue human monoclonal antibody prevents severe pathologies and death from Zika virus infections," JCI Insight, Apr. 20, 2017, 2(8):e92428.
Marchalonis et al., "Antigenic mapping of a human lambda light chain: correlation with three dimensional structure," J Protein Chem, Apr. 1992, 11(2):129-137.
Mazor et al., "Improving target cell specificity using a novel monovalent bispecific IgG design," mAbs, Mar./Apr. 2015, 7(2):377-389.
Muller et al., "The first constant domain ($C_H1$ and $C_L$) of an antibody used as heterodimerization domain for bispecific miniantibodies," FEBS Lett, Jan. 30, 1998, 422(2):259-264.
Priyamvada et al., "Human antibody responses after dengue virus infection are highly cross-reactive to Zika virus," Proc Natl Acad Sci USA, Jul. 12, 2016, 113(28):7852-7.
Screenshots of Genetyx software, 3 pages (document cited by opponent during the EPO opposition proceedings of EP 2 202 245 on May 22, 2020).
Screenshots of the web-based calculator, 9 pages (document cited by opponent during the EPO opposition proceedings of EP 2 202 245 on May 22, 2020).
Sections of the Genetyx manual pertaining to isoelectric point, 5 pages (document cited by opponent during the EPO opposition proceedings of EP 2 202 245 on May 22, 2020) (with English translation).
Xu et al., "A potent neutralizing antibody with therapeutic potential against all four serotypes of dengue virus," NPJ Vaccines, Jan. 23, 2017, 2(2), 10 pages.

* cited by examiner

SEQUENCE LISTING

<160> NUMBER OF SEQ ID NOS: 58

<210> SEQ ID NO 1
<211> LENGTH: 330
<212> TYPE: PRT
<213> ORGANISM: Homo sapiens

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 2
<211> LENGTH: 326
<212> TYPE: PRT
<213> ORGANISM: Homo sapiens

```
<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 3
<211> LENGTH: 327
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 4
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 4

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 5
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 5

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95
```

```
Thr Val Glu Arg Lys Ser Cys Val Glu Cys Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro

<210> SEQ ID NO 6
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
```

```
                130                 135                 140
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
                195                 200                 205

Ala Pro Ile Glu Lys Thr Ile Ser Lys Thr Lys Gly Gln Pro Arg Glu
                210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Val Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
                290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 7
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
                130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
```

```
                165                 170                 175
Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro

<210> SEQ ID NO 8
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205
```

```
Ser Ser Ile Glu Lys Thr Ile Ser Lys Ala Lys Gly Gln Pro Arg Glu
            210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 9
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240
```

```
Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Glu Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Leu

<210> SEQ ID NO 10
<211> LENGTH: 329
<212> TYPE: PRT
<213> ORGANISM: Artificial
<220> FEATURE:
<223> OTHER INFORMATION: An artificially synthesized peptide sequence

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270
```

```
Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
        290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

```
<210> SEQ ID NO 11
<211> LENGTH: 327
<212> TYPE: PRT
<213> ORGANISM: Artificial
<220> FEATURE:
<223> OTHER INFORMATION: An artificially synthesized peptide sequence

<400> SEQUENCE: 11
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
        290                 295                 300
```

-continued

Phe Ser Cys Ser Val Met His Glu Ala Leu His Asn His Tyr Thr Gln
305                 310                 315                 320

Lys Ser Leu Ser Leu Ser Pro
            325

<210> SEQ ID NO 12
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 12

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

-continued

```
Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 13
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 13

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
```

```
                    245                 250                 255
Val Thr Cys Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 14
<211> LENGTH: 446
<212> TYPE: PRT
<213> ORGANISM: Artificial
<220> FEATURE:
<223> OTHER INFORMATION: An artificially synthesized peptide sequence

<400> SEQUENCE: 14

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                    165                 170                 175
Gln Ser Ser Gly Leu Tyr Ser Leu Ser Ser Val Thr Val Pro Ser
                180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
        210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 15
<211> LENGTH: 107
<212> TYPE: PRT
<213> ORGANISM: Artificial
<220> FEATURE:
<223> OTHER INFORMATION: An artificially synthesized peptide sequence

<400> SEQUENCE: 15

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
```

Thr Phe Gly Gln Gly Thr Lys Val Glu Ile Glu
             100                 105

<210> SEQ ID NO 16
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 16

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser

```
                340                 345                 350
Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 17
<211> LENGTH: 446
<212> TYPE: PRT
<213> ORGANISM: Artificial
<220> FEATURE:
<223> OTHER INFORMATION: An artificially synthesized peptide sequence

<400> SEQUENCE: 17

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
```

```
                260                 265                 270
Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 18
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 18

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
            180                 185                 190
Ser Asn Phe Gly Thr Gln Thr Tyr Thr Cys Asn Val Asp His Lys Pro
        195                 200                 205
Ser Asn Thr Lys Val Asp Lys Thr Val Glu Arg Lys Ser Cys Val Glu
        210                 215                 220
Cys Pro Pro Cys Pro Ala Pro Pro Val Ala Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Phe Arg Val Val Ser Val Leu
    290                 295                 300
Thr Val Val His Gln Asp Trp Leu Asn Gly Lys Glu Tyr Lys Cys Lys
305                 310                 315                 320
Val Ser Asn Lys Gly Leu Pro Ala Pro Ile Glu Lys Thr Ile Ser Lys
                325                 330                 335
Thr Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Met Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 19
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 19

Gln Val Gln Leu Gln Glu Ser Gly Pro Gly Leu Val Arg Pro Ser Gln
1               5                   10                  15
Thr Leu Ser Leu Thr Cys Thr Val Ser Gly Tyr Ser Ile Thr Ser Asp
            20                  25                  30
His Ala Trp Ser Trp Val Arg Gln Pro Pro Gly Arg Gly Leu Glu Trp
        35                  40                  45
Ile Gly Tyr Ile Ser Tyr Ser Gly Ile Thr Thr Tyr Asn Pro Ser Leu
    50                  55                  60
Lys Ser Arg Val Thr Met Leu Arg Asp Thr Lys Asn Gln Phe Ser
65                  70                  75                  80
Leu Arg Leu Ser Ser Val Thr Ala Ala Asp Thr Ala Val Tyr Tyr Cys
                85                  90                  95
Ala Arg Ser Leu Ala Arg Thr Thr Ala Met Asp Tyr Trp Gly Gln Gly
```

```
                100             105               110
Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Ser Cys Val Glu
        210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
            435                 440

<210> SEQ ID NO 20
<211> LENGTH: 446
<212> TYPE: PRT
<213> ORGANISM: Artificial
<220> FEATURE:
<223> OTHER INFORMATION: An artificially synthesized peptide sequence

<400> SEQUENCE: 20

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
```

-continued

```
                20                  25                  30
His Ala Trp Ser Trp Val Arg Gln Pro Gly Arg Gly Leu Glu Trp
            35                  40                  45
Ile Gly Tyr Ile Ser Tyr Ser Gly Ile Thr Thr Tyr Asn Pro Ser Leu
50                  55                  60
Lys Ser Arg Val Thr Met Leu Arg Asp Thr Ser Lys Asn Gln Phe Ser
65                  70                  75                  80
Leu Arg Leu Ser Ser Val Thr Ala Ala Asp Thr Ala Val Tyr Tyr Cys
                85                  90                  95
Ala Arg Ser Leu Ala Arg Thr Thr Ala Met Asp Tyr Trp Gly Gln Gly
            100                 105                 110
Ser Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
        210                 215                 220
Thr His Thr Cys Pro Pro Cys Pro Ala Pro Pro Val Ala Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro
            435                 440                 445
```

<210> SEQ ID NO 21
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 21

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365
```

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu
            435                 440

<210> SEQ ID NO 22
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 22

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

```
Pro Arg Glu Glu Gln Phe Asn Ser Thr Phe Arg Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro
    435                 440

<210> SEQ ID NO 23
<211> LENGTH: 15
<212> TYPE: PRT
<213> ORGANISM: Artificial
<220> FEATURE:
<223> OTHER INFORMATION: An artificially synthesized peptide sequence

<400> SEQUENCE: 23

Gly Gly Gly Gly Ser Gly Gly Gly Ser Gly Gly Gly Gly Ser
1               5                   10                  15

<210> SEQ ID NO 24
<211> LENGTH: 267
<212> TYPE: PRT
<213> ORGANISM: Homo sapiens

<400> SEQUENCE: 24

Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
                20                  25                  30

Gln Gln Tyr Leu Ser Tyr Asn Ser Leu Arg Gly Glu Ala Glu Pro Cys
                35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
                100                 105                 110

Asn Gly Glu Glu Phe Met Asn Phe Asp Leu Lys Gln Gly Thr Trp Gly
                115                 120                 125

Gly Asp Trp Pro Glu Ala Leu Ala Ile Ser Gln Arg Trp Gln Gln Gln
    130                 135                 140
```

```
Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
            165                 170                 175

Lys Glu Pro Pro Ser Met Arg Leu Lys Ala Arg Pro Ser Ser Pro Gly
        180                 185                 190

Phe Ser Val Leu Thr Cys Ser Ala Phe Ser Phe Tyr Pro Pro Glu Leu
    195                 200                 205

Gln Leu Arg Phe Leu Arg Asn Gly Leu Ala Ala Gly Thr Gly Gln Gly
    210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
            245                 250                 255

Ala Gly Leu Ala Gln Pro Leu Arg Val Glu Leu
            260                 265
```

<210> SEQ ID NO 25
<211> LENGTH: 99
<212> TYPE: PRT
<213> ORGANISM: Homo sapiens

<400> SEQUENCE: 25

```
Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met
```

<210> SEQ ID NO 26
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 26

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95
```

```
Ala Arg Ser Leu Ala Arg Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 27
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 27

Gln Val Gln Leu Gln Glu Ser Gly Pro Gly Leu Val Arg Pro Ser Gln
1               5                   10                  15
```

```
Thr Leu Ser Leu Thr Cys Thr Val Ser Gly Tyr Ser Ile Thr Ser Asp
            20                  25                  30

His Ala Trp Ser Trp Val Arg Gln Pro Gly Arg Gly Leu Glu Trp
            35                  40                  45

Ile Gly Tyr Ile Ser Tyr Ser Gly Ile Thr Thr Tyr Asn Pro Ser Leu
 50                  55                  60

Lys Ser Arg Val Thr Met Leu Arg Asp Thr Ser Lys Asn Gln Phe Ser
 65                  70                  75                  80

Leu Arg Leu Ser Ser Val Thr Ala Ala Asp Thr Ala Val Tyr Tyr Cys
            85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
 130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
 210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
 290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430
```

```
Ala Leu His Ala His Tyr Thr Gln Lys Ser Leu Ser Leu Ser Pro Gly
            435                 440                 445

Lys

<210> SEQ ID NO 28
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 28

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
```

```
                    340                 345                 350
Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
        435                 440

<210> SEQ ID NO 29
<211> LENGTH: 119
<212> TYPE: PRT
<213> ORGANISM: Mus musculus

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Gln Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ala Arg Ala Thr Ala Met Asp Tyr Trp Gly Gln Gly
            100                 105                 110

Ile Leu Val Thr Val Ser Ser
        115

<210> SEQ ID NO 30
<211> LENGTH: 107
<212> TYPE: PRT
<213> ORGANISM: Mus musculus

<400> SEQUENCE: 30

Asp Ile Gln Met Thr Gln Ser Pro Ser Ser Leu Ser Ala Ser Val Gly
1               5                   10                  15

Asp Ser Val Thr Ile Thr Cys Gln Ala Ser Glu Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu Glu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu
```

-continued

<210> SEQ ID NO 31
<211> LENGTH: 120
<212> TYPE: PRT
<213> ORGANISM: Mus musculus

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Ile Met Asn Trp Val Arg Gln Ala Pro Gly Gln Gly Leu Glu Trp Met
            35                  40                  45

Gly Leu Ile Asn Pro Tyr Asn Gly Gly Thr Ser Tyr Asn Gln Lys Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
                100                 105                 110

Gln Gly Thr Leu Val Thr Val Ser
            115                 120

<210> SEQ ID NO 32
<211> LENGTH: 107
<212> TYPE: PRT
<213> ORGANISM: Mus musculus

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Phe
                20                  25                  30

Leu Ala Trp Tyr Gln Gln Lys Pro Gly Lys Ala Pro Lys Leu Leu Ile
            35                  40                  45

Tyr Asn Ala Lys Thr Leu Ala Lys Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys
            100                 105

<210> SEQ ID NO 33
<211> LENGTH: 122
<212> TYPE: PRT
<213> ORGANISM: Mus musculus

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

```
Ser Gly Ile Thr Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
                100                 105                 110

Gly Gln Gly Thr Leu Val Thr Val Ser Ser
            115                 120

<210> SEQ ID NO 34
<211> LENGTH: 108
<212> TYPE: PRT
<213> ORGANISM: Mus musculus

<400> SEQUENCE: 34

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Gly Arg
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Arg Thr Phe Gly Gln Gly Thr Lys Val Glu Ile Lys
                100                 105

<210> SEQ ID NO 35
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125
```

```
Thr Leu Met Ile Ser Arg Thr Pro Glu Val Thr Cys Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro

<210> SEQ ID NO 36
<211> LENGTH: 330
<212> TYPE: PRT
<213> ORGANISM: Artificial
<220> FEATURE:
<223> OTHER INFORMATION: An artificially synthesized peptide sequence

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                        165                 170                 175
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Ala His Tyr Thr
305                 310                 315                 320

Gln Lys Ser Leu Ser Leu Ser Pro Gly Lys
                325                 330

<210> SEQ ID NO 37
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
```

```
                 195                 200                 205
Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
            290                 295                 300

Ser Val Met His Glu Ala Leu His Ala His Tyr Thr Gln Lys Ser Leu
305                 310                 315                 320

Ser Leu Ser Pro

<210> SEQ ID NO 38
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 38

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240
```

```
Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 39
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 39

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270
```

```
Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 40
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 40

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300
```

Ser Val Met His Glu Ala Leu His Asn His Tyr Thr Gln Lys Ser Leu
305                 310                 315                 320

Ser Leu Ser Pro Gly Lys
                325

<210> SEQ ID NO 41
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 41

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

```
Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 42
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 42

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Ser Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255
```

```
Val Thr Cys Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 43
<211> LENGTH: 328
<212> TYPE: PRT
<213> ORGANISM: Artificial
<220> FEATURE:
<223> OTHER INFORMATION: An artificially synthesized peptide sequence

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Ala His Tyr Thr
305                 310                 315                 320

Gln Lys Ser Leu Ser Leu Ser Pro
                325

<210> SEQ ID NO 44
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

His Ala Val Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Thr Leu
    50                  55                  60

Gln Asp Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ala Arg Ala Thr Ala Met Asp Val Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

```
Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Ala His Tyr Thr Gln Lys Ser Leu Ser Leu Ser Pro
        435                 440                 445

<210> SEQ ID NO 45
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 45

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu Glu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 46
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 46

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270
```

```
Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
            420                 425                 430

His Tyr Thr Gln Lys Ser Leu Ser Leu Ser Pro
            435                 440

<210> SEQ ID NO 47
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 47

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 48
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 48

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Thr Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

```
Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Ala
                420                 425                 430

His Tyr Thr Gln Lys Ser Leu Ser Leu Ser Pro
                435                 440
```

<210> SEQ ID NO 49
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 49

```
Asp Ile Gln Met Thr Gln Ser Pro Ser Ser Leu Ser Ala Ser Val Gly
1               5                   10                  15

Asp Ser Val Thr Ile Thr Cys Gln Ala Ser Arg Asp Ile Ser Ser His
            20                  25                  30

Leu Asn Trp Tyr Gln Gln Lys Pro Gly Lys Ala Pro Glu Leu Leu Ile
            35                  40                  45

Tyr Tyr Gly Ser His Leu Leu Ser Gly Val Pro Ser Arg Phe Ser Gly
        50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 50
<211> LENGTH: 445
<212> TYPE: PRT
<213> ORGANISM: Artificial

<220> FEATURE:
<223> OTHER INFORMATION: An artificially synthesized peptide sequence

<400> SEQUENCE: 50

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400
```

```
Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 51
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 51

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Ser Cys Val Glu
        210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320
```

-continued

```
Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
            435                 440
```

<210> SEQ ID NO 52
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 52

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Val Ala Gly Pro Ser Val Phe Leu
225                 230                 235                 240
```

```
Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Gln
        260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
        290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 53
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 53

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 54
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

```
Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
           100                 105                 110

Pro Val Ala Gly Pro Ser Val Phe Leu Phe Pro Pro Lys Pro Lys Asp
           115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
               165                 170                 175

Ser Thr Phe Arg Val Val Ser Val Leu Thr Val Val His Gln Asp Trp
           180                 185                 190

Leu Asn Gly Lys Glu Tyr Lys Cys Lys Val Ser Asn Lys Gly Leu Pro
           195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
               245                 250                 255

Ala Val Glu Trp Glu Ser Asn Gly Gln Pro Glu Asn Asn Tyr Lys Thr
           260                 265                 270

Thr Pro Pro Met Leu Asp Ser Asp Gly Ser Phe Phe Leu Tyr Ser Lys
           275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 55
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
               20                  25                  30

Phe Pro Glu Pro Val Thr Val Ser Trp Asn Ser Gly Ala Leu Thr Ser
           35                  40                  45

Gly Val His Thr Phe Pro Ala Val Leu Gln Ser Ser Gly Leu Tyr Ser
       50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
           100                 105                 110
```

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro

<210> SEQ ID NO 56
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 57
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

```
Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro

<210> SEQ ID NO 58
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 58

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

```
                   210                 215                 220
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Ala His Tyr Thr Gln Lys Ser Leu Ser Leu Ser Pro
            435                 440                 445
```

MODIFIED ANTIBODY CONSTANT REGION

CROSS-REFERENCE TO RELATED APPLICATIONS

This application is a divisional of U.S. application Ser. No. 12/680,082, having a 371(c) date of Jun. 25, 2010, which is the National Stage of International Application Serial No. PCT/JP2008/067483, filed on Sep. 26, 2008, which claims priority to Japanese Application Serial No. 2007-250147, filed on Sep. 26, 2007. The contents of the applications referenced above are hereby incorporated by reference in their entireties in this application.

TECHNICAL FIELD

The present invention relates to antibody constant regions that have improved physicochemical properties (stability and homogeneity), immunogenicity (antigenicity), and safety, and/or half-life in plasma; and antibodies comprising the constant regions.

BACKGROUND ART

Antibodies are drawing attention as pharmaceuticals as they are highly stable in plasma (blood) and have few adverse effects. Of them, a number of IgG-type antibody pharmaceuticals are available on the market and many antibody pharmaceuticals are currently under development (Non-patent Documents 1 and 2).

Almost all antibody pharmaceuticals currently available on the market are of the IgG1 subclass. IgG1 type antibodies are expected be useful as anti-cancer antibody pharmaceuticals since they can bind to Fcγ receptor and exert ADCC activity. However, binding of the Fc domain to Fcγ receptor, which is important for effector function such as ADCC, can cause unnecessary adverse effects, and thus it is preferable to eliminate such binding activity from antibody pharmaceuticals intended for neutralizing biological activity (Non-patent Document 3). Furthermore, since Fcγ receptor is expressed in antigen-presenting cells, molecules that bind to Fcγ receptor tend to be presented as antigens. It has been reported that immunogenicity is and can be enhanced by linking a protein or peptide to the Fc domain of IgG1 (Non-patent Document 4 and Patent Document 1). Interaction between the antibody Fc domain and Fcγ receptor is thought to be a cause of the serious adverse effects encountered in phase-I clinical trials of TGN1412 (Non-patent Document 5). Thus, binding to Fcγ receptor is considered unfavorable in antibody pharmaceuticals intended for neutralizing the biological activity of an antigen from the perspective of adverse effect and immunogenicity.

A method for impairing the binding to Fcγ receptor is to alter the subtype of the IgG antibody from IgG1 to IgG2 or IgG4; however, this method cannot completely inhibit the binding (Non-patent Document 6). One of the methods reported for completely inhibiting the binding to Fcγ receptor is to artificially alter the Fc domain. For example, the effector functions of anti-CD3 antibodies and anti-CD4 antibodies cause adverse effects. Thus, amino acids that are not present in the wild type sequence were introduced into the Fcγ-receptor-binding domain of Fc (Non-patent Documents 3 and 7), and clinical trials are currently being conducted to assess anti-CD3 antibodies that do not bind to Fcγ receptor and anti-CD4 antibodies that have a mutated Fc domain (Non-patent Documents 5 and 8). Alternatively, Fcγ receptor-nonbinding antibodies can be prepared by altering the FcγR-binding domain of IgG1 (at positions 233, 234, 235, 236, 327, 330, and 331 in the EU numbering system) to an IgG2 or IgG4 sequence (Non-patent Document 9 and Patent Document 2). However, these molecules contain novel non-natural peptide sequences of nine to twelve amino acids, which may constitute a T-cell epitope peptide and thus pose immunogenicity risk. There is no previous report on Fcγ receptor-nonbinding antibodies that have overcome these problems.

Meanwhile, physicochemical properties of antibody proteins, in particular, homogeneity and stability, are very crucial in the development of antibody pharmaceuticals. For the IgG2 subtype, heterogeneity originated from disulfide bonds in the hinge region has been reported (Non-patent Document 10 and Patent Document 3). It is not easy to manufacture them as a pharmaceutical in large-scale while maintaining the objective substances/related substances related heterogeneity between productions. Thus, single substances are desirable as much as possible for antibody molecules developed as pharmaceuticals.

IgG2 and IgG4 are unstable under acidic conditions. IgG type antibodies are in general exposed to acidic conditions in the purification process using Protein A and the virus inactivation process. Thus, attention is needed regarding the stability of IgG2 and IgG4 during these processes, and it is preferable that antibody molecules developed as pharmaceuticals are also stable under acidic conditions. Natural IgG2 and IgG4, and Fcγ receptor-nonbinding antibodies derived from IgG2 or IgG4 (Non-patent Documents 6 and 7 and Patent Document 2) have such problems. It is desirable to solve these problems when developing antibodies into pharmaceuticals.

IgG1-type antibodies are relatively stable under acidic conditions, and the degree of heterogeneity originated from disulfide bonds in the hinge region is also lower in this type of antibodies. However, IgG1-type antibodies are reported to undergo non-enzymatic peptide bond cleavage in the hinge region in solutions when they are stored as formulations, and Fab fragments are generated as impurities as a result (Non-patent Document 11). It is desirable to overcome the generation of impurity when developing antibodies into pharmaceuticals.

Furthermore, for heterogeneity of the C-terminal sequence of an antibody, deletion of C-terminal amino acid lysine residue, and amidation of the C-terminal amino group due to deletion of both of the two C-terminal amino acids, glycine and lysine, have been reported (Non-patent Document 12). It is preferable to eliminate such heterogeneity when developing antibodies into pharmaceuticals.

The constant region of an antibody pharmaceutical aimed for neutralizing an antigen preferably has a sequence that overcomes all the problems described above. However, a constant region that meets all the requirements has not been reported.

A preferred form of antibody pharmaceutical administration is thought to be subcutaneous formulation in chronic autoimmune diseases and such. Low-cost, convenient antibody pharmaceuticals that can be administered subcutaneously in longer intervals can be provided by increasing the half-life of an antibody in the plasma to prolong its therapeutic effect and thereby reduce the amount of protein administered, and by conferring the antibody with high stability so that high concentration formulations can be prepared.

In general, it is necessary that subcutaneous formulations are high-concentration formulations. From the perspective of stability or such, the concentration limit of IgG-type antibody formulations is in general thought to be about 100 mg/ml (Non-patent Document 13). Thus, it is a challenge to secure stability at high concentration. However, there is no report published on the improvement of the stability of IgG at high concentrations by introducing amino acid substitutions into its constant region. A method for prolonging the antibody half-life in plasma has been reported and it substitutes amino acids in the constant region (Non-patent Documents 14 and 15); however, introduction of non-natural sequences into the constant region is not unpreferable from the perspective of immunogenicity risk.

As described above, when the purpose of an antibody pharmaceutical is to neutralize an antigen, it is preferable that all the problems described above have been overcome with regard to its constant-region sequence. However, a constant region that meets all the requirements has not been reported. Thus, there are demands for antibody constant regions that have overcome the problems described above.

Documents of related prior arts for the present invention are described below.

[Non-patent Document 1] Janice M Reichert, Clark J Rosensweig, Laura B Faden & Matthew C Dewitz. Monoclonal antibody successes in the clinic. Nature Biotechnology (2005) 23, 1073-1078

[Non-patent Document 2] Pavlou A K, Belsey M J. The therapeutic antibodies market to 2008. Eur. J. Pharm. Biopharm. 2005 April; 59(3):389-96

[Non-patent Document 3] Reddy M P, Kinney C A, Chaikin M A, Payne A, Fishman-Lobell J, Tsui P, Dal Monte P R, Doyle M L, Brigham-Burke M R, Anderson D, Reff M, Newman R, Hanna N, Sweet R W, Truneh A. Elimination of Fc receptor-dependent effector functions of a modified IgG4 monoclonal antibody to human CD4. J. Immunol. 2000 Feb. 15; 164(4):1925-33

[Non-patent Document 4] Guyre P M, Graziano R F, Goldstein J, Wallace P K, Morganelli P M, Wardwell K, Howell A L. Increased potency of Fc-receptor-targeted antigens. Cancer Immunol. Immunother. 1997 November-December; 45(3-4):146-8

[Non-patent Document 5] Strand V, Kimberly R, Isaacs J D. Biologic therapies in rheumatology: lessons learned, future directions. Nat. Rev. Drug Discov. 2007 January; 6(1):75-92

[Non-patent Document 6] Gessner J E, Heiken H, Tamm A, Schmidt R E. The IgG Fc receptor family. Ann. Hematol. 1998 June; 76(6):231-48

[Non-patent Document 7] Cole M S, Anasetti C, Tso J Y. Human IgG2 variants of chimeric anti-CD3 are nonmitogenic to T cells. J. Immunol. 1997 Oct. 1; 159(7):3613-21

[Non-patent Document 8] Chau L A, Tso J Y, Melrose J, Madrenas J. HuM291(Nuvion), a humanized Fc receptor-nonbinding antibody against CD3, anergizes peripheral blood T cells as partial agonist of the T cell receptor. Transplantation 2001 Apr. 15; 71(7):941-50

[Non-patent Document 9] Armour K L, Clark M R, Hadley A G, Williamson L M. Recombinant human IgG molecules lacking Fcgamma receptor I binding and monocyte triggering activities. Eur. J. Immunol. 1999 August; 29(8):2613-24

[Non-patent Document 10] Chu G C, Chelius D, Xiao G, Khor H K, Coulibaly S, Bondarenko P V. Accumulation of Succinimide in a Recombinant Monoclonal Antibody in Mildly Acidic Buffers Under Elevated Temperatures. Pharm. Res. 2007 Mar. 24; 24(6):1145-56

[Non-patent Document 11] A J Cordoba, B J Shyong, D Breen, R J Harris. Nonenzymatic hinge region fragmentation of antibodies in solution. J. Chromatogr. B. Anal. Technol. Biomed. Life Sci. (2005) 818, 115-121

[Non-patent Document 12] Johnson K A, Paisley-Flango K, Tangarone B S, Porter T J, Rouse J C. Cation exchange-HPLC and mass spectrometry reveal C-terminal amidation of an IgG1 heavy chain. Anal. Biochem. 2007 Jan. 1; 360(1):75-83

[Non-patent Document 13] Shire S J, Shahrokh Z, Liu J. Challenges in the development of high protein concentration formulations. J. Pharm. Sci. 2004 June; 93(6):1390-402

[Non-patent Document 14] Hinton P R, Xiong J M, Johlfs M G, Tang M T, Keller S, Tsurushita N. An engineered human IgG1 antibody with longer serum half-life. J. Immunol. 2006 Jan. 1; 176(1):346-56

[Non-patent Document 15] Ghetie V, Popov S, Borvak J, Radu C, Matesoi D, Medesan C, Ober R J, Ward E S. Increasing the serum persistence of an IgG fragment by random mutagenesis. Nat. Biotechnol. 1997 July; 15(7):637-40

[Patent Document 1] US 20050261229A1
[Patent Document 2] WO 99/58572
[Patent Document 3] US 2006/0194280

DISCLOSURE OF THE INVENTION

Problems to be Solved by the Invention

The present invention was achieved in view of the above circumstances. An objective of the present invention is to provide antibody constant regions that have improved physicochemical properties (stability and homogeneity), immunogenicity, safety, and pharmacokinetics (retention in plasma (blood)) by amino acid alteration.

Means for Solving the Problems

The present inventors conducted dedicated studies to generate antibody constant regions that are improved through alternation of their amino acid sequences and have improved physicochemical properties (stability and homogeneity), immunogenicity, and safety, and pharmacokinetics. As a result, the present inventors successfully improved antibody constant region to have increased stability under acid conditions, reduced heterogeneity originated from disulfide bonds in the hinge region, reduced heterogeneity originated from the H-chain C terminus, and increased stability at high concentrations, as well as discovered novel constant region sequences having reduced Fcγ receptor-binding activity, while minimizing the generation of novel T-cell epitope peptides.

The present invention relates to antibody constant regions that are superior in terms of safety, immunogenicity risk, physicochemical properties (stability and homogeneity), and pharmacokinetics a through improvement by amino acid alteration; antibodies comprising such antibody constant region; pharmaceutical compositions comprising such antibody; and methods for producing them. More specifically, the present invention provides:

[1] a human antibody constant region of any one of:
(a) a human antibody constant region that comprises deletions of both Gly at position 329 (position 446 in the EU numbering system, see sequences of proteins of immunological interest, NIH Publication No.91-3242) and Lys at position 330 (position 447 in the EU numbering system) in the amino acid sequence of SEQ ID NO: 1;

(b) a human antibody constant region that comprises deletions of both Gly at position 325 (position 446 in the EU numbering system) and Lys at position 326 (position 447 in the EU numbering system) in the amino acid sequence of SEQ ID NO: 2; and (c) a human antibody constant region that comprises deletions of both Gly at position 326 (position 446 in the EU numbering system) and Lys at position 327 (position 447 in the EU numbering system) in the amino acid sequence of SEQ ID NO: 3;

[2] an IgG2 constant region in which the amino acids at positions 209 (position 330 in the EU numbering system), 210 (position 331 in the EU numbering system), and 218 (position 339 in the EU numbering system) in the amino acid sequence of SEQ ID NO: 2 have been substituted with other amino acids;

[3] an IgG2 constant region in which the amino acid at position 276 (position 397 in the EU numbering system) in the amino acid sequence of SEQ ID NO: 2 has been substituted with another amino acid;

[4] an IgG2 constant region in which the amino acids at positions 14 (position 131 in the EU numbering system), 102 (position 219 in the EU numbering system), and/or 16 (position 133 in the EU numbering system) in the amino acid sequence of SEQ ID NO: 2 have been substituted with another amino acid;

[5] the IgG2 constant region of [4], in which the amino acids at positions 20 (position 137 in the EU numbering system) and 21 (position 138 in the EU numbering system) in the amino acid sequence of SEQ ID NO: 2 have been substituted with other amino acids;

[6] an IgG2 constant region in which His at position 147 (position 268 in the EU numbering system), Arg at position 234 (position 355 in the EU numbering system), and/or Gln at position 298 (position 419 in the EU numbering system) in the amino acid sequence of SEQ ID NO: 2 have been substituted with other amino acids;

[7] an IgG2 constant region in which the amino acids at positions 209 (position 330 in the EU numbering system), 210 (position 331 in the EU numbering system), 218 (position 339 in the EU numbering system), 276 (position 397 in the EU numbering system), 14 (position 131 in the EU numbering system), 16 (position 133 in the EU numbering system), 102 (position 219 in the EU numbering system), 20 (position 137 in the EU numbering system), and 21 (position 138 in the EU numbering system) in the amino acid sequence of SEQ ID NO: 2 have been substituted with other amino acids;

[8] the IgG2 constant region of [7], which further comprises deletions of both Gly at position 325 (position 446 in the EU numbering system) and Lys at position 326 (position 447 in the EU numbering system);

[9] an IgG2 constant region in which the amino acids at positions 276 (position 397 in the EU numbering system), 14 (position 131 in the EU numbering system), 16 (position 133 in the EU numbering system), 102 (position 219 in the EU numbering system), 20 (position 137 in the EU numbering system), and 21 (position 138 in the EU numbering system) in the amino acid sequence of SEQ ID NO: 2 have been substituted with other amino acids;

[10] the IgG2 constant region of [9], which further comprises deletions of both Gly at position 325 (position 446 in the EU numbering system) and Lys at position 326 (position 447 in the EU numbering system);

[11] an IgG2 constant region in which Cys at position 14 (position 131 in the EU numbering system), Arg at position 16 (position 133 in the EU numbering system), Cys at position 102 (position 219 in the EU numbering system), Glu at position 20 (position 137 in the EU numbering system), Ser at position 21 (position 138 in the EU numbering system), His at position 147 (position 268 in the EU numbering system), Arg at position 234 (position 355 in the EU numbering system), and Gln at position 298 (position 419 in the EU numbering system) in the amino acid sequence of SEQ ID NO: 2 have been substituted with other amino acids;

[12] the IgG2 constant region of [11], which further comprises deletions of both Gly at position 325 (position 446 in the EU numbering system) and Lys at position 326 (position 447 in the EU numbering system);

[13] an IgG2 constant region in which Cys at position 14 (position 131 in the EU numbering system), Arg at position 16 (position 133 in the EU numbering system), Cys at position 102 (position 219 in the EU numbering system), Glu at position 20 (position 137 in the EU numbering system), Ser at position 21 (position 138 in the EU numbering system), His at position 147 (position 268 in the EU numbering system), Arg at position 234 (position 355 in the EU numbering system), Gln at position 298 (position 419 in the EU numbering system), and Asn at position 313 (position 434 in the EU numbering system) in the amino acid sequence of SEQ ID NO: 2 have been substituted with other amino acids;

[14] the IgG2 constant region of [13], which further comprises deletions of both Gly at position 325 (position 446 in the EU numbering system) and Lys at position 326 (position 447 in the EU numbering system);

[15] an IgG4 constant region in which the amino acid at position 289 (position 409 in the EU numbering system) in the amino acid sequence of SEQ ID NO: 3 has been substituted with another amino acid;

[16] an IgG4 constant region in which the amino acids at position 289 (position 409 in the EU numbering system), positions 14, 16, 20, 21, 97, 100, 102, 103, 104, and 105 (positions 131, 133, 137, 138, 214, 217, 219, 220, 221, and 222 in the EU numbering system, respectively), and positions 113, 114, and 115 (positions 233, 234, and 235 in the EU numbering system, respectively), have been substituted with other amino acids, and the amino acid at position 116 (position 236 in the EU numbering system) has been deleted from the amino acid sequence of SEQ ID NO: 3;

[17] the IgG4 constant region of [16], which further comprises deletions of both Gly at position 326 (position 446 in the EU numbering system) and Lys at position 327 (position 447 in the EU numbering system);

[18] an IgG1 constant region in which Asn at position 317 (position 434 in the EU numbering system) in the amino acid sequence of SEQ ID NO: 1 has been substituted with another amino acid;

[19] the IgG1 constant region of [18], which further comprises deletions of both Gly at position 329 (position 446 in the EU numbering system) and Lys at position 330 (position 447 in the EU numbering system);

[20] an IgG2 constant region in which Ala at position 209 (position 330 in the EU numbering system), Pro at position 210 (position 331 in the EU numbering system), Thr at position 218 (position 339 in the EU numbering system), Cys at position 14 (position 131 in the EU numbering system), Arg at position 16 (position 133 in the EU numbering system), Cys at position 102 (position 219 in the EU numbering system), Glu at position 20 (position 137 in the EU numbering system), and Ser at position 21

(position 138 in the EU numbering system) in the amino acid sequence of SEQ ID NO: 2 have been substituted with other amino acids;

[21] the IgG2 constant region of [20], which further comprises deletions of both Gly at position 325 (position 446 in the EU numbering system) and Lys at position 326 (position 447 in the EU numbering system);

[22] an IgG2 constant region in which Cys at position 14 (position 131 in the EU numbering system), Arg at position 16 (position 133 in the EU numbering system), Cys at position 102 (position 219 in the EU numbering system), Glu at position 20 (position 137 in the EU numbering system), and Ser at position 21 (position 138 in the EU numbering system) in the amino acid sequence of SEQ ID NO: 2 have been substituted with other amino acids;

[23] the IgG2 constant region of [22], which further comprises deletions of both Gly at position 325 (position 446 in the EU numbering system) and Lys at position 326 (position 447 in the EU numbering system);

[24] a human antibody constant region comprising the amino acid sequence of SEQ ID NO: 5;

[25] a human antibody constant region comprising the amino acid sequence of SEQ ID NO: 7;

[26] a human antibody constant region comprising the amino acid sequence of SEQ ID NO: 9;

[27] a human antibody constant region comprising the amino acid sequence of SEQ ID NO: 35;

[28] a human antibody constant region comprising the amino acid sequence of SEQ ID NO: 36;

[29] a human antibody constant region comprising the amino acid sequence of SEQ ID NO: 37;

[30] a human antibody constant region comprising the amino acid sequence of SEQ ID NO: 43;

[31] a human antibody constant region comprising the amino acid sequence of SEQ ID NO: 57 (M40ΔGK);

[32] a human antibody constant region comprising the amino acid sequence of SEQ ID NO: 55 (M86ΔGK);

[33] an antibody comprising the constant region of any one of [1] to [32];

[34] an anti-IL-6 receptor antibody comprising the constant region of any one of [1] to [32]; and

[35] a pharmaceutical composition comprising the constant region of any one of [1] to [32].

MODE FOR CARRYING OUT THE INVENTION

Figure 1:
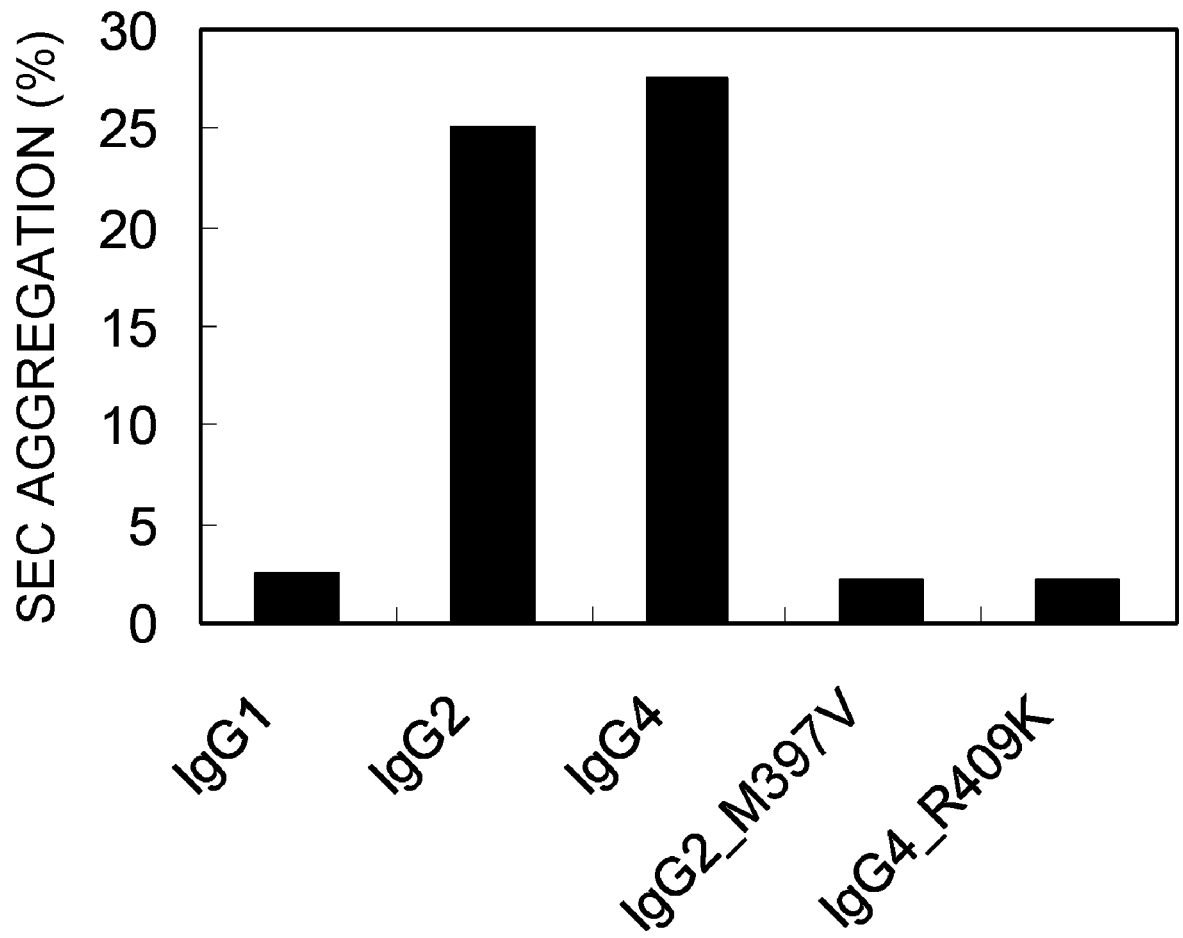
FIG. 1 is a graph showing the result of using gel filtration chromatography to analyze the content of aggregates in WT-IgG1, WT-IgG2, WT-IgG4, IgG2-M397V, and IgG4-R409K purified by hydrochloric acid elution.

The present invention provides antibody constant regions whose physicochemical properties (stability and homogeneity), immunogenicity, safety, and/or pharmacokinetics have been improved by altering the amino acid sequence of an antibody constant region; antibodies comprising such constant region; pharmaceutical compositions comprising such antibody; and methods for producing them.

Herein, the constant region refers to IgG1, IgG2, or IgG4 type constant region. The antibody constant region is preferably a human antibody constant region. The amino acid sequences of human IgG1, IgG2, and IgG4 constant regions are known (human IgG1 constant region, SEQ ID NO: 1; human IgG2 constant region, SEQ ID NO: 2; and human IgG4 constant region, SEQ ID NO: 3). The amino acid substitution-containing antibody constant regions of the present invention may comprise other amino acid substitutions or modifications as long as they comprise the amino acid substitutions of the present invention. Therefore, IgG2 constant regions comprising the amino acid substitutions of the present invention in the IgG2 constant region comprising the amino acid sequence of SEQ ID NO: 2 include IgG2 constant regions that comprise one or more amino acid substitutions and/or modifications in the amino acid sequence of SEQ ID NO: 2 and further comprise the amino acid substitutions of the present invention, as well as IgG2 constant regions that comprise the amino acid substitutions of the present invention and further comprise one or more amino acid substitutions and/or modifications. The same applies to IgG1 constant regions comprising the amino acid sequence of SEQ ID NO: 1 and IgG4 constant regions comprising the amino acid sequence of SEQ ID NO: 3. The sequence of human IgG4 constant region has been altered to improve the stability of the hinge region (Mol. Immunol. 1993 January; 30(1):105-8). Furthermore, the sugar chain at position 297 in the EU numbering system may be of any sugar-chain structure, or there may not be any sugar chain linked at this site (for example, can be produced with *E. coli*).

<IgG2 Having Altered Amino Acids>

The present invention provides IgG2 constant regions with an improved stability under acid conditions.

More specifically, the present invention provides IgG2 constant regions in which Met at position 276 (position 397 in the EU numbering system) in the amino acid sequence of SEQ ID NO: 2 has been substituted with another amino acid. The type of amino acid after substitution is not particularly limited; however, substitution to Val is preferred. The antibody stability under acidic conditions can be improved by substituting Met at position 276 (position 397 in the EU numbering system) in the amino acid sequence of SEQ ID NO: 2 with another amino acid.

The IgG2 constant regions provided by the present invention, which have an improved stability under acid conditions, may also have other amino acid substitutions, deletions, additions, and/or insertions, as long as they have at least the amino acid substitution described above.

The present invention provides IgG2 constant regions with reduced heterogeneity of hinge region.

More specifically, the present invention provides IgG2 constant regions in which Cys at position 14 (position 131 in the EU numbering system), Arg at position 16 (position 133 in the EU numbering system), and/or Cys at position 102 (position 219 in the EU numbering system) in the amino acid sequence of SEQ ID NO: 2 have been substituted with other amino acids. The type of amino acid after substitution is not particularly limited; however, substitutions of Ser for Cys at position 14 (position 131 in the EU numbering system), Lys for Arg at position 16 (position 133 in the EU numbering system), and Ser for Cys at position 102 (position 219 in the EU numbering system) (IgG2-SKSC) are preferred.

These substitutions can reduce the heterogeneity originated from the hinge region of IgG2. The IgG2 constant regions of the present invention comprising amino acid substitutions include IgG2 constant regions comprising at least one of the three types of amino acid substitutions described above; however, the IgG2 constant regions preferably comprise substitutions of Cys at position 14 and Cys at position 102 with other amino acids or all three types of the amino acid substitutions described above.

The IgG2 constant regions provided by the present invention, which have reduced heterogeneity, may also have other amino acid substitutions, deletions, additions, and/or insertions, as long as they have at least the amino acid substitution described above.

For example, mutating Cys at position 14 and Arg at position 16 in an IgG2 constant region comprising the amino acid sequence of SEQ ID NO: 2 may generate non-natural, novel peptide sequences of nine to twelve amino acids, which can become T-cell epitope peptides, and thus generate immunogenicity risk. Even with the introduction of the amino acid substitutions described above, the generation of non-natural T-cell epitope peptides can be avoided by substituting Glu at position 20 (position 137 in the EU numbering system) and Ser at position 21 (position 138 in the EU numbering system) with other amino acids. The type of amino acid after substitution is not particularly limited; however, substitutions of Gly for Glu at position 20 and Gly for Ser at position 21 are preferred.

The present invention also provides IgG2 constant regions with reduced Fcγ receptor-binding activity.

More specifically, the present invention also provides IgG2 constant regions comprising an amino acid sequence in which Ala at position 209 (EU330), Pro at position 210 (EU331), and/or Thr at position 218 (EU339) of the amino acid sequence of SEQ ID NO: 2 have been substituted with Ser, Ser, and Ala, respectively. The substitutions for Ala at position 209 (EU330) and for Pro at position 210 (EU331) have already been reported to enable the impairment of the Fcγ receptor binding (Eur. J. Immunol. 1999 August; 29(8): 2613-24). From the perspective of immunogenicity risk, however, these alterations are not preferred because they result in generation of non-human derived peptides that can become T-cell epitopes. However, the Fcγ receptor binding of IgG2 can be reduced by substituting Ala for Thr at position 218 (EU339) at the same time, and the 9-12 amino acid peptides which can become T-cell epitopes are derived from human only.

The IgG2 constant regions of the present invention comprising amino acid substitutions comprise at least one of the three types of amino acid substitutions described above; however, the IgG2 constant regions preferably comprise all three types of the amino acid substitutions described above. In a preferred embodiment, the IgG2 constant regions of the present invention comprising amino acid substitutions include IgG2 constant regions comprising an amino acid sequence in which Ala at position 209 (EU330), Pro at position 210 (EU331), and Thr at position 218 (EU339) in the amino acid sequence of SEQ ID NO: 2 have been substituted with Ser, Ser, and Ala, respectively.

The IgG2 constant regions provided by the present invention, which have reduced Fcγ receptor-binding activity, may also have other amino acid substitutions, deletions, additions, and/or insertions, as long as they have at least the amino acid substitution described above.

The present invention provides IgG2 constant regions with reduced C-terminal heterogeneity.

More specifically, the present invention provides IgG2 constant regions comprising an amino acid sequence in which Gly at position 325 (position 446 in the EU numbering system) and Lys at position 326 (position 447 in the EU numbering system) have been deleted in the amino acid sequence of SEQ ID NO: 2. The heterogeneity originated from the C terminus of antibody H chain can be reduced only when both of the amino acids are deleted.

The IgG2 constant regions provided by the present invention, which have reduced C-terminal heterogeneity, may also have other amino acid substitutions, deletions, additions, and/or insertions, as long as they have at least the amino acid substitution described above.

The present invention further provides IgG2 constant regions with improved pharmacokinetics.

Specifically, the present invention provides IgG2 constant regions in which His at position 147 (position 268 in the EU numbering system), Arg at position 234 (position 355 in the EU numbering system), and Gln at position 298 (position 419 in the EU numbering system) in the amino acid sequence of SEQ ID NO: 2 have been substituted with other amino acids. These amino acid substitutions enable to improve antibody pharmacokinetics. The type of amino acid after substitution is not particularly limited; however, substitutions of Gln for His at position 147 (position 268 in the EU numbering system), Gln for Arg at position 234 (position 355 in the EU numbering system), and Glu for Gln at position 298 (position 419 in the EU numbering system) are preferred. The IgG2 constant regions with amino acid substitutions of the present invention include IgG2 constant regions comprising at least one of the three types of the amino acid substitutions described above; however, the IgG2 constant regions preferably comprise all three types of the amino acid substitutions described above.

Below is a preferred embodiment of IgG2 of the present invention, which has improved stability under acidic conditions, reduced heterogeneity in the hinge region, and/or reduced Fcγ receptor-binding activity.

Antibodies comprising an IgG2 constant region comprising an amino acid sequence in which Ala at position 209, Pro at position 210, Thr at position 218, Met at position 276, Cys at position 14, Arg at position 16, Cys at position 102, Glu at position 20, and Ser at position 21 in the amino acid sequence of SEQ ID NO: 2 have been substituted with other amino acids.

The type of amino acid after substitution is not particularly limited; however, substitutions of Ser for Ala at position 209 (position 330 in the EU numbering system), Ser for Pro at position 210 (position 331 in the EU numbering system), Ala for Thr at position 218 (position 339 in the EU numbering system), Val for Met at position 276 (position 397 in the EU numbering system), Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

Such IgG2 constant regions include, for example, IgG2 constant regions comprising the amino acid sequence of SEQ ID NO: 4 (M14).

In another preferred embodiment, IgG2 constant regions of the present invention include IgG2 constant regions resulting from the deletion of Gly at position 325 and Lys at position 326 in the above-described IgG2 constant regions to reduce C-terminal heterogeneity. Such antibodies include, for example, IgG2 that comprises a constant region comprising the amino acid sequence of SEQ ID NO: 5 (M14ΔGK).

Below is a preferred embodiment of IgG2 of the present invention, which has reduced heterogeneity in the hinge region and/or reduced Fcγ receptor-binding activity.

Antibodies comprising an IgG2 constant region comprising an amino acid sequence in which Ala at position 209, Pro at position 210, Thr at position 218, Cys at position 14, Arg at position 16, Cys at position 102, Glu at position 20, and Ser at position 21 in the amino acid sequence of SEQ ID NO: 2 have been substituted with other amino acids.

The type of amino acid after substitution is not particularly limited; however, substitutions of Ser for Ala at position 209 (position 330 in the EU numbering system), Ser for Pro at position 210 (position 331 in the EU numbering system), Ala for Thr at position 218 (position 339 in the EU numbering system), Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

Such IgG2 constant regions include, for example, IgG2 constant regions comprising the amino acid sequence of SEQ ID NO: 54 (M86).

In another preferred embodiment, IgG2 constant regions of the present invention include IgG2 constant regions resulting from the deletion of Gly at position 325 and Lys at position 326 in the above-described IgG2 constant regions to reduce C-terminal heterogeneity. Such antibodies include, for example, IgG2 that comprises a constant region comprising the amino acid sequence of SEQ ID NO: 55 (M86ΔGK).

Below is another preferred embodiment of the IgG2 constant regions of the present invention, which have improved stability under acidic conditions and reduced heterogeneity in the hinge region.

IgG2 constant regions comprising an amino acid sequence in which Met at position 276, Cys at position 14, Arg at position 16, Cys at position 102, Glu at position 20, and Ser at position 21 in the amino acid sequence of SEQ ID NO: 2 have been substituted with other amino acids.

The type of amino acid after substitution is not particularly limited; however, substitutions of Val for Met at position 276 (position 397 in the EU numbering system), Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

Such IgG2 constant regions include, for example, IgG2 constant regions comprising the amino acid sequence of SEQ ID NO: 6 (M31).

In another preferred embodiment, the IgG2 constant regions of the present invention include IgG2 constant regions further comprising the deletion of Gly at position 325 and Lys at position 326 in the above-described IgG2 constant regions. Such antibodies include, for example, IgG2 constant regions comprising the amino acid sequence of SEQ ID NO: 7 (M31ΔGK).

Below is another preferred embodiment of the IgG2 constant regions of the present invention, which have reduced heterogeneity in the hinge region.

IgG2 constant regions comprising an amino acid sequence in which Cys at position 14, Arg at position 16, Cys at position 102, Glu at position 20, and Ser at position 21 in the amino acid sequence of SEQ ID NO: 2 have been substituted with other amino acids.

The type of amino acid after substitution is not particularly limited; however, substitutions of Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

Such IgG2 constant regions include, for example, IgG2 constant regions comprising the amino acid sequence of SEQ ID NO: 56 (M40).

In another preferred embodiment, the IgG2 constant regions of the present invention include IgG2 constant regions further comprising the deletion of Gly at position 325 and Lys at position 326 in the above-described IgG2 constant regions. Such antibodies include, for example, IgG2 constant regions comprising the amino acid sequence of SEQ ID NO: 57 (M40ΔGK).

The present invention provides IgG2 constant regions comprising an amino acid sequence in which Cys at position 14 (position 131 in the EU numbering system), Arg at position 16 (position 133 in the EU numbering system), Cys at position 102 (position 219 in the EU numbering system), Glu at position 20 (position 137 in the EU numbering system), Ser at position 21 (position 138 in the EU numbering system), His at position 147 (position 268 in the EU numbering system), Arg at position 234 (position 355 in the EU numbering system), and Gln at position 298 (position 419 in the EU numbering system) have been substituted with other amino acids, and simultaneously Gly at position 325 (position 446 in the EU numbering system) and Lys at position 326 (position 447 in the EU numbering system) have been deleted in the amino acid sequence of SEQ ID NO: 2.

The type of amino acid after substitution is not particularly limited; however, substitutions of Ser for Cys at position 14, Lys for Arg at position 16, Ser for Cys at position 102, Gly for Glu at position 20, Gly for Ser at position 21, Gln for His at position 147, Gln for Arg at position 234, and Glu for Gln at position 298 are preferred.

Specifically, the present invention provides an antibody constant region comprising the amino acid sequence of SEQ ID NO: 35 (M58).

The present invention provides IgG2 constant regions comprising an amino acid sequence in which Cys at position 14 (position 131 in the EU numbering system), Arg at position 16 (position 133 in the EU numbering system), Cys at position 102 (position 219 in the EU numbering system), Glu at position 20 (position 137 in the EU numbering system), Ser at position 21 (position 138 in the EU numbering system), His at position 147 (position 268 in the EU numbering system), Arg at position 234 (position 355 in the EU numbering system), Gln at position 298 (position 419 in the EU numbering system), and Asn at position 313 (position 434 in the EU numbering system) have been substituted with other amino acids, and simultaneously Gly at position 325 (position 446 in the EU numbering system) and Lys at position 326 (position 447 in the EU numbering system) have been deleted in the amino acid sequence of SEQ ID NO: 2.

The type of amino acid after substitution is not particularly limited; however, substitutions of Ser for Cys at position 14, Lys for Arg at position 16, Ser for Cys at position 102, Gly for Glu at position 20, Gly for Ser at position 21, Gln for His at position 147, Gln for Arg at position 234, Glu for Gln at position 298, and Ala for Asn at position 313 are preferred.

Specifically, the present invention provides an antibody constant region comprising the amino acid sequence of SEQ ID NO: 37 (M73).

These antibody constant regions have been optimized to have reduced Fcγ receptor binding activity, reduced immunogenicity risk, improved stability under acidic conditions, reduced heterogeneity, improved pharmacokinetics, and/or higher stability in preparations in comparison with the IgG1 constant region.

<IgG4 Having Altered Amino Acids>

The present invention provides IgG4 constant regions that are stable at acidic conditions.

More specifically, the present invention provides IgG4 constant regions comprising an amino acid sequence in which Arg at position 289 (position 409 in the EU numbering system) of the amino acid sequence of SEQ ID NO: 3 has been substituted with another amino acid. The type of amino acid after substitution is not particularly limited; however, substitution to Lys is preferred. The antibody stability under acidic conditions can be improved by substituting Arg at position 277 (position 409 in the EU numbering system) in the amino acid sequence of SEQ ID NO: 3 with another amino acid.

The IgG4 constant regions provided by the present invention, which have an improved stability under acidic conditions, may also have other amino acid substitutions, deletions, additions, and/or insertions, as long as they have at least the amino acid substitution described above.

The present invention provides IgG4 constant regions with reduced C-terminal heterogeneity.

The present invention provides IgG4 constant regions in which Gly at position 326 (position 446 in the EU numbering system) and Lys at position 327 (position 447 in the EU numbering system) have been deleted in the IgG4 constant region comprising the amino acid sequence of SEQ ID NO: 3. The heterogeneity originated from the C terminus of antibody H chain can be reduced only when both of the amino acids are deleted.

The IgG4 constant regions provided by the present invention, which have reduced C-terminal heterogeneity, may also have other amino acid substitutions, deletions, additions, and/or insertions, as long as they have at least the amino acid substitution described above.

Another preferred embodiment of IgG4 of the present invention, which has improved stability under acidic conditions, reduced heterogeneity in the hinge region, and/or reduced Fcγ receptor-binding activity, includes IgG4 comprising the constant region described below.

IgG4 constant regions comprising an amino acid sequence in which Cys at position 14, Arg at position 16, Glu at position 20, Ser at position 21, Arg at position 97, Ser at position 100, Tyr at position 102, Gly at position 103, Pro at position 104, Pro at position 105, Glu at position 113, Phe at position 114, Leu at position 115, and Arg at position 289 have been substituted with other amino acids, and simultaneously Gly at position 116 has been deleted in the amino acid sequence of SEQ ID NO: 3.

The type of amino acid after substitution is not particularly limited; however, substitutions of Ser for Cys at position 14 (position 131 in the EU numbering system), Lys for Arg at position 16 (position 133 in the EU numbering system), Gly for Glu at position 20 (position 137 in the EU numbering system), Gly for Ser at position 21 (position 138 in the EU numbering system), Thr for Arg at position 97 (position 214 in the EU numbering system), Arg for Ser at position 100 (position 217 in the EU numbering system), Ser for Tyr at position 102 (position 219 in the EU numbering system), Cys for Gly at position 103 (position 220 in the EU numbering system), Val for Pro at position 104 (position 221 in the EU numbering system), Glu for Pro at position 105 (position 222 in the EU numbering system), Pro for Glu at position 113 (position 233 in the EU numbering system), Val for Phe at position 114 (position 234 in the EU numbering system), Ala for Leu at position 115 (position 235 in the EU numbering system), and Lys for Arg at position 289 (position 409 in the EU numbering system) are preferred.

Such IgG4 constant regions include, for example, IgG4 constant regions comprising the amino acid sequence of SEQ ID NO: 8 (M11).

In another preferred embodiment, the IgG4 constant regions of the present invention include IgG4 constant regions further comprising the deletion of Gly at position 325 (position 446 in the EU numbering system) and Lys at position 326 (position 447 in the EU numbering system) in the above-described IgG4 constant region. Such antibodies include, for example, IgG4 constant regions comprising the amino acid sequence of SEQ ID NO: 9 (M11ΔGK).

<IgG1 Having Altered Amino Acids>

The present invention provides IgG1 constant regions with reduced C-terminal heterogeneity.

More specifically, the present invention provides IgG1 constant regions having the deletion of Gly at position 329 (position 446 in the EU numbering system) and Lys at position 330 (position 447 in the EU numbering system) in the IgG1 constant region comprising the amino acid sequence of SEQ ID NO: 1. The heterogeneity originated from the H-chain C terminus of an antibody can be reduced only when both of the amino acids are deleted.

The present invention provides IgG1 constant regions with improved pharmacokinetics.

The present invention provides IgG1 constant regions comprising an amino acid sequence in which Asn at position 317 (position 434 in the EU numbering system) in the amino acid sequence of SEQ ID NO: 1 has been substituted with another amino acid. The type of amino acid after substitution is not particularly limited; however, substitution to Ala is preferred.

The present invention provides a constant region having the deletion of Gly at position 329 and Lys at position 330 in the amino acid sequence of SEQ ID NO: 36. More specifically, the present invention provides an antibody constant region comprising the amino acid sequence of SEQ ID NO: 43 (M83).

The IgG1 constant regions provided by the present invention, which have reduced C-terminal heterogeneity, may also have other amino acid substitutions, deletions, additions, and/or insertions, as long as they have at least the amino acid deletions described above.

The present invention also provides antibodies comprising any one of the antibody constant regions described above. The type and origin of antibodies of the present invention are not particularly limited, as long as they comprise the antibody constant region described above, and can be any antibodies.

The antibodies of the present invention also include modified products of antibodies comprising any of the amino acid substitutions described above. The origin of antibodies is not particularly limited. The antibodies include human, mouse, rat, and rabbit antibodies. The antibodies of the present invention may be chimeric, humanized, fully humanized antibodies, or such. In a preferred embodiment, the antibodies of the present invention are humanized antibodies.

Alternatively, the antibody constant regions described above and/or antibody molecules comprising an antibody constant region described above can be linked as a form of Fc fusion molecule to antibody-like binding molecule (scaffold molecules), bioactive peptides, binding peptides, or such.

The antibodies of the present invention also include modification products of an antibody comprising any one of the constant regions described above.

Such antibody modification products include, for example, antibodies linked with various molecules such as polyethylene glycol (PEG) and cytotoxic substances. Such antibody modification products can be obtained by chemically modifying antibodies of the present invention. Methods for modifying antibodies are already established in this field.

The antibodies of the present invention may also be bispecific antibodies. "Bispecific antibody" refers to an antibody that has in a single molecule variable regions that recognize different epitopes. The epitopes may be present in a single molecule or in separate molecules.

The antibody constant regions described above can be used as a constant region in an antibody against an arbitrary antigen. The antigen is not particularly limited.

The antibodies of the present invention can also be obtained by, for example, the following methods. In one embodiment to obtain antibodies of the present invention, one or more amino acid residues are first deleted or substituted with amino acids of interest in the constant region. Methods for substituting one or more amino acid residues with amino acids of interest include, for example, site-directed mutagenesis (Hashimoto-Gotoh, T., Mizuno, T., Ogasahara, Y., and Nakagawa, M. An oligodeoxyribonucleotide-directed dual amber method for site-directed mutagenesis. Gene (1995) 152, 271-275; Zoller, M. J., and Smith, M. Oligonucleotide-directed mutagenesis of DNA fragments cloned into M13 vectors. Methods Enzymol. (1983) 100, 468-500; Kramer, W., Drutsa, V., Jansen, H. W., Kramer, B., Pflugfelder, M., and Fritz, H. J. The gapped duplex DNA approach to oligonucleotide-directed mutation construction. Nucleic Acids Res. (1984) 12, 9441-9456; Kramer W., and Fritz H. J. Oligonucleotide-directed construction of mutations via gapped duplex DNA Methods. Enzymol. (1987) 154, 350-367; Kunkel, T. A. Rapid and efficient site-specific mutagenesis without phenotypic selection. Proc. Natl. Acad. Sci. USA (1985) 82, 488-492). These methods can be used to substitute target amino acids in the constant region of an antibody with amino acids of interest.

In another embodiment to obtain antibodies, an antibody that binds to an antigen of interest is first prepared by methods known to those skilled in the art. When the prepared antibody is derived from a nonhuman animal, it can be humanized. The binding activity of the antibody can be determined by known methods. Next, one or more amino acid residues in the constant region of the antibody are deleted or substituted with amino acids of interest.

More specifically, the present invention relates to methods for producing antibodies, which comprise the steps of:

(a) expressing a DNA encoding an H chain in which one or more amino acid residues in the constant region are deleted or substituted with amino acids of interest, and a DNA encoding an L chain; and (b) collecting the expression products of step (a).

The first step of the production methods of the present invention is expressing a DNA encoding an antibody H chain in which one or more amino acid residues in the constant region are deleted or substituted with amino acids of interest, and a DNA encoding an antibody L chain. A DNA encoding an H chain in which one or more amino acid residues in the constant region are deleted or substituted with amino acids of interest can be prepared, for example, by obtaining a DNA encoding the constant region of a wild type H chain, and introducing an appropriate substitution so that a codon encoding a particular amino acid in the constant region encodes an amino acid of interest.

Alternatively, a DNA encoding an H chain in which one or more amino acid residues in the constant region are deleted or substituted with amino acids of interest can also be prepared by designing and then chemically synthesizing a DNA encoding a protein in which one or more amino acid residues in the constant region of the wild type H chain are deleted or substituted with amino acids of interest.

The type of amino acid substitution includes the substitutions described herein, but is not limited thereto.

Alternatively, a DNA encoding an H chain in which one or more amino acid residues in the constant region are deleted or substituted with amino acids of interest can also be prepared as a combination of partial DNAs. Such combinations of partial DNAs include, for example, the combination of a DNA encoding a variable region and a DNA encoding a constant region, and the combination of a DNA encoding an Fab region and a DNA encoding an Fc region, but are not limited thereto. A DNA encoding an L chain can also be prepared as a combination of partial DNAs.

Methods for expressing the above-described DNAs include the methods described below. For example, an H chain expression vector is constructed by inserting a DNA encoding an H chain variable region into an expression vector along with a DNA encoding an H chain constant region. Likewise, an L chain expression vector is constructed by inserting a DNA encoding an L chain variable region into an expression vector along with a DNA encoding an L chain constant region. Alternatively, these H and L chain genes may be inserted into a single vector. Expression vectors include, for example, SV40 virus-based vectors, EB virus-based vectors, and BPV (papilloma virus)-based vectors, but are not limited thereto.

Host cells are co-transformed with an antibody expression vector constructed by the methods described above. Such host cells include the above-described cells such as CHO (Chinese hamster ovary) cells as well as microorganisms such as *E. coli*, yeast, and *Bacillus subtilis*, and plants and animals (Nature Biotechnology (2007) 25, 563-565; Nature Biotechnology (1998) 16, 773-777; Biochemical and Biophysical Research Communications (1999) 255, 444-450; Nature Biotechnology (2005) 23, 1159-1169; Journal of Virology (2001) 75, 2803-2809; Biochemical and Biophysical Research Communications (2003) 308, 94-100). The transformation can be preferably achieved by using electroporation, the lipofectin method (R. W. Malone et al., Proc. Natl. Acad. Sci. USA (1989) 86, 6077; P. L. Felgner et al., Proc. Natl. Acad. Sci. USA (1987) 84, 7413), calcium phosphate method (F. L. Graham & A. J. van der Eb, Virology (1973) 52, 456-467), DEAE-Dextran method, and the like.

In the next step of antibody production, the expression products obtained in step (a) are collected. The expression products can be collected, for example, by culturing the transformants and then separating the products from the transformed cells or culture media. Separation and purification of antibodies can be achieved by an appropriate combination of methods such as centrifugation, ammonium sulfate fractionation, salting out, ultrafiltration, columns of Iq, FcRn, Protein A, and Protein G, affinity chromatography, ion exchange chromatography, and gel filtration chromatography.

<Methods for Improving the IgG2 Constant Region Stability under Acidic Conditions>

The present invention also relates to methods for improving antibody stability under acidic conditions, which comprise the step of substituting Met at position 276 (position 397 in the EU numbering system) in the amino acid sequence of SEQ ID NO: 2 (IgG2) with another amino acid. The methods of the present invention for improving antibody stability under acidic conditions may comprise other steps of amino acid substitution, as long as they comprise the step of substituting Met at position 276 (position 397 in the EU numbering system) in the amino acid sequence of SEQ ID NO: 2 (IgG2) with another amino acid. The type of amino acid after substitution is not particularly limited; however, substitution to Val is preferred. The method for amino acid substitution is not particularly limited. The substitution can be achieved, for example, by site-directed mutagenesis described above or a method described in the Examples.

<Methods for Reducing the Heterogeneity Originated from the Hinge Region of IgG2 Constant Region>

The present invention also relates to methods for reducing antibody heterogeneity, which comprise the step of substituting Cys at position 14 (position 131 in the EU numbering system), Arg at position 16 (position 133 in the EU numbering system), and/or Cys at position 102 (position 219 in the EU numbering system) in the amino acid sequence of SEQ ID NO: 2 (IgG2) with other amino acids. The type of amino acid after substitution is not particularly limited; however, substitutions of Ser for Cys at position 14, Lys for Arg at position 16, and Ser for Cys at position 102 are preferred. The methods of the present invention for reducing antibody heterogeneity may comprise other steps of amino acid substitution, as long as they comprise the step of substituting Cys at position 14 (position 131 in the EU numbering system), Arg at position 16 (position 133 in the EU numbering system), and/or Cys at position 102 (position 219 in the EU numbering system) in the amino acid sequence of SEQ ID NO: 2 (IgG2). The method for amino acid substitution is not particularly limited. The substitutions can be achieved, for example, by site-directed mutagenesis described above or a method described in the Examples. In the amino acid substitution, all of the three amino acids described above may be substituted or one or two (for example, positions 14 and 102) of them may be substituted.

<Methods for Reducing the Heterogeneity Originated from Deletion of C-terminal Amino Acids in an IgG2 Constant Region>

The present invention also relates to methods for reducing antibody heterogeneity, which comprise the step of deleting Gly at position 325 (position 446 in the EU numbering system) and Lys at position 326 (position 447 in the EU numbering system) in an IgG2 constant region comprising the amino acid sequence of SEQ ID NO: 2. The methods of the present invention for reducing antibody heterogeneity may comprise other steps of amino acid substitution, as long as they comprise the step of deleting Gly at position 325 (position 446 in the EU numbering system) and Lys at position 326 (position 447 in the EU numbering system) in an IgG2 constant region comprising the amino acid sequence of SEQ ID NO: 2. The method for amino acid substitution is not particularly limited. The substitution can be achieved, for example, by site-directed mutagenesis described above or a method described in the Examples.

<Methods for Improving the Pharmacokinetics by Substituting Amino Acids of IgG2 Constant Region>

The present invention also relates to methods for improving the pharmacokinetics of an antibody, which comprise the step of substituting His at position 14 (EU268), Arg at position 234 (EU355), and/or Gln at position 298 (EU419) in an IgG2 constant region comprising the amino acid sequence of SEQ ID NO: 2. The methods of the present invention for improving the pharmacokinetics of an antibody may comprise other steps of amino acid substitution, as long as they comprise the above-described step. The type of amino acid after substitution is not particularly limited; however, substitutions of Gln for His at position 147 (EU268), Gln for Arg at position 234 (EU355), and Glu for Gln at position 298 (EU419) are preferred.

The present invention also relates to methods for improving the pharmacokinetics of an antibody, which comprise the step of substituting Asn at position 313 (EU434) in an IgG2 constant region comprising the amino acid sequence of SEQ ID NO: 2 or 35 (M58). The type of amino acid after substitution is not particularly limited; however, substitution to Ala is preferred. The methods of the present invention for improving the pharmacokinetics of an antibody may comprise other steps of amino acid substitution, as long as they comprise the above-described step.

<Methods for Improving the Pharmacokinetics by Substituting Amino Acids of IgG1 Constant Region>

The present invention also relates to methods for improving the pharmacokinetics of an antibody, which comprise the step of substituting Asn at position 317 (EU434) in an IgG1 constant region comprising the amino acid sequence of SEQ ID NO: 1. The type of amino acid after substitution is not particularly limited; however, substitution to Ala is preferred. The methods of the present invention for improving the pharmacokinetics of an antibody may comprise other steps of amino acid substitution, as long as they comprise the above-described step.

The present invention also relates to methods for improving the pharmacokinetics of an antibody and reducing the heterogeneity originated from deletion of C-terminal amino acids, which comprise the step of substituting Asn at position 317 (EU434) and deleting Gly at position 329 (EU446) and Lys at position 330 (EU447) in an IgG1 constant region comprising the amino acid sequence of SEQ ID NO: 1. The type of amino acid after substitution is not particularly limited; however, substitution to Ala is preferred. The methods of the present invention for improving the pharmacokinetics of an antibody may comprise other steps of amino acid substitution, as long as they comprise the above-described step.

<Methods for Reducing the FcγR Binding while Maintaining the Human Sequence in the IgG2 Constant Region>

The present invention also relates to methods for reducing the FcγR binding of an antibody, which comprise the step of substituting Ser for Ala at position 209 (EU330), Ser for Pro at position 210 (EU331), and Ala for Thr at position 218 (EU339) in an IgG2 constant region comprising the amino acid sequence of SEQ ID NO: 2. The methods of the present invention for reducing the FcγR binding of an antibody may comprise other steps of amino acid substitution, as long as they comprise the step of substituting Ser for Ala at position 209 (EU330), Ser for Pro at position 210 (EU331), and Ala for Thr at position 218 (EU339) in an IgG2 constant region comprising the amino acid sequence of SEQ ID NO: 2. The method for amino acid substitution is not particularly limited. The substitution can be achieved, for example, by site-directed mutagenesis described above or a method described in the Examples.

The present invention also relates to methods for reducing the heterogeneity originated from the hinge region of IgG2, methods for improving antibody stability under acidic conditions, methods for reducing antibody heterogeneity originated from C-terminus, and/or methods for reducing the FcγR binding of an antibody, all of which comprise, in an IgG2 constant region comprising the amino acid sequence of SEQ ID NO: 2 (M14ΔGK), the steps of:

(a) substituting Ala at position 209 (position 330 in the EU numbering system) in the amino acid sequence of SEQ ID NO: 2 with another amino acid;

(b) substituting Pro at position 210 (position 331 in the EU numbering system) in the amino acid sequence of SEQ ID NO: 2 with another amino acid;

(c) substituting Thr at position 218 (position 339 in the EU numbering system) in the amino acid sequence of SEQ ID NO: 2 with another amino acid;

(d) substituting Met at position 276 (position 397 in the EU numbering system) in the amino acid sequence of SEQ ID NO: 2 with another amino acid;

(e) substituting Cys at position 14 (position 131 in the EU numbering system) in the amino acid sequence of SEQ ID NO: 2 with another amino acid;

(f) substituting Arg at position 16 (position 133 in the EU numbering system) in the amino acid sequence of SEQ ID NO: 2 with another amino acid;

(g) substituting Cys at position 102 (position 219 in the EU numbering system) in the amino acid sequence of SEQ ID NO: 2 with another amino acid;

(h) substituting Glu at position 20 (position 137 in the EU numbering system) in the amino acid sequence of SEQ ID NO: 2 with another amino acid;

(i) substituting Ser at position 21 (position 138 in the EU numbering system) in the amino acid sequence of SEQ ID NO: 2 with another amino acid; and (j) deleting Gly at position 325 and Lys at position 326 (positions 446 and 447 in the EU numbering system, respectively) in the amino acid sequence of SEQ ID NO: 2.

The type of amino acid after substitution is not particularly limited; however, substitutions of Ser for Ala at position 209 (position 330 in the EU numbering system), Ser for Pro at position 210 (position 331 in the EU numbering system), Ala for Thr at position 218 (position 339 in the EU numbering system), Val for Met at position 276 (position 397 in the EU numbering system), Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

The present invention also relates to methods for reducing the heterogeneity originated from the hinge region of IgG2, methods for reducing antibody heterogeneity originated from C-terminus, and/or methods for reducing the FcγR binding of an antibody, all of which comprise, in an IgG2 constant region comprising the amino acid sequence of SEQ ID NO: 2 (M86ΔGK), the steps of:

(a) substituting Ala at position 209 (position 330 in the EU numbering system) in the amino acid sequence of SEQ ID NO: 2 with another amino acid;

(b) substituting Pro at position 210 (position 331 in the EU numbering system) in the amino acid sequence of SEQ ID NO: 2 with another amino acid;
(c) substituting Thr at position 218 (position 339 in the EU numbering system) in the amino acid sequence of SEQ ID NO: 2 with another amino acid;
(d) substituting Cys at position 14 (position 131 in the EU numbering system) in the amino acid sequence of SEQ ID NO: 2 with another amino acid;
(e) substituting Arg at position 16 (position 133 in the EU numbering system) in the amino acid sequence of SEQ ID NO: 2 with another amino acid;
(f) substituting Cys at position 102 (position 219 in the EU numbering system) in the amino acid sequence of SEQ ID NO: 2 with another amino acid;
(g) substituting Glu at position 20 (position 137 in the EU numbering system) in the amino acid sequence of SEQ ID NO: 2 with another amino acid;
(h) substituting Ser at position 21 (position 138 in the EU numbering system) in the amino acid sequence of SEQ ID NO: 2 with another amino acid; and
(i) deleting Gly at position 325 and Lys at position 326 (positions 446 and 447 in the EU numbering system, respectively) in the amino acid sequence of SEQ ID NO: 2.

The type of amino acid after substitution is not particularly limited; however, substitutions of Ser for Ala at position 209 (position 330 in the EU numbering system), Ser for Pro at position 210 (position 331 in the EU numbering system), Ala for Thr at position 218 (position 339 in the EU numbering system), Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

The methods of the present invention may comprise other steps such as amino acid substitution and deletion, as long as they comprise the steps described above. The methods for amino acid substitution and deletion are not particularly limited. The substitution and deletion can be achieved, for example, by site-directed mutagenesis described above or a method described in the Examples.

The present invention also relates to methods for reducing the heterogeneity originated from the hinge region of IgG2, methods for improving antibody stability under acidic conditions, and/or methods for reducing antibody heterogeneity originated from C-terminus, all of which comprise in an IgG2 constant region comprising the amino acid sequence of SEQ ID NO: 2 (M31ΔGK), the steps of:
(a) substituting Met at position 276 (position 397 in the EU numbering system) in the amino acid sequence of SEQ ID NO: 2 with another amino acid;
(b) substituting Cys at position 14 (position 131 in the EU numbering system) in the amino acid sequence of SEQ ID NO: 2 with another amino acid;
(c) substituting Arg at position 16 (position 133 in the EU numbering system) in the amino acid sequence of SEQ ID NO: 2 with another amino acid;
(d) substituting Cys at position 102 (position 219 in the EU numbering system) in the amino acid sequence of SEQ ID NO: 2 with another amino acid;
(e) substituting Glu at position 20 (position 137 in the EU numbering system) in the amino acid sequence of SEQ ID NO: 2 with another amino acid;
(f) substituting Ser at position 21 (position 138 in the EU numbering system) in the amino acid sequence of SEQ ID NO: 2 with another amino acid; and
(g) deleting Gly at position 325 and Lys at position 326 (positions 446 and 447 in the EU numbering system, respectively) in the amino acid sequence of SEQ ID NO: 2.

The type of amino acid after substitution is not particularly limited; however, substitutions of Val for Met at position 276 (position 397 in the EU numbering system), Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

The present invention further relates to methods for reducing the heterogeneity originated from the hinge region of IgG2 and/or methods for reducing antibody heterogeneity originated from C-terminus, all of which comprise in an IgG2 constant region comprising the amino acid sequence of SEQ ID NO: 2 (M40ΔGK), the steps of:
(a) substituting Cys at position 14 (position 131 in the EU numbering system) in the amino acid sequence of SEQ ID NO: 2 with another amino acid;
(b) substituting Arg at position 16 (position 133 in the EU numbering system) in the amino acid sequence of SEQ ID NO: 2 with another amino acid;
(c) substituting Cys at position 102 (position 219 in the EU numbering system) in the amino acid sequence of SEQ ID NO: 2 with another amino acid;
(d) substituting Glu at position 20 (position 137 in the EU numbering system) in the amino acid sequence of SEQ ID NO: 2 with another amino acid;
(e) substituting Ser at position 21 (position 138 in the EU numbering system) in the amino acid sequence of SEQ ID NO: 2 with another amino acid; and
(f) deleting Gly at position 325 and Lys at position 326 (positions 446 and 447 in the EU numbering system, respectively) in the amino acid sequence of SEQ ID NO: 2.

The type of amino acid after substitution is not particularly limited; however, substitutions of Ser for Cys at position 14 (position 131 in the EU numbering system), Lys for Arg at position 16 (position 133 in the EU numbering system), Ser for Cys at position 102 (position 219 in the EU numbering system), Gly for Glu at position 20 (position 137 in the EU numbering system), and Gly for Ser at position 21 (position 138 in the EU numbering system) are preferred.

The present invention also relates to methods for reducing antibody heterogeneity originated from the hinge region of IgG2, methods for improving pharmacokinetics, and/or methods for reducing antibody heterogeneity originated from C-terminus, all of which comprise in an IgG2 constant region comprising the amino acid sequence of SEQ ID NO: 2 (M58), the steps of:
(a) substituting Ser for Cys at position 14 (position 131 in the EU numbering system) in the amino acid sequence of SEQ ID NO: 2;
(b) substituting Lys for Arg at position 16 (position 133 in the EU numbering system) in the amino acid sequence of SEQ ID NO: 2;
(c) substituting Ser for Cys at position 102 (position 219 in the EU numbering system) in the amino acid sequence of SEQ ID NO: 2;

(d) substituting Gly for Glu at position 20 (position 137 in the EU numbering system) in the amino acid sequence of SEQ ID NO: 2;
(e) substituting Gly for Ser at position 21 (position 138 in the EU numbering system) in the amino acid sequence of SEQ ID NO: 2;
(f) substituting Gln for His at position 147 (position 268 in the EU numbering system) in the amino acid sequence of SEQ ID NO: 2;
(g) substituting Gln for Arg at position 234 (position 355 in the EU numbering system) in the amino acid sequence of SEQ ID NO: 2;
(h) substituting Glu for Gln at position 298 (position 419 in the EU numbering system) in the amino acid sequence of SEQ ID NO: 2; and
(i) deleting Gly at position 325 and Lys at position 326 (positions 446 and 447 in the EU numbering system, respectively) in the amino acid sequence of SEQ ID NO: 2.

The present invention also relates to methods for reducing antibody heterogeneity originated from the hinge region of IgG2, methods for improving pharmacokinetics, and/or methods for reducing antibody heterogeneity originated from C-terminus, all of which comprise in an IgG2 constant region comprising the amino acid sequence of SEQ ID NO: 2 (M73), the steps of:
(a) substituting Ser for Cys at position 14 (position 131 in the EU numbering system) in the amino acid sequence of SEQ ID NO: 2;
(b) substituting Lys for Arg at position 16 (position 133 in the EU numbering system) in the amino acid sequence of SEQ ID NO: 2;
(c) substituting Ser for Cys at position 102 (position 219 in the EU numbering system) in the amino acid sequence of SEQ ID NO: 2;
(d) substituting Gly for Glu at position 20 (position 137 in the EU numbering system) in the amino acid sequence of SEQ ID NO: 2;
(e) substituting Gly for Ser at position 21 (position 138 in the EU numbering system) in the amino acid sequence of SEQ ID NO: 2;
(f) substituting Gln for His at position 147 (position 268 in the EU numbering system) in the amino acid sequence of SEQ ID NO: 2;
(g) substituting Gln for Arg at position 234 (position 355 in the EU numbering system) in the amino acid sequence of SEQ ID NO: 2;
(h) substituting Glu for Gln at position 298 (position 419 in the EU numbering system) in the amino acid sequence of SEQ ID NO: 2;
(i) substituting Ala for Asn at position 313 (position 434 in the EU numbering system) in the amino acid sequence of SEQ ID NO: 2; and
(j) deleting Gly at position 325 and Lys at position 326 (positions 446 and 447 in the EU numbering system, respectively) in the amino acid sequence of SEQ ID NO: 2.

The methods of the present invention may comprise other steps such as amino acid substitution and deletion, as long as they comprise the steps described above. The methods for amino acid substitution and deletion are not particularly limited. The substitution and deletion can be achieved, for example, by site-directed mutagenesis described above or a method described in the Examples.

<Methods for Improving the Stability of an IgG4 Constant Region under Acidic Conditions>

The present invention also relates to methods for improving antibody stability under acidic conditions, which comprise the step of substituting Arg at position 289 (position 409 in the EU numbering system) of an IgG4 constant region comprising the amino acid sequence of SEQ ID NO: 3 with another amino acid. The methods of the present invention for improving antibody stability under acidic conditions may comprise other steps of amino acid substitution, as long as they comprise the step of substituting Arg at position 289 (position 409 in the EU numbering system) in the amino acid sequence of SEQ ID NO: 3 (human IgG4 constant region) with another amino acid. The type of amino acid after substitution is not particularly limited; however, substitution to Lys is preferred. The method for amino acid substitution is not particularly limited. The substitution can be achieved, for example, by site-directed mutagenesis described above or a method described in the Examples.

<Methods for Reducing the Heterogeneity Originated from Deletion of C-terminal Amino Acids in an IgG4 Constant Region>

The present invention also relates to methods for reducing the heterogeneity of an antibody, which comprise the step of deleting Gly at position 326 (position 446 in the EU numbering system) and Lys at position 327 (position 447 in the EU numbering system) in an IgG4 constant region comprising the amino acid sequence of SEQ ID NO: 3 (Mol. Immunol. 1993 January; 30(1):105-8). The methods of the present invention for reducing the heterogeneity may comprise other steps of amino acid substitution, as long as they comprise the step of deleting Lys at position 327 (position 447 in the EU numbering system) and/or Gly at position 326 (position 446 in the EU numbering system) in an IgG4 constant region comprising the amino acid sequence of SEQ ID NO: 3. The method for amino acid substitution is not particularly limited. The substitution can be achieved, for example, by site-directed mutagenesis described above or a method described in the Examples.

The present invention also relates to methods for improving the stability under acidic conditions, methods for reducing the heterogeneity originated from C-terminus, and/or methods for reducing the FcγR binding of an antibody, all of which comprise, in an IgG4 constant region comprising the amino acid sequence of SEQ ID NO: 3 (M11ΔGK), the steps of:
(a) substituting Cys at position 14 (position 131 in the EU numbering system) in the amino acid sequence of SEQ ID NO: 3 with another amino acid;
(b) substituting Arg at position 16 (position 133 in the EU numbering system) in the amino acid sequence of SEQ ID NO: 3 with another amino acid;
(c) substituting Glu at position 20 (position 137 in the EU numbering system) in the amino acid sequence of SEQ ID NO: 3 with another amino acid;
(d) substituting Ser at position 21 (position 138 in the EU numbering system) in the amino acid sequence of SEQ ID NO: 3 with another amino acid;
(e) substituting Arg at position 97 (position 214 in the EU numbering system) in the amino acid sequence of SEQ ID NO: 3 with another amino acid;
(f) substituting Ser at position 100 (position 217 in the EU numbering system) in the amino acid sequence of SEQ ID NO: 3 with another amino acid;
(g) substituting Tyr at position 102 (position 219 in the EU numbering system) in the amino acid sequence of SEQ ID NO: 3 with another amino acid;

(h) substituting Gly at position 103 (position 220 in the EU numbering system) in the amino acid sequence of SEQ ID NO: 3 with another amino acid;
(i) substituting Pro at position 104 (position 221 in the EU numbering system) in the amino acid sequence of SEQ ID NO: 3 with another amino acid;
(j) substituting Pro at position 105 (position 222 in the EU numbering system) in the amino acid sequence of SEQ ID NO: 3 with another amino acid;
(k) substituting Glu at position 113 (position 233 in the EU numbering system) in the amino acid sequence of SEQ ID NO: 3 with another amino acid;
(l) substituting Phe at position 114 (position 234 in the EU numbering system) in the amino acid sequence of SEQ ID NO: 3 with another amino acid;
(m) substituting Leu at position 115 (position 235 in the EU numbering system) in the amino acid sequence of SEQ ID NO: 3 with another amino acid;
(n) deleting Gly at position 116 (position 236 in the EU numbering system) in the amino acid sequence of SEQ ID NO: 3;
(o) substituting Arg at position 289 (position 409 in the EU numbering system) in the amino acid sequence of SEQ ID NO: 3 with another amino acid; and
(p) deleting Gly at position 236 and Lys at position 237 (positions 446 and 447 in the EU numbering system, respectively) in the amino acid sequence of SEQ ID NO: 3.

The type of amino acid after substitution is not particularly limited; however, substitutions of Ser for Cys at position 14 (position 131 in the EU numbering system), Lys for Arg at position 16 (position 133 in the EU numbering system), Gly for Glu at position 20 (position 137 in the EU numbering system), Gly for Ser at position 21 (position 138 in the EU numbering system), Thr for Arg at position 97 (position 214 in the EU numbering system), Arg for Ser at position 100 (position 217 in the EU numbering system), Ser for Tyr at position 102 (position 219 in the EU numbering system), Cys for Gly at position 103 (position 220 in the EU numbering system), Val for Pro at position 104 (position 221 in the EU numbering system), Glu for Pro at position 105 (position 222 in the EU numbering system), Pro for Glu at position 113 (position 233 in the EU numbering system), Val for Phe at position 114 (position 234 in the EU numbering system), Ala for Leu at position 115 (position 235 in the EU numbering system), and Lys for Arg at position 289 (position 409 in the EU numbering system) are preferred.

The methods of the present invention may comprise other steps, such as amino acid substitution and deletion, as long as they comprise the steps described above. The method for amino acid substitution and deletion are not particularly limited. The substitution and deletion can be achieved, for example, by site-directed mutagenesis described above or a method described in the Examples.

<Methods for Reducing the Heterogeneity Originated from Deletion of C-terminal Amino Acids in an IgG1 Constant Region>

The present invention also relates to methods for reducing antibody heterogeneity, which comprise the step of deleting Gly at position 329 (position 446 in the EU numbering system) and Lys at position 330 (position 447 in the EU numbering system) in an IgG1 constant region comprising the amino acid sequence of SEQ ID NO: 1. The methods of the present invention for reducing antibody heterogeneity may comprise other steps of amino acid substitutions, as long as they comprise the step of deleting Lys at position 330 (position 447 in the EU numbering system) and Gly at position 329 (position 446 in the EU numbering system) in an IgG1 constant region comprising the amino acid sequence of SEQ ID NO: 1. The method for amino acid substitution is not particularly limited. The substitution can be achieved, for example, by site-directed mutagenesis described above or a method described in the Examples.

The antibody constant regions described above are not particularly limited, and may be used for any antibodies. Examples of antibodies which use the constant region of the present invention include:
(a) a heavy chain that comprises the amino acid sequence of SEQ ID NO: 48 (VH4-M73);
(b) a heavy chain that comprises the amino acid sequence of SEQ ID NO: 46 (VH3-M73);
(c) a heavy chain that comprises the amino acid sequence of SEQ ID NO: 44 (VH5-M83);
(d) a light chain that comprises the amino acid sequence of SEQ ID NO: 49 (VL1-kappa);
(e) a light chain that comprises the amino acid sequence of SEQ ID NO: 47 (VL3-kappa);
(f) a light chain that comprises the amino acid sequence of SEQ ID NO: 45 (VL5-kappa);
(g) an antibody that comprises the heavy chain of (a) and the light chain of (d) (FV3-M73);
(h) an antibody that comprises the heavy chain of (b) and the light chain of (e) (FV4-M73); and
(i) an antibody that comprises the heavy chain of (c) and the light chain of (f) (FV5-M83).

<Pharmaceutical Compositions Comprising Antibodies>

The present invention provides pharmaceutical compositions comprising an antibody of the present invention.

The pharmaceutical compositions of the present invention can be formulated, in addition to the antibodies, with pharmaceutically acceptable carriers by known methods. For example, the compositions can be used parenterally, when the antibodies are formulated in a sterile solution or suspension for injection using water or any other pharmaceutically acceptable liquid. For example, the compositions can be formulated by appropriately combining the antibodies with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical implementations. The content of the active ingredient in such a formulation is adjusted so that an appropriate dose within the required range can be obtained.

Sterile compositions for injection can be formulated using vehicles such as distilled water for injection, according to standard protocols.

Aqueous solutions used for injection include, for example, physiological saline and isotonic solutions containing glucose or other adjuvants such as D-sorbitol, D-mannose, D-mannitol, and sodium chloride. These can be used in conjunction with suitable solubilizers such as alcohol, specifically ethanol, polyalcohols such as propylene glycol and polyethylene glycol, and non-ionic surfactants such as Polysorbate 80™ and HCO-50.

Oils include sesame oils and soybean oils, and can be combined with solubilizers such as benzyl benzoate or benzyl alcohol. These may also be formulated with buffers, for example, phosphate buffers or sodium acetate buffers; analgesics, for example, procaine hydrochloride; stabilizers, for example, benzyl alcohol or phenol; or antioxidants. The prepared injections are typically aliquoted into appropriate ampules.

The administration is preferably carried out parenterally, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected according to the age and symptoms of the patient. A single dose of the pharmaceutical composition containing an antibody or a polynucleotide encoding an antibody can be selected, for example, from the range of 0.0001 to 1,000 mg per kg of body weight. Alternatively, the dose may be, for example, in the range of 0.001 to 100,000 mg/person. However, the dose is not limited to these values. The dose and method of administration vary depending on the patient's body weight, age, and symptoms, and can be appropriately selected by those skilled in the art.

As used herein, the three-letter and single-letter codes for respective amino acids are as follows:
Alanine: Ala (A)
Arginine: Arg (R)
Asparagine: Asn (N)
Aspartic acid: Asp (D)
Cysteine: Cys (C)
Glutamine: Gln (Q)
Glutamic acid: Glu (E)
Glycine: Gly (G)
Histidine: His (H)
Isoleucine: Ile (I)
Leucine: Leu (L)
Lysine: Lys (K)
Methionine: Met (M)
Phenylalanine: Phe (F)
Proline: Pro (P)
Serine: Ser (S)
Threonine: Thr (T)
Tryptophan: Trp (W)
Tyrosine: Tyr (Y)
Valine: Val (V)

All prior art documents cited herein are incorporated by reference in their entirety.

EXAMPLES

Hereinbelow, the present invention is further specifically described with reference to the Examples, but it is not to be construed as being limited thereto.

Example 1

Improvement of the Stability of IgG2 and IgG4 Under Acidic Condition

Construction of Expression Vectors for IgG2- or IgG4-converted Humanized IL-6 Receptor Antibodies and Expression of the Antibodies To reduce the Fcγ receptor-binding activity, the constant region of a humanized anti-human IL-6 receptor antibody, humanized PM-1 antibody (Cancer Res. 1993 Feb. 15; 53(4):851-6), which is of the IgG1 isotype, was substituted with IgG2 or IgG4 (Mol. Immunol. 1993 January; 30(1): 105-8) to generate molecules WT-IgG2 (SEQ ID NO: 13) and WT-IgG4 (SEQ ID NO: 14). An animal cell expression vector was used to express the IgGs. An expression vector, in which the constant region of humanized PM-1 antibody (IgG1) used in Reference Example 1 was digested with NheI/NotI and then substituted with the IgG2 or IgG4 constant region by ligation, was constructed. The nucleotide sequence of each DNA fragment was determined with a DNA sequencer (ABI PRISM 3730xL DNA Sequencer or ABI PRISM 3700 DNA Sequencer (Applied Biosystems)) using the BigDye Terminator Cycle Sequencing Kit (Applied Biosystems) according to the attached instruction manual. Using the WT L chain (SEQ ID NO: 15), WT-IgG1, WT-IgG2, and WT-IgG4 were expressed by the method described below. Human embryonic kidney cancer-derived HEK293H cells (Invitrogen) were suspended in DMEM (Invitrogen) supplemented with 10% Fetal Bovine Serum (Invitrogen). The cells (10-ml/plate; cell density of 5 to $6 \times 10^5$ cells/ml) were plated on dishes for adherent cells (10 cm in diameter; CORNING) and cultured in a $CO_2$ incubator (37° C., 5% $CO_2$) for one whole day and night. Then, the medium was removed by aspiration, and 6.9 ml of CHO-S-SFM-II medium (Invitrogen) was added. The prepared plasmid DNA mixture (13.8 μg in total) was combined with 20.7 μl of 1 μg/ml Polyethylenimine (Polysciences Inc.) and 690 μl of CHO-S-SFMII medium. The resulting mixture was incubated at room temperature for 10 minutes, and then added to the cells in each dish. The cells were incubated in a $CO_2$ incubator (at 37° C. under 5% $CO_2$) for 4 to 5 hours. Then, 6.9 ml of CHO-S-SFM-II medium (Invitrogen) was added to the dishes, and the cells were incubated in a $CO_2$ incubator for three days. The culture supernatants were collected and centrifuged (approx. 2000 g, 5 min, room temperature) to remove the cells, and sterilized through 0.22-μm filter MILLEX®-GV (Millipore). The samples were stored at 4° C. until use.

(1) Humanized PM-1 antibody (PM-1 VH+IgG1) H chain, SEQ ID NO: 12 (amino acid sequence)
(2) Humanized PM-1 VH+IgG2 H chain, SEQ ID NO: 13 (amino acid sequence)
(3) Humanized PM-1 VH+IgG4 H chain, SEQ ID NO: 14 (amino acid sequence)

Purification of WT-IgG1, WT-IgG2, and WT-IgG4 through Elution from Protein A using Hydrochloric Acid 50 μl of rProtein A Sepharose™ Fast Flow (Amersham Biosciences) suspended in TBS was added to the obtained culture supernatants, and the combined solutions were mixed by inversion at 4° C. for four hours or more. The solutions were transferred into 0.22-μm filter cups of Ultrafree®-MC (Millipore). After washing three times with 500 μl of TBS, the rProtein A Sepharose™ resins were suspended in 100 μl of 10 mM HCl/150 mM NaCl (pH 2.0) and the mixtures were incubated for two minutes to elute the antibodies (hydrochloric acid elution). Immediately, the eluates were neutralized by adding 6.7 μl of 1.5 M Tris-HCl (pH 7.8). The elution was carried out twice, yielding 200 μl of purified antibodies.

Gel Filtration Chromatography Analysis of WT-IgG1, WT-IgG2, and WT-IgG4 Purified by Hydrochloric Acid Elution The contents of aggregate in the purified samples obtained by hydrochloric acid elution were assessed by gel filtration chromatography analysis.

Aggregation Assessment Method:
 System: Waters Alliance
 Column: G3000SWxl (TOSOH)
 Mobile phase: 50 mM sodium phosphate, 300 mM KCl pH 7.0
 Flow rate, wavelength: 0.5 ml/min, 220 nm The result is shown in FIG. 1. While the content of aggregate in WT-IgG1 after purification was about 2%, those of WT-IgG2 and WT-IgG4 after purification were about 25%. This suggests that IgG1 is stable to acid during hydrochloric acid elution, and by contrast, IgG2 and IgG4 are unstable and underwent denaturation/aggregation. Thus, the stability of IgG2 and IgG4 under acidic condition was demonstrated to be lower than that of IgG1. Protein A has been frequently used to purify IgG molecules, and the IgG molecules are eluted from Protein A under acidic condition. In addition, virus inactivation, which is required when developing IgG molecules as pharmaceuticals, is generally carried out under acidic condition. It is thus desirable that the stability of IgG molecules under acidic condition is higher. However, the stability of IgG2 and IgG4 molecules under acidic condition was found to be lower than that of IgG1, and suggests for the first time that there is a problem of denaturation/aggregation under acidic condition in developing IgG2 and IgG4 molecules as pharmaceuticals. It is desirable that this problem of denaturation/aggregation be overcome when developing them as pharmaceuticals. To date, however, no report has been published on a method for solving this problem through amino acid substitution.

Preparation and Assessment of WT-IgG2 and WT-IgG4 having an Altered CH3 Domain

The stability of IgG2 and IgG4 molecules under acidic condition was demonstrated to be lower than that of IgG1. Thus, altered forms of IgG2 and IgG4 molecules were tested to improve the stability under acidic condition. According to models for the constant regions of IgG2 and IgG4 molecules, one of the potential destabilizing factors under acidic condition was thought to be the instability at the CH3-CH3 domain interface. Methionine at position 397 in the EU numbering system in IgG2, or arginine at position 409 in the EU numbering system in IgG4 was thought to destabilize the CH3/CH3 interface. Since positions 397 and 409 of IgG1 in the EU numbering system are valine and lysine, respectively, an altered IgG2 antibody that comprises the substitution of valine for methionine at position 397 in the EU numbering system (IgG2-M397V, SEQ ID NO: 16 (amino acid sequence)) and an altered IgG4 antibody that comprises the substitution of lysine for arginine at position 409 in the EU numbering system (IgG4-R409K, SEQ ID NO: 17 (amino acid sequence)) are prepared.

The methods used for constructing expression vectors for the antibodies of interest, and expressing and purifying the antibodies, were the same as those used for the hydrochloric acid elution described above. Gel filtration chromatography analysis was carried out to estimate the contents of aggregate in the purified samples obtained by hydrochloric acid elution from Protein A.

Aggregation Assessment Method:
  System: Waters Alliance
  Column: G3000SWxl (TOSOH)
  Mobile phase: 50 mM sodium phosphate, 300 mM KCl, pH 7.0
  Flow rate, wavelength: 0.5 ml/min, 220 nm The result is shown in FIG. 1. While the content of aggregate in WT-IgG1 after purification was about 2%, those in WT-IgG2 and WT-IgG4 after purification were about 25%. By contrast, the contents of aggregate in variants with altered CH3 domain, IgG2-M397V and IgG4-R409K, were comparable (approx. 2%) to that in IgG1. This finding demonstrates that the stability of an IgG2 or IgG4 antibody under acidic condition can be improved by substituting valine for methionine of IgG2 at position 397 in the EU numbering system or lysine for arginine of IgG4 at position 409 in the EU numbering system, respectively. The purified antibodies of were dialyzed against a solution of 20 mM sodium acetate, 150 mM NaCl, pH 6.0 (EasySEP, TOMY). DSC measurement (measurements of midpoint temperature and Tm value) was carried out at a heating rate of 1° C./min from 40 to 100° C. at a protein concentration of about 0.1 mg/ml. Furthermore, the midpoint temperatures of thermal denaturation of WT-IgG2, WT-IgG4, IgG2-M397V, and IgG4-R409K were determined. The result showed that the Tm value for the altered CH3 domain was higher in IgG2-M397V and IgG4-R409K as compared to WT-IgG2 and WT-IgG4, respectively. This suggests that IgG2-M397V and IgG4-R409K are also superior in terms of thermal stability as compared to WT-IgG2 and WT-IgG4, respectively.

IgG2 and IgG4 are exposed to acidic condition in virus inactivation process and in the purification process using Protein A. Thus, denaturation/aggregation in the above processes was problematic. However, it was discovered that the problem could be solved by using IgG2-M397V and IgG4-R409K for the sequences of IgG2 and IgG4 constant regions. Thus, these alterations were revealed to be very useful in developing IgG2 and IgG4 antibody pharmaceuticals. Furthermore, the usefulness of IgG2-M397V and IgG4-R409K was also demonstrated by the finding that they are superior in thermal stability.

Example 2

Improvement of Heterogeneity Derived from Disulfide Bonds in IgG2

Purification of WT-IgG1, WT-IgG2, and WT-IgG4 through Acetic Acid Elution from Protein A 50 μl of rProtein A Sepharose™ Fast Flow (Amersham Biosciences) suspended in TBS was added to the culture supernatants obtained in Example 1, and the combined solutions were mixed by inversion at 4° C. for four hours or more. The solutions were transferred into 0.22-μm filter cups of Ultrafree®-MC (Millipore). After washing three times with 500 μl of TBS, the rProtein A Sepharose™ resins were suspended in 100 μl of aqueous solution of 50 mM sodium acetate (pH 3.3) and the mixtures were incubated for two minutes to elute the antibodies. Immediately, the eluates were neutralized by adding 6.7 μl of 1.5 M Tris-HCl (pH 7.8). The elution was carried out twice, yielding 200 μl of purified antibodies.

Analysis of WT-IgG1, WT-IgG2, and WT-IgG4 by Cation Exchange Chromatography (IEC)

Purified WT-IgG1, WT-IgG2, and WT-IgG4 were analyzed for homogeneity by cation exchange chromatography.

Assessment Method using IEC:
  System: Waters Alliance
  Column: ProPac WCX-10 (Dionex)
  Mobile phase A: 25 mM MES-NaOH, pH 6.1
    B: 25 mM MES-NaOH, 250 mM Na-Acetate, pH 6.1
  Flow rate, wavelength: 0.5 ml/min, 280 nm
  GradientB: 50%-75% (75 min) in the analysis of WT-IgG1
    B: 30%-55% (75 min) in the analysis of WT-IgG2 and WT-IgG4

Figure 2:
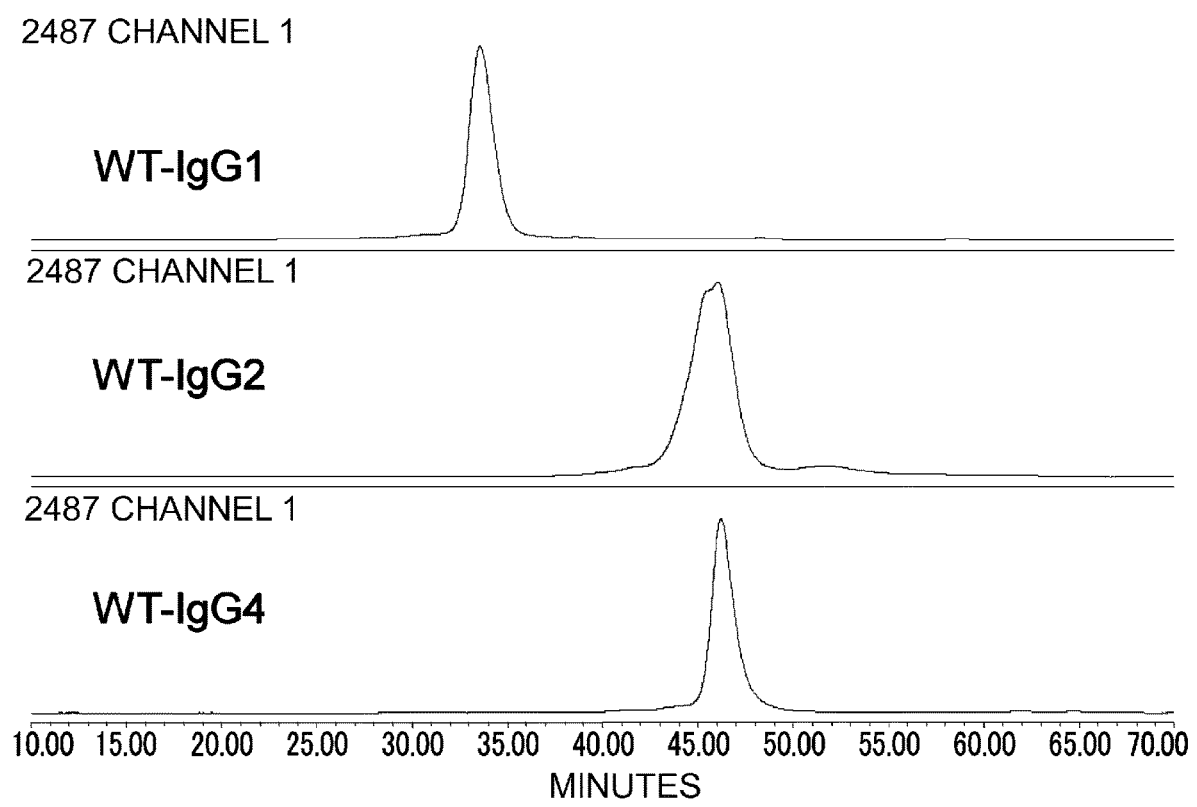
FIG. 2 is a diagram showing the result of cation exchange chromatography (IEC) analysis of WT-IgG1, WT-IgG2, and WT-IgG4.

The result is shown in FIG. 2. WT-IgG2 showed more than one peak in the ion exchange analysis while WT-IgG1 and WT-IgG4 exhibited a single peak. This suggests that the IgG2 molecule is more heterogeneous as compared to IgG1 and IgG4. Indeed, IgG2 isotypes have been reported to have heterogeneity derived from disulfide bonds in the hinge region (Non-patent Document 10). Thus, the hetero-peaks of IgG2 shown in FIG. 2 are also assumed to be objective substance/related substances derived from the disulfide bonds. It is not easy to manufacture them as a pharmaceutical in large-scale while maintaining the objective substances/related substances related heterogeneity between productions. Thus, homogeneous (less heterogeneous) substances are desirable as much as possible for antibody molecules developed as pharmaceuticals. For wild type IgG2, there is a problem of homogeneity which is important in developing antibody pharmaceuticals. Indeed, US20060194280 (A1) has shown that natural IgG2 gives various hetero-peaks as a result of the disulfide bonds in ion exchange chromatography analysis, and that the biological activity varies among these peaks. US20060194280 (A1) reports refolding in the purification process as a method for combining the hetero-peaks into a single one, but use of such a process in the production is costly and complicated. Thus, a preferred method for combining the hetero-peaks into a single one is based on amino acid substitution. Although the heterogeneity originated from disulfide bonds in the hinge region should be overcome to develop IgG2 as pharmaceuticals, no report has been published to date on a method for solving this problem through amino acid substitution.

Preparation and Assessment of Altered WT-IgG2 CH1 Domain and Hinge Region

Figure 3:
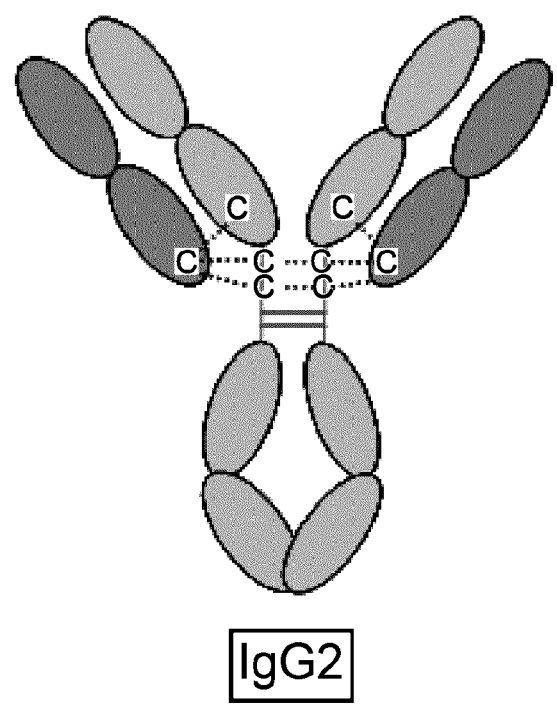
FIG. 3 is a diagram showing predicted disulfide bonding in the hinge region of WT-IgG2.

As shown in FIG. 3, there are various potential disulfide bond patterns for an IgG2 molecule. Possible causes of the heterogeneity derived from the hinge region of IgG2 were differential pattern of disulfide bonding and free cysteines. IgG2 has two cysteines (at positions 219 and 220 in the EU numbering system) in the upper hinge region, and cysteines adjacent to the two upper-hinge cysteines include cysteine at position 131 in the EU numbering system in the H chain CH1 domain and L chain C-terminal cysteine, and two corresponding cysteines in the H chain upper hinge of the dimerization partner. Specifically, there are eight cysteines in total in the vicinity of the upper hinge region of IgG2 when the antibody is in the associated form of H2L2. This may be the reason for the various heterogeneous patterns due to wrong disulfide bonding and free cysteines.

Figure 4:
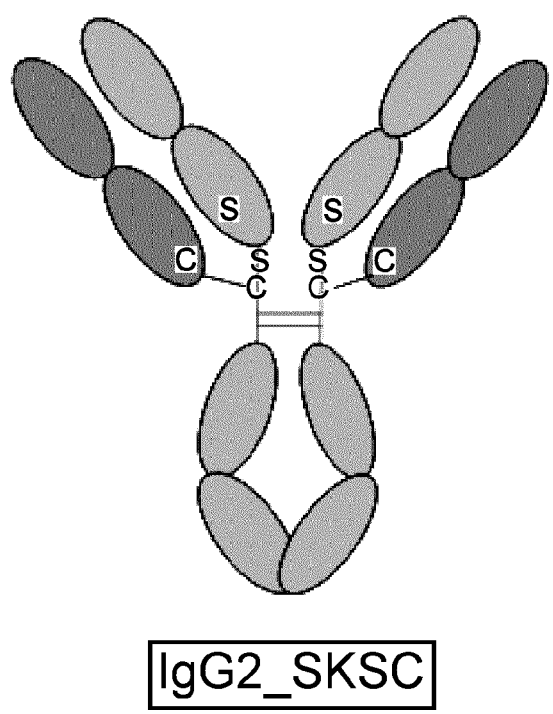
FIG. 4 is a diagram showing predicted disulfide bonding in the hinge region of IgG2-SKSC.

The hinge region sequence and CH1 domain of IgG2 were altered to reduce the heterogeneity originated from the IgG2 hinge region. Examinations were conducted to avoid the heterogeneity of IgG2 due to differential pattern of disulfide bonding and free cysteines. The result of examining various altered antibodies suggested that the heterogeneity could be avoided without decreasing the thermal stability by substituting serine and lysine for cysteine and arginine at positions 131 and 133 in the EU numbering system, respectively, in the H chain CH1 domain, and substituting serine for cysteine at position 219, EU numbering, in the upper hinge of H chain of the wild type IgG2 constant region sequence (hereinafter IgG2-SKSC) (IgG2-SKSC, SEQ ID NO: 18). These substitutions would enable IgG2-SKSC to form a homogenous covalent bond between H and L chains, which is a disulfide bond between the C-terminal cysteine of the L chain and cysteine at position 220 in the EU numbering system (FIG. 4).

The methods described in Reference Example 1 were used to construct an expression vector for IgG2-SKSC and to express and purify IgG2-SKSC. The purified IgG2-SKSC and wild type IgG2 (WT-IgG2) were analyzed for homogeneity by cation exchange chromatography.

Assessment Method using IEC:
 System: Waters Alliance
 Column: ProPac WCX-10 (Dionex)
 Mobile phase A: 25 mM MES-NaOH, pH 5.6
 B: 25 mM MES-NaOH, 250 mM Na-Acetate, pH 5.6
 Flow rate, wavelength: 0.5 ml/min, 280 nm
 Gradient B: 50%-100% (75 min)

Figure 5:
FIG. 5 is a diagram showing the result of cation exchange chromatography (IEC) analysis of WT-IgG2 and IgG2-SKSC.

The result is shown in FIG. 5. As expected above, IgG2-SKSC was shown to be eluted at a single peak while WT-IgG2 gave multiple peaks. This suggests that the heterogeneity derived from disulfide bonds in the hinge region of IgG2 can be avoided by using alterations such as those used to generate IgG2-SKSC, which allow formation of a single disulfide bond between the C-terminal cysteine of the L chain and cysteine at position 220 in the EU numbering system. The midpoint temperatures of thermal denaturation of WT-IgG1, WT-IgG2, and IgG2-SKSC were determined by the same methods as described in Example 1. The result showed that WT-IgG2 gave a peak for Fab domain which has a lower Tm value than WT-IgG1, while IgG2-SKSC did not give such a peak. This suggests that IgG2-SKSC is also superior in thermal stability as compared to WT-IgG2.

Although wild type IgG2 was thought to have a homogeneity problem which is important in developing antibody pharmaceuticals, it was found that this problem could be solved by using IgG2-SKSC for the constant region sequence of IgG2. Thus, IgG2-SKSC is very useful in developing IgG2 antibody pharmaceuticals. Furthermore, the usefulness of IgG2-SKSC was also demonstrated by the finding that it is superior in thermal stability.

Example 3

Improvement of C-terminal Heterogeneity in IgG Molecules

Construction of an Expression Vector for H Chain C-terminal ΔGK Antibody from WT-IgG1

For heterogeneity of the C-terminal sequences of an antibody, deletion of C-terminal amino acid lysine residue, and amidation of the C-terminal amino group due to deletion of both of the two C-terminal amino acids, glycine and lysine, have been reported (Non-patent Document 12). The absence of such heterogeneity is preferred when developing antibody pharmaceuticals. Actually, in humanized PM-1 antibody TOCILIZUMAB, the major component is the sequence that lacks the C-terminal amino acid lysine, which is encoded by the nucleotide sequence but deleted in post-translational modification, and the minor component having the lysine also coexists as heterogeneity. Thus, the C-terminal amino acid sequence was altered to reduce the C-terminal heterogeneity. Specifically, the present inventors altered the nucleotide sequence of wild type IgG1 to delete the C-terminal lysine and glycine from the H chain constant region of the IgG1, and assessed whether the amidation of the C-terminal amino group could be suppressed by deleting the two C-terminal amino acids glycine and lysine.

Mutations were introduced into the C-terminal sequence of the H chain using pB-CH vector encoding the humanized PM-1 antibody (WT) obtained in Reference Example 1. The nucleotide sequence encoding Lys at position 447 and/or Gly at position 446 in the EU numbering system was converted into a stop codon by introducing a mutation using the QuikChange Site-Directed Mutagenesis Kit (Stratagene) according to the method described in the attached instruction manual. Thus, expression vectors for antibody engineered to lack the C-terminal amino acid lysine (position 447 in the EU numbering system) and antibody engineered to lack the two C-terminal amino acids glycine and lysine (positions 446 and 447 in the EU numbering system, respectively) were constructed. H chain C-terminal ΔK and ΔGK antibodies were obtained by expressing the engineered H chains and the L chain of the humanized PM-1 antibody. The antibodies were expressed and purified by the method described in Reference Example 1.

Purified H chain C-terminal ΔGK antibody was analyzed by cation exchange chromatography according to the following procedure. The effect of the C-terminal deletion on heterogeneity was assessed by cation exchange chromatography analysis using the purified H chain C-terminal ΔGK antibody according to the method described below. The conditions of cation exchange chromatography analysis are described below. Chromatograms for humanized PM-1 antibody, H chain C-terminal ΔK antibody, and H chain C-terminal ΔGK antibody were compared.

Figure 6:
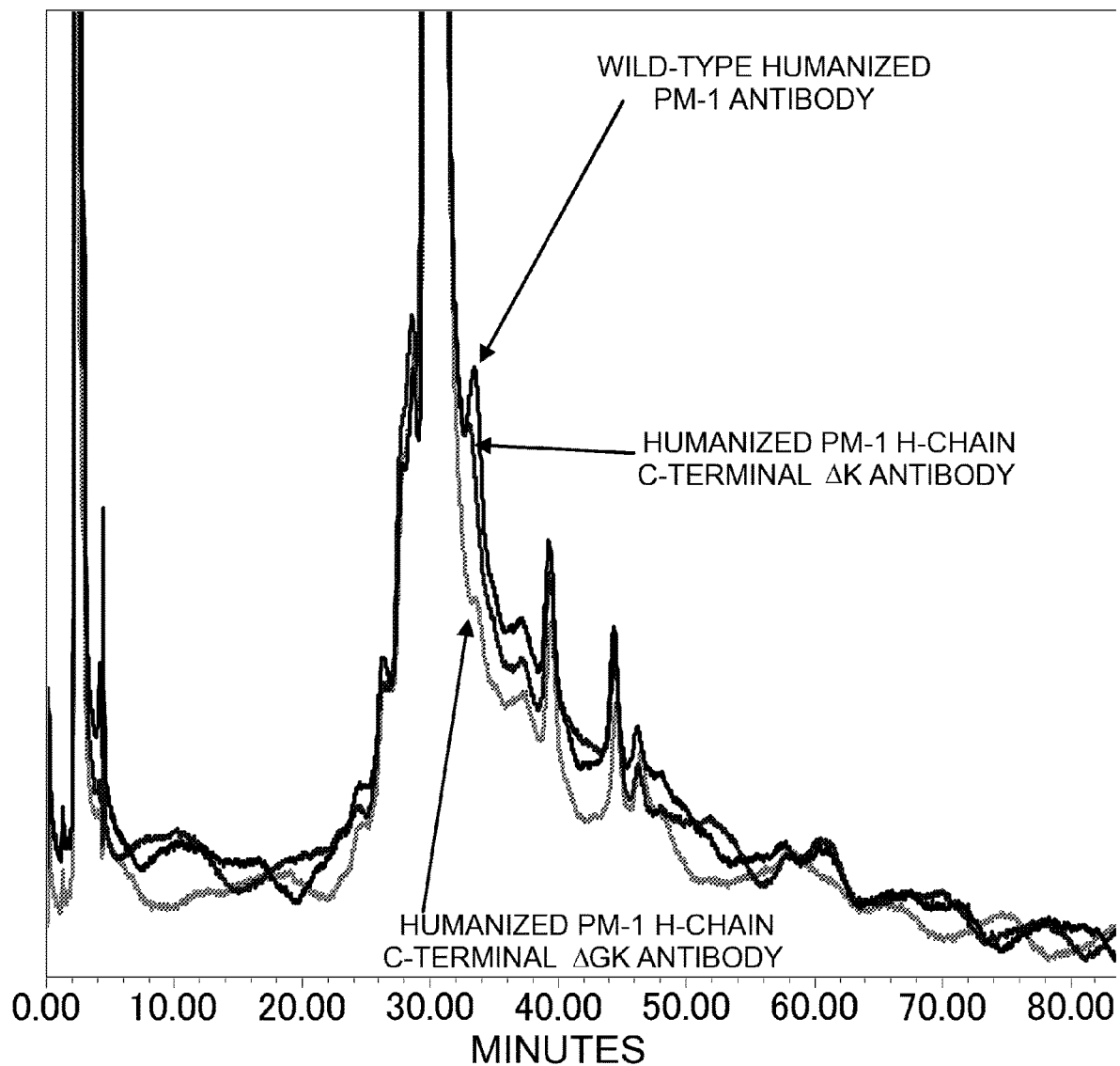
FIG. 6 is a diagram showing the result of cation exchange chromatography (IEC) analysis of humanized PM-1 antibody, H chain C-terminal ΔK antibody, and H chain C-terminal ΔGK antibody.

Column: ProPac WCX-10 (Dionex)
Mobile phase A: 25 mmol/l MES/NaOH, pH 6.1
    B: 25 mmol/l MES/NaOH, 250 mmol/l NaCl, pH 6.1
Flow rate: 0.5 ml/min
Gradient: 25% B (5 min)->(105 min)->67% B->(1 min)->100% B (5 min)
Detection: 280 nm The analysis result for the non-altered humanized PM-1 antibody, H chain C-terminal ΔK antibody, and H chain C-terminal ΔGK antibody is shown in FIG. 6. Non-patent Document 10 reports a basic peak with more prolonged retention time than that of the main peak. Analysis of a basic peak corresponding to that reported in Non-patent Document 10 shows that the basic peak contains an H chain C terminus with Lys at position 449 and an H chain C terminus with amidated Pro at position 447. The intensity of the basic peak was significantly reduced in the H chain C-terminal ΔGK antibody, while no such significant reduction was observed in the H chain C-terminal ΔK antibody. This suggests that the C-terminal heterogeneity of the H chain can be reduced only when the two C-terminal amino acids are deleted from the H chain.

The temperature of thermal denaturation of the H chain C-terminal ΔGK antibody was determined by DSC to assess the effect of the deletion of the two residues at the H chain C terminus on thermal stability. For the DSC measurement, the antibody was dialyzed against 20 mM acetic acid buffer (pH 6.0) containing 150 mM NaCl to change the buffer. After thorough deaeration, the humanized PM-1 antibody and H chain C-terminal ΔGK antibody solutions, and the reference solution (outer dialysate) were enclosed in calorimetric cells, and thoroughly thermally equilibrated at 40° C. Then, the samples were scanned at from 40 to 100° C. with a rate of about 1K/min. The resulting denaturation peaks were assigned (Rodolfo et al., Immunology Letters, 1999, p 47-52). The result showed that the C-terminal deletion had no effect on the thermal denaturation temperature of CH3 domain.

Thus, the heterogeneity originated from the C-terminal amino acid can be reduced without affecting the thermal stability of antibody by deleting the C-terminal lysine and glycine from the H chain constant region at the nucleotide sequence level. Since all of the constant regions of human antibodies IgG1, IgG2, and IgG4 contain Gly and Lys at positions 446 and 447 in the EU numbering system in their C-terminal sequences, the method for reducing the C-terminal amino acid heterogeneity discovered in this example and others is also expected to be applicable to IgG2 and IgG4 constant regions.

Example 4

Construction of M14ΔGK with a Novel Optimized Constant Region Sequence

When an antibody pharmaceutical is aimed at neutralizing an antigen, effector functions such as ADCC of Fc domain are unnecessary and therefore the binding to Fcγ receptor is unnecessary. The binding to Fcγ receptor is assumed to be unfavorable from the perspectives of immunogenicity and adverse effect (Non-patent Documents 5 and 6). The humanized anti-IL-6 receptor IgG1 antibody TOCILIZUMAB does not need to bind to Fcγ receptor, because it only needs to specifically bind to IL-6 receptor and neutralize its biological activity in order to be used as a therapeutic agent for diseases associated with IL-6, such as rheumatoid arthritis.

Construction and Assessment of M14ΔGK, M11ΔGK, and M17ΔGK, Fcγ Receptor-nonbinding, Optimized Constant Regions A possible method for impairing the Fcγ receptor binding is to convert the IgG antibody from IgG1 isotype to IgG2 or IgG4 isotype (Ann. Hematol. 1998 June; 76(6):231-48). As a method for completely eliminating the binding to Fcγ receptor, a method of introducing an artificial alteration into Fc domain has been reported. For example, since the effector functions of anti-CD3 antibody and anti-CD4 antibody cause adverse effects, amino acid mutations that are not present in the wild type sequence have been introduced into the Fcγ receptor-binding region of Fc domain (Non-patent Documents 3 and 7), and the resulting Fcγ receptor-nonbinding anti-CD3 and anti-CD4 antibodies are currently under clinical trials (Non-patent Documents 5 and 8). According to another report (Patent Document 3), Fcγ receptor-nonbinding antibodies can be prepared by converting the FcγR-binding domain of IgG1 (at positions 233, 234, 235, 236, 327, 330, and 331 in the EU numbering system) into the sequence of IgG2 (at positions 233, 234, 235, and 236 in the EU numbering system) or IgG4 (at positions 327, 330, and 331 in the EU numbering system). However, if all of the above mutations are introduced into IgG1, novel peptide sequences of nine amino acids, which potentially serve as non-natural T-cell epitope peptides, will be generated, and this increases the immunogenicity risk. The immunogenicity risk should be minimized in developing antibody pharmaceuticals.

To overcome the above problem, alterations in the IgG2 constant region were considered. In the FcγR-binding domain of IgG2 constant region, residues at positions 327, 330, and 331 in the EU numbering system are different from the nonbinding sequence of IgG4 while those at positions 233, 234, 235, and 236 in the EU numbering system are amino acids of nonbinding type. Thus, it is necessary to alter the amino acids at positions 327, 330, and 331 in the EU numbering system to the sequence of IgG4 (G2Δa described in Eur. J. Immunol. 1999 August; 29(8):2613-24). However, since the amino acid at position 339 in the EU numbering system in IgG4 is alanine while the corresponding residue in IgG2 is threonine, a simple alteration of the amino acids at positions 327, 330, and 331 in the EU numbering system to the sequence of IgG4 unfavorably generates a novel peptide sequence of 9 amino acids, potentially serving as a non-natural T-cell epitope peptide, and thus increases the immunogenicity risk. Then, the present inventors found that the generation of novel peptide sequence could be prevented by introducing the substitution of alanine for threonine at position 339 in the EU numbering system in IgG2, in addition to the alteration described above.

In addition to the mutations described above, other mutations were introduced, and they were the substitution of valine for methionine at position 397 in the EU numbering system in IgG2, which was discovered in Example 1 to improve the stability of IgG2 under acidic condition; and the substitution of serine for cysteine at position 131 in the EU numbering system, the substitution of lysine for arginine at position 133 in the EU numbering system, and the substitution of serine for cysteine at position 219 in the EU numbering system, which were discovered in Example 2 to improve the heterogeneity originated from disulfide bonds in the hinge region. Furthermore, since the mutations at positions 131 and 133 generate a novel peptide sequence of 9 amino acids, potentially serving as a non-natural T-cell epitope peptide, and thus generate the immunogenicity risk, the peptide sequence around positions 131 to 139 was converted into a natural human sequence by introducing the substitution of glycine for glutamic acid at position 137 in the EU numbering system and the substitution of glycine for serine at position 138 in the EU numbering system. Furthermore, glycine and lysine at positions 446 and 447 in the EU numbering system were deleted from the C terminus of H chain to reduce the C-terminal heterogeneity. The constant region sequence having all of the mutations introduced was named M14ΔGK (M14ΔGK, SEQ ID NO: 5). Although there is a mutation of cysteine at position 219 to serine in M14ΔGK as a novel 9-amino acid peptide sequence which potentially serves as a T-cell epitope peptide, the immunogenicity risk was considered very low since the amino acid property of serine is similar to that of cysteine. The immunogenicity prediction by TEPITOPE also suggested that there was no difference in immunogenicity.

An expression vector for the antibody H chain sequence whose variable region was WT and constant region was M14ΔGK (M14ΔGK, SEQ ID NO: 5; WT-M14ΔGK, SEQ ID NO: 19) was constructed by the method described in Reference Example 1. An antibody having WT-M14ΔGK as H chain and WT as L chain was expressed and purified by the method described in Reference Example 1.

Furthermore, in WT-M11ΔGK (M11ΔGK, SEQ ID NO: 8; WT-M11ΔGK, SEQ ID NO: 21), mutations were introduced with the same method into the IgG4 constant region at positions 233, 234, 235, and 236 in the EU numbering system (G4Δb described in Eur. J. Immunol. 1999 August; 29(8):2613-24; this alteration newly generates non-human sequence and thus increases the immunogenicity risk) to reduce the Fcγ receptor binding. In addition to the above alteration, to reduce the immunogenicity risk, mutations were introduced at positions 131, 133, 137, 138, 214, 217, 219, 220, 221, and 222 in the EU numbering system so that the pattern of disulfide bonding in the hinge region was the same as that of M14ΔGK; a mutation was introduced at position 409 in the EU numbering system (Example 1) to improve the stability under acidic condition; and the amino acids at positions 446 and 447 in the EU numbering system were deleted (Example 3) to reduce the C-terminal heterogeneity.

Furthermore, WT-M17ΔGK (M17ΔGK, SEQ ID NO: 10; WT-M17ΔGK, SEQ ID NO: 20) was constructed by introducing mutations into the IgG1 constant region at positions 233, 234, 235, 236, 327, 330, 331, and 339 in the EU numbering system (G1Δab described in Eur. J. Immunol. 1999 August; 29(8):2613-24) to impair the Fcγ receptor binding and by deleting the amino acids at positions 446 and 447 in the EU numbering system to reduce the C-terminal heterogeneity (Example 3).

WT-M17ΔGK or WT-M11ΔGK was used as the H chain, and WT was used as the L chain. These antibodies were expressed and purified by the method described in Example 1.

Assessment of WT-M14ΔGK, WT-M17ΔGK, and WT-M11ΔGK for Fcγ Receptor Binding

Figure 7:
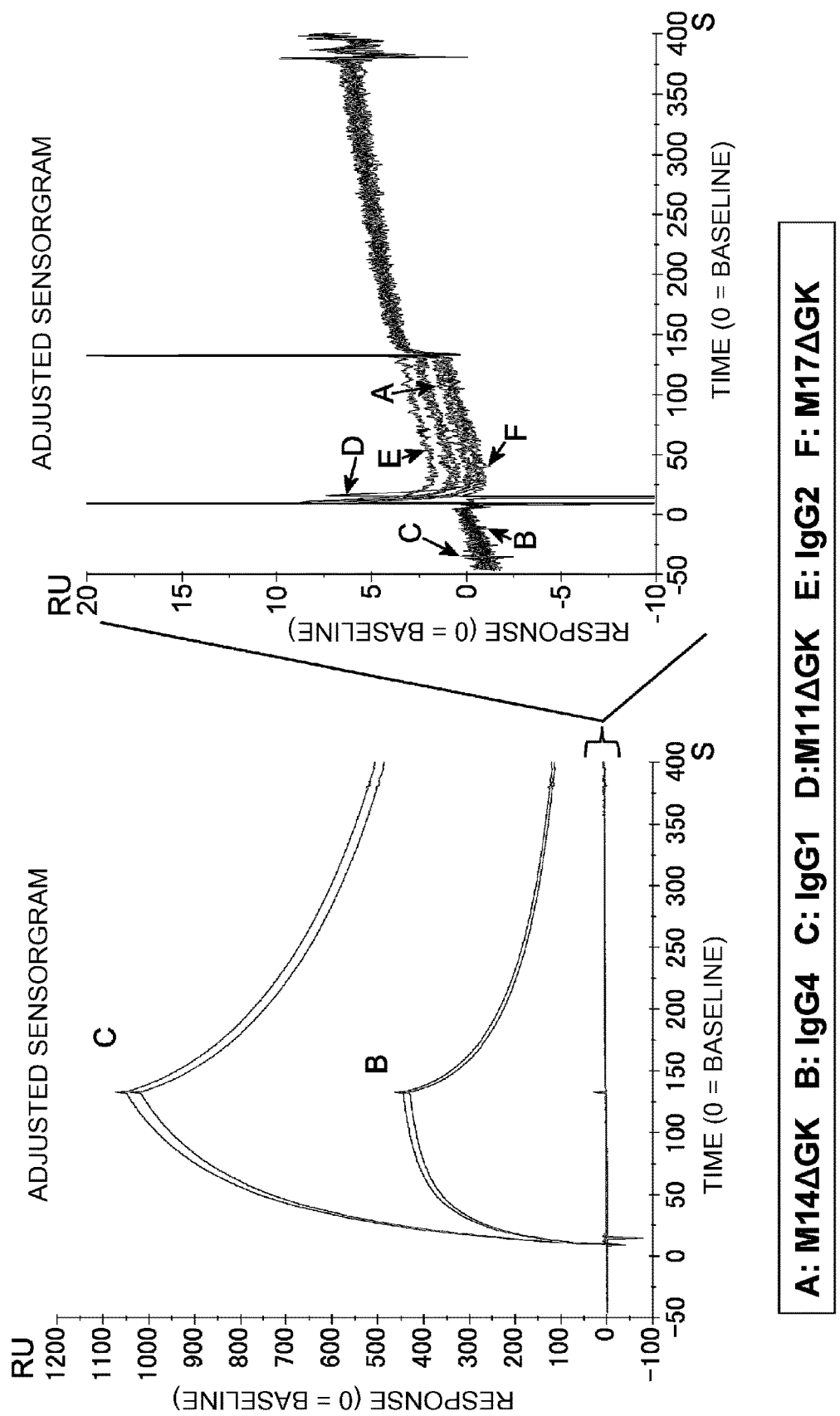
FIG. 7 shows comparison of the amounts WT-IgG1, WT-IgG2, WT-IgG4, WT-M14ΔGK, WT-M17ΔGK, and WT-M11ΔGK bound to FcγRI.

The FcγRI binding was assessed by the procedure described below. Using Biacore T100, human-derived Fcγ receptor I (hereinafter FcγRI) immobilized onto a sensor chip was allowed to interact with IgG1, IgG2, IgG4, M11ΔGK, M14ΔGK, or M1ΔGK 7 as an analyte. The amounts of bound antibody were compared. The measurement was conducted using Recombinant Human FcRIA/CD64 (R&D systems) as human-derived FcγRI, and IgG1, IgG2, IgG4, M11ΔGK, M14ΔGK, and M17ΔGK as samples. FcγRI was immobilized onto the sensor chip CM5 (BIACORE) by the amine coupling method. The final amount of immobilized hFcγRI was about 13000 RU. The running buffer used was HBS-EP+, and the flow rate was 20 µl/min. The sample concentration was adjusted to 100 µg/ml using HBS-EP+. The analysis included two steps: two minutes of association phase where 10 µl of an antibody solution was injected and the subsequent four minutes of dissociation phase where the injection was switched with HBS-EP+. After the dissociation phase, the sensor chip was regenerated by injecting 20 µl of 5 mM sodium hydroxide. The association, dissociation, and regeneration constitute one analysis cycle. Various antibody solutions were injected to obtain sensorgrams. As analytes, IgG4, IgG2, IgG1, M11, M14, and M17 were injected in this order. This series of injection was repeated twice. The result of comparison of data on the determined amounts of bound antibody is shown in FIG. 7. The comparison shows that the amount of bound antibody is reduced in the order of: IgG1>IgG4>>IgG2=M11ΔGK=M14ΔGK=M17ΔGK.

Thus, it was revealed that the FcγRI binding of wild type IgG2, M11ΔGK, M14ΔGK, and M17ΔGK was weaker than that of wild type IgG1 and IgG4.

Figure 8:
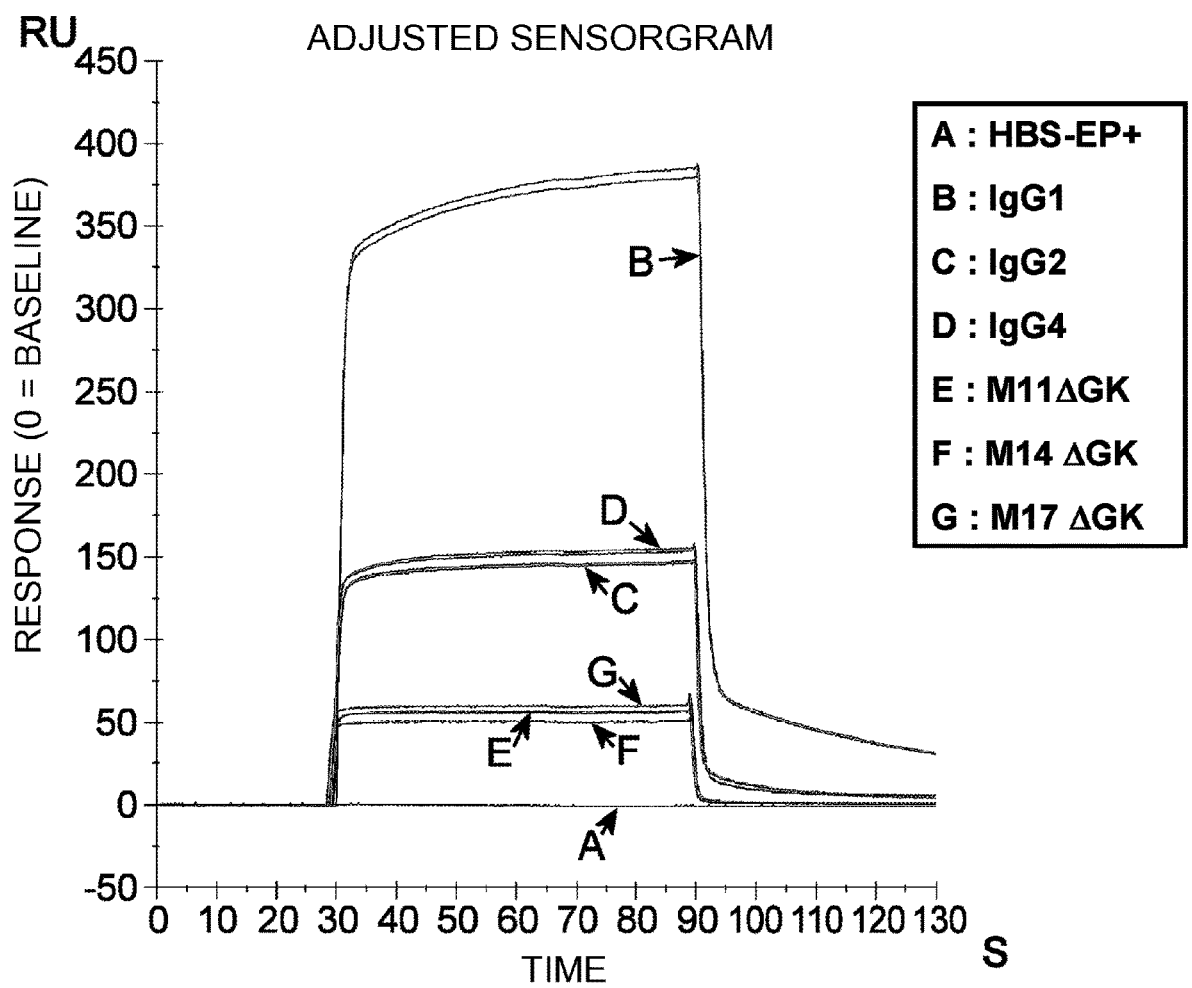
FIG. 8 is a graph showing comparison of the amounts WT-IgG1, WT-IgG2, WT-IgG4, WT-M14ΔGK, WT-M17ΔGK, and WT-M11ΔGK bound to FcγRIIa.

The FcγRIIa binding was assessed by the procedure described below. Using Biacore T100, human-derived Fcγ receptor IIa (hereinafter FcγRIIa) immobilized onto a sensor chip was allowed to interact with IgG1, IgG2, IgG4, M11ΔGK, M14ΔGK, or M17ΔGK as an analyte. The amounts of bound antibody were compared. The measurement was conducted using Recombinant Human FcRIIA/CD32a (R&D systems) as human-derived FcγRIIa, and IgG1, IgG2, IgG4, M11ΔGK, M14ΔGK, and M17ΔGK as samples. FcγRIIa was immobilized onto the sensor chip CM5 (BIACORE) by the amine coupling method. The final amount of immobilized FcγRIIa was about 3300 RU. The running buffer used was HBS-EP+, and the flow rate was 20 µl/min. Then, the running buffer was injected until the baseline was stabilized. The measurement was carried out after the baseline was stabilized. The immobilized FcγRIIa was allowed to interact with an antibody of each IgG isotype (IgG1, IgG2, or IgG4) or antibody introduced with mutations (M11ΔGK, M14ΔGK, or M17ΔGK) as an analyte. The amount of bound antibody was observed. The running buffer used was HBS-EP+, and the flow rate was 20 µl/min. The measurement temperature was 25° C. The concentration of each IgG or altered form thereof was adjusted to 100 µg/ml. 20 µl of an analyte was injected and allowed to interact with the immobilized FcγRIIa. After interaction, the analyte was dissociated from FcγRIIa and the sensor chip was regenerated by injecting 200 µl of the running buffer. As analytes, IgG4, IgG2, IgG1, M11ΔGK, M14ΔGK, and M17ΔGK were injected in this order. This series of injection was repeated twice. The result of comparison of data on the amounts of bound antibody determined is shown in FIG. 8. The comparison shows that the amount of bound antibody is reduced in the order of: IgG1>IgG2=IgG4>M11ΔGK=M14ΔGK=M17ΔGK. Thus, it was revealed that the FcγRIIa binding of M11ΔGK, M14ΔGK, and M17ΔGK was weaker than that of wild type IgG1, IgG2, and IgG4.

Figure 9:
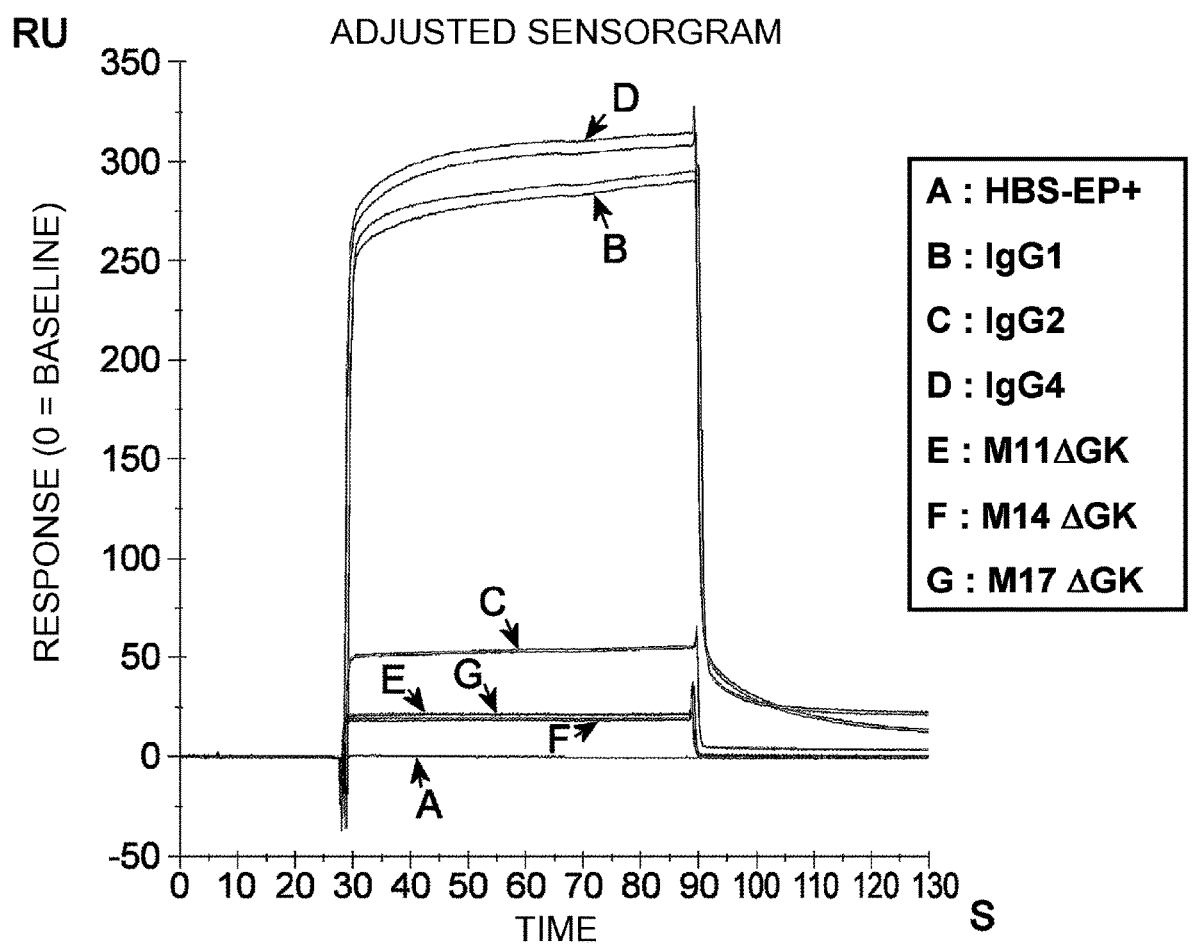
FIG. 9 is a graph showing comparison of the amounts WT-IgG1, WT-IgG2, WT-IgG4, WT-M14ΔGK, WT-M17ΔGK, and WT-M11ΔGK bound to FcγRIIb.

The FcγRIIb binding was assessed by the procedure described below. Using Biacore T100, human-derived Fcγ receptor IIb (hereinafter FcγRIIb) immobilized onto a sensor chip was allowed to interact with IgG1, IgG2, IgG4, M11ΔGK, M14ΔGK, or M17ΔGK as an analyte. The amounts of bound antibody were compared. The measurement was conducted using Recombinant Human FcRIIB/C (R&D systems) as human-derived FcγRIIb, and IgG1, IgG2, IgG4, M11ΔGK, M14ΔGK, and M17ΔGK as samples. FcγRIIb was immobilized onto the sensor chip CM5 (BIA-CORE) by the amine coupling method. The final amount of immobilized FcγRIIb was about 4300 RU. Then, the running buffer was injected until the baseline was stabilized. The measurement was carried out after the baseline was stabilized. The immobilized FcγRIIb was allowed to interact with an antibody of each IgG isotype (IgG1, IgG2, or IgG4) or antibody introduced with mutations (M11ΔGK, M14ΔGK, or M17ΔGK) as an analyte. The amount of bound antibody was observed. The running buffer used was HBS-EP+and the flow rate was 20 µl/min. The measurement temperature was 25° C. The concentration of each IgG or altered form thereof was adjusted to 200 µg/ml. 20 µl of an analyte was injected and allowed to interact with the immobilized FcγRIIb. After interaction, the analyte was dissociated from FcγRIIb and the sensor chip was regenerated by injecting 200 µl of the running buffer. As analytes, IgG4, IgG2, IgG1, M11ΔGK, M14ΔGK, and M17ΔGK were injected in this order. This series of injection was repeated twice. The result of comparison of data on the amounts of bound antibody determined is shown in FIG. 9. The comparison shows that the amount of bound antibody is reduced in the order of: IgG4>IgG1>IgG2>M11ΔGK=M14ΔGK=M17ΔGK. Thus, it was revealed that the FcγRIIb binding of M11ΔGK, M14ΔGK, and M17ΔGK was weaker than that of wild type IgG1, IgG2, and IgG4.

Figure 10:
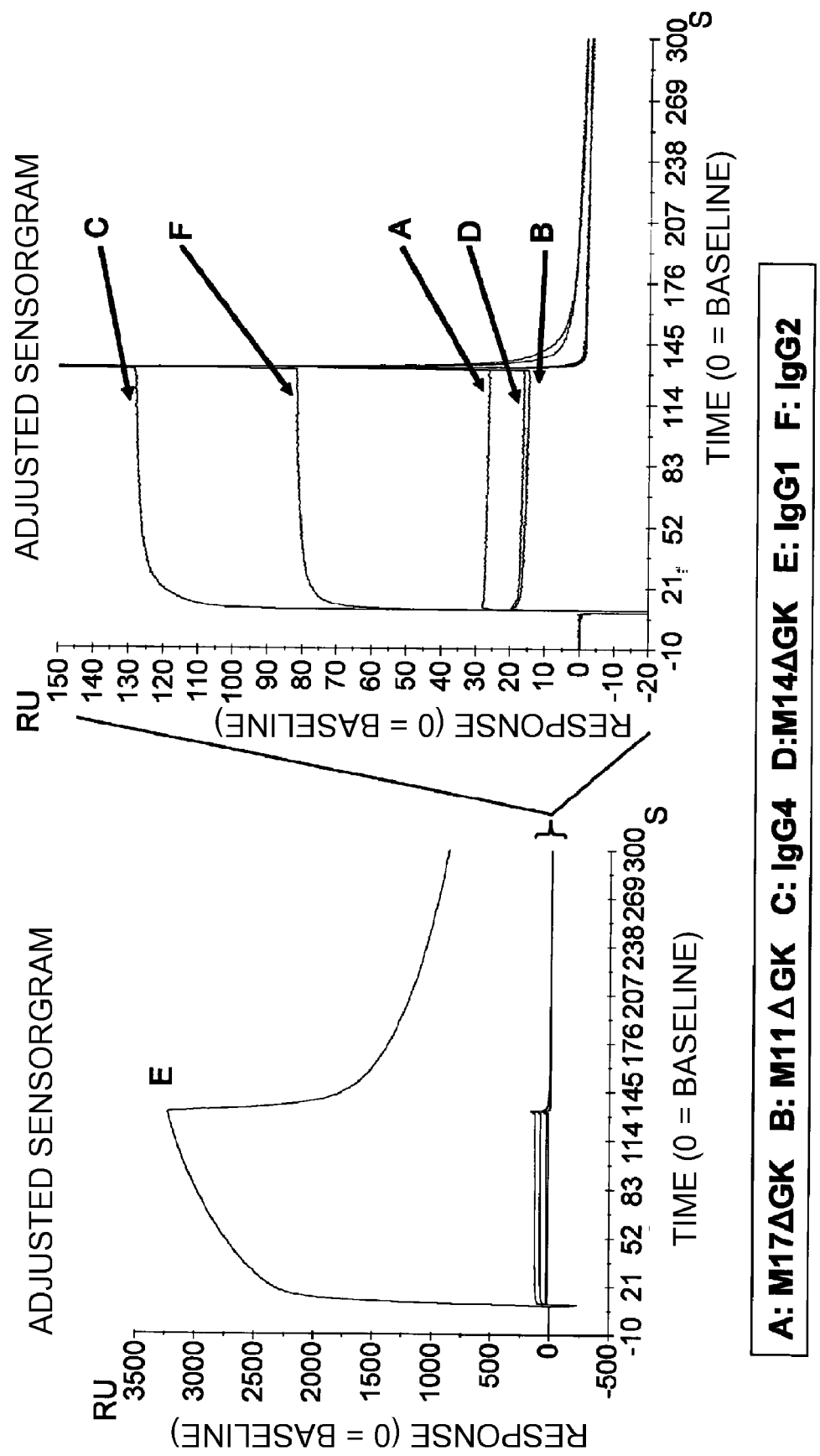
FIG. 10 is a graph showing comparison of the amounts WT-IgG1, WT-IgG2, WT-IgG4, WT-M14ΔGK, WT-M17ΔGK, and WT-M11ΔGK bound to FcγRIIIa (Val).

The FcγRIIIa binding was assessed by the procedure described below. Using Biacore T100, human-derived Fcγ receptor IIIa (hereinafter FcγRIIIa) immobilized onto a sensor chip was allowed to interact with IgG1, IgG2, IgG4, M11ΔGK, M14ΔGK, or M17ΔGK as an analyte. The amounts of bound antibody were compared. The measurement was conducted using hFcγRIIIaV-His6 (recombinant hFcγRIIIaV-His6 prepared in the applicants' company) as human-derived FcγRIIIa, and IgG1, IgG2, IgG4, M11ΔGK, M14ΔGK, and M17ΔGK as samples. FcγRIIIa was immobilized onto the sensor chip CM5 (BIACORE) by the amine coupling method. The final amount of immobilized hFcγRIIIaV-His6 was about 8200 RU. The running buffer used was HBS-EP+, and the flow rate was 5 µl/min. The sample concentration was adjusted to 250 µg/ml using HBS-EP+. The analysis included two steps: two minutes of association phase where 10 µl of an antibody solution was injected and the subsequent four minutes of dissociation phase where the injection was switched with HBS-EP+. After the dissociation phase, the sensor chip was regenerated by injecting 20 µl of 5 mM hydrochloric acid. The association, dissociation, and regeneration constitute one analysis cycle. Various antibody solutions were injected to obtain sensorgrams. As analytes, IgG4, IgG2, IgG1, M11ΔGK, M14ΔGK, and M17ΔGK were injected in this order. The result of comparison of data on the determined amounts of bound antibody is shown in FIG. 10. The comparison shows that the amount of bound antibody is reduced in the order of: IgG1>>IgG4>IgG2>M17ΔGK>M11ΔGK=M14ΔGK.
Thus, it was revealed that the FcγRIIIa binding of M11ΔGK, M14ΔGK, and M17ΔGK was weaker than that of wild type IgG1, IgG2, and IgG4. Furthermore, the FcγRIIIa binding of M11ΔGK and M14ΔGK was found to be weaker than that of M17ΔGK containing the mutation G1Δab reported in Eur. J. Immunol. 1999 August; 29(8):2613-24.

The finding described above demonstrates that the Fcγ receptor binding of WT-M14ΔGK, WT-M17ΔGK, and WT-M11ΔGK is markedly reduced as compared to wild type IgG1. The immunogenicity risk due to Fcγ receptor-mediated internalization into APC and adverse effects caused by the effector function such as ADCC can be avoided by using WT-M14ΔGK, WT-M17ΔGK, or WT-M11ΔGK as a constant region. Thus, WT-M14ΔGK, WT-M17ΔGK, and WT-M11ΔGK are useful as constant region sequence of antibody pharmaceuticals aimed at neutralizing antigens.

Assessment of WT-M14ΔGK, WT-M17ΔGK, and WT-M11ΔGK for Stability at High Concentrations WT-M14ΔGK, WT-M17ΔGK, and WT-M11ΔGK were assessed for stability at high concentrations. The purified antibodies of WT-IgG1, WT-M14ΔGK, WT-M17ΔGK, and WT-M11ΔGK were dialyzed against a solution of 20 mM histidine chloride, 150 mM NaCl, pH 6.5 (EasySEP, TOMY), and then concentrated by ultrafilters. The antibodies were tested for stability at high concentrations. The conditions were as follows.

Figure 11:
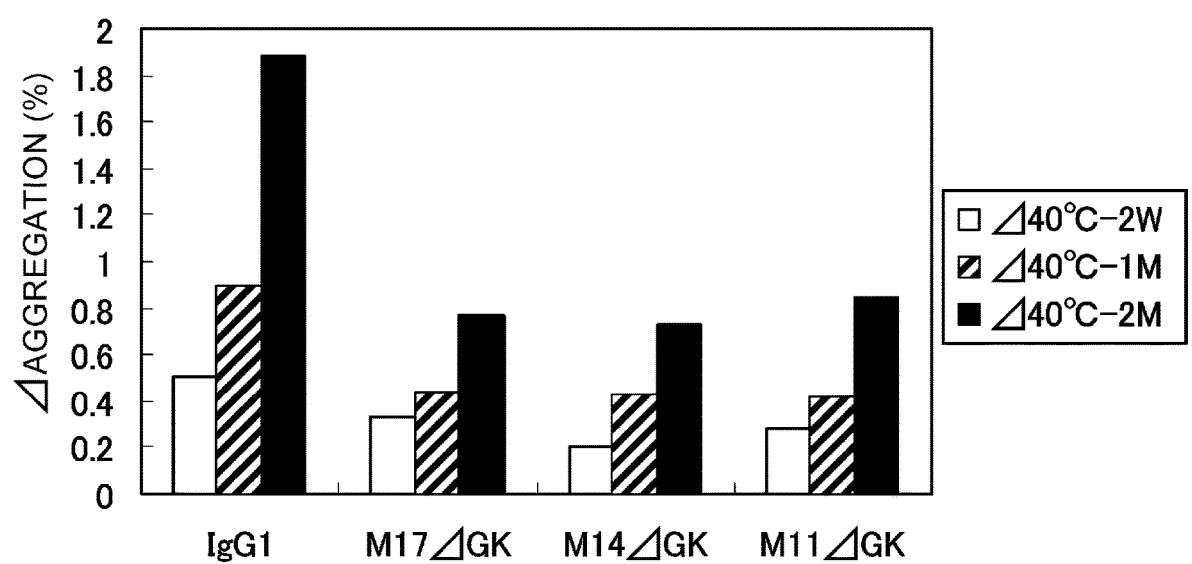
FIG. 11 is a graph showing the increase of aggregation in a stability test for WT-IgG1, WT-M14ΔGK, WT-M17ΔGK, and WT-M11ΔGK at high concentrations.
Figure 12:
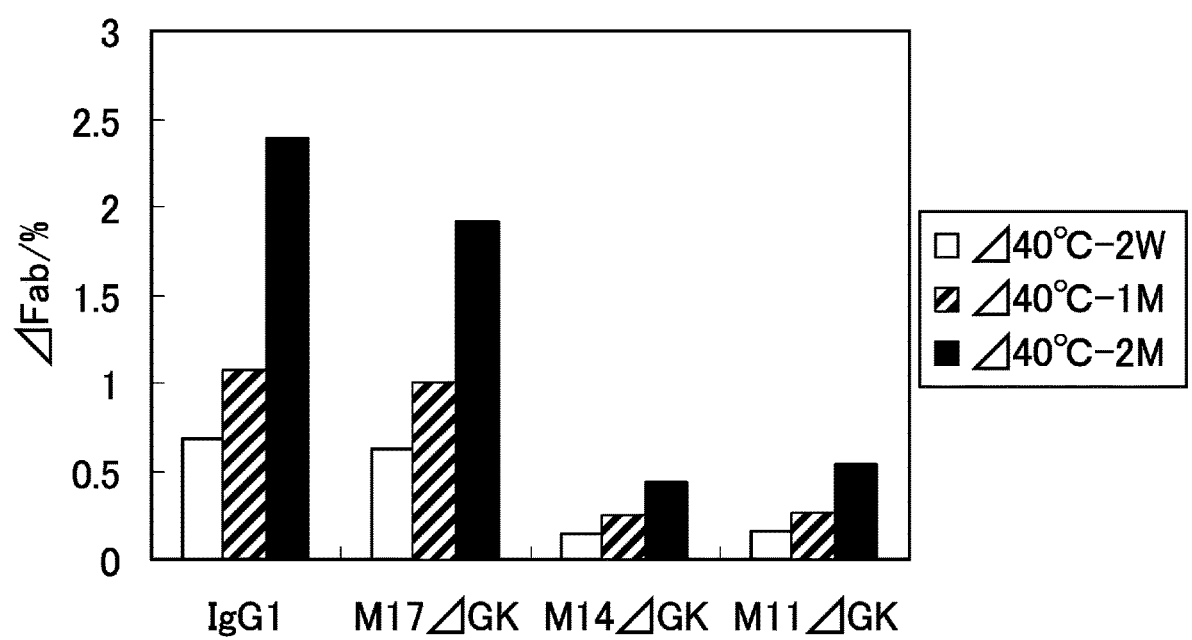
FIG. 12 is a graph showing the increase of Fab fragments in a stability test for WT-IgG1, WT-M14ΔGK, WT-M17ΔGK, and WT-M11ΔGK at high concentrations.

Antibodies: WT-IgG1, WT-M14ΔGK, WT-M17ΔGK, and WT-M11ΔGK
Buffer: 20 mM histidine chloride, 150 mM NaCl, pH 6.5
Concentration: 61 mg/ml
Storage temperature and time period: 40° C. for two weeks, 40° C. for one month, 40° C. for two months
Aggregation Assessment Method:
System: Waters Alliance
Column: G3000SWxl (TOSOH)
Mobile phase: 50 mM sodium phosphate, 300 mM KCl pH 7.0
Flow rate, wavelength: 0.5 ml/min, 220 nm
100 times diluted samples were analyzed The contents of aggregate in the initial formulations (immediately after preparation) and formulations stored under various conditions were estimated by gel filtration chromatography described above. Differences (amounts increased) in the content of aggregate relative to the initial formulations are shown in FIG. 11. The result showed that the amounts of aggregate in WT-M14ΔGK, WT-M17ΔGK, and WT-M11ΔGK increased only slightly as compared to WT-IgG1 and were about half of the content in WT. Furthermore, as shown in FIG. 12, the amount of increased Fab fragment was comparable between WT-IgG1 and WT-M17ΔGK, while the amounts increased in WT-M14ΔGK and WT-M11ΔGK were about one quarter of the amount in WT. Degeneration pathways of IgG type antibody formulations include formation of aggregate and generation of Fab degradate as described in WO 2003/039485. Based on the two criteria, aggregation and Fab fragment generation, WT-M14ΔGK and WT-M11ΔGK were demonstrated to have a superior stability in formulations as compared to WT-IgG1. Thus, even for antibodies that have an IgG1 constant region with poor stability and could not be prepared as antibody pharmaceuticals in high-concentration liquid formulations, the use of WT-M14ΔGK, WT-M17ΔGK, or WT-M11ΔGK as a constant region was expected to allow production of more stable high-concentration liquid formulations.

In particular, M14ΔGK was expected to be very useful as a novel constant region sequence that would (1) overcome the instability of the original IgG2 molecule under acidic condition; (2) improve the heterogeneity originated from disulfide bonds in the hinge region; (3) not bind to Fcγ receptor; (4) have a minimized number of novel peptide sequences of 9 amino acids which potentially serve as T-cell epitope peptides; and (5) have a better stability than IgG1 in high-concentration formulations.

Example 5

Preparation and Assessment of M31ΔGK

M14ΔGK prepared in Example 4 was altered by substituting the IgG2 sequence for the amino acids at positions 330, 331, and 339 in the EU numbering system to construct M31ΔGK (M31ΔGK, SEQ ID NO: 7). An expression vector for a sequence of antibody H chain whose variable region is WT and constant region sequence is M31ΔGK (WT-M31ΔGK, SEQ ID NO: 22) was constructed by the method described in Reference Example 1. Using WT-M31ΔGK H chain and WT L chain, WT-M31ΔGK was expressed and purified by the method described in Reference Example 1.
In addition to WT-M31ΔGK, WT-IgG2 and WT-M14ΔGK were expressed and purified at the same time, and analyzed by cation exchange chromatography by the procedure described below. The conditions used in the cation exchange chromatography analysis were as follows. Chromatograms for WT-IgG2, WT-M14ΔGK, and WT-M31ΔGK were compared.

Figure 13:
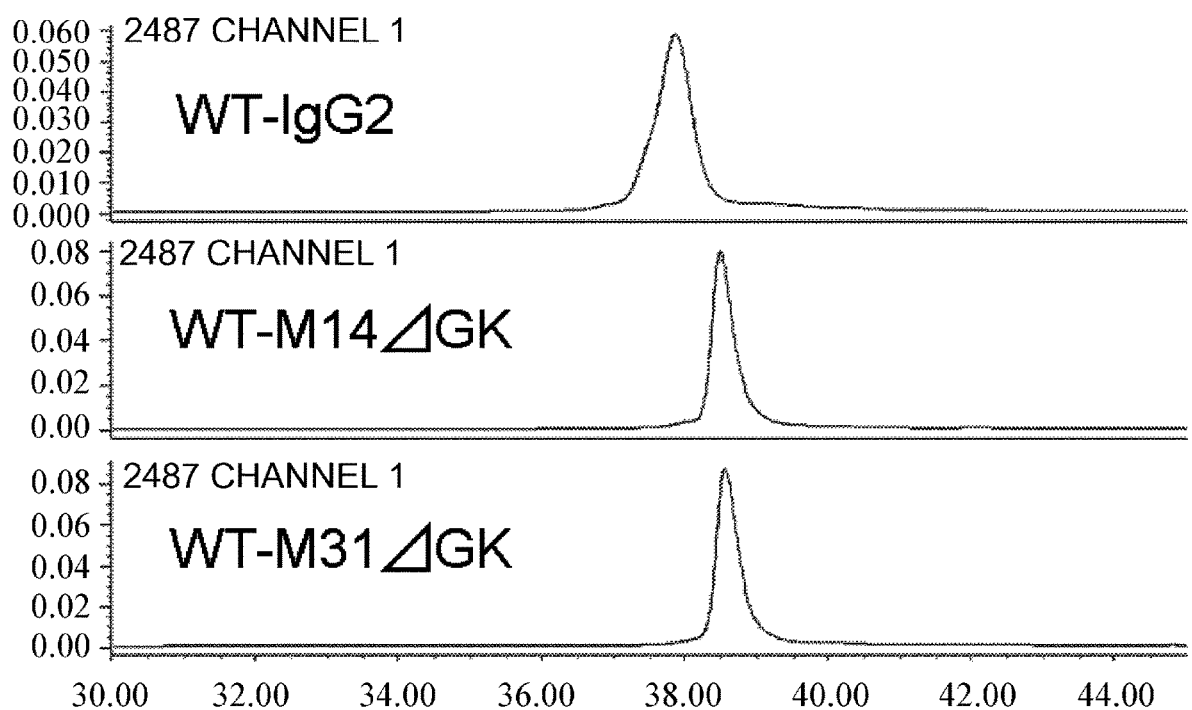
FIG. 13 is a diagram showing the result of cation exchange chromatography (IEC) analysis of WT-IgG2, WT-M14ΔGK, and WT-M31ΔGK.

Column: ProPac WCX-10 (Dionex)
Mobile phase A: 25 mmol/l MES/NaOH, pH 6.1
    B: 25 mmol/l MES/NaOH, 250 mmol/l NaCl, pH 6.1
Flow rate: 0.5 ml/min
Gradient: 0% B (5 min)->(65 min)->100% B->(1 min)
Detection: 280 nm The analysis result for WT-IgG2, WT-M14ΔGK, and WT-M31ΔGK is shown in FIG. 13. Like WT-M14ΔGK, WT-M31ΔGK was demonstrated to be eluted as a single peak, while WT-IgG2 gave multiple peaks. This indicates that the heterogeneity derived from disulfide bonds in the hinge region of IgG2 can also be avoided in WT-M31ΔGK.

Example 6

Assessment of the Plasma Retention of WT-M14

Method for Estimating the Retention in Human Plasma

The prolonged retention (slow elimination) of IgG molecule in plasma is known to be due to the function of FcRn which is known as a salvage receptor of IgG molecule (Nat. Rev. Immunol. 2007 September; 7(9):715-25). When taken up into endosomes via pinocytosis, under the acidic conditions within endosome (approx. pH 6.0), IgG molecules bind to FcRn expressed in endosomes. While IgG molecules that do not bind to FcRn are transferred and degraded in lysosomes, those bound to FcRn are translocated to the cell surface and then released from FcRn back into plasma again under the neutral conditions in plasma (approx. pH 7.4).

Known IgG-type antibodies include the IgG1, IgG2, IgG3, and IgG4 isotypes. The plasma half-lives of these isotypes in human are reported to be about 36 days for IgG1 and IgG2; about 29 days for IgG3; and 16 days for IgG4 (Nat. Biotechnol. 2007 December; 25(12):1369-72). Thus, the retention of IgG1 and IgG2 in plasma is believed to be the longest. In general, the isotypes of antibodies used as pharmaceutical agents are IgG1, IgG2, and IgG4. Methods reported for further improving the pharmacokinetics of these IgG antibodies include methods for improving the above-described binding to human FcRn, and this is achieved by altering the sequence of IgG constant region (J. Biol. Chem. 2007 Jan. 19; 282(3):1709-17; J. Immunol. 2006 Jan. 1; 176(1):346-56).

There are species-specific differences between mouse FcRn and human FcRn (Proc. Natl. Acad. Sci. USA. 2006 Dec. 5; 103(49):18709-14). Therefore, to predict the plasma retention of IgG antibodies that have an altered constant region sequence in human, it is desirable to assess the binding to human FcRn and retention in plasma in human FcRn transgenic mice (Int. Immunol. 2006 December; 18(12):1759-69).

Assessment of the Binding to Human FcRn

FcRn is a complex of FcRn and β2-microglobulin. Oligo-DNA primers were prepared based on the human FcRn gene sequence disclosed (J. Exp. Med. (1994) 180 (6), 2377-2381). A DNA fragment encoding the whole gene was prepared by PCR using human cDNA (Human Placenta Marathon-Ready cDNA, Clontech) as a template and the prepared primers. Using the obtained DNA fragment as a template, a DNA fragment encoding the extracellular domain containing the signal region (Met1-Leu290) was amplified by PCR, and inserted into an animal cell expression vector (the amino acid sequence of human FcRn as set forth in SEQ ID NO: 24). Likewise, oligo-DNA primers were prepared based on the human β2-microglobulin gene sequence disclosed (Proc. Natl. Acad. Sci. USA. (2002) 99 (26), 16899-16903). A DNA fragment encoding the whole gene was prepared by PCR using human cDNA (Hu-Placenta Marathon-Ready cDNA, CLONTECH) as a template and the prepared primers. Using the obtained DNA fragment as a template, a DNA fragment encoding the whole β2-microglobulin containing the signal region (Met1-Met119) was amplified by PCR and inserted into an animal cell expression vector (the amino acid sequence of human β2-microglobulin as set forth in SEQ ID NO: 25).

Soluble human FcRn was expressed by the following procedure. The plasmids constructed for human FcRn and β2-microglobulin were introduced into cells of the human embryonic kidney cancer-derived cell line HEK293H (Invitrogen) using 10% Fetal Bovine Serum (Invitrogen) by lipofection. The resulting culture supernatant was collected, and FcRn was purified using IgG Sepharose 6 Fast Flow (Amersham Biosciences) by the method described in J. Immunol. 2002 Nov. 1; 169(9):5171-80, followed by further purification using HiTrap Q HP (GE Healthcare).

The binding to human FcRn was assessed using Biacore 3000. An antibody was bound to Protein L or rabbit anti-human IgG Kappa chain antibody immobilized onto a sensor chip, human FcRn was added as an analyte for interaction with the antibody, and the affinity (KD) was calculated from the amount of bound human FcRn. Specifically, Protein L or rabbit anti-human IgG Kappa chain antibody was immobilized onto sensor chip CM5 (BIACORE) by the amine coupling method using 50 mM Na-phosphate buffer (pH 6.0) containing 150 mM NaCl as the running buffer. Then, an antibody was diluted with a running buffer containing 0.02% Tween20, and injected to be bound to the chip. Human FcRn was then injected and the binding of the human FcRn to antibody was assessed.

The affinity was computed using BIAevaluation Software. The obtained sensorgram was used to calculate the amount of hFcRn bound to the antibody immediately before the end of human FcRn injection. The affinity of the antibody for human FcRn was calculated by fitting with the steady state affinity method.

Assessment for the Plasma Retention in Human FcRn Transgenic Mice

The pharmacokinetics in human FcRn transgenic mice (B6.mFcRn-/-.hFcRn Tg line 276 +/+ mice; Jackson Laboratories) was assessed by the following procedure. An antibody was intravenously administered once at a dose of 1 mg/kg to mice, and blood was collected at appropriate time points. The collected blood was immediately centrifuged at 15,000 rpm and 4° C. for 15 minutes to obtain blood plasma. The separated plasma was stored in a freezer at −20° C. or below until use. The plasma concentration was determined by ELISA.

Predictive Assessment of the Plasma Retention of WT-M14 in Human

The bindings of WT-IgG1 and WT-M14 to human FcRn were assessed by BIAcore. As shown in Table 1, the result indicated that the binding of WT-M14 was slightly greater than that of WT-IgG1.

TABLE 1

|  | KD (μM) |
|---|---|
| WT-IgG1 | 2.07 |
| WT-M14 | 1.85 |

Figure 14:
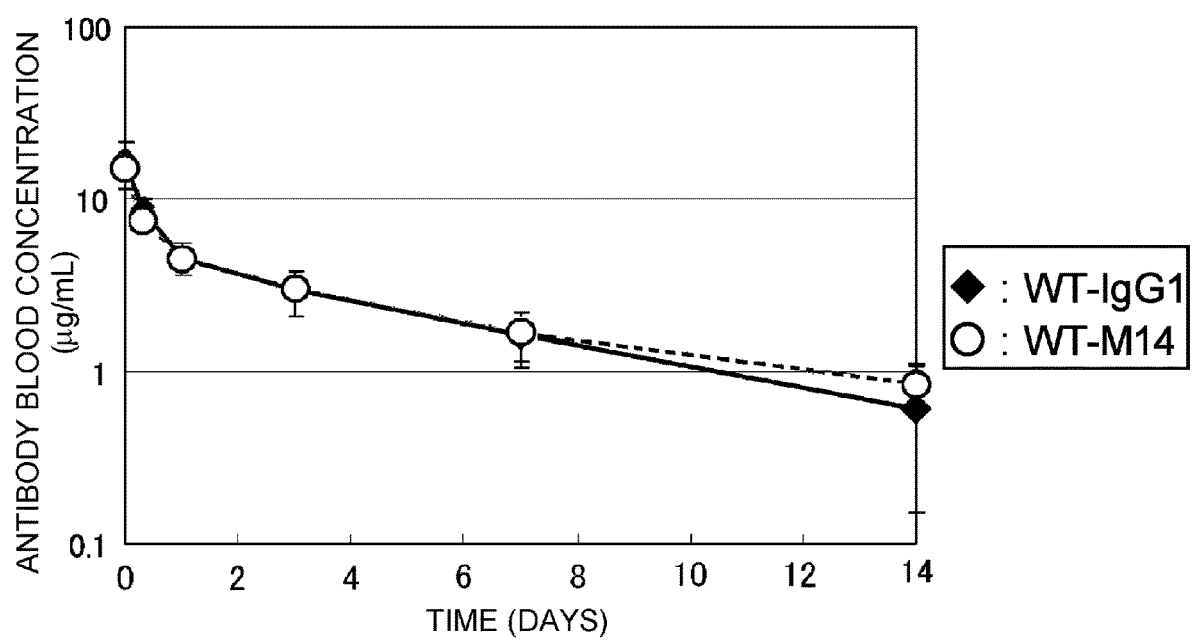
FIG. 14 is a graph showing the time courses of plasma concentrations of WT-IgG1 and WT-M14 after intravenous administration to human FcRn transgenic mice.

As shown in FIG. 14, however, the retention in plasma was comparable between WT-IgG1 and WT-M14 when assessed using human FcRn transgenic mice. This finding suggests that the plasma retention of the M14 constant region in human is comparable to that of the IgG1 constant region.

Example 7

Preparation of WT-M44, WT-M58, and WT-M73 which have Improved Pharmacokinetics

Preparation of the WT-M58 Molecule

As described in Example 6, the plasma retention of WT-M14 in human FcRn transgenic mice was comparable to that of WT-IgG1. Known methods to improve pharmacokinetics include those to lower the isoelectric point of an antibody and those to enhance the binding to FcRn. Here, the modifications described below were introduced to improve the pharmacokinetics of WT-M14. Specifically, the following substitutions were introduced into WT-M31ΔGK, which was prepared from WT-M14 as described in Example 4: substitution of methionine for valine at position 397; substitution of glutamine for histidine at position 268; substitution of glutamine for arginine at position 355; and substitution of glutamic acid for glutamine at position 419 in the EU numbering system. These four substitutions were introduced into WT-M31ΔGK to generate WT-M58 (amino acid sequence of SEQ ID NO: 26). Expression vectors were prepared by the same method described in Example 1. WT-M58 and L(WT) were used as H chain and L chain, respectively. WT-M58 was expressed and purified by the method described in Example 1.

Construction of the WT-M73 Molecule

On the other hand, WT-M44 (amino acid sequence of SEQ ID NO: 27) was generated by introducing into IgG1 a substitution of alanine for the amino acid at position 434, EU numbering. WT-M83 (amino acid sequence of SEQ ID NO: 58) was also generated by deletions of glycine at position 446, EU numbering and lysine at position 447, EU numbering to reduce H chain C-terminal heterogeneity. Furthermore, WT-M73 (amino acid sequence of SEQ ID NO: 28) was generated by introducing into WT-M58 a substitution of alanine at position 434, EU numbering.

Expression vectors for the above antibodies were constructed by the method described in Example 1. WT-M44, WT-M58, or WT-M73 was used as H chain, while L (WT) was used as L chain. WT-M44, WT-M58, and WT-M73 were expressed and purified by the method described in Example 1.

Predictive Assessment of the Plasma Retention of WT-M44, WT-M58, and WT-M73 in Human The bindings of WT-IgG1, WT-M44, WT-M58, and WT-M73 to human FcRn were assessed by BIAcore. As shown in Table 2, the result indicates that the bindings of WT-M44, WT-M58, and WT-M73 are greater than WT-IgG1, and about 2.7, 1.4, and 3.8 times of that of WT-IgG1, respectively.

TABLE 2

|  | KD (μM) |
|---|---|
| WT-IgG1 | 1.62 |
| WT-M44 | 0.59 |
| WT-M58 | 1.17 |
| WT-M73 | 0.42 |

Figure 15:
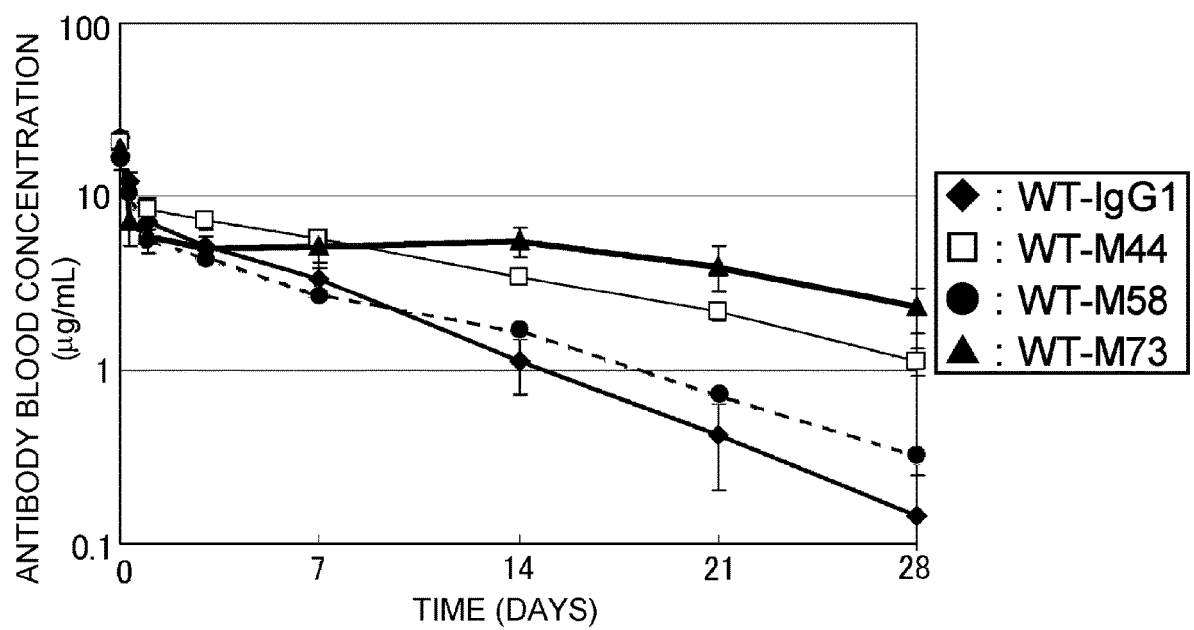
FIG. 15 is a graph showing the time courses of plasma concentrations of WT-IgG1, WT-M44, WT-M58, and WT-M73 after intravenous administration to human FcRn transgenic mice.
Figure 24:
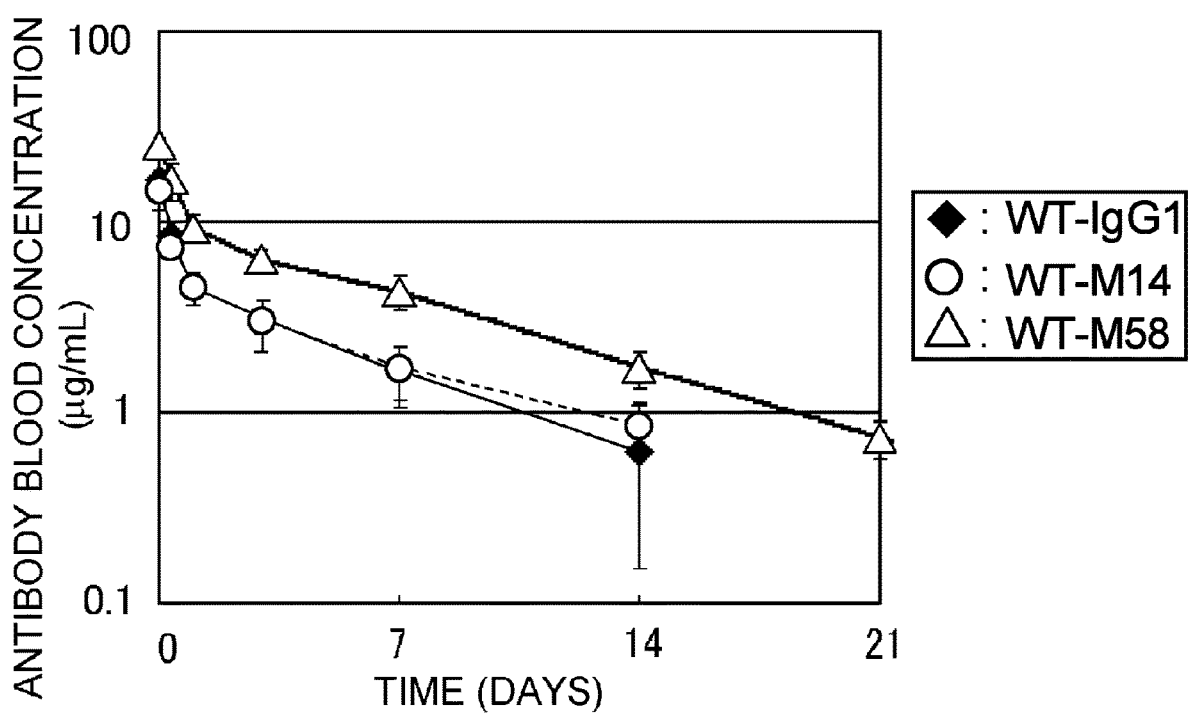
FIG. 24 is a graph showing the time courses of plasma concentrations of WT-IgG1, WT-M14, and WT-M58 after intravenous administration to human FcRn transgenic mice.

As a result of assessing WT-IgG1, WT-M14, and WT-M58 for their plasma retention in human FcRn transgenic mice, as shown in FIG. 24, WT-M58 was confirmed to have increased retention in plasma relative to WT-IgG1 and WT-M14. Furthermore, WT-IgG1, WT-M44, WT-M58, and WT-M73 were assessed for their plasma retention in human FcRn transgenic mice. As shown in FIG. 15, all of WT-M44, WT-M58, and WT-M73 were confirmed to have improved pharmacokinetics relative to WT-IgG1. The pharmacokinetics-improving effect correlated with the binding activity to human FcRn. In particular, the plasma level of WT-M73 at Day 28 was improved to about 16 times of that of WT-IgG1. This finding suggests that the pharmacokinetics of antibodies with the M73 constant region in human is also significantly enhanced when compared to antibodies with the IgG1 constant region.

Example 8

Effect of the Novel Constant Regions M14 and M58 in Reducing Heterogeneity in Various Antibodies As described in Example 4, it was demonstrated that the heterogeneity originated from the hinge region of IgG2 could be reduced by converting the IgG2 constant region to M14 in the humanized anti-IL-6 receptor PM1 antibody (WT). IgG2 type antibodies other than the humanized PM1 antibody were also tested to assess whether the heterogeneity can be reduced by converting their constant regions into M14 or M58.

Antibodies other than the humanized PM1 antibody were: the anti IL-6 receptor antibody F2H/L39 (the amino acid sequences of F2H/L39_VH and F2H/L39 VL as set forth in SEQ ID NOs: 29 and 30, respectively); anti-IL-31 receptor antibody H0L0 (the amino acid sequences of H0L0_VH and H0L0_VL as set forth in SEQ ID NOs: 31 and 32, respectively); and anti-RANKL antibody DNS (the amino acid sequences of DNS_VH and DNS_VL as set forth in SEQ ID NOs: 33 and 34, respectively). For each of these antibodies, antibodies with IgG1 constant region (SEQ ID NO: 1), IgG2 constant region (SEQ ID NO: 2), or M14 (SEQ ID NO: 5) or M58 (SEQ ID NO: 35) were generated.

The generated antibodies were assessed for heterogeneity by cation exchange chromatography using an adequate gradient and an appropriate flow rate on a ProPac WCX-10 (Dionex) column (mobile phase A: 20 mM sodium acetate (pH 5.0), mobile phase B: 20 mM sodium acetate/1M NaCl (pH 5.0)). The assessment result obtained by cation exchange chromatography (IEC) is shown in FIG. 16.

Figure 16:
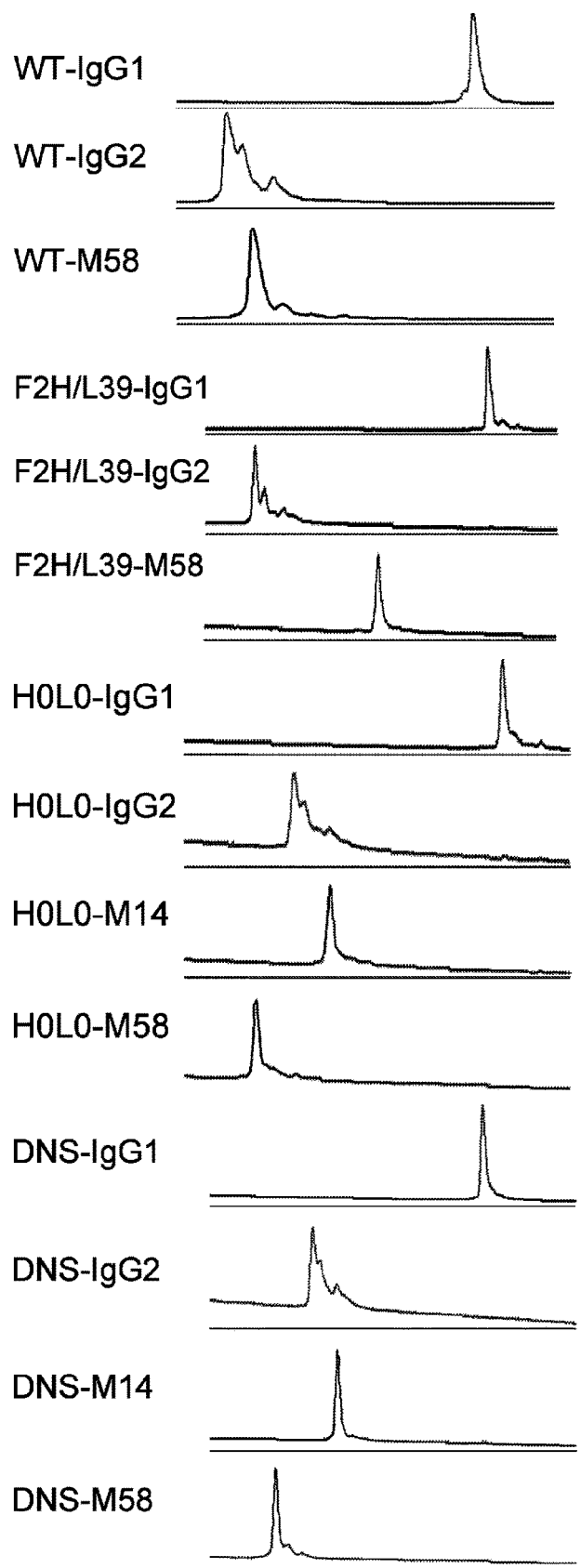
FIG. 16 is a diagram showing a cation exchange chromatography-based assessment of the effect on heterogeneity by the constant region of anti IL-6 receptor antibodies WT and F2H/L39, anti-IL-31 receptor antibody H0L0, and anti-RANKL antibody DNS.

As shown in FIG. 16, conversion of the constant region from an IgG1 type into an IgG2 type was demonstrated to increase heterogeneity not only in the humanized anti-IL-6 receptor PM1 antibody (WT), but also in the anti-IL-6 receptor antibody F2H/L39, anti-IL-31 receptor antibody H0L0, and anti-RANKL antibody DNS. In contrast, heterogeneity could be decreased in all of these antibodies by converting their constant region into M14 or M58. Thus, it was demonstrated that, regardless of the type of antigen or antibody variable region sequence, the heterogeneity originated from natural IgG2 could be reduced by substituting serines for cysteines at position 131, EU numbering, in the H-chain CH1 domain and at position 219, EU numbering, in the upper hinge of H chain.

Example 9

Effect of the Novel Constant Region M58 to Improve the Pharmacokinetics in Various Antibodies As described in Example 7, it was demonstrated that conversion of the constant region from IgG1 into M58 in the humanized anti-IL-6 receptor PM1 antibody (WT) improved the binding to human FcRn and pharmacokinetics in human FcRn transgenic mice. So, IgG1 type antibodies other than the humanized PM1 antibody were also tested to assess whether their pharmacokinetics can be improved by converting their constant region into M58.

Antibodies other than the humanized PM1 antibody (WT) were the anti-IL-31 receptor antibody H0L0 (the amino acid sequences of H0L0_VH and H0L0_VL as set forth in SEQ ID NOs: 31 and 32, respectively) and anti-RANKL antibody DNS (the amino acid sequences of DNS_VH and DNS_VL as set forth in SEQ ID NOs: 33 and 34, respectively). For each of these antibodies, antibodies with IgG1 constant region (SEQ ID NO: 1) or M58 (SEQ ID NO: 35) were generated and assessed for their binding to human FcRn by the method described in Example 6. The result is shown in Table 3.

TABLE 3

| | KD (μM) | | |
| --- | --- | --- | --- |
| | WT | H0L0 | DNS |
| IgG1 | 1.42 | 1.07 | 1.36 |
| M58 | 1.03 | 0.91 | 1.03 |

As shown in Table 3, it was demonstrated that as a result of conversion of the constant region from the IgG1 type to M58, as with anti-IL-6 receptor antibody WT, the bindings of both the anti-IL-31 receptor antibody H0L0 and anti-RANKL antibody DNS to human FcRn were improved. This suggests the possibility that regardless of the type of antigen or sequence of antibody variable region, the pharmacokinetics in human is improved by converting the constant region from the IgG1 type to M58.

Example 10

Effect of Cysteine in the CH1 Domain on Heterogeneity and Stability

As described in Example 2, cysteines in the hinge region and CH1 domain of IgG2 were substituted to decrease the heterogeneity of natural IgG2. Assessment of various altered antibodies revealed that heterogeneity could be reduced without decreasing stability by using SKSC (SEQ ID NO: 38). SKSC (SEQ ID NO: 38) is an altered constant region obtained by substituting serine for cysteine at position 131 and lysine for arginine at position 133, EU numbering, in the H-chain CH1 domain, and serine for cysteine at position 219, EU numbering, in the H-chain upper hinge of the wild type IgG2 constant region sequence.

Meanwhile, another possible method for decreasing heterogeneity is a single substitution of serine for cysteine at position 219, or serine for cysteine at position 220, EU numbering, in the H-chain upper hinge. The altered IgG2 constant region SC (SEQ ID NO: 39) was prepared by substituting serine for cysteine at position 219 and CS (SEQ ID NO: 40) was prepared by substituting serine for cysteine at position 220, EU numbering, in IgG2. WT-SC (SEQ ID NO: 41) and WT-CS (SEQ ID NO: 42) were prepared to have SC and CS, respectively, and compared with WT-IgG1, WT-IgG2, WT-SKSC, and WT-M58 in terms of heterogeneity and thermal stability. Furthermore, F2H/L39-IgG1, F2H/L39-IgG2, F2H/L39-SC, F2H/L39-CS, F2H/L39-SKSC, and F2H/L39-M14, which have the constant region of IgG1 (SEQ ID NO: 1), IgG2 (SEQ ID NO: 2), SC (SEQ ID NO: 39), CS (SEQ ID NO: 40), SKSC (SEQ ID NO: 38), or M14 (SEQ ID NO: 5), respectively, were prepared from F2H/L39 (the amino acid sequences of F2H/L39_VH and F2H/L39_VL as set forth in SEQ ID NOs: 29 and 30, respectively), which is an anti IL-6 receptor antibody different from WT. The antibodies were compared with regard to heterogeneity.

WT-IgG1, WT-IgG2, WT-SC, WT-CS, WT-SKSC, WT-M58, F2H/L39-IgG1, F2H/L39-IgG2, F2H/L39-SC, F2H/L39-CS, F2H/L39-SKSC, and F2H/L39-M14 were assessed for heterogeneity by cation exchange chromatography using an adequate gradient and an appropriate flow rate on a ProPac WCX-10 (Dionex) column (mobile phase A: 20 mM sodium acetate (pH 5.0), mobile phase B: 20 mM sodium acetate/1M NaCl (pH 5.0)). The assessment result obtained by cation exchange chromatography is shown in FIG. 17.

Figure 17:
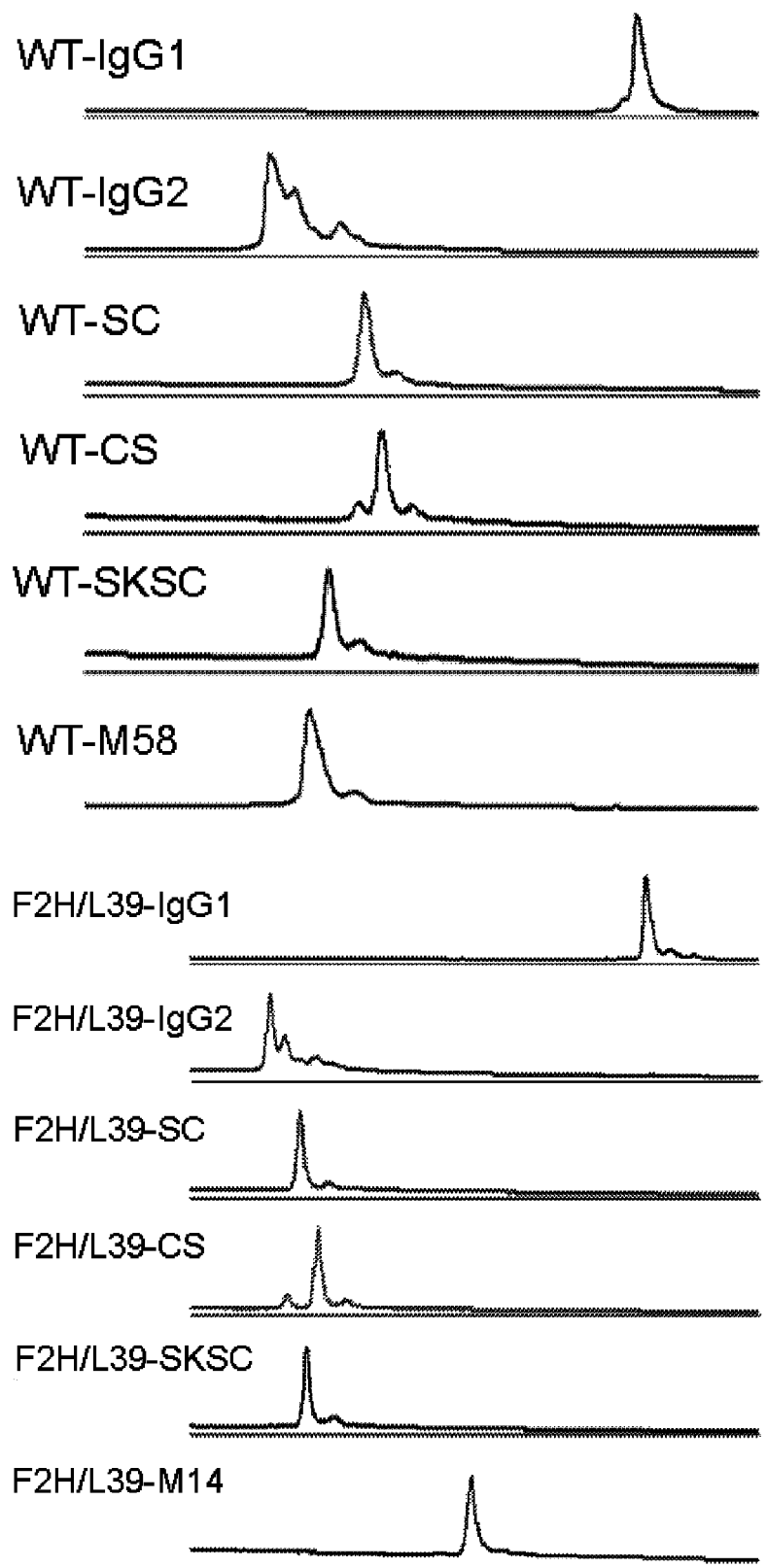
FIG. 17 is a diagram showing a cation exchange chromatography-based assessment of the effect on heterogeneity by the CH1 domain cysteine of anti IL-6 receptor antibodies WT and F2H/L39.

As shown in FIG. 17, conversion of the constant region from an IgG1 type to an IgG2 type was demonstrated to increase heterogeneity in both WT and F2H/L39. In contrast, heterogeneity was significantly decreased by converting the constant region into SKSC and M14 or M58. Meanwhile, conversion of the constant region into SC significantly decreased heterogeneity, as in the case of SKSC. However, conversion into CS did not sufficiently improve heterogeneity.

Figure 18:
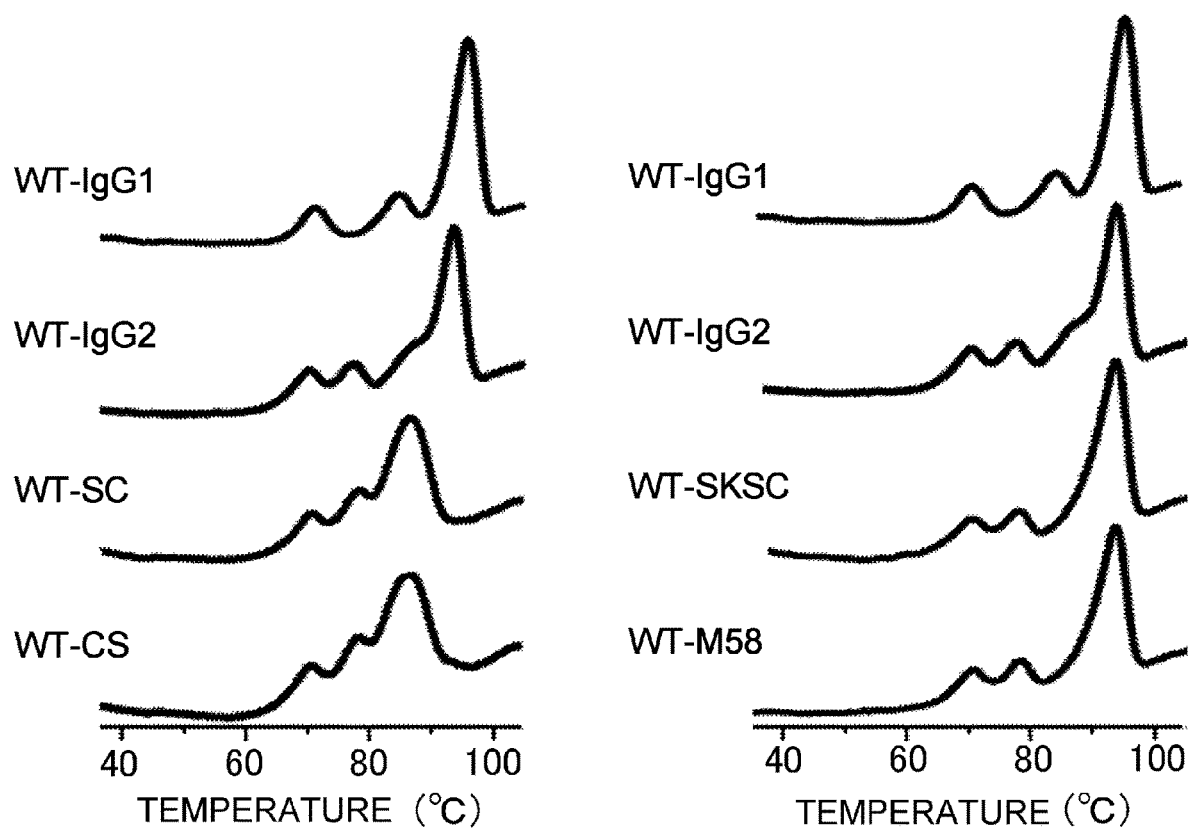
FIG. 18 is a diagram showing a DSC-based assessment of the effect on denaturation peak by the CH1 domain cysteine of anti IL-6 receptor antibody WT and F2H/L39.

In addition to low heterogeneity, high stability is generally desired when preparing stable formulations in development of antibody pharmaceuticals. Thus, to assess stability, the midpoint temperature of thermal denaturation (Tm value) was determined by differential scanning calorimetry (DSC) (VP-DSC; Microcal). The midpoint temperature of thermal denaturation (Tm value) serves as an indicator of stability. In order to prepare stable formulations as pharmaceutical agents, a higher midpoint temperature of thermal denaturation (Tm value) is preferred (J. Pharm. Sci. 2008 April; 97(4):1414-26). WT-IgG1, WT-IgG2, WT-SC, WT-CS, WT-SKSC, and WT-M58 were dialyzed (EasySEP; TOMY) against a solution of 20 mM sodium acetate, 150 mM NaCl, pH 6.0. DSC measurement was carried out at a heating rate of 1° C./min in a range of 40 to 100° C., and at a protein concentration of about 0.1 mg/ml. The denaturation curves obtained by DSC are shown in FIG. 18. The Tm values of the Fab domains are listed in Table 4 below.

TABLE 4

|  | Tm/° C. |
| --- | --- |
| WT-IgG1 | 94.8 |
| WT-IgG2 | 93.9 |
| WT-SC | 86.7 |
| WT-CS | 86.4 |
| WT-SKSC | 93.7 |
| WT-M58 | 93.7 |

The Tm values of WT-IgG1 and WT-IgG2 were almost the same (about 94° C.; Tm of IgG2 was about 1° C. lower). Meawhile, the Tm values of WT-SC and WT-CS were about 86° C., and thus significantly lower than those of WT-IgG1 and WT-IgG2. On the other hand, the Tm values of WT-M58 and WT-SKSC were about 94° C., and comparable to those of WT-IgG1 and WT-IgG2. This suggests that WT-SC and WT-CS are markedly unstable as compared to IgG2, and thus, WT-SKSC and WT-M58, both of which also comprise substituion of serine for cysteine in the CH1 domain, are preferred in the development of antibody pharmaceuticals. The reason for the significant decrease of Tm in WT-SC and WT-CS relative to IgG2 is thought to be differences in the disulfide-bonding pattern between WT-SC or WT-CS and IgG2.

Furthermore, comparison of DSC denaturation curves showed that WT-IgG1, WT-SKSC, and WT-M58 each gave a sharp and single denaturation peak for the Fab domain. In contrast, WT-SC and WT-CS each gave a broader denaturation peak for the Fab domain. WT-IgG2 also gave a shoulder peak on the lower temperature side of the Fab domain denaturation peak. In general, it is considered that a single component gives a sharp DSC denaturation peak, and when two or more components with different Tm values (namely, heterogeneity) are present, the denaturation peak becomes broader. Specifically, the above-described result suggests the possibility that each of WT-IgG2, WT-SC, and WT-CS contains two or more components, and thus the natural-IgG2 heterogeneity has not been sufficiently reduced in WT-SC and WT-CS. This finding suggests that not only cysteines in the hinge region but also those in the CH1 domain are involved in the wild type-IgG2 heterogeneity, and it is necessary to alter not only cysteines in the hinge region but also those in the CH1 domain to decrease the DSC heterogeneity. Furthermore, as described above, stability comparable to that of wild type IgG2 can be acheived only when cysteines in both the hinge region and CH1 domain are substituted.

The above finding suggests that from the perspective of heterogeneity and stability, SC and CS, which are constant regions introduced with serine substitution for only the hinge region cysteine, are insufficient as constant regions to decrease heterogeneity originated from the hinge region of IgG2. It was thus discovered that the heterogeneity could be significantly decreased while maintaining an IgG2-equivalent stability, only when the cysteine at position 131, EU numbering, in the CH1 domain was substituted with serine in addition to cysteine at hinge region. Such constant regions include M14, M31, M58, and M73 described above. In particular, M58 and M73 are stable and less heterogeneous, and exhibit improved pharmacokinetics, and therefore are expected to be very useful as constant regions for antibody pharmaceuticals.

Example 11

Generation of Fully Humanized anti-IL-6 Receptor Antibodies with Improved PK/PD

To generate a fully humanized anti-IL-6 receptor antibody with improved PK/PD, the molecules described below were created by altering TOCILIZUMAB (H chain, WT-IgG1 (SEQ ID NO: 12); L chain, WT (SEQ ID NO: 15). The following fully humanized IL-6 receptor antibodies were prepared which use as constant region M73 or M83 prepared in Example 7: Fv3-M73 (H chain, VH4-M73, SEQ ID NO: 48; L chain, VL1-kappa, SEQ ID NO: 49), Fv4-M73 (H chain, VH3-M73, SEQ ID NO: 46; L chain, VL3-kappa, SEQ ID NO: 47), and Fv5-M83 (H chain, VH5-M83, SEQ ID NO: 44; L chain, VL5-kappa, SEQ ID NO: 45).

Figure 19:
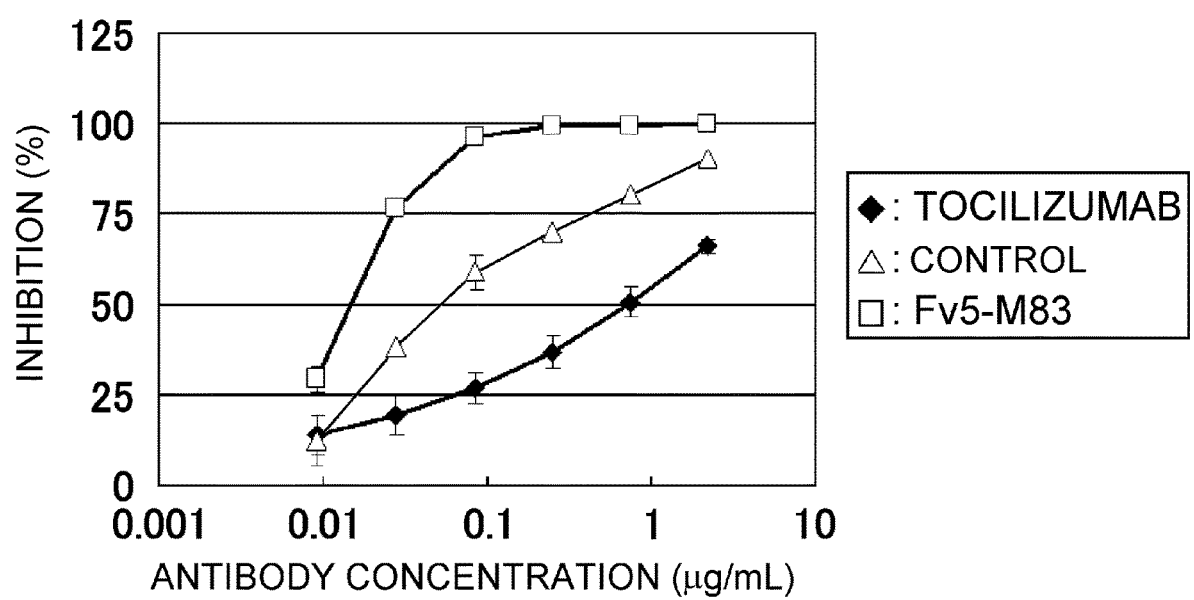
FIG. 19 is a graph showing the activities of TOCILIZUMAB, the control, and Fv5-M83 to neutralize BaF/g130.
Figure 20:
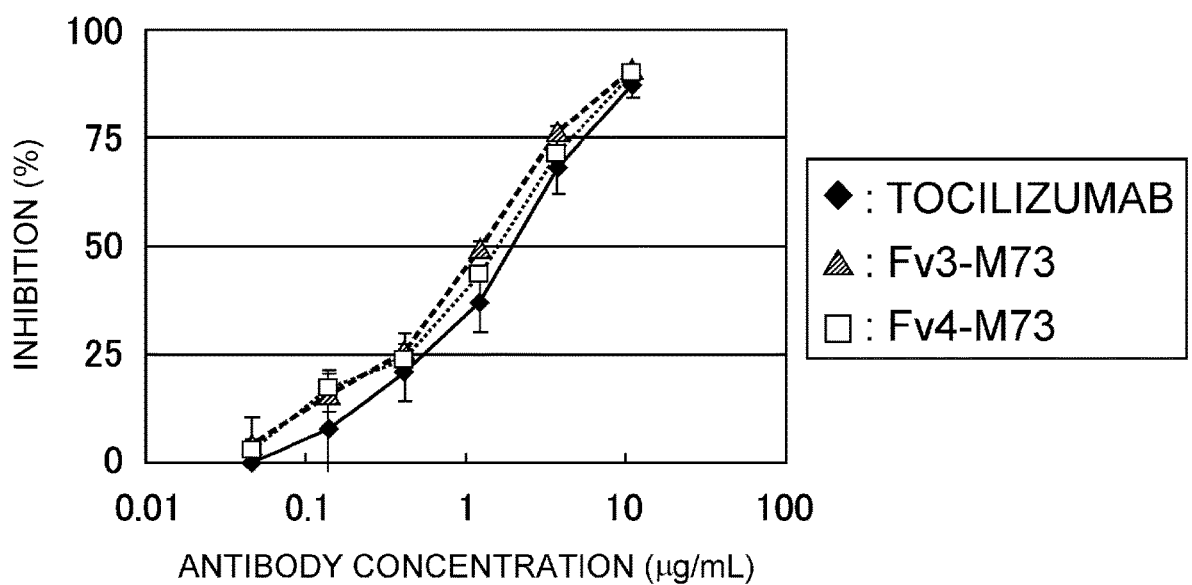
FIG. 20 is a graph showing the activities of TOCILIZUMAB, Fv3-M73, and Fv4-M73 to neutralize BaF/gp130.

The affinities of prepared Fv3-M73, Fv4-M73, and Fv5-M83 against IL-6 receptor were compared to that of TOCILIZUMAB. The affinities of these anti-IL-6 receptor antibodies determined are shown in Table 5 (see Reference Example for method). Furthermore, their BaF/gp130-neutralizing activities were compared to those of TOCILIZUMAB and the control (the known high affinity anti-IL-6 receptor antibody described in Reference Example, and VQ8F11-21 hIgG1 described in US 2007/0280945) (see Reference Example for method). The results obtained by determining the biological activities of these antibodies using BaF/gp130 are shown in FIG. 19 (TOCILIZUMAB, the control, and Fv5-M83 with a final IL-6 concentration of 300 ng/ml) and FIG. 20 (TOCILIZUMAB, Fv3-M73, and Fv4-M73 with a final IL-6 concentration of 30 ng/ml). As shown in Table 5, Fv3-M73 and Fv4-M73 have about two to three times higher affinity than TOCILIZUMAB, while Fv5-M83 exhibits about 100 times higher affinity than TOCILIZUMAB (since it was difficult to measure the affinity of Fv5-M83, instead the affinity was determined using Fv5-IgG1, which has an IgG1-type constant region; the constant region is generally thought to have no effect on affinity). As shown in FIG. 20, Fv3-M73 and Fv4-M73 exhibit slightly stronger activities than TOCILIZUMAB. As shown in FIG. 19, Fv5-M83 has a very strong activity, which is more than 100 times greater than that of TOCILIZUMAB in terms of 50% inhibitory concentration. Fv5-M83 also exhibits about 10 times higher neutralizing activity in terms of 50% inhibitory concentration than the control (the known high-affinity anti-IL-6 receptor antibody).

TABLE 5

|  | $k_a$ (1/Ms) | $k_d$ (1/s) | KD (M) |
| --- | --- | --- | --- |
| TOCILIZUMAB | 4.0E+05 | 1.1E−03 | 2.7E−09 |
| Fv3-M73 | 8.5E+05 | 8.7E−04 | 1.0E−09 |
| Fv4-M73 | 7.5E+05 | 1.0E−03 | 1.4E−09 |
| Fv5-M83 | 1.1E+06 | 2.8E−05 | 2.5E−11 |

The isoelectric points of TOCILIZUMAB, the control, Fv3-M73, Fv4-M73, and Fv5-M83 were determined by isoelectric focusing using a method known to those skilled in the art. The result showed that the isoelectric point was about 9.3 for TOCILIZUMAB; about 8.4 to 8.5 for the control; about 5.7 to 5.8 for Fv3-M73; about 5.6 to 5.7 for Fv4-M73; and 5.4 to 5.5 for Fv5-M83. Thus, each antibody had a significantly lowered isoelectric point when compared to TOCILIZUMAB and the control. Furthermore, the theoretical isoelectric point of the variable regions VH/VL was calculated by GENETYX (GENETYX CORPORATION). The result showed that the theoretical isoelectric point was 9.20 for TOCILIZUMAB; 7.79 for the control; 5.49 for Fv3-M73; 5.01 for Fv4-M73; and 4.27 for Fv5-M83. Thus, each antibody had a significantly lowered isoelectric point when compared to TOCILIZUMAB and the control. Accordingly, the pharmacokinetics of Fv3-M73, Fv4-M73, and Fv5-M83 was thought to be improved when compared to TOCILIZUMAB and the control.

T-cell epitopes in the variable region sequence of TOCILIZUMAB, Fv3-M73, Fv4-M73, or Fv5-M83 were analyzed using TEPITOPE (Methods. 2004 December; 34(4):468-75). As a result, TOCILIZUMAB was predicted to have T-cell epitopes, of which many could bind to HLA. In contrast, the number of sequences that were predicted to bind to T-cell epitopes was significantly reduced in Fv3-M73, Fv4-M73, and Fv5-M83. In addition, the framework of Fv3-M73, Fv4-M73, or Fv5-M83 has no mouse sequence and is thus fully humanized. These suggest the possibility that immunogenicity risk is significantly reduced in Fv3-M73, Fv4-M73, and Fv5-M83 when compared to TOCILIZUMAB.

Example 12

PK/PD Test of Fully Humanized Anti-IL-6 Receptor Antibodies in Monkeys

Figure 21:
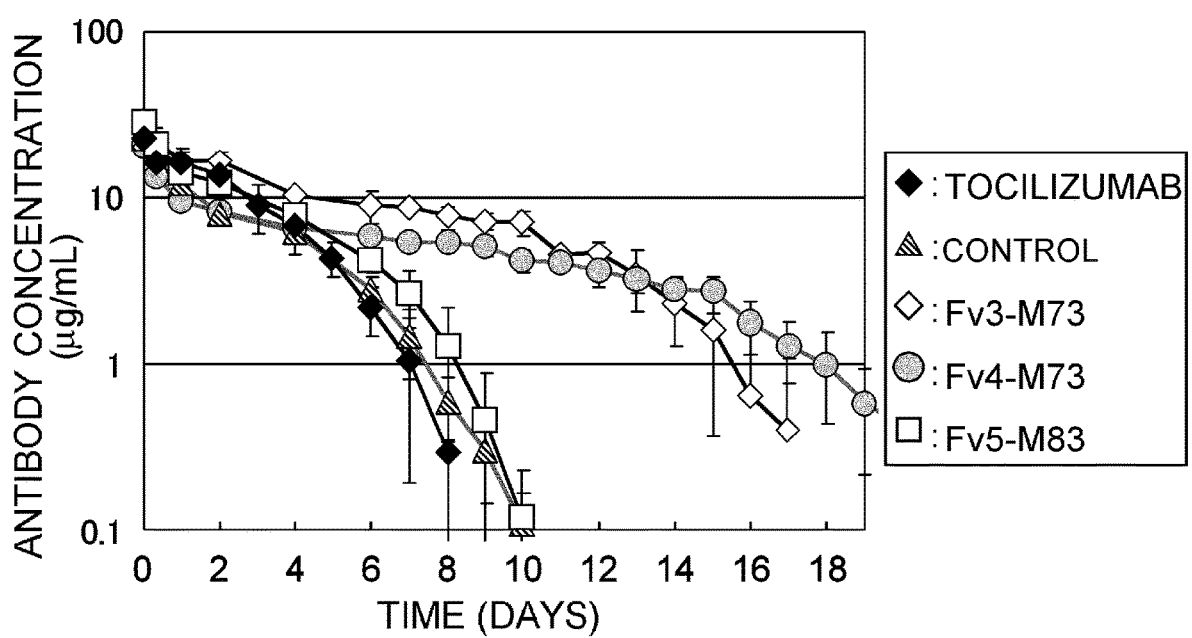
FIG. 21 is a graph showing the plasma concentration time courses of TOCILIZUMAB, the control, Fv3-M73, Fv4-M73, and Fv5-M83 in cynomolgus monkeys after intravenous administration.

Each of TOCILIZUMAB, the control, Fv3-M73, Fv4-M73, and Fv5-M83 was intravenously administered once at a dose of 1 mg/kg to cynomolgus monkeys to assess the time courses of their plasma concentrations (see Reference Example for method). The plasma concentration time courses of TOCILIZUMAB, Fv3-M73, Fv4-M73, and Fv5-M83 after intravenous administration are shown in FIG. 21. The result showed that each of Fv3-M73, Fv4-M73, and Fv5-M83 exhibited significantly improved pharmacokinetics in cynomolgus monkeys when compared to TOCILIZUMAB and the control. Of them, Fv3-M73 and Fv4-M73 exhibited substantially improved pharmacokinetics when compared to TOCILIZUMAB.

Figure 22:
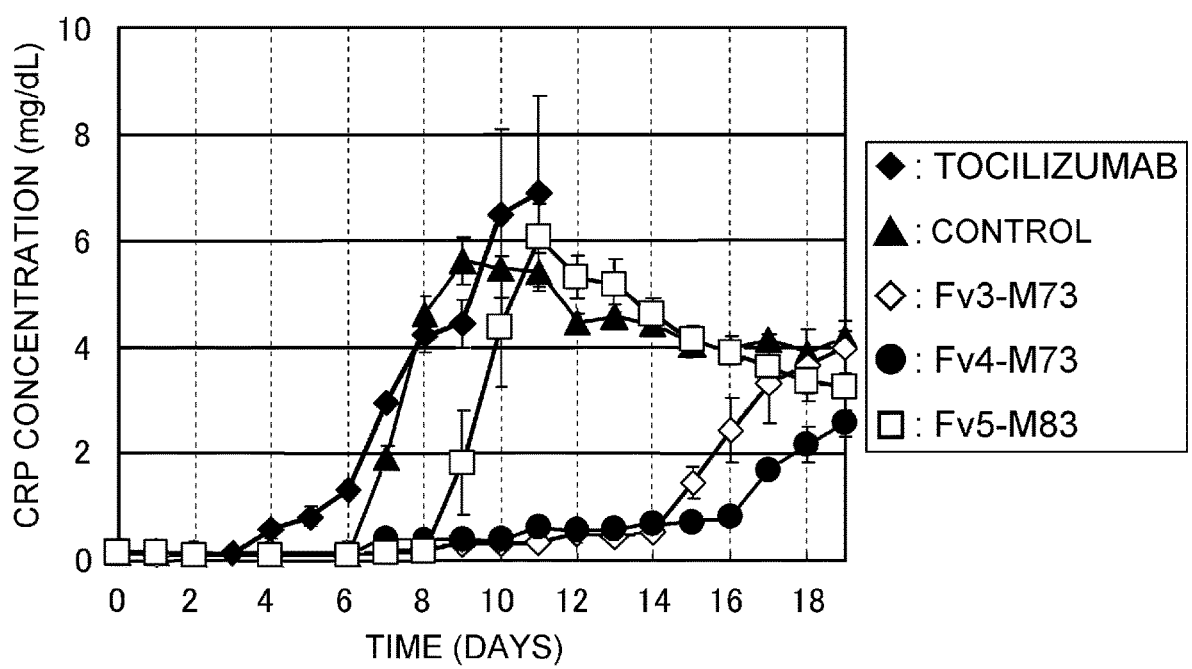
FIG. 22 is a graph showing the time courses of CRP concentration in cynomolgus monkeys after intravenous administration of TOCILIZUMAB, the control, Fv3-M73, Fv4-M73, or Fv5-M83.
Figure 23:
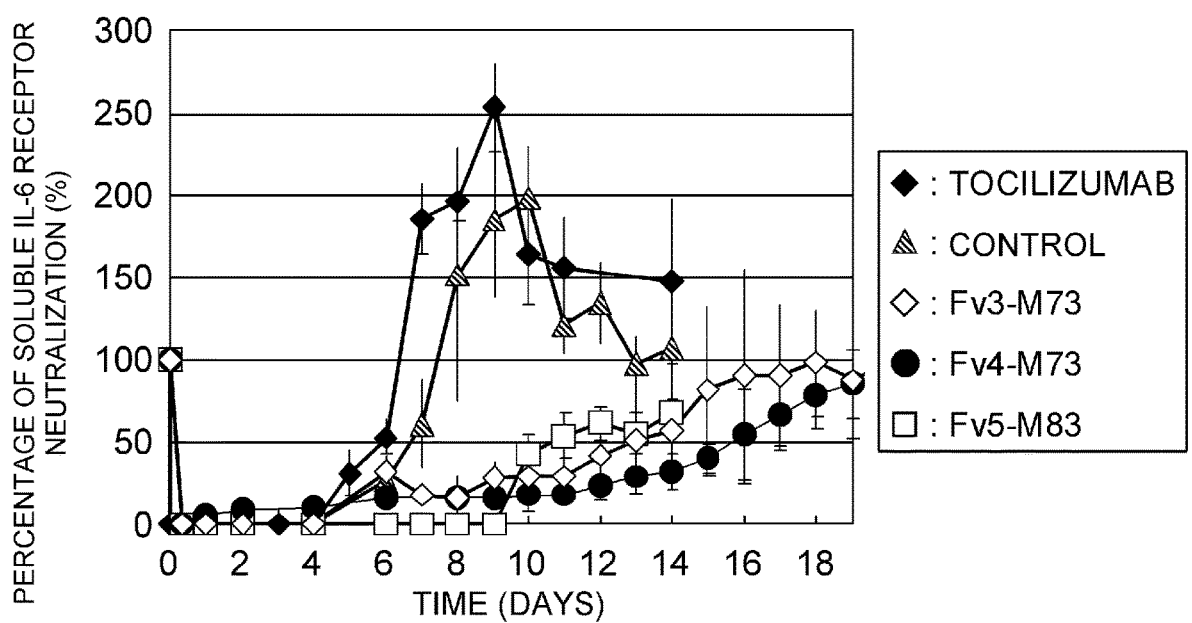
FIG. 23 is a graph showing the time courses of concentration of free soluble IL-6 receptor in cynomolgus monkeys after intravenous administration of TOCILIZUMAB, the control, Fv3-M73, Fv4-M73, or Fv5-M83.

The efficacy of each antibody to neutralize membrane-bound cynomolgus monkey IL-6 receptor was assessed. Cynomolgus monkey IL-6 was administered subcutaneously in the lower back at 5 μg/kg every day from Day 6 to Day 18 after antibody administration (Day 3 to Day 10 for TOCILIZUMAB), and the CRP concentration in each animal was determined 24 hours later (see Reference Example for method). The time course of CRP concentration after administration of each antibody is shown in FIG. 22. To assess the efficacy of each antibody to neutralize soluble cynomolgus monkey IL-6 receptor, the plasma concentration of free soluble cynomolgus monkey IL-6 receptor in the cynomolgus monkeys was determined and percentage of soluble IL-6 receptor neutralization were calculated (see Reference Example for method). The time course of percentage of soluble IL-6 receptor neutralization after administration of each antibody is shown in FIG. 23.

Each of Fv3-M73, Fv4-M73, and Fv5-M83 neutralized membrane-bound cynomolgus monkey IL-6 receptor in a more sustainable way, and suppressed the increase of CRP over a longer period when compared to TOCILIZUMAB and the control (the known high-affinity anti-IL-6 receptor antibody). Furthermore, each of Fv3-M73, Fv4-M73, and Fv5-M83 neutralized soluble cynomolgus monkey IL-6 receptor in a more sustainable way, and suppressed the increase of free soluble cynomolgus monkey IL-6 receptor over a longer period when compared to TOCILIZUMAB and the control. These findings demonstrate that all of Fv3-M73, Fv4-M73, and Fv5-M83 are superior in sustaining the neutralization of membrane-bound and soluble IL-6 receptors than TOCILIZUMAB and the control. Of them, Fv3-M73 and Fv4-M73 are remarkably superior in sustaining the neutralization. Meanwhile, Fv5-M83 suppressed CRP and free soluble cynomolgus monkey IL-6 receptor more strongly than Fv3-M73 and Fv4-M73. Thus, Fv5-M83 is considered to be stronger than Fv3-M73, Fv4-M73, and the control (the known high-affinity anti-IL-6 receptor antibody) in neutralizing membrane-bound and soluble IL-6 receptors. It was considered that results in in vivo of cynomolgus monkeys reflect the stronger affinity of Fv5-M83 for IL-6 receptor and stronger biological activity of Fv5-M83 in the BaF/gp130 assay system relative to the control.

These findings suggest that Fv3-M73 and Fv4-M73 are highly superior in sustaining their activities as an anti-IL-6 receptor-neutralizing antibody when compared to TOCILIZUMAB and the control, and thus enable to significantly reduce the dosage and frequency of administration. Furthermore, Fv5-M83 was demonstrated to be remarkably superior in terms of the strength of activity as an anti-IL-6 receptor-neutralizing antibody as well as sustaining their activity. Thus, Fv3-M73, Fv4-M73, and Fv5-M83 are expected to be useful as pharmaceutical IL-6 antagonists.

Reference Example

Preparation of Soluble Recombinant Cynomolgus Monkey IL-6 Receptor (cIL-6R)

Oligo-DNA primers were prepared based on the disclosed gene sequence for Rhesus monkey IL-6 receptor (Birney et al., Ensembl 2006, Nucleic Acids Res. 2006 Jan. 1; 34 (Database issue):D556-61). A DNA fragment encoding the whole cynomolgus monkey IL-6 receptor gene was prepared by PCR using the primers, and as a template, cDNA prepared from the pancreas of cynomolgus monkey. The resulting DNA fragment was inserted into an animal cell expression vector, and a stable expression CHO line (cyno.sIL-6R-producing CHO cell line) was prepared using the vector. The culture medium of cyno.sIL-6R-producing CHO cells was purified using a HisTrap column (GE Healthcare Bioscience) and then concentrated with Amicon Ultra-15 Ultracel-10k (Millipore). A final purified sample of soluble cynomolgus monkey IL-6 receptor (hereinafter cIL-6R) was obtained through further purification on a Superdex 200 pg 16/60 gel filtration column (GE Healthcare Bioscience).

Preparation of Recombinant Cynomolgus Monkey IL-6 (cIL-6)

Cynomolgus monkey IL-6 was prepared by the procedure described below. The nucleotide sequence encoding 212 amino acids deposited under SWISSPROT Accession No. P79341 was prepared and cloned into an animal cell expression vector. The resulting vector was introduced into CHO cells to prepare a stable expression cell line (cyno.IL-6- producing CHO cell line). The culture medium of cyno.IL-6-producing CHO cells was purified using a SP-Sepharose/FF column (GE Healthcare Bioscience) and then concentrated with Amicon Ultra-15 Ultracel-5k (Millipore). A final purified sample of cynomolgus monkey IL-6 (hereinafter cIL-6) was obtained through further purification on a Superdex 75 pg 26/60 gel filtration column (GE Healthcare Bioscience), followed by concentration with Amicon Ultra-15 Ultracel-5k (Millipore).

Preparation of a known High-affinity Anti-IL-6 Receptor Antibody

An animal cell expression vector was constructed to express VQ8F11-21 hIgG1, a known high-affinity anti-IL-6 receptor antibody. VQ8F11-21 hIgG1 is described in US 2007/0280945 A1 (US 2007/0280945 A1; the amino acid sequences of H chain and L chain as set forth in SEQ ID NOs: 19 and 27, respectively). The antibody variable region was constructed by PCR using a combination of synthetic oligo DNAs (assembly PCR). IgG1 was used as the constant region. The antibody variable and constant regions were combined together by assembly PCR, and then inserted into an animal cell expression vector to construct expression vectors for the H chain and L chain of interest. The nucleotide sequences of the resulting expression vectors were determined by a method known to those skilled in the art. The high-affinity anti-IL-6 receptor antibody (hereinafter abbreviated as "control") was expressed and purified using the constructed expression vectors by the method described in Example 1.

Assessment for the Biological Activity by Human gp130-expressing BaF3 Cells (BaF/gp130)

The IL-6 receptor neutralizing activity was assessed using BaF3/gp130 which proliferates in an IL-6/IL-6 receptor-dependent manner. After three washes with RPMI1640 supplemented with 10% FBS, BaF3/gp130 cells were suspended at $5 \times 10^4$ cells/ml in RPMI1640 supplemented with 600 ng/ml or 60 ng/ml human interleukin-6 (TORAY) (final concentration of 300 ng/ml or 30 ng/ml, respectively), appropriate amount of recombinant soluble human IL-6 receptor (SR344), and 10% FBS. The cell suspensions were dispensed (50 µl/well) into 96-well plates (CORNING). Then, the purified antibodies were diluted with RPMI1640 containing 10% FBS, and added to each well (50 µl/well). The cells were cultured at 37° C. under 5% $CO_2$ for three days. WST-8 Reagent (Cell Counting Kit-8; Dojindo Laboratories) was diluted two-fold with PBS. Immediately after 20 µl of the reagent was added to each well, the absorbance at 450 nm (reference wavelength: 620 nm) was measured using SUNRISE CLASSIC (TECAN). After culturing for two hours, the absorbance at 450 nm (reference wavelength: 620 nm) was measured again. The IL-6 receptor neutralizing activity was assessed using the change of absorbance during two hours as an indicator.

Biacore-based Analysis of Binding to IL-6 Receptor

Antigen-antibody reaction kinetics was analyzed using Biacore T100 (GE Healthcare). The SR344-antibody interaction was measured by immobilizing appropriate amounts of anti-IgG (γ-chain specific) F(ab')$_2$ onto a sensor chip by amine coupling method, binding antibodies of interest onto the chip at pH7.4, and then running IL-6 receptor SR344 adjusted to be various concentrations at pH7.4 over the chip as an analyte. All measurements were carried out at 37° C. The kinetic parameters, association rate constant $k_a$ (1/Ms) and dissociation rate constant $k_d$ (1/s) were calculated from the sensorgrams obtained by measurement. Then, $K_D$ (M) was determined based on the rate constants. The respective parameters were determined using Biacore T100 Evaluation Software (GE Healthcare).

PK/PD Test to Determine the Plasma Concentrations of Antibodies, CRP, and Free Soluble IL-6 Receptor in Monkeys The plasma concentrations in cynomolgus monkeys were determined by ELISA using a method known to those skilled in the art.

The concentration of CRP was determined with an automated analyzer (TBA-120FR; Toshiba Medical Systems Co.) using Cias R CRP (KANTO CHEMICAL CO., INC.).

The plasma concentration of free soluble cynomolgus monkey IL-6 receptor in cynomolgus monkeys was determined by the procedure described below. All IgG antibodies (cynomolgus monkey IgG, anti-human IL-6 receptor antibody, and anti-human IL-6 receptor antibody-soluble cynomolgus monkey IL-6 receptor complex) in the plasma were adsorbed onto Protein A by loading 30 µl of cynomolgus monkey plasma onto an appropriate amount of rProtein A Sepharose Fast Flow resin (GE Healthcare) dried in a 0.22-µm filter cup (Millipore). Then, the solution in cup was spinned down using a high-speed centrifuge to collect the solution that passed through. The solution that passed through does not contain Protein A-bound anti-human IL-6 receptor antibody-soluble cynomolgus monkey IL-6 receptor complex. Therefore, the concentration of free soluble IL-6 receptor can be determined by measuring the concentration of soluble cynomolgus monkey IL-6 receptor in the solution that passed through Protein A. The concentration of soluble cynomolgus monkey IL-6 receptor was determined using a method known to those skilled in the art for measuring the concentrations of soluble human IL-6 receptor. Soluble cynomolgus monkey IL-6 receptor (cIL-6R) prepared as described above was used as a standard.

Then the percentage of soluble IL-6 receptor neutralization was calculated by following formula.

$$\frac{\text{Free soluble IL-6 receptor concentration after antibody administration}}{\text{Soluble IL-6 receptor concentration before antibody administration}} \times 100$$

INDUSTRIAL APPLICABILITY

The present invention provides antibody constant regions suitable for pharmaceuticals, whose physicochemical properties (stability and homogeneity), immunogenicity, safety, and pharmacokinetics have been improved by amino acid alteration.

The invention claimed is:

1. An IgG4 antibody comprising two polypeptides that are antibody heavy chains, each of which comprises an identical heavy chain constant region comprising the amino acid sequence of SEQ ID NO: 3 with only the following amino acid changes:
  (i) deletions of the amino acids at EU numbering positions 446 and 447;
  (ii) optionally an amino acid substitution, relative to SEQ ID NO: 3, at one or more of the following EU numbering positions: 131, 133, 137, 138, 214, 217, 219, 220, 221, 222, 233, 234, 235 and 409; and
  (iii) optionally a deletion of the amino acid at EU numbering position 236,
  wherein the amino acid at EU numbering position 445 is not amidated and is at the C-terminus of each of the two polypeptides.

2. The IgG4 antibody of claim 1, wherein the amino acids at EU numbering positions 233, 234, and 235 are substituted relative to the sequence of SEQ ID NO: 3, and the amino acid at EU numbering position 236 is deleted.

3. The IgG4 antibody of claim 1, wherein the amino acids at EU numbering positions 131, 133, 137, 138, 214, 217, 219, 220, 221, and 222 are substituted relative to the sequence of SEQ ID NO: 3.

4. The IgG4 antibody of claim 1, wherein the amino acid at EU numbering position 409 is substituted relative to the sequence of SEQ ID NO: 3.

5. The IgG4 antibody of claim 1, wherein the amino acids at EU numbering positions 131, 133, 137, 138, 214, 217, 219, 220, 221, 222, 233, 234, 235, and 409 are substituted relative to the sequence of SEQ ID NO: 3, and the amino acid at EU numbering position 236 is deleted.

6. A pharmaceutical composition comprising the antibody of claim 1.

7. An IgG4 antibody comprising two polypeptides that are antibody heavy chains, each of which comprises an identical heavy chain constant region comprising the amino acid sequence of SEQ ID NO: 3 with only the following amino acid changes:
  (i) deletions of the amino acids at EU numbering positions 446 and 447;
  (ii) one or more substitutions relative to the sequence of SEQ ID NO: 3, including a substitution at one or more of the following EU numbering positions: 131, 133, 137, 138, 214, 217, 219, 220, 221, 222, 233, 234, 235 and 409; and
  (iii) optionally a deletion of the amino acid at EU numbering position 236,
  wherein the amino acid at EU numbering position 445 is the C-terminal amino acid of each of the two polypeptides and is not amidated.

8. The IgG4 antibody of claim 7, wherein the amino acids at EU numbering positions 233, 234, and 235 are substituted relative to the sequence of SEQ ID NO: 3, and the amino acid at EU numbering position 236 is deleted.

9. The IgG4 antibody of claim 7, wherein the amino acids at EU numbering positions 131, 133, 137, 138, 214, 217, 219, 220, 221, and 222 are substituted relative to the sequence of SEQ ID NO: 3.

10. The IgG4 antibody of claim 7, wherein the amino acid at EU numbering position 409 is substituted relative to the sequence of SEQ ID NO: 3.

11. The IgG4 antibody of claim 7, wherein the amino acids at EU numbering positions 131, 133, 137, 138, 214, 217, 219, 220, 221, 222, 233, 234, 235, and 409 are substituted relative to the sequence of SEQ ID NO: 3, and the amino acid at EU numbering position 236 is deleted.

12. A pharmaceutical composition comprising the antibody of claim 7.

13. An IgG4 antibody comprising two polypeptides that are antibody heavy chains, each of which comprises an identical heavy chain constant region comprising the amino acid sequence of SEQ ID NO: 3 with changes including:
  deletions of the amino acids at EU numbering positions 446 and 447; and
  (ii) at least one additional change at any of EU numbering positions 118-445 in the amino acid sequence of SEQ ID NO: 3, each additional change being independently selected from the group consisting of substitution, deletion, and insertion, wherein the at least one additional change includes a change selected from the group consisting of:
    an amino acid substitution at EU numbering position 131,
    an amino acid substitution at EU numbering position 133,
    an amino acid substitution at EU numbering position 137,
    an amino acid substitution at EU numbering position 138,
    an amino acid substitution at EU numbering position 214,
    an amino acid substitution at EU numbering position 217,
    an amino acid substitution at EU numbering position 219,
    an amino acid substitution at EU numbering position 220,
    an amino acid substitution at EU numbering position 221,
    an amino acid substitution at EU numbering position 222,
    an amino acid substitution at EU numbering position 233,
    an amino acid substitution at EU numbering position 234,
    an amino acid substitution at EU numbering position 235,
    an amino acid substitution at EU numbering position 409, and
    a deletion of the amino acid at EU numbering position 236,
  wherein the amino acid at EU numbering position 445 may be substituted but is not deleted, is the C-terminal amino acid of each of the two polypeptides, and is not amidated.

14. The IgG4 antibody of claim 13, wherein the amino acids at EU numbering positions 233, 234, and 235 are substituted relative to the sequence of SEQ ID NO: 3, and the amino acid at EU numbering position 236 is deleted.

15. The IgG4 antibody of claim 13, wherein the amino acids at EU numbering positions 131, 133, 137, 138, 214, 217, 219, 220, 221, and 222 are substituted relative to the sequence of SEQ ID NO: 3.

16. The IgG4 antibody of claim 13, wherein the amino acid at EU numbering position 409 is substituted relative to the sequence of SEQ ID NO: 3.

17. The IgG4 antibody of claim 13, wherein the amino acid at EU numbering position 236 is deleted.

18. A pharmaceutical composition comprising the antibody of claim 13.

19. A method of producing an IgG4 antibody comprising two identical modified human IgG4 heavy chain constant regions with reduced C-terminal heterogeneity, the method comprising:
  (a) preparing nucleic acid encoding the IgG4 antibody of claim 1;
  (b) introducing the nucleic acid in a host cell;
  (c) culturing the host cell to express the nucleic acid; and
  (d) collecting the IgG4 antibody from the host cell,
  wherein C-terminal heterogeneity of the IgG4 antibody in a composition comprising multiple copies of the IgG4 antibody is reduced compared to C-terminal heterogeneity in a composition comprising multiple copies of a naturally occurring human IgG4.

20. A method of producing an IgG4 antibody comprising two identical modified human IgG4 heavy chain constant regions with reduced C-terminal heterogeneity, the method comprising:
  (a) preparing nucleic acid encoding the IgG4 antibody of claim 7;
  (b) introducing the nucleic acid in a host cell;
  (c) culturing the host cell to express the nucleic acid; and
  (d) collecting the IgG4 antibody from the host cell,
  wherein C-terminal heterogeneity of the IgG4 antibody in a composition comprising multiple copies of the IgG4 antibody is reduced compared to C-terminal heterogeneity in a composition comprising multiple copies of a naturally occurring human IgG4.

21. A method of producing an IgG4 antibody comprising two identical modified human IgG4 heavy chain constant regions with reduced C-terminal heterogeneity, the method comprising:
  (a) preparing nucleic acid encoding the IgG4 antibody of claim 13;
  (b) introducing the nucleic acid in a host cell;
  (c) culturing the host cell to express the nucleic acid; and
  (d) collecting the IgG4 antibody from the host cell,
  wherein C-terminal heterogeneity of the IgG4 antibody in a composition comprising multiple copies of the IgG4 antibody is reduced compared to C-terminal heterogeneity in a composition comprising multiple copies of a naturally occurring human IgG4.

* * * * *